United States Patent
He et al.

(10) Patent No.: US 9,549,921 B2
(45) Date of Patent: Jan. 24, 2017

(54) HETEROCYCLIC COMPOUNDS AND METHODS OF USE THEREOF FOR THE TREATMENT OF HEPATITIS C

(71) Applicants: Shuwen He, Fanwood, NJ (US); Zhong Lai, East Brunswick, NJ (US); Xing Dai, Cranford, NJ (US); Dong Xiao, Warren, NJ (US); Clare London, Chatham, NJ (US); Nicolas Zorn, Durmenach (FR); Ravi Nargund, East Brunswick, NJ (US); Anandan Palani, Bridgewater, NJ (US); Casey C. McComas, Phoenixville, PA (US); Peng Li, Shanghai (CN); Xuanjia Peng, Shanghai (CN); Richard Soll, Middleton, MA (US)

(72) Inventors: Shuwen He, Fanwood, NJ (US); Zhong Lai, East Brunswick, NJ (US); Xing Dai, Cranford, NJ (US); Dong Xiao, Warren, NJ (US); Clare London, Chatham, NJ (US); Nicolas Zorn, Durmenach (FR); Ravi Nargund, East Brunswick, NJ (US); Anandan Palani, Bridgewater, NJ (US); Casey C. McComas, Phoenixville, PA (US); Peng Li, Shanghai (CN); Xuanjia Peng, Shanghai (CN); Richard Soll, Middleton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/897,966

(22) PCT Filed: Jun. 19, 2014

(86) PCT No.: PCT/US2014/043075
§ 371 (c)(1),
(2) Date: Dec. 11, 2015

(87) PCT Pub. No.: WO2014/209729
PCT Pub. Date: Dec. 31, 2014

(65) Prior Publication Data
US 2016/0143895 A1    May 26, 2016

(51) Int. Cl.
| A61K 31/454 | (2006.01) |
|---|---|
| C07D 487/04 | (2006.01) |
| A61K 31/498 | (2006.01) |
| A61K 31/4525 | (2006.01) |
| A61K 31/4545 | (2006.01) |
| A61K 31/5377 | (2006.01) |
| A61K 31/496 | (2006.01) |
| A61K 31/55 | (2006.01) |
| A61K 31/502 | (2006.01) |

(Continued)

(52) U.S. Cl.
CPC .......... *A61K 31/454* (2013.01); *A61K 31/404* (2013.01); *A61K 31/423* (2013.01); *A61K 31/4525* (2013.01); *A61K 31/4545* (2013.01); *A61K 31/496* (2013.01); *A61K 31/498* (2013.01); *A61K 31/502* (2013.01); *A61K 31/5377* (2013.01); *A61K 31/55* (2013.01); *A61K 45/06* (2013.01); *C07D 405/04* (2013.01); *C07D 405/14* (2013.01); *C07D 413/14* (2013.01); *C07D 417/14* (2013.01); *C07D 471/04* (2013.01); *C07D 487/04* (2013.01); *C07D 495/04* (2013.01); *C07D 498/04* (2013.01); *C07D 513/04* (2013.01)

(58) Field of Classification Search
None
See application file for complete search history.

(56) References Cited

U.S. PATENT DOCUMENTS

| 2004/0132720 A1 | 7/2004 | Marshall et al. |
|---|---|---|
| 2004/0162318 A1 | 8/2004 | Saha et al. |

(Continued)

FOREIGN PATENT DOCUMENTS

| CN | 1731993 | 2/2006 |
|---|---|---|
| WO | WO2008082484 | 7/2008 |

(Continued)

OTHER PUBLICATIONS

Beaulieu et al., Inhibitors of the HCV NS5B polymerase: New hope for the treatment of hepatitis C infections, Current Opinions in Investigational Drugs, 2004, 838, 5.

(Continued)

*Primary Examiner* — Brian J Davis
(74) *Attorney, Agent, or Firm* — Alysia A. Finnegan; Gloria M. Fuentes

(57) ABSTRACT

The present invention relates to compounds of formula I that are useful as hepatitis C virus (HCV) NS5B polymerase inhibitors, the synthesis of such compounds, and the use of such compounds for inhibiting HCV NS5B polymerase activity, for treating or preventing HCV infections and for inhibiting HCV viral replication and/or viral production in a cell-based system.(I)

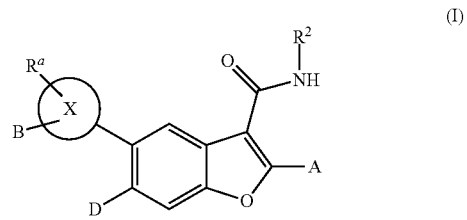

17 Claims, No Drawings

(51) Int. Cl.

| | |
|---|---|
| A61K 31/423 | (2006.01) |
| A61K 31/404 | (2006.01) |
| A61K 45/06 | (2006.01) |
| C07D 413/14 | (2006.01) |
| C07D 498/04 | (2006.01) |
| C07D 471/04 | (2006.01) |
| C07D 405/04 | (2006.01) |
| C07D 417/14 | (2006.01) |
| C07D 405/14 | (2006.01) |
| C07D 513/04 | (2006.01) |
| C07D 495/04 | (2006.01) |

(56) References Cited

U.S. PATENT DOCUMENTS

| | | |
|---|---|---|
| 2009/0081636 A1 | 3/2009 | Huang et al. |
| 2012/0328569 A1 | 12/2012 | McComas et al. |

FOREIGN PATENT DOCUMENTS

| | | | |
|---|---|---|---|
| WO | WO2008082488 | 7/2008 | |
| WO | WO2008083351 | 7/2008 | |
| WO | WO2008136815 | 11/2008 | |
| WO | WO2009032116 | 3/2009 | |
| WO | WO2009032123 | 3/2009 | |
| WO | WO2009032124 | 3/2009 | |
| WO | WO2009032125 | 3/2009 | |
| WO | WO2009137500 | 11/2009 | |
| WO | WO2010111483 | 9/2010 | |
| WO | WO2011103063 | 8/2011 | |
| WO | WO 2011/112191 A1 * | 9/2011 | ........... C07D 307/79 |
| WO | WO2011106992 | 9/2011 | |
| WO | WO2011112769 | 9/2011 | |
| WO | WO2014209726 | 12/2014 | |
| WO | WO2014209727 | 12/2014 | |

OTHER PUBLICATIONS

Carroll et al., Inhibition of Hepatitis C Virus RNA Replication by 2'-Modified Nucleoside Analogs, J. Biol. Chem., 2003, 11979-11984, 278(14).

Database Registry [Online] Columbus, Ohio, US: Chemical Abstracts Service [retrieved on Jun. 9, 2008] Retrieved from STN International, Columbus, USA. RN 1026673-40-4.

Ni et al., Progress and Development of Small Molecule HCV Antivirals, Current Opinion in Drug Discovery and Development, 2004, 446, 7(4).

Sven-Erik Behrens, Identification and properties of the RNA-dependnt RNA polymerase of hepatitis C virus, EMBO. J., 1996, 12-22, 15(1).

Tan et al., Hepatitis C Therapeutics: Current Status and Emerging Strategies, Nature Reviews, 2002, 867-881, 1.

* cited by examiner

HETEROCYCLIC COMPOUNDS AND METHODS OF USE THEREOF FOR THE TREATMENT OF HEPATITIS C

CROSS-REFERENCE TO RELATED APPLICATIONS

This application is a §371 National Stage Application of PCT/US2014/043075, international filing date of Jun. 19, 2014, which claims the benefit of International Application No. PCT/CN2013/000745, filed Jun. 24, 2013, now expired.

FIELD OF THE INVENTION

The present disclosure relates to compounds that are useful as inhibitors of the hepatitis C virus (HCV) NS5B (non-structural protein 5B) polymerase, compositions comprising such compounds, the use of such compounds for treating HCV infection and/or reducing the likelihood or severity of symptoms of HCV infection, methods for inhibiting the function of the NS5B polymerase, and methods for inhibiting HCV viral replication and/or viral production.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

One identified target for therapeutic intervention is HCV NS5B polymerase. Sven-Erik Behrens et al., *Identification and properties of the RNA-dependent RNA polymerase of hepatitis C virus*, 15(1) EMBO J. 12-22 (1996). Antagonists of NS5B activity are inhibitors of HCV replication. Steven S. Carroll et al., *Inhibition of Hepatitis C Virus RNA Replication by 2'-Modified Nucleoside Analogs*, 278(14) J. BIOL. CHEM. 11979-84 (2003).

There is a clear and long-felt need to develop effective therapeutics for treatment of HCV infection. Specifically, there is a need to develop compounds that inhibit HCV viral replication and that would be useful for treating HCV-infected patients.

SUMMARY OF THE INVENTION

The present disclosure relates to novel compounds of formula I and pharmaceutically acceptable salts thereof. These compounds are useful, either as compounds or their pharmaceutically acceptable salts (when appropriate), in the inhibition of HCV (hepatitis C virus) NS5B (non-structural 5B) polymerase, the prevention or treatment of one or more of the symptoms of HCV infection, the inhibition of HCV viral replication and/or HCV viral production, and/or as pharmaceutical composition ingredients. As pharmaceutical composition ingredients, these compounds and their salts may be the primary active therapeutic agent, and, when appropriate, may be combined with other therapeutic agents including but not limited to other HCV antivirals, anti-infectives, immunomodulators, antibiotics or vaccines, as well as the present Standard of Care treatment options for HCV.

In one aspect, the present invention relates to a compound of formula I:

or a pharmaceutically acceptable salt thereof,
wherein:

X is a 5 or 6-membered saturated monocyclic ring with 1 or 2 heteroatom ring atoms independently selected from N and O;

A is fluorophenyl;

B is a) hydrogen;
b) —C(O)CH═C(CH$_3$)$_2$;
c) Ar;
d) —C(O)—Ar;
e) —C(O)CHR$^y$—Ar;
f) —C(O)CH(NHR$^x$)—Ar;
g) —SO$_2$(CH$_2$)$_{0-2}$—Ar;
h) —SO$_2$—CH═CH—Ar;
i) —CO-Cyc;
j) —COCH$_2$-Cyc;
k) —SO$_2$-Cyc;

Ar is an aromatic ring system selected from:
(i) 5-6 membered monocyclic ring with 0, 1, or 2 heteroatom ring atoms independently selected from N or O, optionally substituted with 1 or 2 substituents independently selected from fluorophenyl, C$_1$-C$_6$ alkyl, and halo; and
(ii) 8-10 membered bicyclic rings with 1, 2 or 3 heteroatom ring atoms selected from N, O and S, optionally substituted with 1, 2 or 3 substituents independently selected from C$_1$-C$_6$ alkyl, C$_1$-C$_6$alkoxy, halo, CF$_3$, cyano, oxo, —NH$_2$, and cyclopropylmethyl;

Cyc is C$_3$-C$_6$ cycloalkyl optionally substituted with fluorophenyl or pyridine; or 3-oxabicyclo[3.1.0]hexane;

D is H or NR$^3$SO$_2$R$^4$;

R$^2$, R$^3$, and R$^4$ are independently C$_1$-C$_6$ alkyl;

R$^a$ is hydrogen or C$_1$-C$_6$ alkyl;

R$^x$ is hydrogen or C(O)OC(CH$_3$)$_3$; and

R$^y$ is hydrogen, morpholinyl or Ar.

The present invention also includes pharmaceutical compositions containing a compound of the present invention and methods of preparing such pharmaceutical compositions. The present invention further includes methods of treating or reducing the likelihood or severity of HCV infection, methods for inhibiting the activity of the NS5B polymerase, and methods for inhibiting HCV viral replication and/or viral production.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are HCV NS5B polymerase inhibitors.

In an aspect of the invention, X is

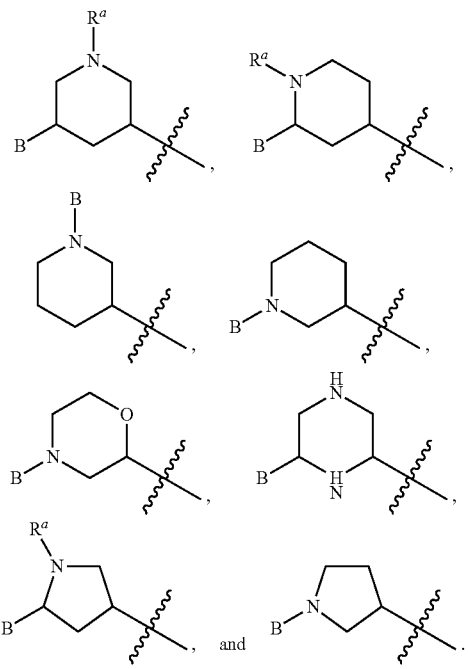

In a first embodiment of the invention, $R^2$, $R^3$ and $R^4$ are methyl, and the other groups are as provided in the general formula above or as in the first aspect.

In a second embodiment of the invention, D is $N(CH_3)SO_2CH_3$, and the other groups are as provided in the general formula above, as in the first aspect, or as in the first embodiment.

In a third embodiment of the invention, each halo is F, and the other groups are as provided in the general formula above, as in the first aspect or as in the first or second embodiments.

In a fourth embodiment of the invention, the compound of the invention has the formula

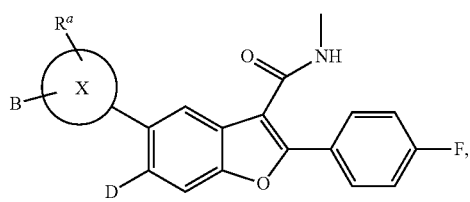

(Ia)

or a pharmaceutically acceptable salt thereof, and the groups are as provided in the general formula above, as in the first aspect or as in the first through third embodiments.

In a fifth embodiment of the invention, X is

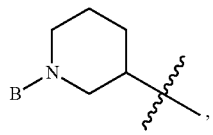

and the other groups are as provided in the general formula above, or as in the first through fourth embodiments.

In a sixth embodiment of the invention, B is Ar, —C(O)—Ar, or —SO$_2$—Ar; wherein Ar is a 9-membered bicyclic ring with 1, 2, or 3 heteroatom ring atoms selected from N, O and S, optionally substituted with 1, 2 or 3 substituents independently selected from $C_1$-$C_6$ alkyl, $C_1$-$C_6$alkoxy, F, $CF_3$, and cyano, and the other groups are as provided in the general formula above, as in the first aspect or as in the first through fifth embodiments. In an aspect of this sixth embodiment, Ar is

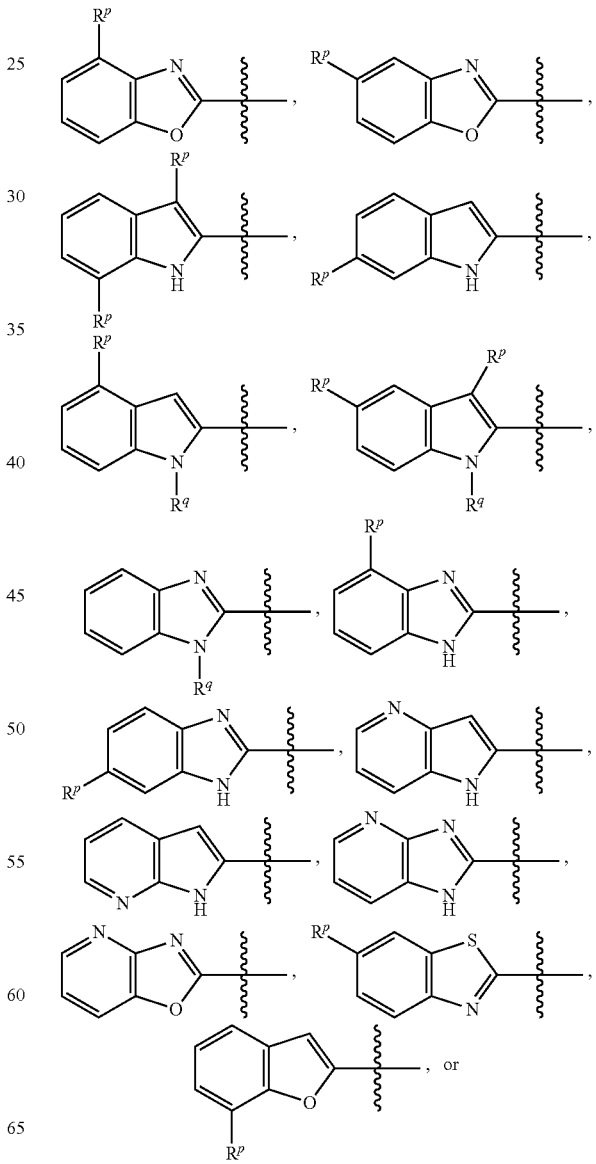

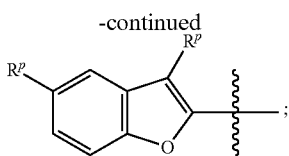

wherein each $R^p$ is independently selected from hydrogen, methyl, methoxy, F, CF$_3$, or cyano, and $R^q$ is hydrogen, methyl or ethyl, and the other groups are as provided in the general formula above, as in the first aspect or as in the first through fifth embodiments.

In a seventh embodiment of the invention, B is —SO$_2$—Ar, —SO$_2$CH$_2$—Ar, —SO$_2$CH$_2$CH$_2$—Ar, —C(O)—Ar; or —C(O)CH$_2$—Ar; wherein Ar is phenyl, methylphenyl, fluorophenyl, difluorophenyl, pyridine, or fluoropyridine, and the other groups are as provided in the general formula above, as in the first aspect or as in the first through sixth embodiments.

In certain aspects of the invention, a fluorophenyl is para-fluorophenyl.

In another embodiment of the invention, the compound of the invention is selected from the exemplary species depicted in Examples 1-144 shown below, and pharmaceutically acceptable salts thereof.

In another embodiment of the invention, the compound of the invention is selected from the exemplary species depicted in Examples 2, 4, 7, 11, 14, 25, 35, 37, 38 and 59 shown below, and pharmaceutically acceptable salts thereof.

Other embodiments of the present invention include the following:

(a) A pharmaceutical composition comprising an effective amount of a compound of formula I and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(d) A pharmaceutical combination that is (i) a compound of formula I and (ii) a second therapeutic agent selected from the group consisting of HCV antiviral agents, immunomodulators, and anti-infective agents; wherein the compound of formula I and the second therapeutic agent are each employed in an amount that renders the combination effective for inhibiting HCV NS5B activity, or for inhibiting HCV viral replication, or for treating HCV infection and/or reducing the likelihood or severity of symptoms of HCV infection.

(e) The combination of (d), wherein the HCV antiviral agents are one or more antiviral agents selected from the group consisting of direct inhibitors of HCV, including but not limited to NS3 and NS3/4A protease inhibitors, NS5A inhibitors and HCV NS5B polymerase inhibitors.

(f) A use of a compound of formula I in the preparation of a medicament for inhibiting HCV NS5B activity in a subject in need thereof.

(g) A use of a compound of formula I in the preparation of a medicament for preventing and/or treating infection by HCV in a subject in need thereof.

(h) A method of treating HCV infection and/or reducing the likelihood or severity of symptoms of HCV infection in a subject in need thereof, which comprises administering to the subject an effective amount of a compound of formula I.

(i) The method of (h), wherein the compound of formula I is administered in combination with an effective amount of at least one second therapeutic agent selected from the group consisting of HCV antiviral agents, immunomodulators, and anti-infective agents.

(j) The method of (i), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(k) A method of inhibiting HCV viral replication and/or HCV viral production in a cell-based system, which comprises administering to the subject an effective amount of a compound of formula I in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(m) A method of inhibiting HCV NS5B activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

Additional embodiments of the invention include the pharmaceutical compositions, combinations, uses and methods set forth in (a) through (n) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) inhibiting HCV NS5B activity, or (b) inhibiting HCV viral replication, or (c) treating HCV infection and/or reducing the likelihood or severity of symptoms of HCV infection, or (d) use in medicine. In these uses, the compounds of the present invention can optionally be employed in combination with one or more second therapeutic agents selected from HCV antiviral agents, anti-infective agents, and immunomodulators.

Chemical names, common names, and chemical structures may be used interchangeably to describe the same structure. If a chemical compound is referred to using both a chemical structure and a chemical name and an ambiguity exists between the structure and the name, the structure is understood to predominate.

As used herein, the term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HCV infection), "administration" and its variants are each understood to include concurrent and sequential provision of the compound or salt and other agents.

As used herein, the term "alkoxy" refers to an "alkyl-O—" group. Alkoxy groups may be substituted as indicated.

The term "alkyl" refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "aryl" (or "aromatic ring system") refers to aromatic mono- and poly-carbocyclic ring systems wherein the individual carbocyclic rings in the polyring systems are fused or attached to each other via a single bond. As used herein, the term aryl includes aromatic mono- and poly-carbocyclic ring systems that include from 0 to 4 heteroatoms (non-carbon atoms) that are independently chosen from N, O and S. Aromatic ring systems also includes ring systems where an aromatic ring is fused to a saturated ring. Suitable aryl groups include phenyl, naphthyl, biphenylenyl, pyridinyl, pyrimidinyl and pyrrolyl, as well as those discussed below. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "composition" is intended to encompass a product comprising the specified ingredients, as well as any product which results from combining the specified ingredients.

The term "compound" is intended to encompass chemical agents described by generic formula I in all forms. Such chemical agents can be present in different forms such as hydrates and solvates.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl, bicyclo[3.1.0] hexyl and adamantyl. The term "3 to 7-membered cycloalkyl" refers to a cycloalkyl group having from 3 to 7 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

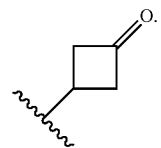 [SMILES: *C1CC(=O)C1]

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5B activity and thereby elicit the response being sought (i.e., an "inhibition effective amount"). When the active compound (i.e., active ingredient) is administered as the salt, references to the amount of active ingredient are to the free acid or free base form of the compound.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "halogen" (or "halo") refers to atoms of fluorine, chlorine, bromine and iodine (alternatively referred to as fluoro, chloro, bromo, and iodo).

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof.

The term "preventing," as used herein with respect to an HCV viral infection or HCV-virus related disorder, refers to reducing the likelihood of HCV infection.

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Unless expressly stated to the contrary, substitution by a named substituent is permitted on any atom provided such substitution is chemically allowed and results in a stable compound. Combinations of substituents and/or variables are permissible only if such combinations result in stable compounds. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (for example, $R^1$ or $R^3$) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Certain of the compounds of the present invention can exist as tautomers. For the purposes of the present invention a reference to a compound of formula I is a reference to the compound per se, or to any one of its tautomers per se, or to mixtures of two or more tautomers.

The compounds of the present inventions are useful in the inhibition of HCV replication (e.g., HCV NS5B activity), the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for identifying resistant HCV replicon cell lines harboring mutations within NS5B, which are excellent screening tools for more powerful antiviral compounds. Furthermore, the compounds of this invention are useful in establishing or determining the binding site of other antivirals to the HCV replicase.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of inhibiting HCV NS5B polymerase, treating HCV infection and/or reducing the likelihood or severity of symptoms of HCV infection and inhibiting HCV viral replication and/or HCV viral production, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, HCV viral genotype, viral resistance, and the host undergoing therapy.

As noted above, the present invention also relates to a method of inhibiting HCV NS5B activity, inhibiting HCV viral replication and/or HCV viral production, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such agents are described in detail below.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759NX-759 (ViroChem Pharma/Vertex), HCV-371 (Wyeth/ViroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo Smith-Kline), ANA598 (Anadys), GSK-625433 (Glaxo Smith-Kline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

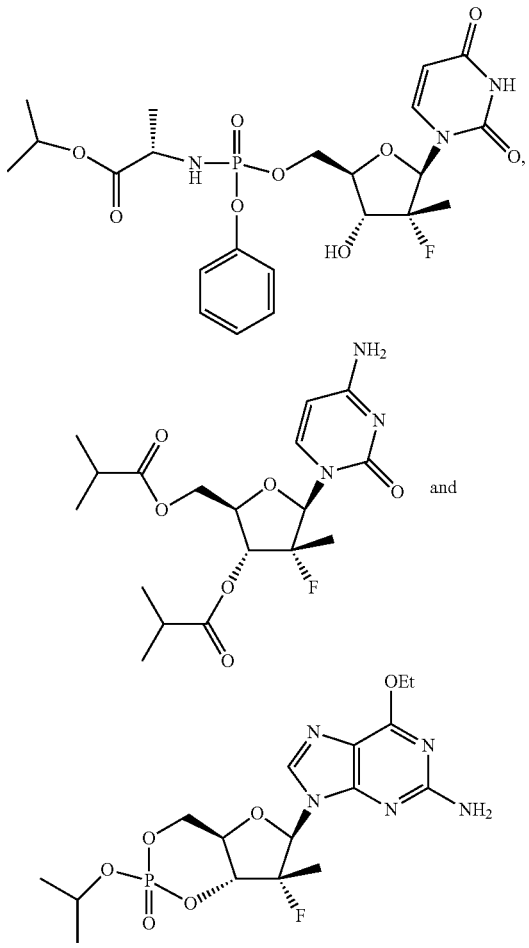

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J. in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhbitors useful in the present compositions and methods include, but are not limited to, an HCV protease inhibitor. Examples of HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

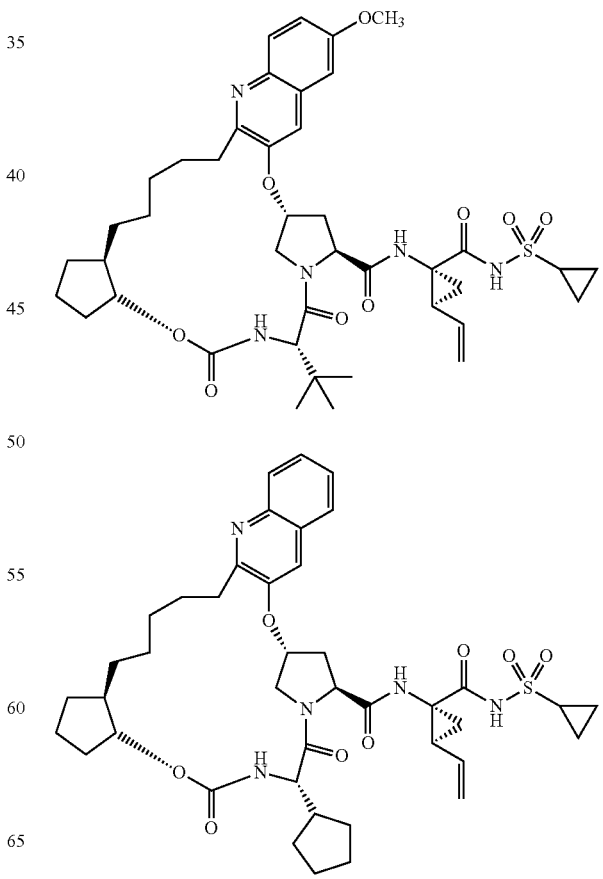

-continued
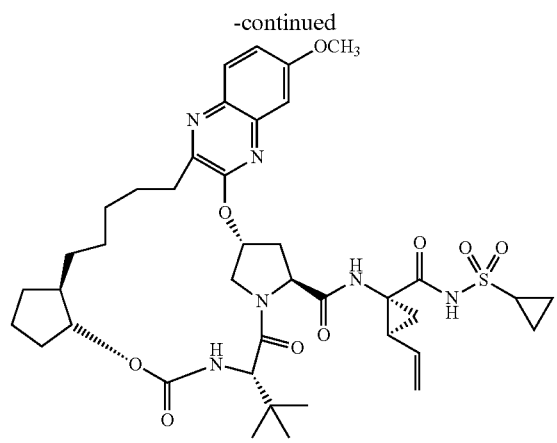
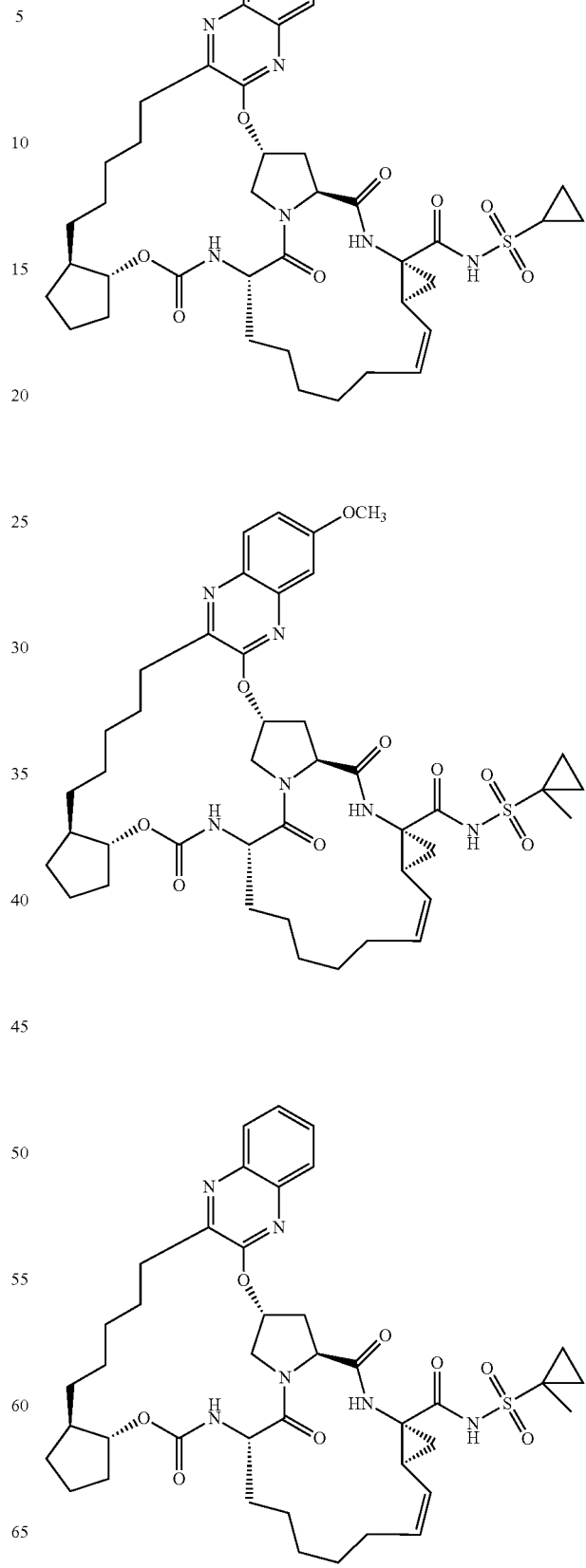

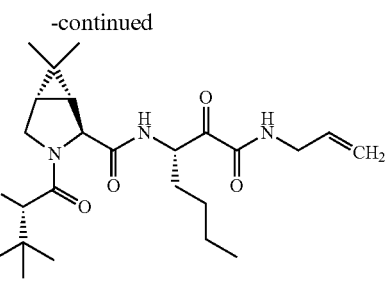
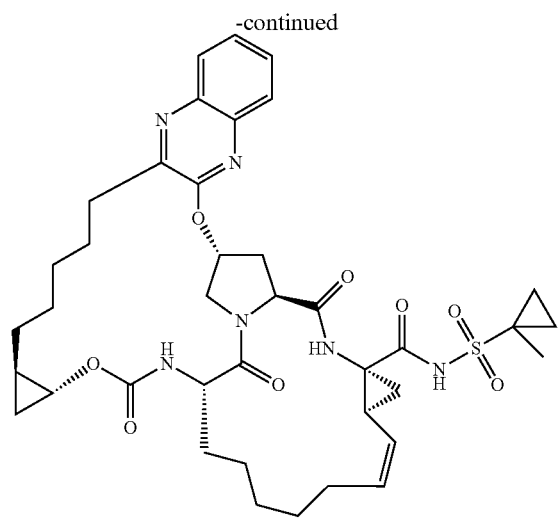
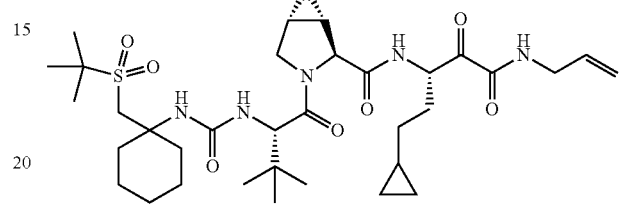
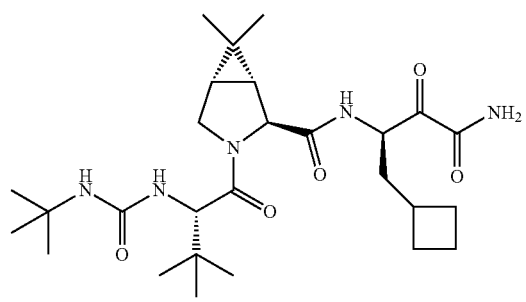
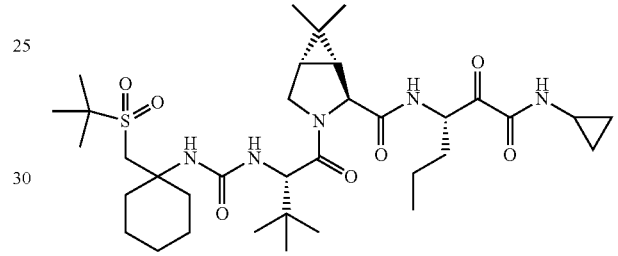
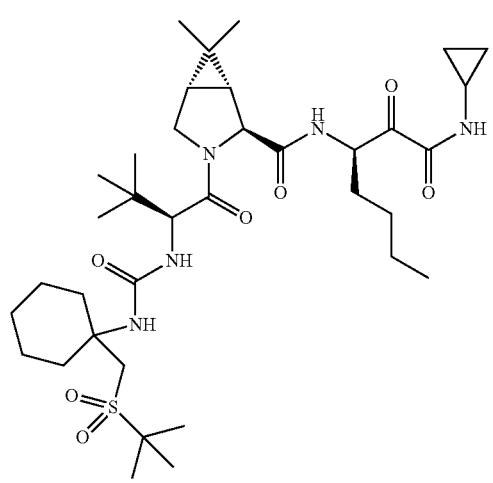
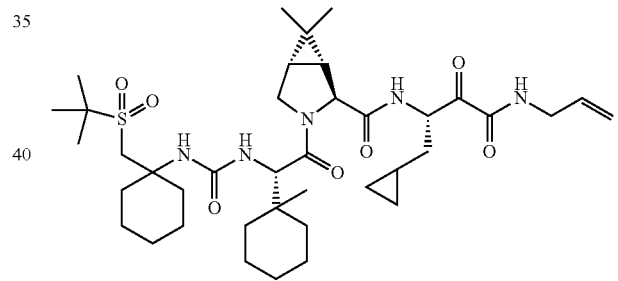
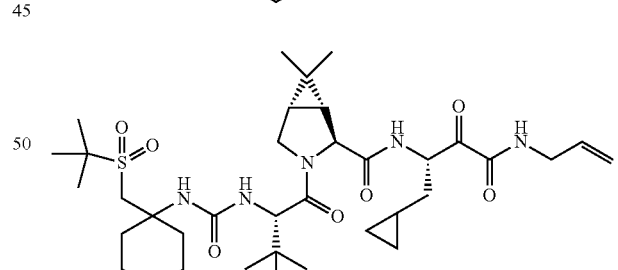
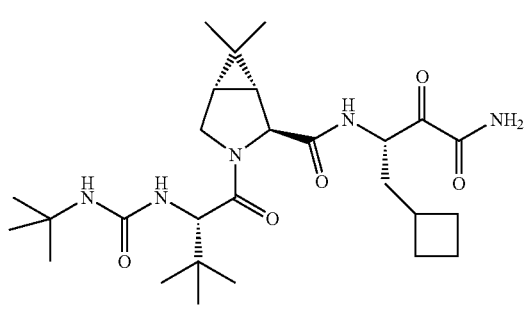
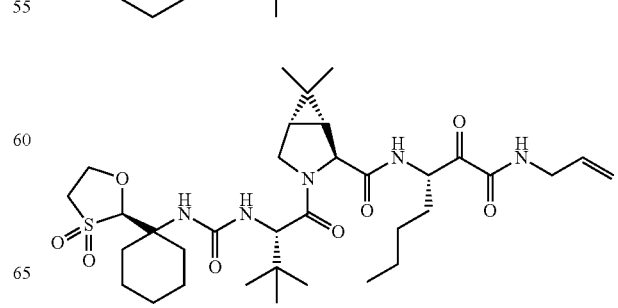

-continued
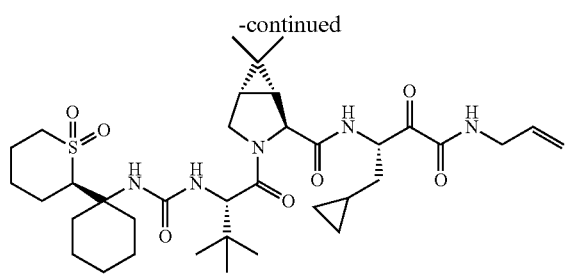
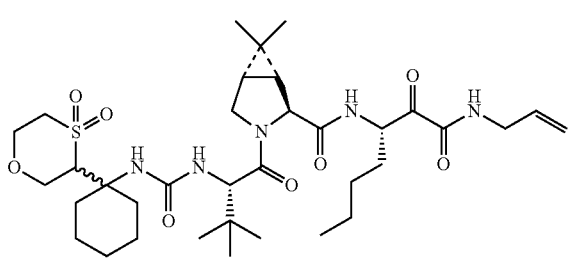
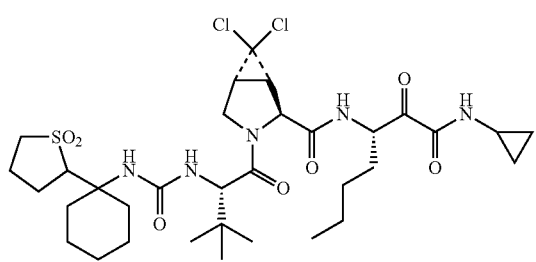
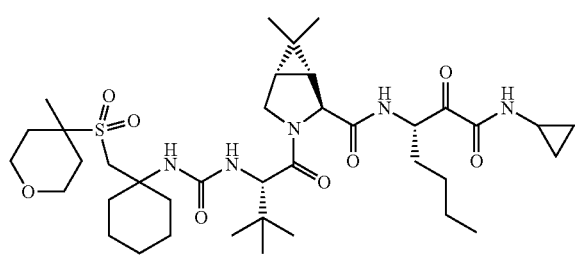
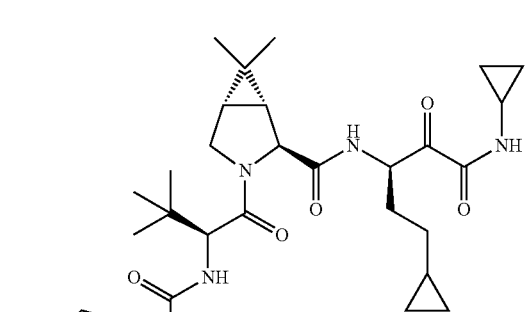
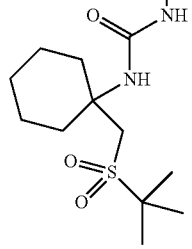
-continued
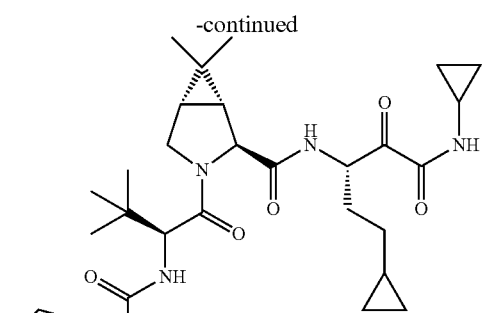
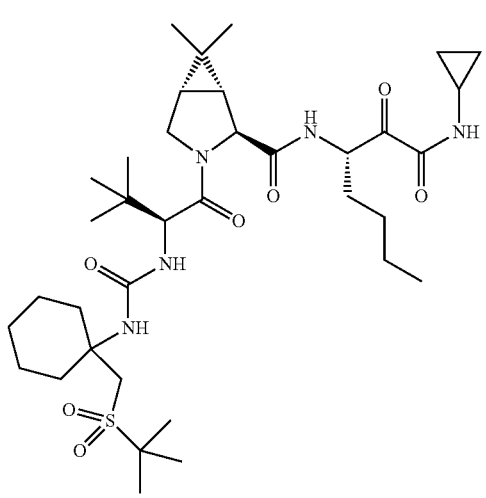
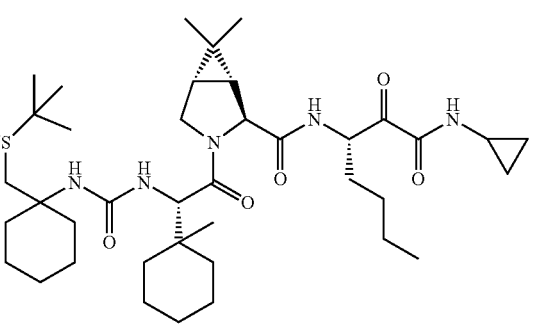
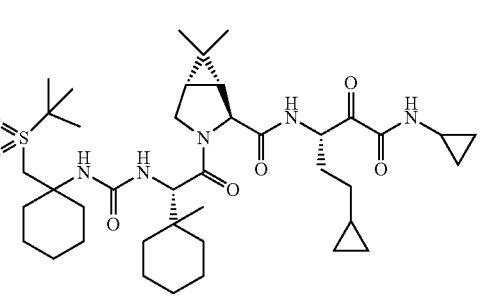
and -continued

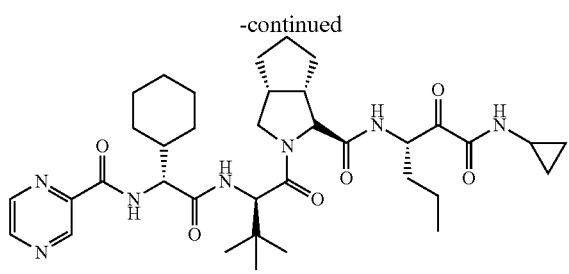

and pharmaceutically acceptable salts thereof

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS5A inhibitors useful as second additional therapeutic agents in the present compositions and methods include, but are not limited to those disclosed in International Publication No. WO 2010/111483 and the following compounds:

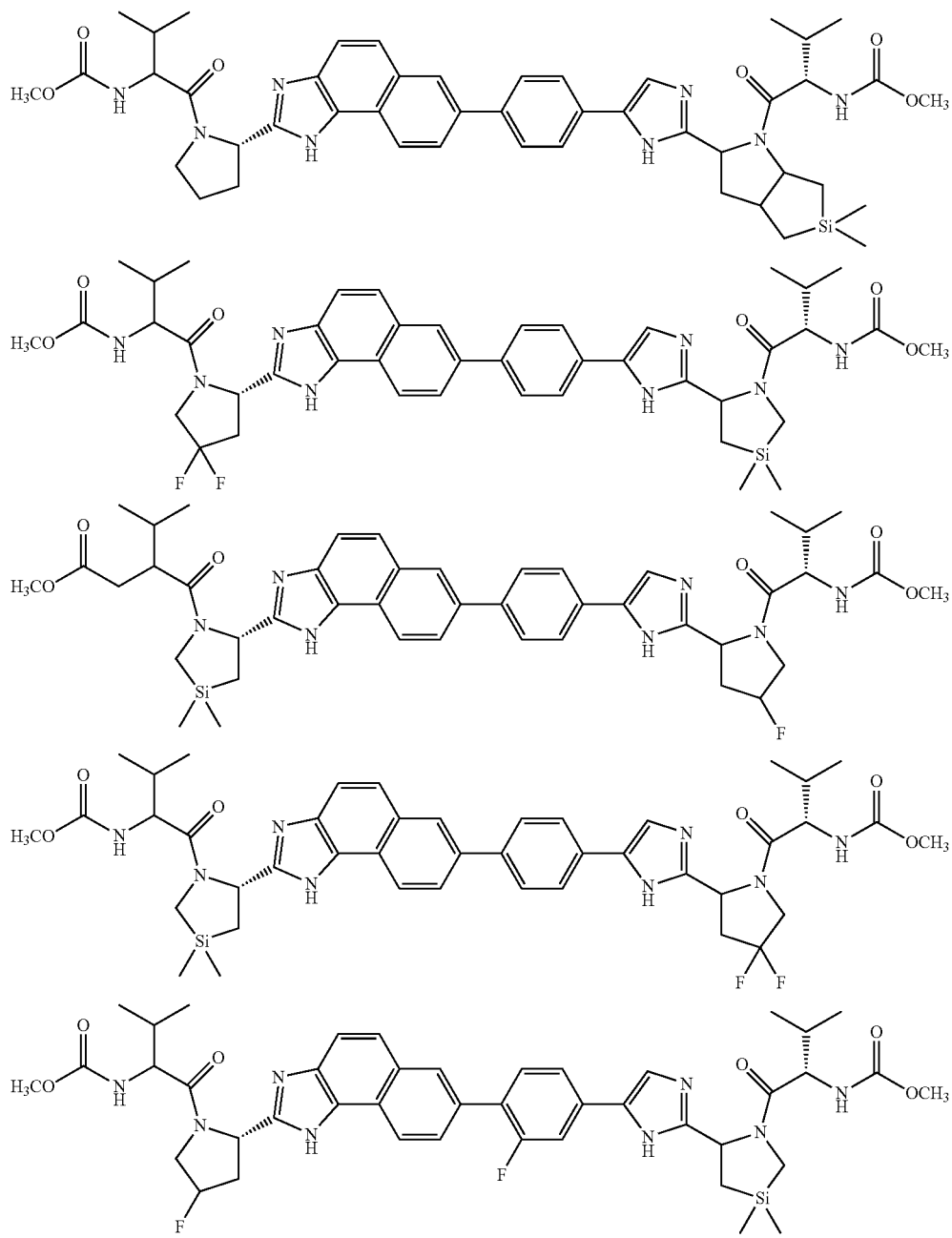

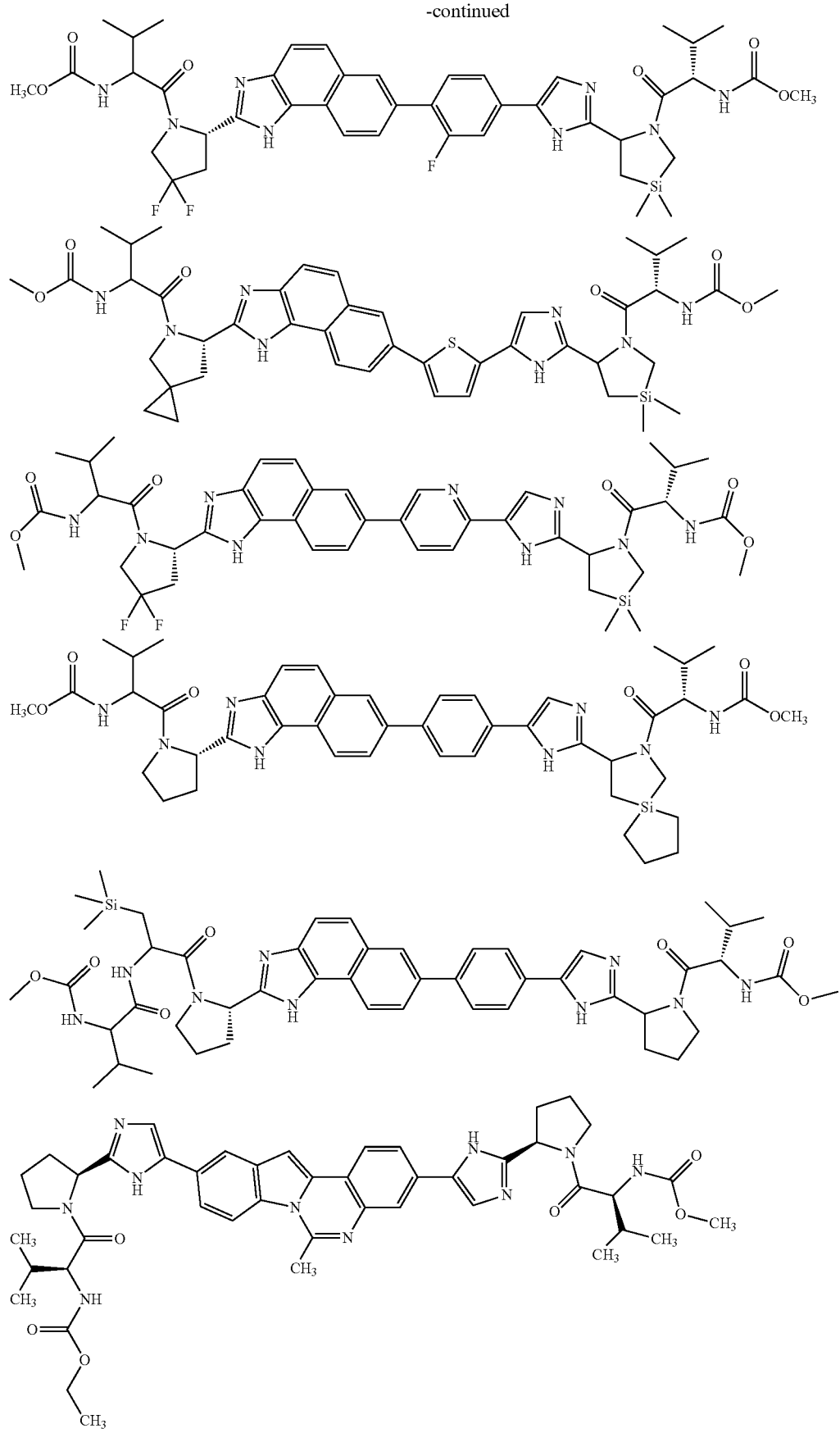

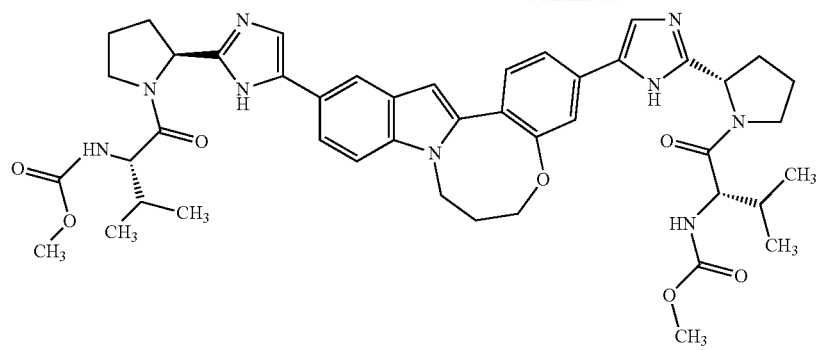
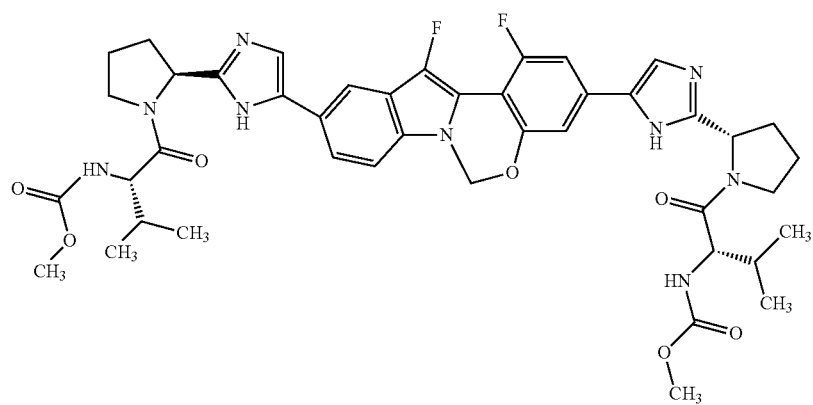
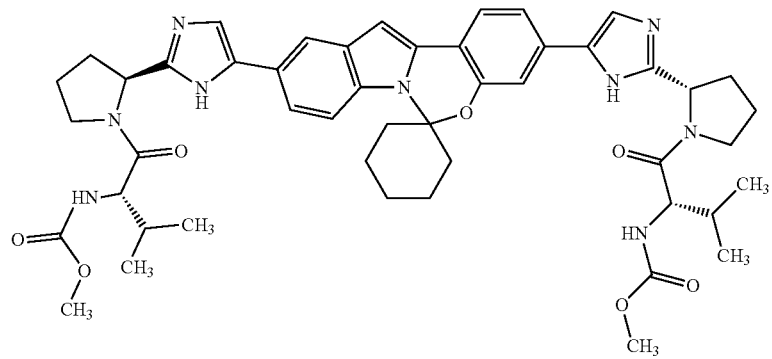
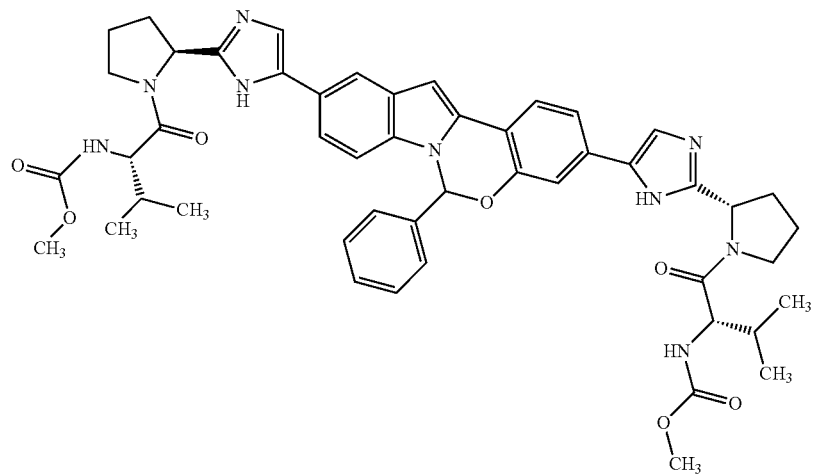

-continued
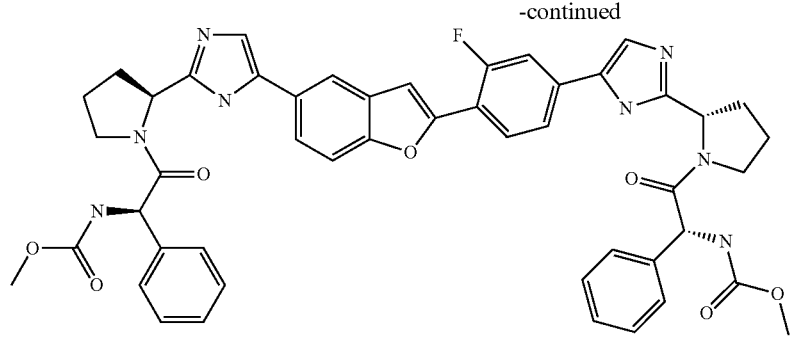
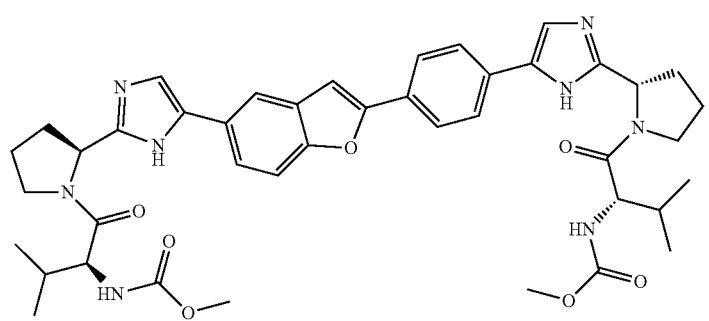
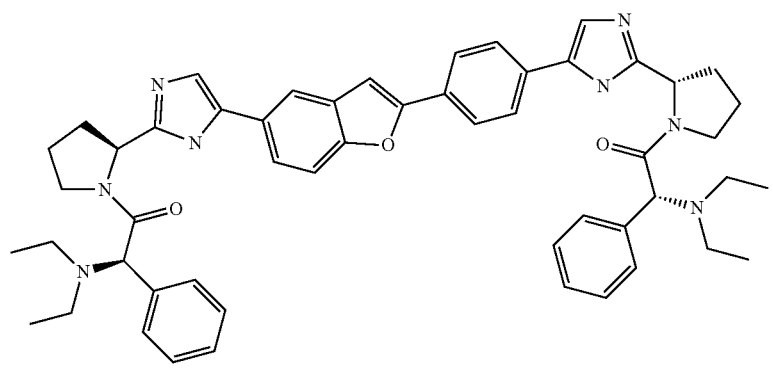
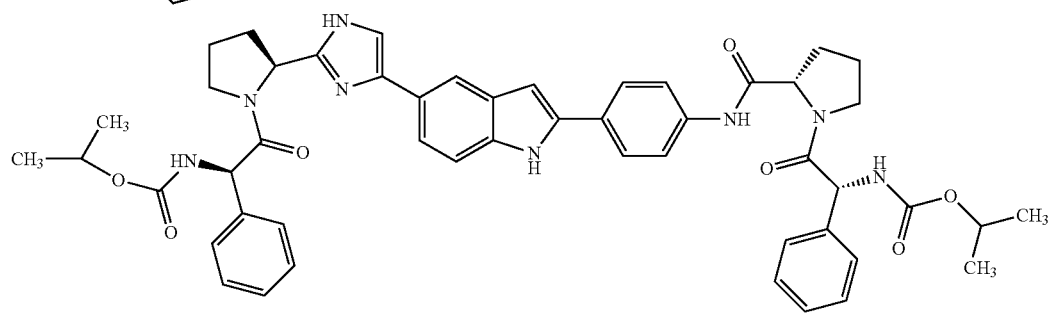
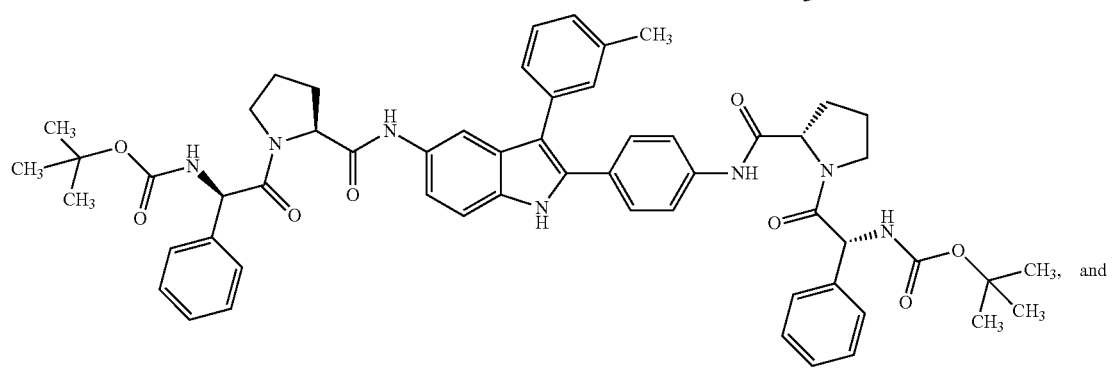
and

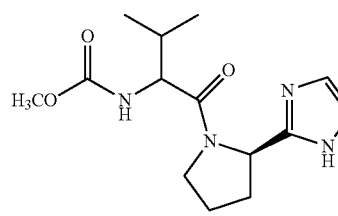
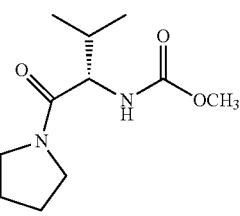

and pharmaceutically acceptable salts thereof.

HCV replicase inhibitors useful in the present compositions and methods include, but are not limited to, those disclosed in U.S. Patent Publication No. US20090081636.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). A compound of the invention and an additional therapeutic agent may be present in fixed amounts (dosage amounts) in a single dosage unit (e.g., a capsule, a tablet and the like).

The HCV NS5B inhibitory activity of the present compounds may be tested using assays known in the art. The HCV NS5B polymerase inhibitors described herein have activities in a genotype 1b replicon assay as described in the Examples. The assay is performed by incubating a replicon harboring cell-line in the presence of inhibitor for a set period of time and measuring the effect of the inhibitor on HCV replicon replication either directly by quantifying replicon RNA level, or indirectly by measuring enzymatic activity of a co-encoded reporter enzyme such as luciferase or β-lactamase. By performing a series of such measurements at different inhibitor concentrations, the effective inhibitory concentration of the inhibitor ($EC_{50}$ or $EC_{90}$) is determined. See Jan M. Vrolijk et al., *A replicons-based bioassay for the measurement of interferons in patients with chronic hepatitis C*, 110 J. VIROLOGICAL METHODS 201 (2003). Such assays may also be run in an automated format for high through-put screening. See Paul Zuck et al., *A cell-based β-lactamase reporter gene assay for the identification of inhibitors of hepatitis C virus replication*, 334 ANALYTICAL BIOCHEMISTRY 344 (2004).

The present invention also includes processes for making compounds of formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

General Schemes

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-2 below. Alternative synthetic pathways and analogous structures will be apparent to those skilled in the art of organic synthesis. All stereoisomers and tautomeric forms of the compounds are contemplated.

Some commercially available starting materials and intermediates used for the synthesis of the Compounds of Formula (I) are available. These starting materials and intermediates are available from commercial suppliers such as Sigma-Aldrich (St. Louis, Mo.) and Acros Organics Co. (Fair Lawn, N.J.). Such starting materials and intermediates compounds are used as received.

Scheme 1 shows methods useful for making a key intermediate (Intermediate 1) and its two individual enantiomers. Other intermediates with structures similar to Intermediate 1 were prepared as described in the experimental section.

Scheme 1

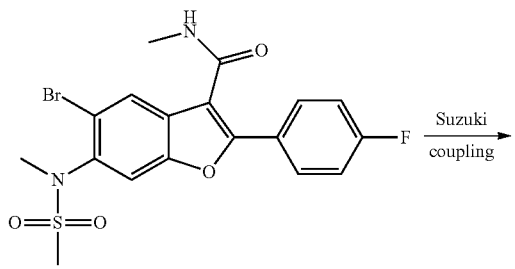

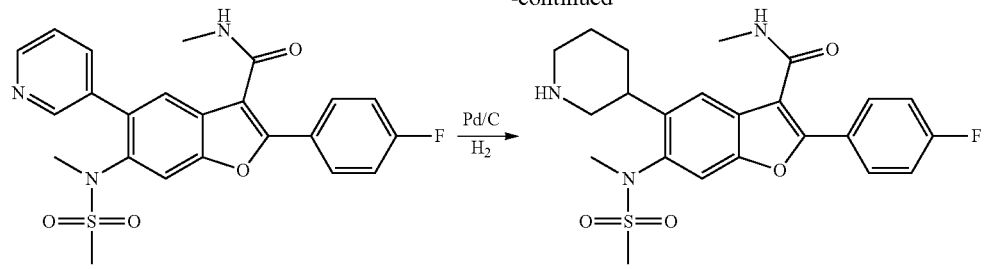

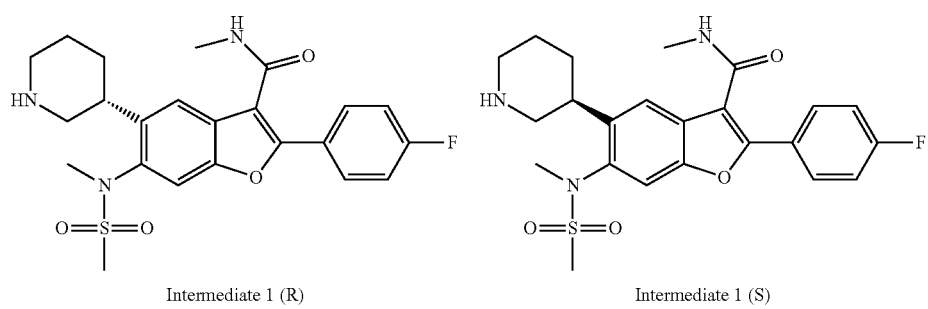

Scheme 2 shows methods useful for converting Intermediate 1 to amides, sulfonamide, or N-aryl compounds. In some cases, Intermediate 1 was used as an individual enantiomer (R or S); in other cases, Intermediate 1 was used as a racemate. In the latter case, the final compounds were separated into single compounds by chiral SFC.

List of Abbreviations
a.q. Aqueous
Boc t-butyloxycarbonyl
Boc₂O Di-tert-butyl-dicarbonate
B(O^iPr)₃ Triisopropyl borate
(Bpin)₂ Bis(pinacolato)diboron

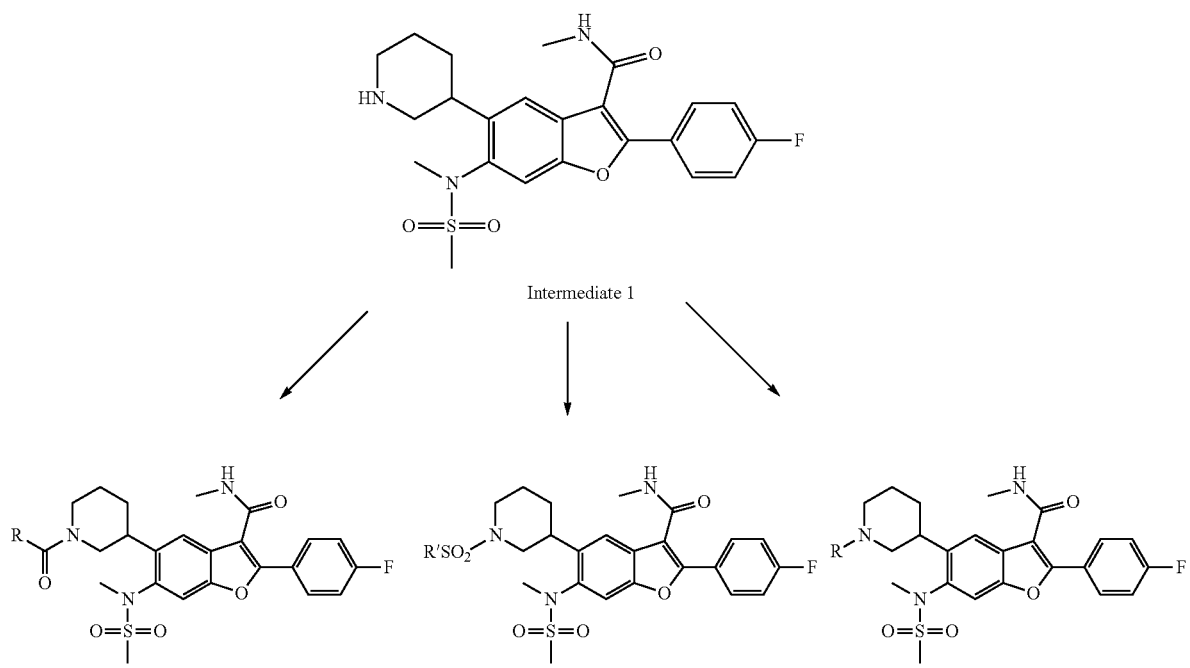

n-BuLi n-butyllithium
CDCl$_3$ Trichloro($^2$H)methane or deuterio-trichloromethane
CO$_2$ Carbon dioxide
DCM, CH$_2$Cl$_2$ Dichloromethane
DEA Diethanolamine
DIEA N,N-Diisopropylethylamine
DMAP 4-dimethylaminopyridine
DMF Dimethylformamide
DMSO Dimethylsulfoxide
EDCl N-(3-Dimethylaminopropyl)-N'-ethylcarbodiimide (also EDC)
Et Ethyl
Et$_3$N Triethylamine
EtOAc, EA Ethyl acetate
EtOH, CH$_3$CH$_2$OH Ethanol
HATU (Dimethylamino)-N,N-dimethyl(3H-[1,2,3]triazolo[4,5-b]pyridin-3 yloxy)methaniminium hexafluorophosphate
HCHO Formaledehyde
HCl Hydrochloric acid
H$_2$ Hydrogen gas or atmosphere
HCOOH Formic acid
H$_2$O Water
H$_2$SO$_4$ Sulfuric acid
HOAc, CH$_3$COOH Acetic acid
HOBT, HOBt 1-Hydroxy benzotriazole
$^1$H-NMR Proton Nuclear Magnetic Resonance
HPLC High Performance Liquid Chromatography
ISCO In situ chemical oxidation
K$_2$CO$_3$ Potassium carbonate
KOAc Potassium acetate
K$_3$PO$_4$ Potassium Phosphate
LDA Lithium diisopropylamide
LiHMDS Lithium hexamethyldisilazide
LiOH Lithium hydroxide
MeCN, CH$_3$CN Acetonitrile
MeI, CH$_3$I Methyl iodide
MeOD Methan($^2$H)ol
MeOH, CH$_3$OH Methanol
MS Mass spectroscopy
Ms Methanesulfonyl (or mesyl) group
MsCl Methanesulfonyl chloride
N$_2$ Nitrogen gas or atmosphere
NaBH(OAc)$_3$ Sodium triacetoxyborohydride
NaHCO$_3$ Sodium bicarbonate
Na$_2$SO$_4$ Sodium sulfate (anhydrous)
NCS N-Chlorosuccinimide
NH$_4$Cl Ammonium chloride
NMO N-Methylmorpholine-N-Oxide
OsO$_4$ Osmium tetroxide
PCC Pyridinium Chlorochromate
Pd Palladium
Pd$_2$(dba)$_3$ Tris(dibenzylideneacetone)dipalladium(0)
Pd(dppf)Cl$_2$ 1,1'-bis(diphenylphosphino)ferrocene-palladium(II)dichloride
Pd(dtbpf)Cl$_2$ 1,1'-bis(di-tert-butylphosphino)ferrocene-dichloropalladium(II)
Pd(PPh$_3$)$_4$ Tetrakis(triphenylphosphine)palladium(0)
PE Petroleum ether
Ph Phenyl
Pt Platinum
PtO$_2$ Platinum (IV) oxide
PTSA p-Toluenesulfonic acid
RT Room temperature, approximately 25° C.
sat saturated
SFC Supercritical fluid chromatography
SO$_2$ Sulfur dioxide
SOCl$_2$ Thionyl chloride
T$_3$P Propylphosphonic Anhydride
TCDI N,N'-Thiocarbonyldiimidazole
TEA Triethylamine
TF$_2$NPh N-phenyltrifluoromethanesulphonimide
TFA Trifluoroacetic acid
THF Tetrahydrofuran
TsOH p-Toluenesulfonic acid
TLC Thin layer chromatography

EXAMPLES

In the examples below, some enantiomer pairs are identified by consecutive example numbers without identifying which enantiomer corresponds to which example number. The example numbers correspond to a specific peak number which was tested for activity.

Example 1

5-(5-(4-fluorobenzo[d]oxazol-2-yl)-1-methylpiperidin-3-yl)-2-(4-fluorophenyl)-N-methyl-6-(N-methylmethylsulfonamido)benzofuran-3-carboxamide

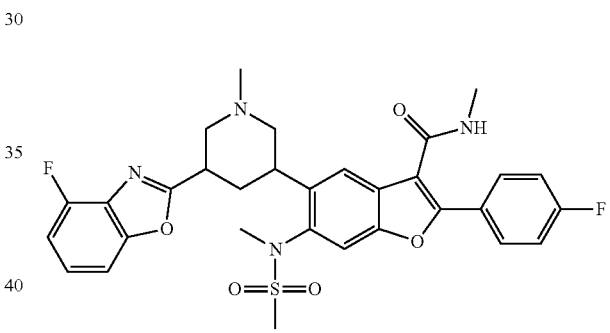

Step 1—Synthesis of methyl 5-bromonicotinate

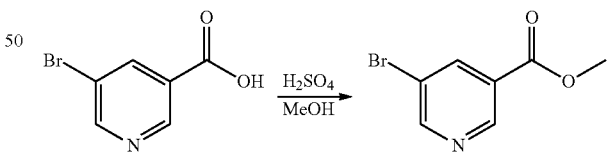

To cooled methanol (20 mL, 0° C.) was added dropwise concentrated H$_2$SO$_4$ (2 mL). To the resulting clear solution was added 5-bromonicotinic acid (2 g, 10 mmol) and the mixture was refluxed for 3 h. After being cooled to room temperature, the solvent was evaporated and the residue was partitioned between EtOAc and water. The organic layer was washed with saturated NaHCO$_3$ (a.q.), dried over Na$_2$SO$_4$ and concentrated to give methyl 5-bromonicotinate (1.5 g, yield: 71%). $^1$H-NMR (CDCl$_3$, 400 MHz) δ 9.10 (d, J=1.6 Hz, 1H), 8.81 (d, J=2.4 Hz, 1H), 8.41 (t, J=2.4 Hz, 1H), 3.94 (s, 3H). MS (M+H)$^+$: 216/218.

Step 2—Synthesis of methyl 5-(4,4,5,5-tetramethyl-1,3,2-dioxaborolan-2-yl)nicotinate

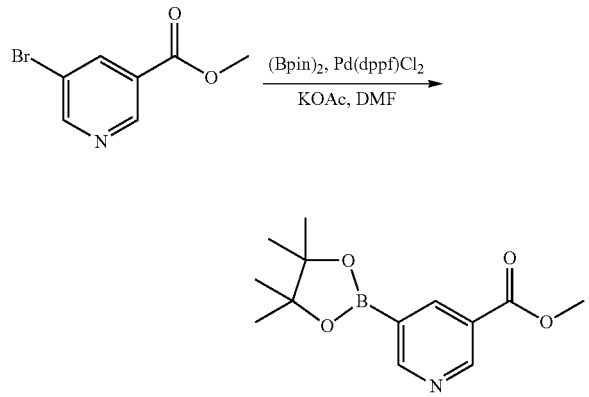

To a solution of methyl 5-bromonicotinate (1 g, 4.6 mmol), KOAc (920 mg, 9.2 mmol) and (Bpin)₂ (1.7 g, 6.9 mmol) in DMF (10 mL) was added Pd(dppf)Cl₂ under N₂, and the resulting reaction mixture was stirred for 4 h at 80° C. After the reaction mixture was concentrated, the residue was dissolved in DCM, then filtered, evaporated and the residue was purified by flash chromatography (PE/EtOAc=4/1) to give the product of methyl 5-(4,4,5,5-tetramethyl-1,3,2-dioxaborolan-2-yl)nicotinate (800 mg, yield: 66%). $^1$H-NMR (CDCl₃, 400 MHz) δ 9.21 (d, J=2.4 Hz, 1H), 9.03 (d, J=2.0 Hz, 1H), 8.61 (t, J=2.0 Hz, 1H), 3.90 (s, 3H), 1.31 (s, 12H). MS (M+H)⁺: 264.

Step 3—Synthesis of methyl 5-(2-(4-fluorophenyl)-3-(methylcarbamoyl)-6-(N-methylmethyl sulfonamido)benzofuran-5-yl)nicotinate

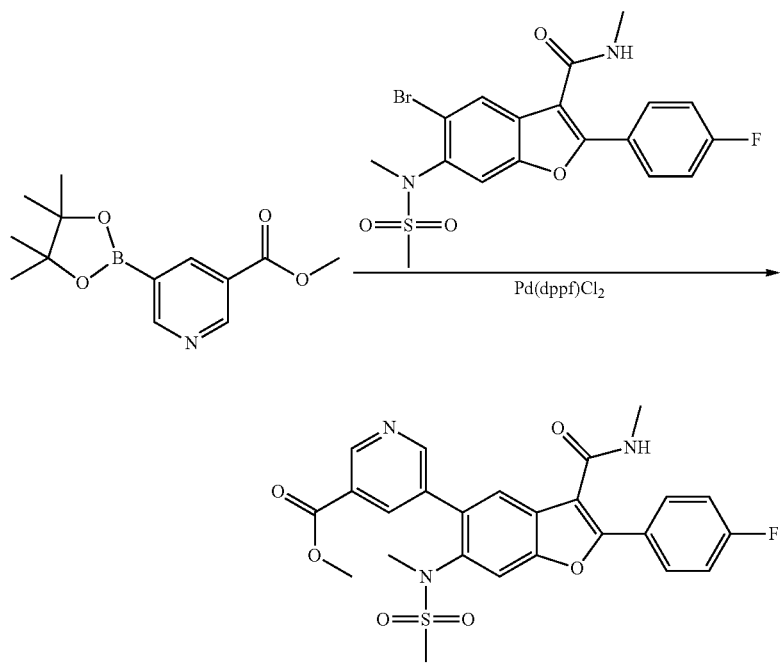

To a solution of methyl 5-(4,4,5,5-tetramethyl-1,3,2-dioxaborolan-2-yl)nicotinate (1.1 g, 2.4 mmol), 5-bromo-2-(4-fluorophenyl)-N-methyl-6-(N-methylmethylsulfonamido)benzofuran-3-carboxamide (763 mg, 2.9 mmol) (prepared according to International Patent Application Publication No. WO 2011106992) and K₃PO₄.3H₂O (1.3 g, 4.8 mmol) in DMF (20 mL) was added Pd(dppf)Cl₂ under N₂, and the resulting reaction mixture was stirred for 3 h at 90° C. After the reaction mixture was concentrated, the residue was dissolved in DCM, then filtered, evaporated and the residue was purified by column chromatography (PE/EtOAc=4/1 to 1/1) to give the product of methyl 5-(2-(4-fluorophenyl)-3-(methylcarbamoyl)-6-(N-methylmethylsulfonamido)benzofuran-5-yl)nicotinate (1 g, yield: 83%). $^1$H-NMR (CDCl₃, 400 MHz) δ 7.17 (d, J=1.2 Hz, 1H), 8.00 (d, J=1.6 Hz, 1H), 8.40 (s, 1H), 7.83~7.87 (m, 3H), 7.59 (s, 1H), 7.16(t, J=8.4 Hz, 2H), 5.76 (d, J=4.0 Hz, 1H), 3.92 (s, 3H), 3.15 (s, 3H), 2.92 (d, J=4.8 Hz, 3H), 2.69(s, 3H). MS (M+H)⁺: 512.

Step 4—Synthesis of methyl 5-(2-(4-fluorophenyl)-3-(methylcarbamoyl)-6-(N-methylmethyl sulfonamido)benzofuran-5-yl)piperidine-3-carboxylate

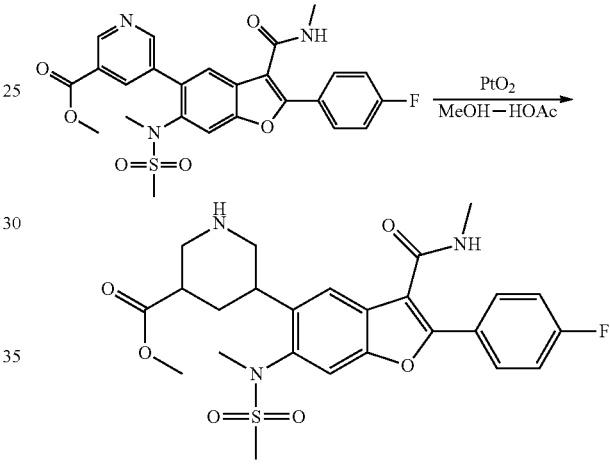

To a solution of methyl 5-(2-(4-fluorophenyl)-3-(methylcarbamoyl)-6-(N-methylmethylsulfonamido)benzofuran-5-yl)nicotinate (650 mg, 1.27 mmol) in MeOH:CH₃COOH=4:1 (100 mL) was added PtO₂, and the resulting reaction mixture was stirred at 35° C. under H₂ at 35 Psi overnight. After being filtered, evaporated, diluted with water and basified with saturated NaHCO₃ (a.q.), the resulting mixture was extracted with DCM, and then the organic layer was dried, concentrated and purified by column chromatography (DCM/MeOH=20/1) to give methyl 5-(2-(4-fluorophenyl)-3-(methylcarbamoyl)-6-(N-methylmethylsulfonamido)benzofuran-5-yl)piperidine-3-carboxylate (600 mg, yield: 91%). ¹H-NMR (CDCl₃, 400 MHz) δ 7.79 (s, 2H), 7.70~7.73 (m, 1H), 7.36~7.39 (m, 1H), 7.11~7.15 (m, 2H), 6.03 (d, J=5.6 Hz, 1H), 3.77~3.80 (m, 3H), 3.61~3.64 (m, 3H), 3.17~3.20 (m, 6H), 3.04 (s, 2H), 2.93~2.97(m, 7H). MS (M+H)⁺: 518.

Step 5—Synthesis of methyl 5-(2-(4-fluorophenyl)-3-(methylcarbamoyl)-6-(N-methylmethyl sulfonamido)benzofuran-5-yl)-1-methylpiperidine-3-carboxylate

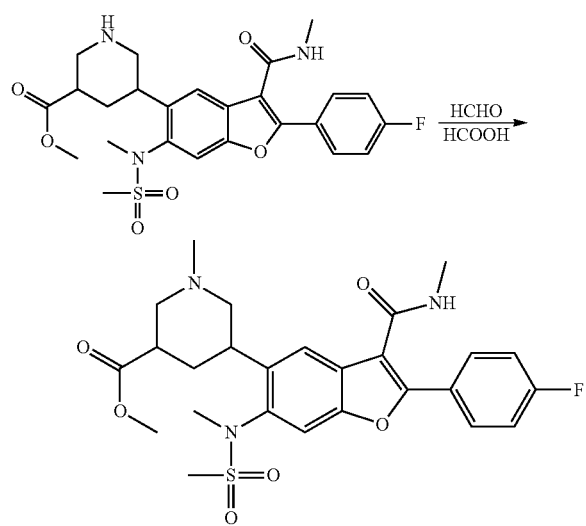

A solution of methyl 5-(2-(4-fluorophenyl)-3-(methylcarbamoyl)-6-(N-methylmethylsulfonamido)benzofuran-5-yl)piperidine-3-carboxylate (400 mg, 0.8 mmol) in HCHO (4 mL) and HCOOH (4 mL) was heated to reflux for 1 h. After being concentrated, diluted with water and basified with saturated NaHCO₃ (aq), the mixture was extracted with DCM, and then the organic layer was dried, concentrated and purified by column chromatography (DCM/MeOH=50/1) to give methyl 5-(2-(4-fluorophenyl)-3-(methylcarbamoyl)-6-(N-methylmethylsulfonamido)benzofuran-5-yl)-1-methylpiperidine-3-carboxylate (380 mg, yield: 92%). ¹H-NMR (CDCl₃, 400 MHz) δ 7.78~7.81 (m, 1H), 7.73 (s, 2H), 7.50~7.59 (m, 1H), 7.15 (d, J=8.8 Hz, 2H), 5.72~5.87 (m, 1H), 3.95~3.98 (m, 1H), 3.61~3.78 (m, 4H), 3.47~3.49 (m, 1H), 3.16~3.42 (m, 6H), 3.08 (s, 1H), 3.00 (s, 1H), 2.78~2.90 (m, 3H), 2.35~2.65 (m, 5H), 2.26~2.28 (m, 1H). MS(M+H)⁺: 532.

Step 6—Synthesis of 5-(2-(4-fluorophenyl)-3-(methylcarbamoyl)-6-(N-methylmethylsulfonamido)benzofuran-5-yl)-1-methylpiperidine-3-carboxylic acid

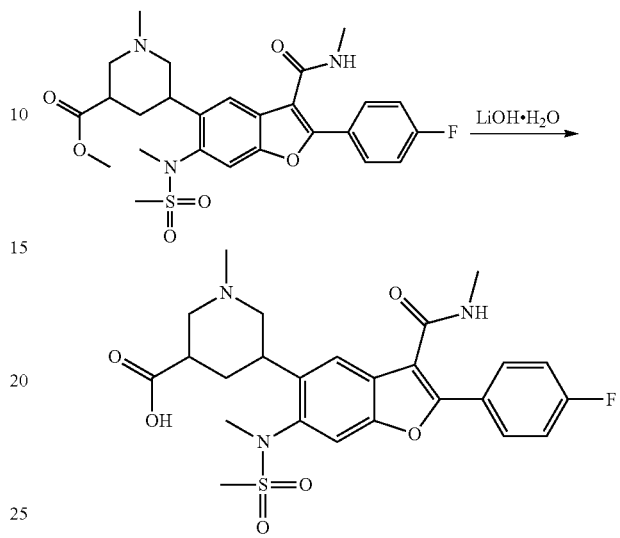

A solution of methyl 5-(2-(4-fluorophenyl)-3-(methylcarbamoyl)-6-(N-methylmethylsulfonamido)benzofuran-5-yl)-1-methylpiperidine-3-carboxylate (450 mg, 0.85 mmol) and LiOH.H₂O (178 mg, 4.3 mmol) in 1,4-dioxane: H₂O=5:1 (18 mL) was heated to reflux and stirred for 1 h. Then the reaction mixture was cooled and diluted with water, followed by adjusting the solution to pH=2~3. The resulting precipitate was collected by filtration, washed with water and dried to give 5-(2-(4-fluorophenyl)-3-(methylcarbamoyl)-6-(N-methylmethylsulfonamido)benzofuran-5-yl)-1-methylpiperidine-3-carboxylic acid (400 mg, yield: 91%), which was used for the next step without further purification. MS (M+H)⁺: 518.

Step 7—Synthesis of N-(2-fluoro-6-hydroxyphenyl)-5-(2-(4-fluorophenyl)-3-(methylcarbamoyl)-6-(N-methylmethylsulfonamido)benzofuran-5-yl)-1-methylpiperidine-3-carboxamide

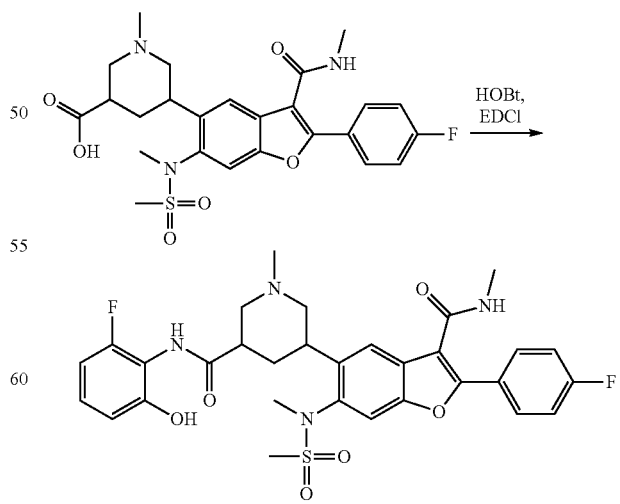

A solution of 5-(2-(4-fluorophenyl)-3-(methylcarbamoyl)-6-(N-methylmethyl sulfonamido)benzofuran-5-yl)-1- methylpiperidine-3-carboxylic acid (100 mg, 0.2 mmol), HOBT (54 mg, 0.4 mmol) and EDCl.HCl (77 mg, 0.4 mmol) in DMF (5 mL) was stirred at room temperature for 1.5 hours. 2-amino-3-fluorophenol (76 mg, 0.6 mmol) was then added and the reaction continued to stir at room temperature overnight. The reaction was then poured into water, then extracted with DCM, washed with NaHCO₃, and dried over Na₂SO₄. After being concentrated, the residue was purified by column chromatography (DCM/MeOH=20/1) to give pure N-(2-fluoro-6-hydroxyphenyl)-5-(2-(4-fluorophenyl)-3-(methylcarbamoyl)-6-(N-methylmethylsulfonamido)benzofuran-5-yl)-1-methylpiperidine-3-carboxamide (80 mg, yield: 66%), which was used for the next step without further purification. MS (M+H)⁺: 627.

Step 8—Synthesis of 5-(5-(4-fluorobenzo oxazol-2-yl)-1-methylpiperidin-3-yl)-2-(4-fluorophenyl)-N-methyl-6-(N-methylmethylsulfonamido)benzofuran-3-carboxamide (Example 1)

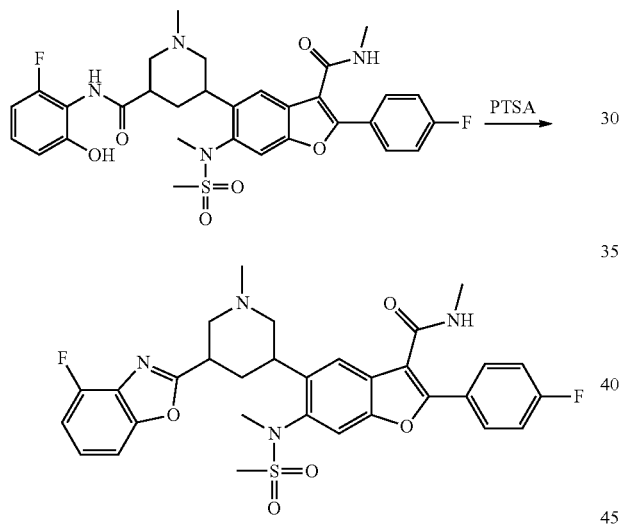

A solution of N-(2-fluoro-6-hydroxyphenyl)-5-(2-(4-fluorophenyl)-3-(methylcarbamoyl)-6-(N-methylmethylsulfonamido)benzofuran-5-yl)-1-methylpiperidine-3-carboxamide (70 mg, 0.11 mmol) and PTSA (11 mg, 0.06 mmol) in toluene (30 mL) was heated to reflux for 24 hours. After being concentrated, diluted with water and extracted with DCM, the organic layer was washed with saturated NaHCO₃, dried over Na₂SO₄ and concentrated. The residue was purified (DCM/CH₃OH=10/1) to give pure 5-(5-(4-fluorobenzo[d]oxazol-2-yl)-1-methylpiperidin-3-yl)-2-(4-fluorophenyl)-N-methyl-6-(N-methylmethylsulfonamido)benzofuran-3-carboxamide (20 mg, yield: 29%). ¹H-NMR (CDCl₃, 400 MHz) δ 7.79 (d, J=8.0 Hz, 3H), 7.43 (d, J=7.2 Hz, 1H), 7.20~7.24 (m, 2H), 7.10~7.14 (m, 2H), 6.94~6.98 (m, 1H), 5.77 (s, 1H), 3.60~3.68 (m, 1H), 3.24~3.47 (m, 2H), 3.08~3.11 (m, 3H), 2.80~3.02 (m, 7H), 2.29~2.55 (m, 1H), 2.17~2.26 (m, 3H), 1.91~1.94 (m, 3H). MS (M+H)⁺: 609.

Example 2

(S)-5-(1-((7-fluoro-1H-indol-2-yl)sulfonyl)piperidin-3-yl)-2-(4-fluorophenyl)-N-methyl-6-(N-methylmethylsulfonamido)benzofuran-3-carboxamide

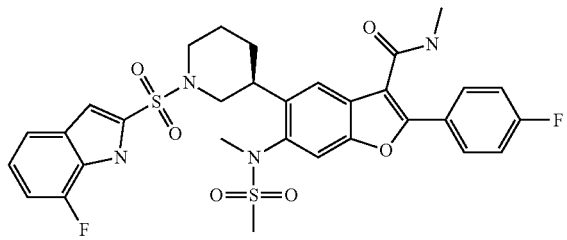 [SMILES: CNC(=O)c1c(-c2ccc(F)cc2)oc2cc(N(C)S(C)(=O)=O)c([C@@H]3CCCN(S(=O)(=O)c4cc5cccc(F)c5[nH]4)C3)cc12]

Step 1—Synthesis of 2-(4-fluorophenyl)-N-methyl-6-(N-methylmethylsulfonamido)-5-(pyridin-3-yl)benzofuran-3-carboxamide

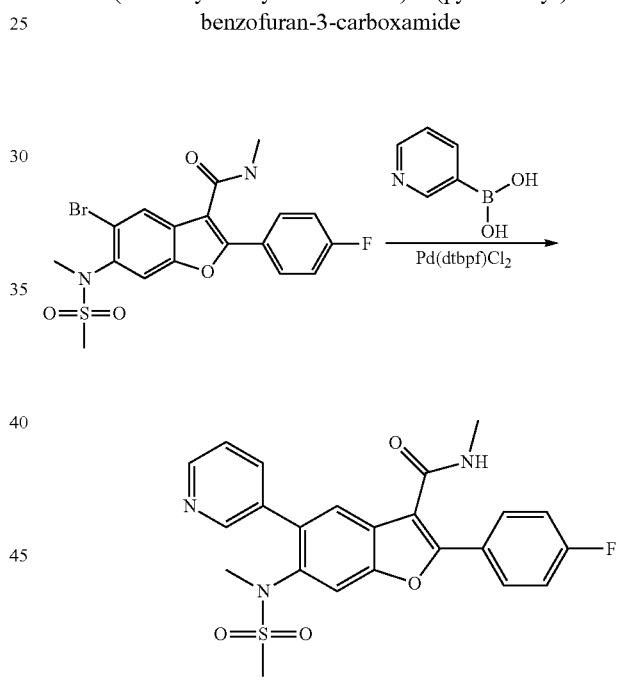

A mixture of 5-bromo-2-(4-fluorophenyl)-N-methyl-6-(N-methylmethyl sulfonamido)benzofuran-3-carboxamide (1.5 g, 3.29 mmol), pyridine-3-boronicacid (0.810 g, 6.59 mmol), potassium phosphate tribasic (5.59 g, 13.18 mmol) and 1,1'-bis(di-tert-butyosphosphino)ferrocene palladium dichloride (0.215 g, 0.329 mmol) was suspended in DMF (15 ml) and heated at 120° C. for 30 min. The reaction mixture was filtered and concentrated under vacuum, applied onto ISCO with normal phase and eluted with EtOAc/Hexane 30-100%. This resulted in 1.2 g (80%) of 2-(4-fluorophenyl)-N-methyl-6-(N-methylmethylsulfonamido)-5-(pyridin-3-yl)benzofuran-3-carboxamide as a white solid. LC-MS (ES, m/z) C₂₃H₂₀FN₃O₄S: 453; Found: 454 [M+H]⁺.

Step 2—Synthesis of 2-(4-fluorophenyl)-N-methyl-6-(N-methylmethylsulfonamido)-5-(piperidin-3-yl)benzofuran-3-carboxamide

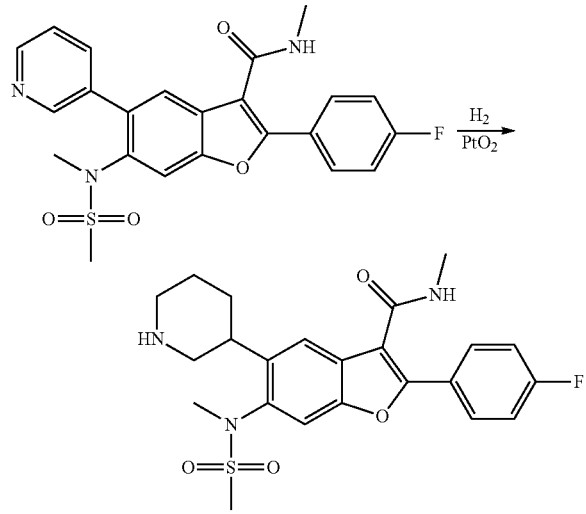

To a solution of 2-(4-fluorophenyl)-N-methyl-6-(N-methylmethylsulfonamido)-5-(pyridin-3-yl)benzofuran-3-carboxamide (1 g, 2.205 mmol) in MeOH (5 mL) and hydrochloric acid (37%, 0.5 ml) was added platinum(IV) oxide (20 mg, 0.088 mmol). The mixture was shaken under $H_2$ (45 Psi) for 2.5 hours. The reaction mixture was filtered and concentrated under vacuum. This resulted in 1.01 g (100%) of 2-(4-fluorophenyl)-N-methyl-6-(N-methylmethyl sulfonamido)-5-(piperidin-3-yl)benzofuran-3-carboxamide as a white solid. LC-MS (ES, m/z) $C_{23}H_{26}FN_3O_4S$: 459; Found: 460 $[M+H]^+$.

Step 3—Synthesis of (S)-2-(4-fluorophenyl)-N-methyl-6-(N-methylmethylsulfonamido)-5-(piperidin-3-yl)benzofuran-3-carboxamide and (R)-2-(4-fluorophenyl)-N-methyl-6-(N-methylmethylsulfonamido)-5-(piperidin-3-yl)benzofuran-3-carboxamide

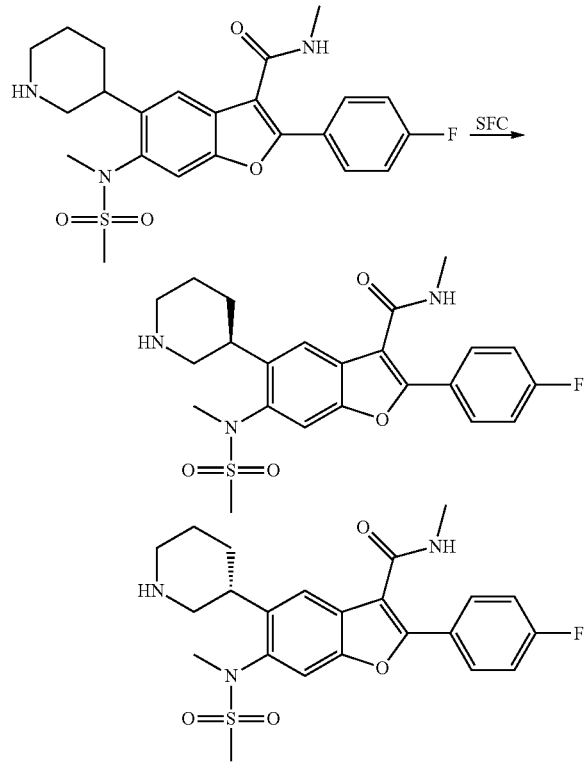

2-(4-fluorophenyl)-N-methyl-6-(N-methylmethylsulfonamido)-5-(piperidin-3-yl)benzofuran-3-carboxamide (2.7 g, 5.88 mmol) was dissolved in DCM, applied onto IC 30×250 mm column and eluted with 35% MeOH (0.2% DEA)/$CO_2$ (100 bar, 35° C.). This resulted in 0.9 g (33.3%) of (S)-2-(4-fluorophenyl)-N-methyl-6-(N-methylmethylsulfonamido)-5-(piperidin-3-yl)benzofuran-3-carboxamide as a white solid. LC-MS (ES, m/z) $C_{23}H_{26}FN_3O_4S$: 459; Found: 460 $[M+H]^+$, and 1 g (37%) of (R)-2-(4-fluorophenyl)-N-methyl-6-(N-methylmethylsulfonamido)-5-(piperidin-3-yl)benzofuran-3-carboxamide as a white solid. LC-MS (ES, m/z) $C_{23}H_{26}FN_3O_4S$: 459; Found: 460 $[M+H]^+$. The absolute configurations were determined by vibrational circular dichroism spectroscopy.

Step 4—Synthesis of tert-butyl 7-fluoro-1H-indole-1-carboxylate

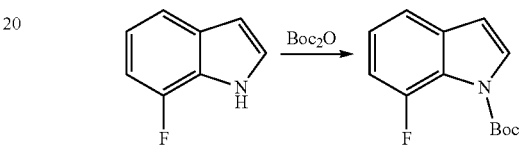

A mixture of 7-fluoro-1H-indole (3 g, 22.2 mmol), DIEA (8.6 g, 66.6 mmol) and DMAP (50 mg) in DCM (50 mL) was stirred at RT under $N_2$ atmosphere. Then $(Boc)_2O$ (5.81 g, 26.6 mmol) was added, and the reaction mixture was stirred at RT for 16 h. The mixture was diluted with water, extracted with EtOAc, concentrated in vacuum and dried over $Na_2SO_4$. The residue was purified by column chromatography (PE:EA=20:1) to afford the desired product tert-butyl 7-fluoro-1H-indole-1-carboxylate (4 g, yield: 77%). $^1$H-NMR (CDCl$_3$, 400 MHz) δ 7.65 (s, 1H), 7.33 (d, J=8.0 Hz, 1H), 7.16~7.17 (m, 1H), 7.02 (t, J=8.0 Hz, 1H), 6.59 (s, 1H), 1.66 (s, 9H). MS $(M+H)^+$: 236.

Step 5—Synthesis of tert-butyl 2-(chlorosulfonyl)-7-fluoro-1H-indole-1-carboxylate

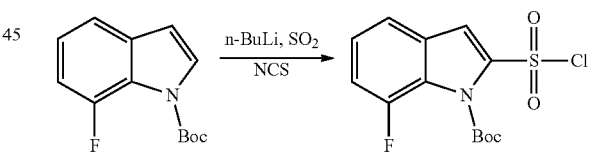

To a mixture of tert-butyl 7-fluoro-1H-indole-1-carboxylate (500 mg, 2.03 mmol) in THF (10 mL) was added n-BuLi (1 mL, 2.5 mmol) under $N_2$ atmosphere at −78° C. The mixture was stirred at −78° C. for 1 h. Then $SO_2$ (g) was bubbled into the mixture for 10 min, and the reaction mixture was allowed to warm to 10° C. over 2 h. After being concentrated in vacuum, the mixture was diluted with DCM (20 mL) followed by addition of NCS (460 mg, 3.05 mmol). The reaction was stirred at RT overnight. Water was added and the reaction mixture was extracted with DCM, dried over $Na_2SO_4$ and concentrated. The residue was purified by column chromatography (PE:EA=20:1) to afford the desired product of tert-butyl 2-(chlorosulfonyl)-7-fluoro-1H-indole-1-carboxylate (500 mg, yield: 65%). $^1$H-NMR (CDCl$_3$, 400 MHz) δ 7.44~7.51 (m, 2H), 7.20 (d, J=8.0 Hz, 2H), 1.63 (s, 9H). MS $(M+H)^+$: 334/336.

Step 6—Synthesis of (S)-tert-butyl 7-fluoro-2-((3-(2-(4-fluorophenyl)-3-(methylcarbamoyl)-6-(N-methylmethylsulfonamido)benzofuran-5-yl)piperidin-1-yl)sulfonyl)-1H-indole-1-carboxylate

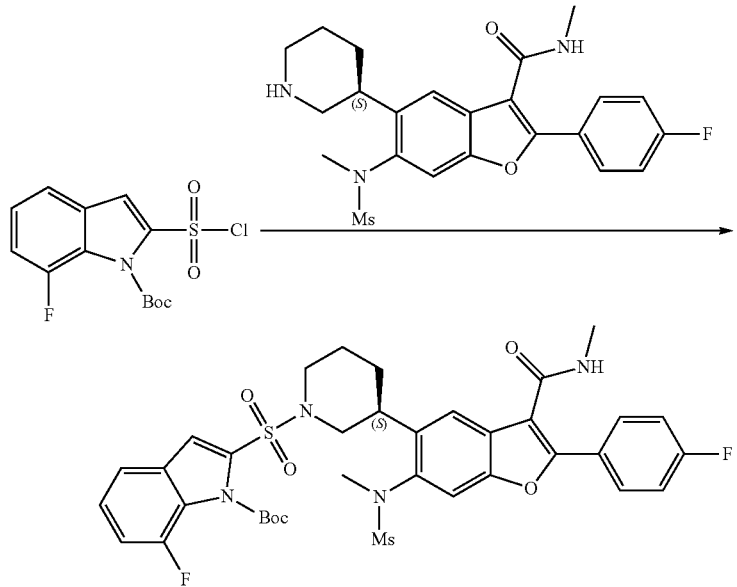

A mixture of tert-butyl 2-(chlorosulfonyl)-7-fluoro-1H-indole-1-carboxylate (64 mg, 0.20 mmol), (S)-2-(4-fluorophenyl)-N-methyl-6-(N-methylmethylsulfonamido)-5-(piperidin-3-yl)benzofuran-3-carboxamide (70 mg, 0.15 mmol) and TEA (45 mg, 0.45 mmol) in DCM (6 mL) was stirred at RT for 6 h under N$_2$ atmosphere. The mixture was diluted with water, extracted with DCM, dried over Na$_2$SO$_4$ and concentrated to give the product (S)-tert-butyl 7-fluoro-2-((3-(2-(4-fluorophenyl)-3-(methylcarbamoyl)-6-(N-methylmethylsulfonamido)benzofuran-5-yl)piperidin-1-yl)sulfonyl)-1H-indole-1-carboxylate (100 mg, yield: 88%), which was used for the next step without further purification. MS (M+H)$^+$: 757.

Step 7—Synthesis of (S)-5-(1-((7-fluoro-1H-indol-2-yl)sulfonyl)piperidin-3-yl)-2-(4-fluorophenyl)-N-methyl-6-(N-methylmethylsulfonamido)benzofuran-3-carboxamide (Example 2)

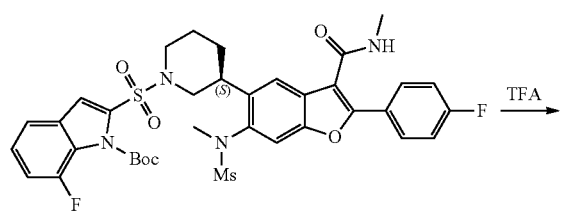

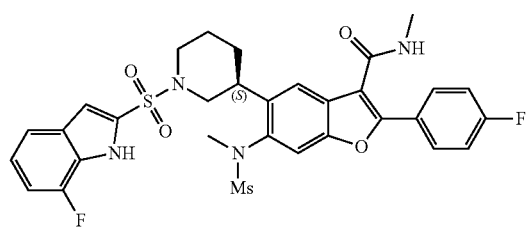

A mixture of (S)-tert-butyl 7-fluoro-2-((3-(2-(4-fluorophenyl)-3-(methylcarbamoyl)-6-(N-methylmethylsulfonamido)benzofuran-5-yl)piperidin-1-yl)sulfonyl)-1H-indole-1-carboxylate (100 mg, 0.13 mmol) and TFA (1 mL) in CH$_2$Cl$_2$ (5 mL) was stirred at RT for 2 h. Then the mixture was concentrated. The residue was purified by prep-HPLC to afford the desired product of (S)-5-(1-((7-fluoro-1H-indol-2-yl)sulfonyl)piperidin-3-yl)-2-(4-fluorophenyl)-N-methyl-6-(N-methylmethylsulfonamido)benzofuran-3-carboxamide (50 mg, yield: 59%). $^1$H-NMR (CDCl$_3$, 400 MHz) δ 9.10~9.55 (m, 1H), 7.77~7.83 (m, 3H), 7.44~7.50 (m, 2H), 7.01~7.17 (m, 5H), 5.76~5.81 (m, 1H), 3.50~4.16 (m, 3H), 3.12~3.33 (m, 6H), 2.9~03.02 (m, 3H), 2.50~2.76 (m, 2H), 1.73~2.02 (m, 4H). MS (M+H)$^+$: 657.

Example 3

(R)-5-(1-((7-fluoro-1H-indol-2-yl)sulfonyl)piperidin-3-yl)-2-(4-fluorophenyl)-N-methyl-6-(N-methylmethylsulfonamido)benzofuran-3-carboxamide

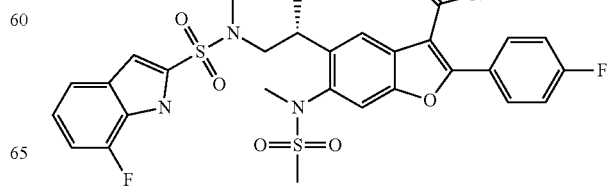

Step 1—Synthesis of (R)-tert-butyl 7-fluoro-2-((3-(2-(4-fluorophenyl)-3-(methylcarbamoyl)-6-(N-methylmethylsulfonamido)benzofuran-5-yl)piperidin-1-yl)sulfonyl)-1H-indole-1-carboxylate

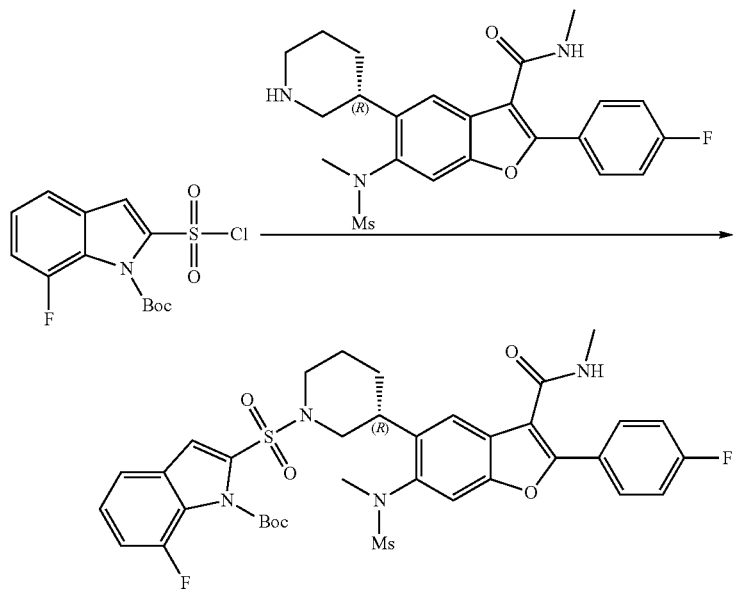

A mixture of tert-butyl 2-(chlorosulfonyl)-7-fluoro-1H-indole-1-carboxylate (64 mg, 0.20 mmol), (R)-2-(4-fluorophenyl)-N-methyl-6-(N-methylmethylsulfonamido)-5-(piperidin-3-yl)benzofuran-3-carboxamide (70 mg, 0.15 mmol) and TEA (45 mg, 0.45 mmol) in DCM (6 mL) was stirred at RT for 6 h under $N_2$ atmosphere. The mixture was diluted with water, extracted with DCM, dried over $Na_2SO_4$ and concentrated to give the product (R)-tert-butyl 7-fluoro-2-((3-(2-(4-fluorophenyl)-3-(methylcarbamoyl)-6-(N-methylmethylsulfonamido) benzofuran-5-yl)piperidin-1-yl)sulfonyl)-1H-indole-1-carboxylate (100 mg, yield: 88%), which was used for the next step without further purification. MS (M+H)$^+$: 757.

Step 2—Synthesis of (R)-5-(1-((7-fluoro-1H-indol-2-yl)sulfonyl)piperidin-3-yl)-2-(4-fluorophenyl)-N-methyl-6-(N-methylmethylsulfonamido)benzofuran-3-carboxamide

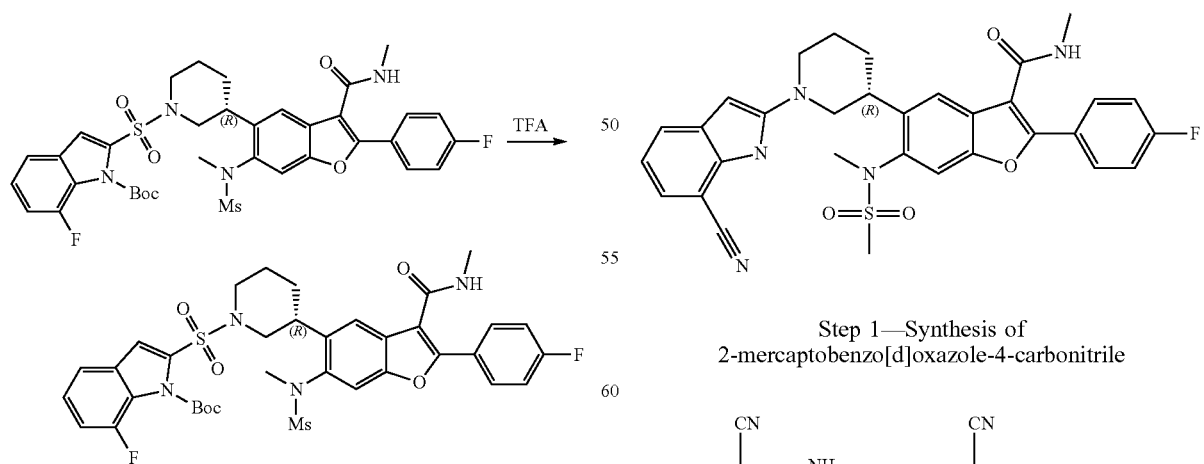

A mixture of (R)-tert-butyl 7-fluoro-2-((3-(2-(4-fluorophenyl)-3-(methylcarbamoyl)-6-(N-methylmethylsulfonamido)benzofuran-5-yl)piperidin-1-yl)sulfonyl)-1H-indole-1-carboxylate (100 mg, 0.13 mmol) and TFA (1 mL) in $CH_2Cl_2$ (5 mL) was stirred at RT for 2 h. Then the mixture was concentrated. The residue was purified by prep-HPLC to afford the desired product of (R)-5-(1-(7-fluoro-1H-indol-2-yl)sulfonyl)piperidin-3-yl)-2-(4-fluorophenyl)-N-methyl-6-(N-methylmethylsulfonamido)benzofuran-3-carboxamide (50 mg, yield: 59%). $^1$H-NMR (CDCl$_3$, 400 MHz) δ 9.10~9.55 (m, 1H), 7.77~7.83 (m, 3H), 7.44~7.50 (m, 2H), 7.01~7.17 (m, 5H), 5.76~5.81 (m, 1H), 3.50~4.16 (m, 3H), 3.12~3.33 (m, 6H), 2.9~03.02 (m, 3H), 2.50~2.76 (m, 2H), 1.73~2.02 (m, 4H). MS (M+H)$^+$: 657.

Example 4

(R)-5-(1-(4-cyanobenzo[d]oxazol-2-yl)piperidin-3-yl)-2-(4-fluorophenyl)-N-methyl-6-(N-methylmethylsulfonamido)benzofuran-3-carboxamide

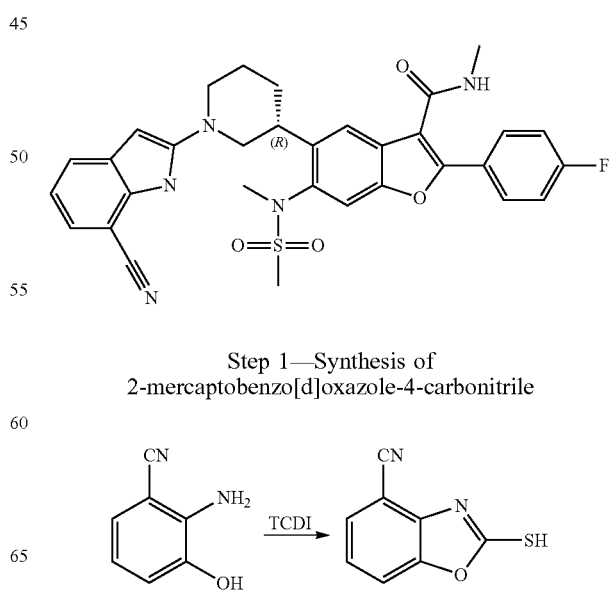

Step 1—Synthesis of 2-mercaptobenzo[d]oxazole-4-carbonitrile

A mixture of 2-amino-3-hydroxybenzonitrile (200 mg, 1.22 mmol), TCDI (260 mg, 1.46 mmol) and in THF (10 mL) was stirred at RT for 6 h under N₂ atmosphere. The mixture was diluted with 1N HCl, extracted with EtOAc, dried over Na₂SO₄ and concentrated in vacuum to give the product 2-mercaptobenzo[d]oxazole-4-carbonitrile (200 mg, yield: 80%), which was used for the next step without further purification. ¹H-NMR (CDCl₃, 400 MHz) δ 7.45 (t, J=8.0 Hz, 2H), 7.25 (t, J=8.0 Hz, 1H). MS (M+H)⁺: 177.

Step 2—Synthesis of 2-chlorobenzo[d]oxazole-4-carbonitrile

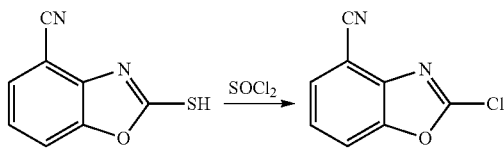

To a mixture of 2-mercaptobenzo[d]oxazole-4-carbonitrile (100 mg, 0.57 mmol) in SOCl₂ (2 mL) was added DMF (1 drop). The mixture was heated to 80° C. for 20 min. The reaction mixture was concentrated in vacuum, diluted with NaHCO₃ (aq), extracted with EtOAc, dried over Na₂SO₄, and concentrated. The residue was purified by column chromatography (PE:EA=5:1) to give the product of 2-chlorobenzo[d]oxazole-4-carbonitrile (60 mg, yield: 60%). ¹H-NMR (CDCl₃, 400 MHz) δ 7.75 (d, J=8.0 Hz, 2H), 7.70 (d, J=8.0 Hz, 1H), 7.47 (t, J=8.0 Hz, 1H). MS (M+H)⁺: 179/181.

Step 3—Synthesis of (R)-5-(1-(4-cyanobenzo[d]oxazol-2-yl)piperidin-3-yl)-2-(4-fluorophenyl)-N-methyl-6-(N-methylmethylsulfonamido)benzofuran-3-carboxamide (Example 4)

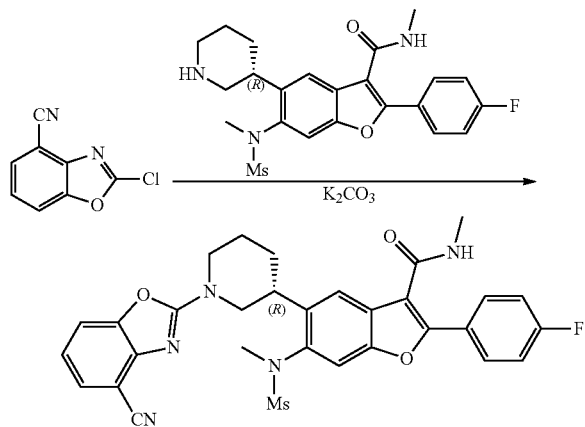

A mixture of 2-chlorobenzo[d]oxazole-4-carbonitrile (33 mg, 0.18 mmol), (R)-2-(4-fluorophenyl)-N-methyl-6-(N-methylmethylsulfonamido)-5-(piperidin-3-yl)benzofuran-3-carboxamide (70 mg, 0.15 mmol) and K₂CO₃ (63 mg, 1.98 mmol) in DMF (5 mL) was stirred at RT overnight under N₂ atmosphere. The mixture was diluted with water, extracted with EtOAc, dried over Na₂SO₄ and concentrated in vacuum. The residue was purified by prep-HPLC to afford the desired product of (R)-5-(1-(4-cyanobenzo[d]oxazol-2-yl)piperidin-3-yl)-2-(4-fluorophenyl)-N-methyl-6-(N-methylmethylsulfonamido)benzofuran-3-carboxamide (50 mg, yield: 56%). ¹H-NMR (CDCl₃, 400 MHz) δ 7.83~7.89 (m, 3H), 7.36~7.62 (m, 3H), 7.18~7.22 (m, 2H), 6.97~6.99 (m, 1H), 5.78 (br s, 1H), 4.39~4.42 (m, 2H), 3.22~3.55 (m, 3H), 2.97~3.16 (m, 8H), 1.79~2.23 (m, 5H). MS (M+H)⁺: 602.

Example 5

(S)-5-(1-(4-cyanobenzo[d]oxazol-2-yl)piperidin-3-yl)-2-(4-fluorophenyl)-N-methyl-6-(N-methylmethylsulfonamido)benzofuran-3-carboxamide

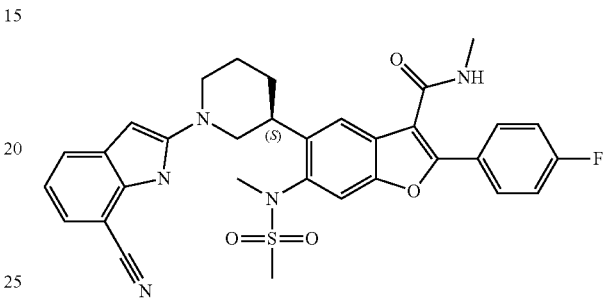

Synthesis of (S)-5-(1-(4-cyanobenzo[d]oxazol-2-yl)piperidin-3-yl)-2-(4-fluorophenyl)-N-methyl-6-(N-methylmethylsulfonamido)benzofuran-3-carboxamide

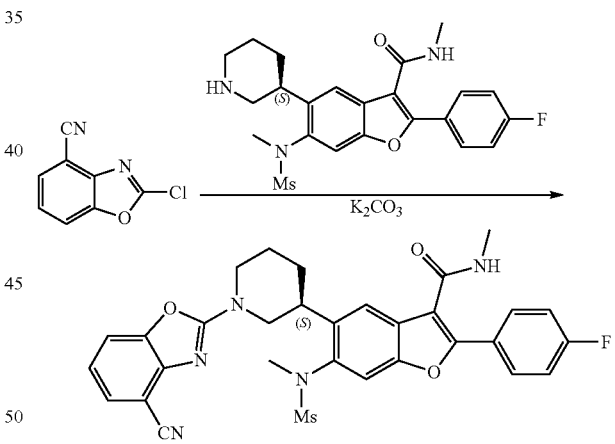

A mixture of 2-chlorobenzo[d]oxazole-4-carbonitrile (33 mg, 0.18 mmol), (S)-2-(4-fluorophenyl)-N-methyl-6-(N-methylmethylsulfonamido)-5-(piperidin-3-yl)benzofuran-3-carboxamide (70 mg, 0.15 mmol) and K₂CO₃ (63 mg, 1.98 mmol) in DMF (5 mL) was stirred at RT overnight under N₂ atmosphere. The mixture was diluted with water, extracted with EtOAc, dried over Na₂SO₄ and concentrated in vacuum. The residue was purified by prep-HPLC to afford the desired product of (S)-5-(1-(4-cyanobenzo[d]oxazol-2-yl)piperidin-3-yl)-2-(4-fluorophenyl)-N-methyl-6-(N-methylmethylsulfonamido)benzofuran-3-carboxamide (50 mg, yield: 56%). ¹H-NMR (CDCl₃, 400 MHz) δ 7.83~7.89 (m, 3H), 7.36~7.62 (m, 3H), 7.18~7.22 (m, 2H), 6.97~6.99 (m, 1H), 5.78 (brs, 1H), 4.39~4.42 (m, 2H), 3.22~3.55 (m, 3H), 2.97~3.16 (m, 8H), 1.79~2.23 (m, 5H). MS (M+H)⁺: 602.

Examples 6 and 7

5-(4-(7-fluoro-1H-indole-2-carbonyl)morpholin-2-yl)-2-(4-fluorophenyl)-N-methyl-6-(N-methylmethylsulfonamido)benzofuran-3-carboxamide (enantiomers 1 and 2)

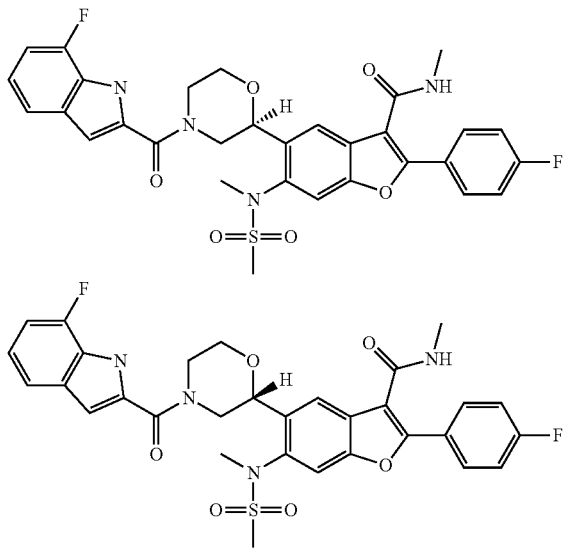

Step 1—Synthesis of 2-(4-fluorophenyl)-N-methyl-6-(N-methylmethylsulfonamido)-5-vinylbenzofuran-3-carboxamide

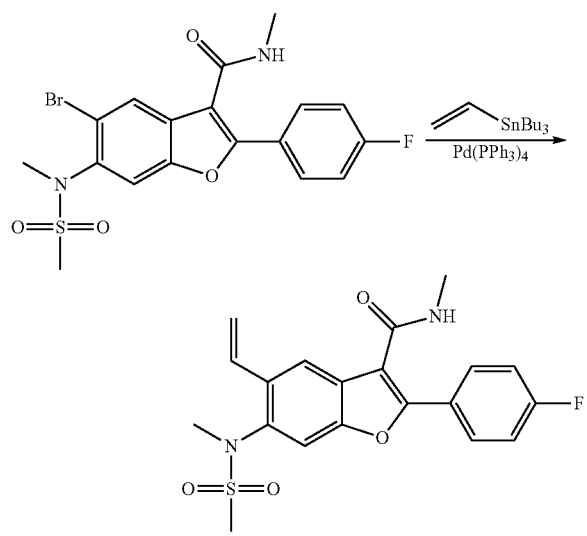

A mixture of 5-bromo-2-(4-fluorophenyl)-N-methyl-6-(N-methylmethyl sulfonamido)benzofuran-3-carboxamide (10 g, 21.96 mmol), tributyl(vinyl)stannane (14 g, 44.15 mmol) and Pd(PPh$_3$)$_4$ (2.54 g, 2.20 mmol) in dioxane (150 mL) was stirred at 90° C. for 20 hours under N$_2$ protection. Then the mixture was cooled to room temperature, diluted with EA (100 mL) and filtered through a Celite pad. The combined organic phase was washed with water and brine, dried over Na$_2$SO$_4$ and concentrated. The residue was purified by silica gel column chromatography (PE:EA=2:1) to afford the desired product of 2-(4-fluorophenyl)-N-methyl-6-(N-methylmethylsulfonamido)-5-vinylbenzofuran-3-carboxamide (8.8 g, yield: 79.5%). $^1$H-NMR (CDCl$_3$, 400 MHz) δ 8.06 (s, 1H), 7.90 (dd, J=5.2, 8.8 Hz, 2H), 7.51 (s, 1H), 7.19 (t, J=8.4 Hz, 2H), 7.09 (dd, J=11.2, 17.6 Hz, 1H), 5.84 (d, J=17.6 Hz, 2H), 5.41 (d, J=11.2 Hz, 1H), 3.28 (s, 3H), 2.97~3.04 (m, 6H). MS (M+H)$^+$: 403.

Step 2—Synthesis of 5-(1,2-dihydroxyethyl)-2-(4-fluorophenyl)-N-methyl-6-(N-methylmethylsulfonamido)benzofuran-3-carboxamide

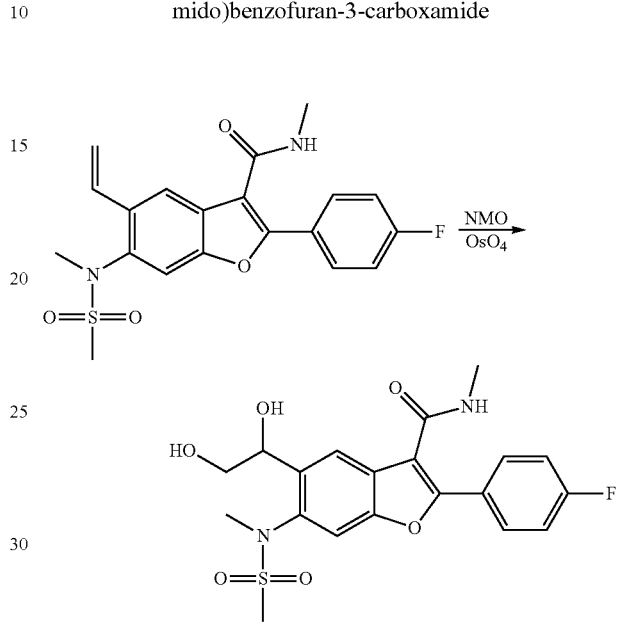

A mixture of 2-(4-fluorophenyl)-N-methyl-6-(N-methylmethylsulfonamido)-5-vinylbenzofuran-3-carboxamide (4 g, 9.94 mmol), NMO (3.49 g, 29.81 mmol) and OsO$_4$ (250 mg, 0.98 mmol) in THF/MeOH/H$_2$O (20 mL/20 mL/5 mL) was stirred at room temperature for 2 hours. Then Na$_2$SO$_3$ (5 g, 39.7 mmol) was added, and the reaction mixture was extracted with EA (10 mL*3). The combined organic layer was washed with brine (30 mL), dried over Na$_2$SO$_4$ and concentrated. The residue was purified by silica gel column chromatography (DCM:MeOH=10:1) to afford the product of 5-(1,2-dihydroxyethyl)-2-(4-fluorophenyl)-N-methyl-6-(N-methylmethylsulfonamido)benzofuran-3-carboxamide (3.5 g, yield: 80.8%). $^1$H-NMR (CDCl$_3$, 400 MHz) δ 7.98~8.05 (m, 1H), 7.88~7.97 (m, 2H), 7.44 (s, 1H), 7.17 (t, J=8.4 Hz, 2H), 6.15~6.29 (m, 1H), 5.39 (dd, J=3.6, 7.6 Hz, 1H), 5.22 (d, J=4.4 Hz, 1H), 3.91~3.99 (m, 1H), 3.81~3.90 (m, 1H), 3.44~3.79 (m, 2H), 3.25~3.37 (m, 3H), 2.82~3.12 (m, 7H). MS (M+H)$^+$: 436.

Step 3—Synthesis of 2-(2-(4-fluorophenyl)-3-(methylcarbamoyl)-6-(N-methylmethylsulfonamido)benzofuran-5-yl)-2-hydroxyethyl methanesulfonate

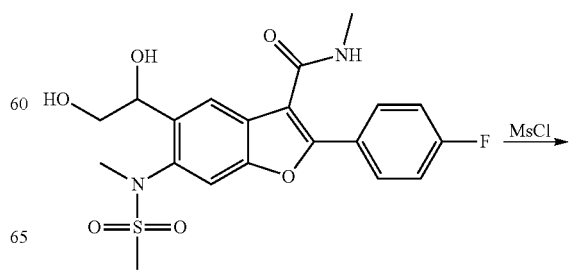

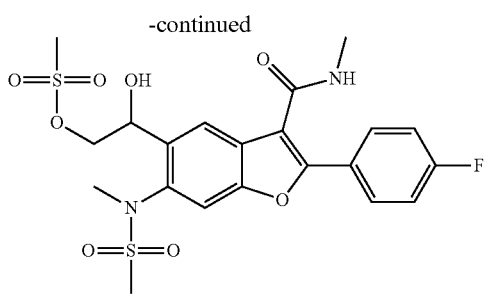

To a solution of 5-(1,2-dihydroxyethyl)-2-(4-fluorophenyl)-N-methyl-6-(N-methylmethylsulfonamido)benzofuran-3-carboxamide (3.5 g, 8.02 mmol) in pyridine (30 mL) was added MsCl (1.5 g, 13.09 mmol). The reaction mixture was stirred at room temperature for 2 hours and then the reaction mixture was diluted with water, and then extracted with EA (20 mL*8). The combined organic layer was washed with brine (150 mL), dried over $Na_2SO_4$ and concentrated, the residue was purified by silica gel column chromatography (DCM:MeOH=20:1) to afford the product 2-(2-(4-fluorophenyl)-3-(methylcarbamoyl)-6-(N-methylmethyl sulfonamido)benzofuran-5-yl)-2-hydroxyethyl methanesulfonate (3.8 g, yield: 92.2%). $^1$H-NMR (CDCl$_3$, 400 MHz) δ 8.03~8.09 (m, 1H), 7.91~8.02 (m, 2H), 7.40~7.54 (m, 1H), 7.19 (t, J=8.4 Hz, 2H), 6.14~5.91 (m, 1H), 5.48~5.68 (m, 1H), 4.39~4.72 (m, 2H), 3.29~3.39 (m, 3H), 2.97~3.15 (m, 9H). MS (M+H)$^+$: 515.

Step 4—Synthesis of 2-(4-fluorophenyl)-5-(1-hydroxy-2-(2-hydroxyethyl)amino)ethyl)-N-methyl-6-(N-methylmethylsulfonamido)benzofuran-3-carboxamide

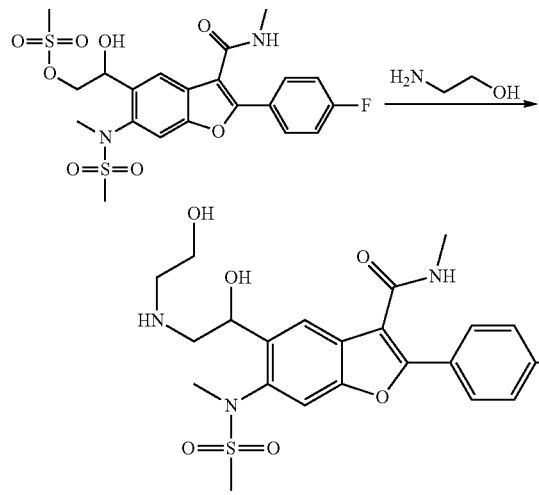

To a solution of 2-(2-(4-fluorophenyl)-3-(methylcarbamoyl)-6-(N-methylmethyl sulfonamido)benzofuran-5-yl)-2-hydroxyethyl methanesulfonate (3.8 g, 7.38 mmol) in DMF (20 mL) was added 2-aminoethanol (2.71 g, 44.32 mmol) and $K_2CO_3$ (3.06 g, 22.16 mmol). The reaction mixture was stirred at 80° C. for 40 hours. Then the reaction mixture was concentrated to afford the crude product 2-(4-fluorophenyl)-5-(1-hydroxy-2-(2-hydroxyethyl)amino)ethyl)-N-methyl-6-(N-methylmethylsulfonamido)benzofuran-3-carboxamide, which was used for next step without purification. MS (M+H)$^+$: 480.

Step 5—Synthesis of ten-butyl (2-(2-(4-fluorophenyl)-3-(methylcarbamoyl)-6-(N-methylmethyl sulfonamido)benzofuran-5-yl)-2-hydroxyethyl)(2-hydroxyethyl)carbamate

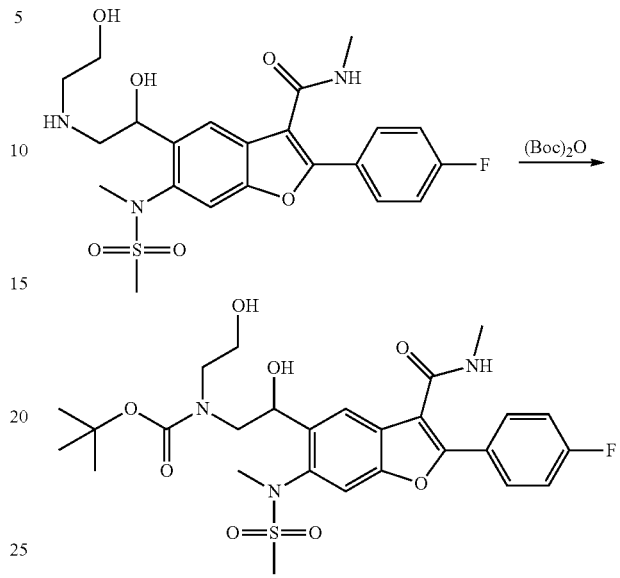

A mixture of 2-(4-fluorophenyl)-5-(1-hydroxy-2-(2-hydroxyethyl)amino)ethyl)-N-methyl-6-(N-methylmethylsulfonamido)benzofuran-3-carboxamide (crude from previous step) and (Boc)$_2$O (15 g, 68.7 mmol) in THF (30 mL) was stirred at room temperature for 18 hours under $N_2$ protection. Then the mixture was quenched with water and extracted with EA (20 mL*5). The organic phase was washed with water and brine, dried over $Na_2SO_4$ and concentrated. The residue was purified by silica gel column chromatography (DCM:MeOH=20:1) to afford the product of tert-butyl (2-(2-(4-fluorophenyl)-3-(methylcarbamoyl)-6-(N-methylmethyl sulfonamido)benzofuran-5-yl)-2-hydroxyethyl)(2-hydroxyethyl)carbamate (2.5 g, yield: 58.1% for 2 steps). $^1$H-NMR (CDCl$_3$, 400 MHz) δ 7.71~8.14 (m, 3H), 7.41 (d, J=15.6 Hz, 1H), 7.17 (d, J=3.6 Hz, 2H), 5.95~6.33 (m, 1H), 5.35~5.64 (m, 1H), 3.59~3.95 (m, 4H), 3.50 (d, J=12.4 Hz, 1H), 3.26~3.43 (m, 4H), 3.15 (br. s., 1H), 2.94~3.10 (m, 5H), 1.39~1.54 (m, 9H). MS (M+H)$^+$: 580.

Step 6—Synthesis of 2-(4-fluorophenyl)-N-methyl-6-(N-methylmethylsulfonamido)-5-(morpholin-2-yl)benzofuran-3-carboxamide

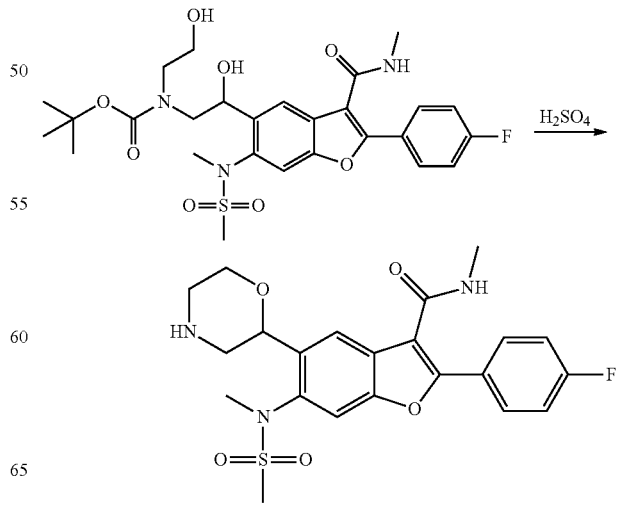

Tert-butyl (2-(2-(4-fluorophenyl)-3-(methylcarbamoyl)-6-(N-methylmethyl sulfonamido)benzofuran-5-yl)-2-hydroxyethyl)(2-hydroxyethyl)carbamate (700 mg, 1.2 mmol) in 70% $H_2SO_4$ aqueous (20 mL) was stirred at room temperature for 12 hours under $N_2$ protection. Then the mixture was quenched with water, adjusted to pH ~8, and extracted with EA (20 mL*5). The combined organic layer was washed with brine (30 mL), dried over $Na_2SO_4$ and concentrated. The residue was purified by silica gel column chromatography (DCM:MeOH=20:1) to afford the product of 2-(4-fluorophenyl)-N-methyl-6-(N-methylmethylsulfonamido)-5-(morpholin-2-yl)benzofuran-3-carboxamide (350 mg, yield: 62.8%). $^1$H-NMR (CDCl$_3$, 400 MHz) δ 8.01 (br s, 1H), 7.87~7.97 (m, 2H), 7.40~7.55 (m, 1H), 7.18 (t, J=8.4 Hz, 2H), 5.85~6.04 (m, 1H), 4.87~5.12 (m, 1H), 3.96~4.10 (m, 1H), 3.76~3.90 (m, 1H), 3.19~3.38 (m, 4H), 2.98~3.15 (m, 8H), 2.76~2.97 (m, 2H). MS (M+H)$^+$: 462.

Step 7—Synthesis of ten-butyl 7-fluoro-2-(2-(2-(4-fluorophenyl)-3-(methylcarbamoyl)-6-(N-methylmethylsulfonamido)benzofuran-5-yl)morpholine-4-carbonyl)-1H-indole-1-carboxylate

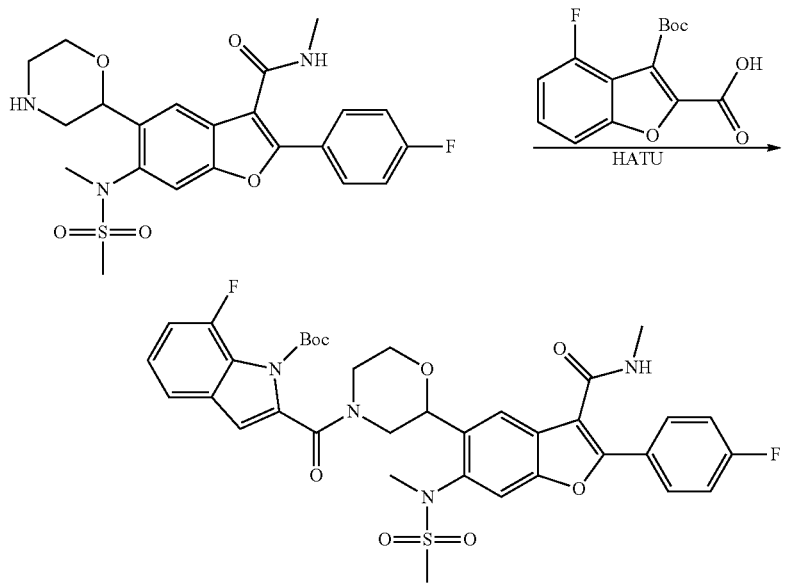

A mixture of 2-(4-fluorophenyl)-N-methyl-6-(N-methylmethylsulfonamido)-5-(morpholin-2-yl)benzofuran-3-carboxamide (150 mg, 0.33 mmol), 1-(tert-butoxycarbonyl)-7-fluoro-1H-indole-2-carboxylic acid (91 mg, 0.33 mmol), HATU (371 mg 0.98 mmol) and Et$_3$N (165 mg 1.6 mmol) in DMF (2 mL) was stirred at RT overnight under $N_2$ protection. Then the mixture was diluted with $H_2O$ (20 mL) and extracted with EtOAc. The organic layer was washed with water, brine, dried over $Na_2SO_4$, and concentrated. The residue was purified by prep-TLC (PE:EA=1:1) to give the product of tert-butyl 7-fluoro-2-(2-(2-(4-fluorophenyl)-3-(methylcarbamoyl)-6-(N-methylmethylsulfonamido)benzofuran-5-yl)morpholine-4-carbonyl)-1H-indole-1-carboxylate (180 mg, yield: 76%). MS (M+H)$^+$: 723.

Step 8—Synthesis of 5-(4-(7-fluoro-1H-indole-2-carbonyl)morpholin-2-yl)-2-(4-fluorophenyl)-N-methyl-6-(N-methylmethylsulfonamido)benzofuran-3-carboxamide (Enantiomers 1 and 2)

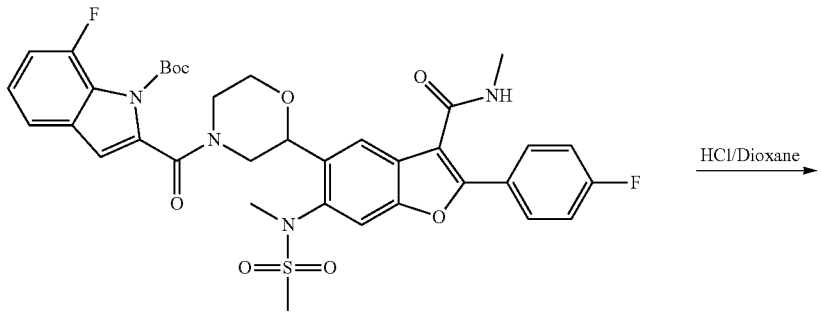

-continued

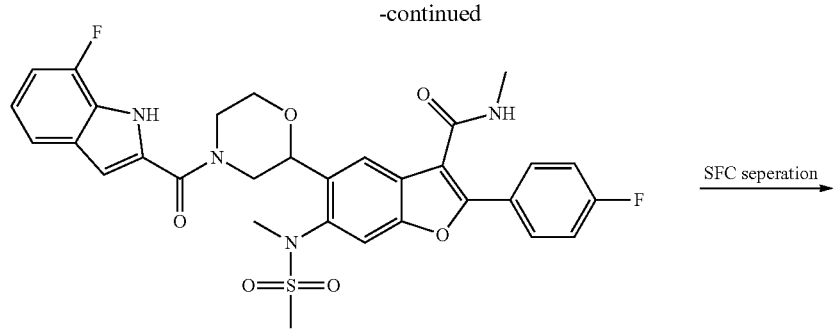

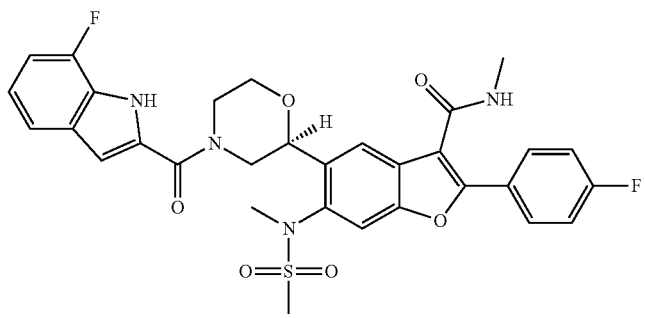

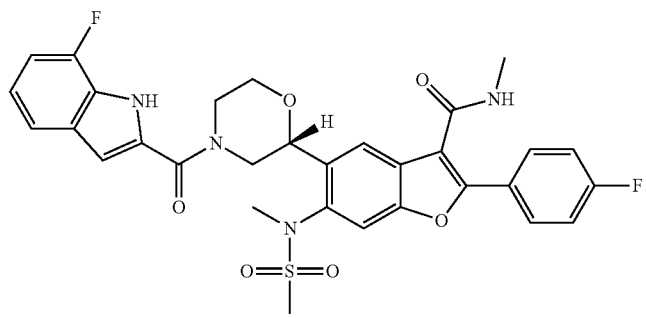

To a solution of tert-butyl 7-fluoro-2-(2-(2-(4-fluorophenyl)-3-(methylcarbamoyl)-6-(N-methylmethylsulfonamido)benzofuran-5-yl)morpholine-4-carbonyl)-1H-indole-1-carboxylate (230 mg, 0.32 mmol) in dioxane (2 mL) was added HCl solution in dioxane (5 mL, 4 M) at RT. The mixture was stirred at RT for 5 hours. The mixture was diluted with water and extracted with DCM. The organic layers were washed with brine, dried over $Na_2SO_4$, and concentrated. The residue was purified by prep-HPLC and SFC to give two single enantiomers.

Example 6 (enantiomer 1, peak 1 on SFC, AS-H_S_3_5_40_3 ML_8 MIN_15 CM, HPLC_RT=5.097 min) (60 mg, yield: 30%). $^1$H-NMR (CDCl$_3$, 400 MHz) δ 9.38 (br s, 1H), 8.10~8.17 (m, 1H), 7.84~7.98 (m, 2H), 7.33~7.57 (m, 2H), 7.15~7.23 (m, 2H), 6.87~7.09 (m, 3H), 5.88 (br s, 1H), 4.87~5.10 (m, 2H), 4.51~4.75 (m, 3H), 4.10~4.25 (m, 1H), 3.80~3.95 (m, 1H), 3.31 (s, 3H), 2.8~3.14 (m, 6H). MS (M+H)$^+$: 623.

Example 7 (enantiomer 2, peak 2 on SFC, AS-H_S_3_5_40_3 ML_8 MIN_15 CM, HPLC_RT=5.582 min) (60 mg, yield: 30%). $^1$H-NMR (CDCl$_3$, 400 MHz) δ 9.38 (br s, 1H), 8.10~8.17 (m, 1H), 7.84~7.98 (m, 2H), 7.33~7.57 (m, 2H), 7.15~7.23 (m, 2H), 6.87~7.09 (m, 3H), 5.88 (br s, 1H), 4.87~5.10 (m, 2H), 4.51~4.75 (m, 3H), 4.10~4.25 (m, 1H), 3.80~3.95 (m, 1H), 3.31 (s, 3H), 2.8~83.14 (m, 6H). MS (M+H)$^+$: 623.

Examples 8 and 9

5-(4-(4-fluoro-1-methyl-1H-indole-2-carbonyl)morpholin-2-yl)-2-(4-fluorophenyl)-N-methyl-6-(N-methylmethylsulfonamido)benzofuran-3-carboxamide (enantiomers 1 and 2)

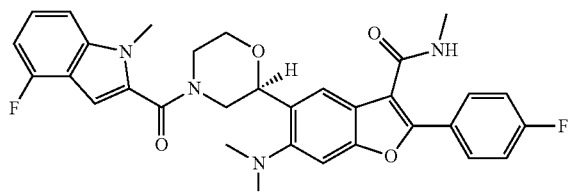

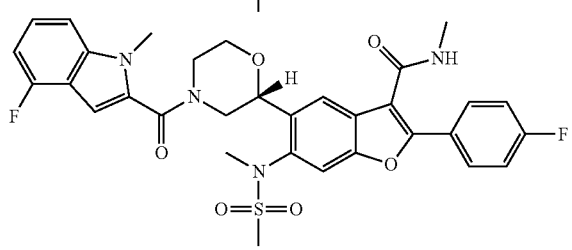

Synthesis of 5-(4-(4-fluoro-1-methyl-1H-indole-2-carbonyl)morpholin-2-yl)-2-(4-fluorophenyl)-N-methyl-6-(N-methylmethylsulfonamido)benzofuran-3-carboxamide (enantiomer 1) and 5-(4-(4-fluoro-1-methyl-1H-indole-2-carbonyl)morpholin-2-yl)-2-(4-fluorophenyl)-N-methyl-6-(N-methylmethylsulfonamido)benzofuran-3-carboxamide (enantiomer 2)

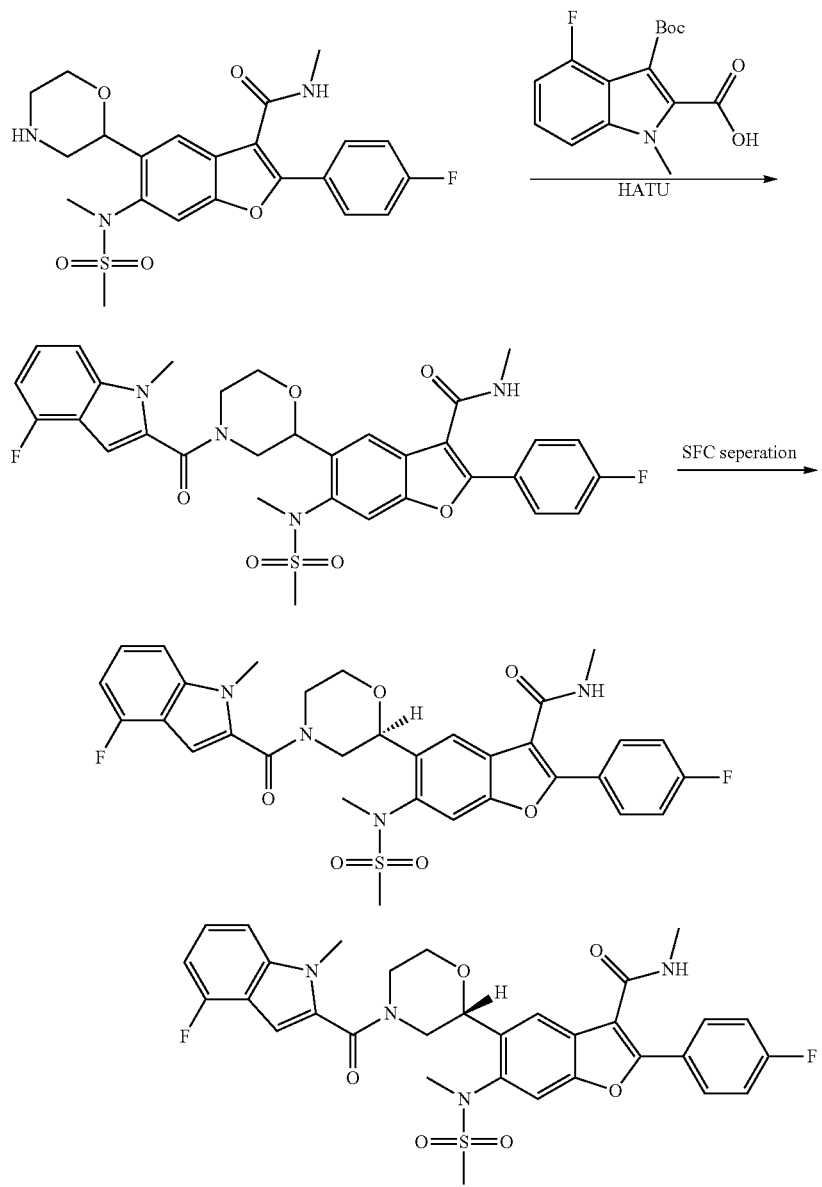

A mixture of 2-(4-fluorophenyl)-N-methyl-6-(N-methylmethylsulfonamido)-5-(morpholin-2-yl)benzofuran-3-carboxamide (150 mg, 0.33 mmol), 4-fluoro-1-methyl-1H-indole-2-carboxylic acid (63 mg, 0.33 mmol), HATU (371 mg 0.98 mmol) and Et$_3$N (165 mg 1.6 mmol) in DMF (2 mL) was stirred at RT overnight under N$_2$ protection. Then the reaction mixture was diluted with H$_2$O (20 mL) and extracted with DCM, the organic layer was washed with water, brine, dried over Na$_2$SO$_4$ and concentrated. The residue was purified by prep-HPLC and SFC to give two single enantiomers.

Example 8 (enantiomer 1, peak 1 on SFC, AS-H_S_3_5_40_2.5 ML_6 MIN_25 CM, HPLC_RT=2.40 min) (80 mg, yield: 38%). $^1$H-NMR (CDCl$_3$, 400 MHz) δ 8.0~28.13 (m, 1H), 7.84~7.96 (m, 2H), 7.30~7.55 (m, 1H), 7.09~7.22 (m, 4H), 6.64~6.86 (m, 2H), 5.97 (br s, 1H), 4.89~5.27 (m, 1H), 4.03~4.76 (m, 3H), 3.78~3.97 (m, 4H), 3.29 (s, 3H), 2.64~3.09 (m, 8H). MS (M+H)$^+$: 637.

Example 9 (enantiomer 2, peak 2 on SFC, AS-H_S_3_5_40_2.5 ML_6 MIN_25 CM, HPLC_RT=3.07 min) (80 mg, yield: 38%). $^1$H-NMR (CDCl$_3$, 400 MHz) δ 8.0~28.13 (m, 1H), 7.84~7.96 (m, 2H), 7.30~7.55 (m, 1H), 7.09~7.22 (m, 4H), 6.64~6.86 (m, 2H), 5.97 (br s, 1H), 4.89~5.27 (m, 1H), 4.03~4.76 (m, 3H), 3.78~3.97 (m, 4H), 3.29 (s, 3H), 2.64~3.09 (m, 8H). MS (M+H)$^+$: 637.

Examples 10 and 11

5-(4-(benzo[d]oxazol-2-yl)morpholin-2-yl)-2-(4-fluorophenyl)-N-methyl-6-(N-methylmethylsulfonamido)benzofuran-3-carboxamide (enantiomers 1 and 2)

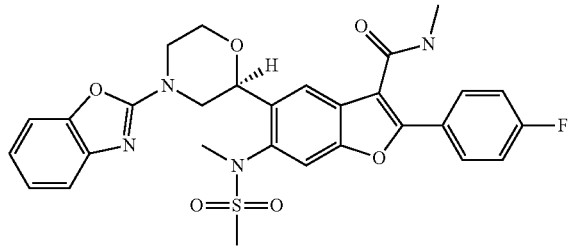

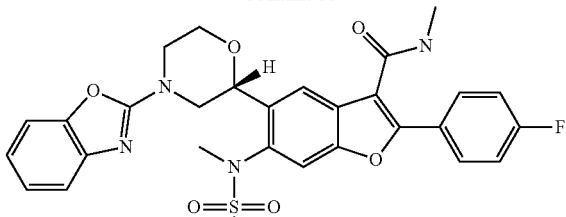

Synthesis of 5-(4-(benzo[d]oxazol-2-yl)morpholin-2-yl)-2-(4-fluorophenyl)-N-methyl-6-(N-methylmethylsulfonamido)benzofuran-3-carboxamide and 5-(4-(benzo[d]oxazol-2-yl)morpholin-2-yl)-2-(4-fluorophenyl)-N-methyl-6-(N-methylmethylsulfonamido)benzofuran-3-carboxamide

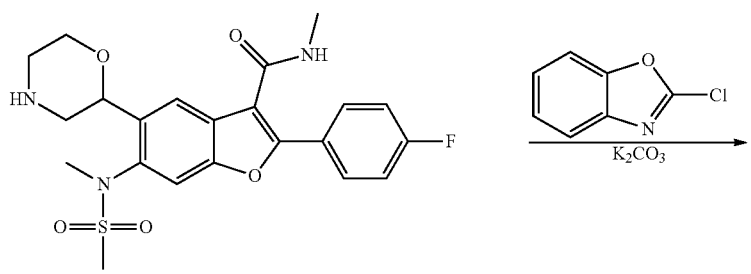

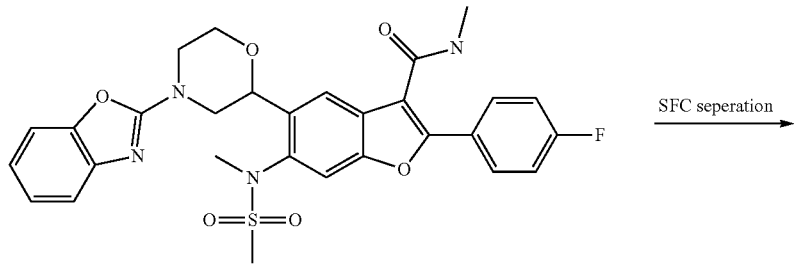

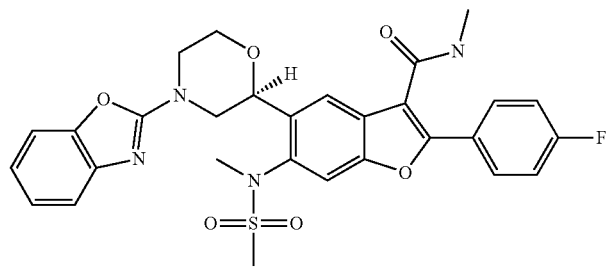

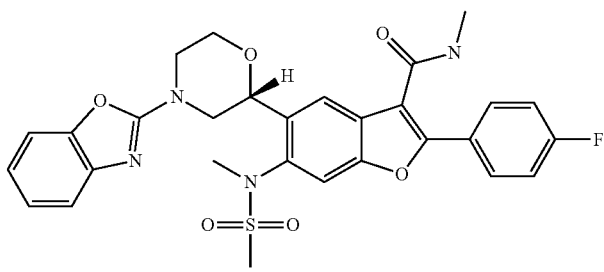

A mixture of 2-(4-fluorophenyl)-N-methyl-6-(N-methylmethylsulfonamido)-5-(morpholin-2-yl)benzofuran-3-carboxamide (229 mg, 0.50 mmol), 2-chlorobenzo[d]oxazole (91 mg, 0.595 mmol) and K$_2$CO$_3$ (206 mg 1.49 mmol) in DMF (5 mL) was stirred at RT for 4 h under N$_2$ protection. Then the reaction mixture was diluted with H$_2$O (20 mL) and extracted with EtOAc. The organic layer was washed with water, brine, dried over Na$_2$SO$_4$ and concentrated. The residue was purified by prep-HPLC and SFC to give two single enantiomers.

Example 10 (enantiomer 1, peak 1 on SFC, OJ-H_3 UM_5_5_40_4 ML_3 MIN, HPLC_RT=1.385 min) (100 mg, yield: 34%). $^1$H-NMR (CDCl$_3$, 400 MHz) δ 8.09 (br s, 1H), 7.88~7.97 (m, 2H), 7.53 (s, 1H), 7.32~7.40 (m, 1H), 7.24~7.31 (m, 1H), 7.13~7.23 (m, 3H), 7.04 (q, J=7.6 Hz, 1H), 5.95 (br s, 1H), 4.99~5.26 (m, 1H), 4.07~4.29 (m, 3H), 3.85~4.03 (m, 1H), 3.36~3.52 (m, 2H), 3.17 (s, 3H), 2.96~3.07 (m, 6H). MS (M+H)$^+$: 579.

Example 11 (enantiomer 2, peak 2 on SFC, OJ-H_3 UM_5_5_40_4 ML_3 MIN, HPLC_RT=1.765 min) (100 mg, yield: 34%). $^1$H-NMR (CDCl$_3$, 400 MHz) δ 8.09 (br s, 1H), 7.88~7.97 (m, 2H), 7.53 (s, 1H), 7.32~7.40 (m, 1H), 7.24~7.31 (m, 1H), 7.13~7.23 (m, 3H), 7.04 (q, J=7.6 Hz, 1H), 5.95 (br s, 1H), 4.99~5.26 (m, 1H), 4.07~4.29 (m, 3H), 3.85~4.03 (m, 1H), 3.36~3.52 (m, 2H), 3.17 (s, 3H), 2.96~3.07 (m, 6H). MS (M+H)$^+$: 579.

Example 12

5-((5S)-5-(4-fluorobenzo[d]oxazol-2-yl)-1-methylpyrrolidin-3-yl)-2-(4-fluorophenyl)-N-methyl-6-(N-methylmethylsulfonamido)benzofuran-3-carboxamide

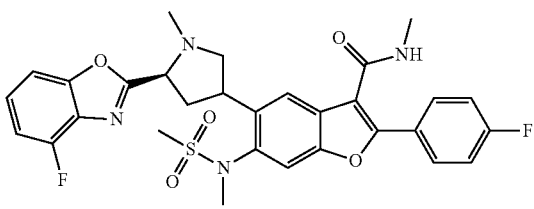 [SMILES: CNC(=O)c1c(-c2ccc(F)cc2)oc2cc(N(C)S(C)(=O)=O)c(C3C[C@@H](c4nc5c(F)cccc5o4)N(C)C3)cc12]

Step 1—Synthesis of (S)-1-tert-butyl 2-methyl 4-oxopyrrolidine-1,2-dicarboxylate

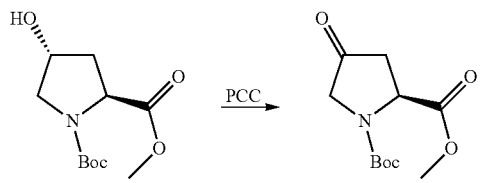

PCC (52.9 g, 244.63 mmol) was added into a solution of (2S,4R)-1-tert-butyl 2-methyl 4-hydroxypyrrolidine-1,2-dicarboxylate (10 g, 81.54 mmol) in DCM (300 mL) under N$_2$ and the mixture was stirred for 48 hours. After being filtered and concentrated, the residue was purified by column chromatography eluted with PE:EtOAc=4:1 to afford (S)-1-tert-butyl 2-methyl 4-oxopyrrolidine-1,2-dicarboxylate (11 g, yield: 55.5%). $^1$H-NMR (CDCl$_3$, 400 MHz) δ 4.67~4.79 (m, 1H), 3.86 (d, J=12.0 Hz, 2H), 3.73 (s, 3H), 2.90~2.93 (m, 1H), 2.56 (d, J=20.0 Hz, 1H), 1.45 (s, 9H). MS (M+H)$^+$: 244.

Step 2—Synthesis of (S)-1-tert-butyl 2-methyl 4-(trifluoromethylsulfonyloxy)-1H-pyrrole-1,2(2H,5H)-dicarboxylate

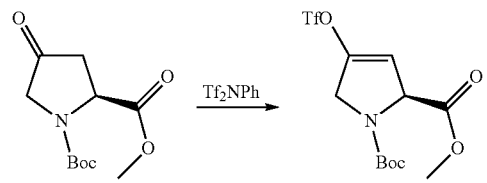 [SMILES: "Tf2NPh" ; COC(=O)[C@@H]1CC(=O)CN1C(=O)OC(C)(C)C ; COC(=O)[C@@H]1C=C(OS(=O)(=O)C(F)(F)F)CN1C(=O)OC(C)(C)C]

LiHMDS (1.51 g, 9.04 mmol) was added into a solution of (S)-1-tert-butyl 2-methyl 4-oxopyrrolidine-1,2-dicarboxylate (2 g, 8.22 mmol) in dry THF (20 mL) under N$_2$ dropwise at −78° C. and the mixture was stirred for 0.5 hours. 1,1,1-trifluoro-N-phenyl-N-(trifluoromethylsulfonyl)methanesulfonamide (3.23 g, 9.04 mmol) in dry THF (20 mL) was added into the reaction mixture under N$_2$ dropwise at −78° C. and stirred for 2 hours. Then the reaction mixture was stirred at RT for 12 hours. After being diluted with NH$_4$Cl (a.q.) and extracted with EtOAc (200 mL*3), the orgranics were washed with brine and dried over Na$_2$SO$_4$. After being filtered and concentrated in vacuo, the residue was purified by column chromatography and eluted with PE:EtOAc=20:1 to afford (5)-1-tert-butyl 2-methyl 4-(trifluoromethylsulfonyloxy)-1H-pyrrole-1,2(2H,5H)-dicarboxylate (1.1 g, yield: 35.5%). $^1$H-NMR (CDCl$_3$, 400 MHz) δ 5.6~95.74 (m, 1H), 4.99~5.08 (m, 1H), 4.23~4.41 (m, 2H), 3.75 (s, 3H), 1.47 (s, 9H). MS (M+H)$^+$: 376.

Step 3—Synthesis of (S)-1-tert-butyl 2-methyl 4-(4,4,5,5-tetramethyl-1,3,2-dioxaborolan-2-yl)-1H-pyrrole-1,2(2H,5H)-dicarboxylate

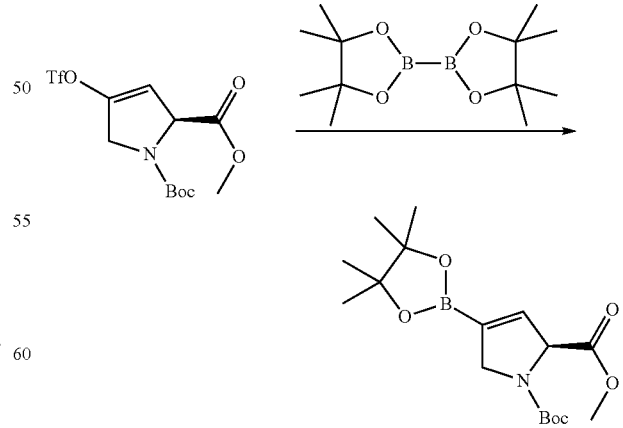

To a degassed solution of (S)-1-tert-butyl 2-methyl 4-(trifluoromethylsulfonyloxy)-1H-pyrrole-1,2(2H,5H)-dicarboxylate (200 mg, 0.53 mmol) and bis(pinacolato)diboron (148 mg, 0.58 mmol) in dry dioxane (3 mL) was added Pd(dppf)Cl$_2$ (1 mg) and KOAc (162 mg, 165 mmol) under N$_2$. The mixture was heated to 100° C. and then stirred overnight. The reaction mixture was cooled to RT and filtered. The filtrate was diluted with EtOAc (50 mL), washed with H$_2$O, brine, dried over Na$_2$SO$_4$. After being concentrated, the residue was purified by prep-TLC (PE:EtOAc=1:1) to afford (S)-1-tert-butyl 2-methyl 4-(4,4,5,5-tetramethyl-1,3,2-dioxaborolan-2-yl)-1H-pyrrole-1,2(2H,5H)-dicarboxylate (160 mg, yield: 85%). $^1$H-NMR (CDCl$_3$, 400 MHz) δ 6.27~6.33 (m, 1H), 5.07~5.10 (m, 1H), 4.26~4.32 (m, 2H), 3.69 (s, 3H), 1.42 (s, 9H), 1.21 (s, 12H). MS (M+H)$^+$: 354.

Step 4—Synthesis of (S)-1-tert-butyl 2-methyl 4-(2-(4-fluorophenyl)-3-(methylcarbamoyl)-6-(N-methylmethylsulfonamido)benzofuran-5-yl)-1H-pyrrole-1,2(2H,5H)-dicarboxylate

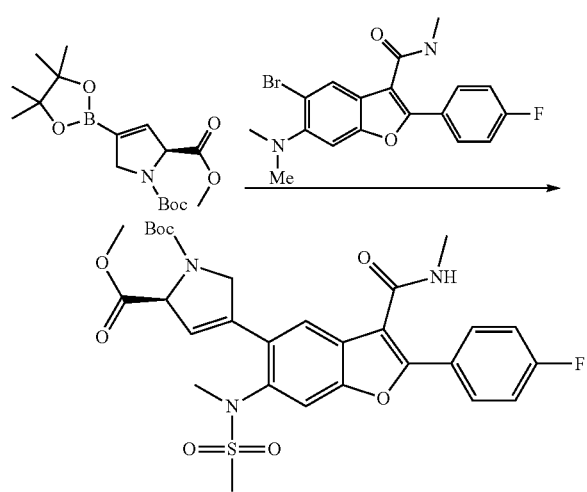

To a degassed solution of 5-bromo-2-(4-fluorophenyl)-N-methyl-6-(N-methylmethylsulfonamido)benzofuran-3-carboxamide (120 mg, 0.26 mmol) and (S)-1-tert-butyl 2-methyl 4-(4,4,5,5-tetramethyl-1,3,2-dioxaborolan-2-yl)-1H-pyrrole-1,2(2H,5H)-dicarboxylate (102 mg, 0.29 mmol) in dry dioxane (3 mL) was added Pd(dppf)Cl$_2$ (2 mg) and K$_3$PO$_4$ (112 mg, 1.05 mmol) under N$_2$. The mixture was heated to 100° C. and then stirred overnight. The reaction mixture was cooled to RT and filtered. The filtrate was diluted with EtOAc (50 mL), washed with H$_2$O, brine, and dried over Na$_2$SO$_4$. After being concentrated, the residue was purified by prep-HPLC (PE:EtOAc=1:2) to give the product of (S)-1-tert-butyl 2-methyl 4-(2-(4-fluorophenyl)-3-(methylcarbamoyl)-6-(N-methylmethylsulfonamido)benzofuran-5-yl)-1H-pyrrole-1,2(2H,5H)-dicarboxylate (50 mg, yield: 31.6%). $^1$H-NMR (CDCl$_3$, 400 MHz) δ 7.86~7.92 (m, 2H), 7.77~7.81 (m, 1H), 7.55 (s, 1H), 7.17~7.22 (m, 2H), 6.04~6.06 (m, 2H), 5.12~5.21 (m, 1H), 4.57~4.67 (m, 2H), 3.78 (s, 3H), 3.25 (s, 3H), 3.00~3.02 (m, 6H), 1.23 (s, 9H). MS (M+H)$^+$: 602.

Step 5—Synthesis of (2S)-1-tert-butyl 2-methyl 4-(2-(4-fluorophenyl)-3-(methylcarbamoyl)-6-(N-methylmethylsulfonamido)benzofuran-5-yl)pyrrolidine-1,2-dicarboxylate

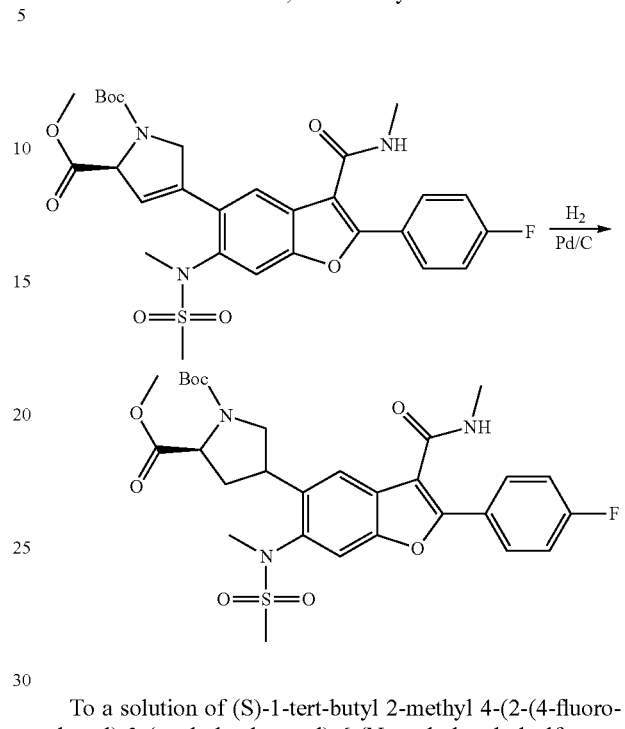

To a solution of (S)-1-tert-butyl 2-methyl 4-(2-(4-fluorophenyl)-3-(methylcarbamoyl)-6-(N-methylmethylsulfonamido)benzofuran-5-yl)-1H-pyrrole-1,2(2H,5H)-dicarboxylate (460 mg, 0.76 mmol) in MeOH (10 mL), Pd/C (200 mg) was added and the resulting reaction mixture was stirred under 40 psi of H$_2$ atmosphere for 24 h at 25° C. Then the reaction mixture was filtered, and the filtrate was evaporated to give the crude product of (2S)-1-tert-butyl 2-methyl 4-(2-(4-fluorophenyl)-3-(methylcarbamoyl)-6-(N-methylmethylsulfonamido)benzofuran-5-yl)pyrrolidine-1,2-dicarboxylate (400 mg, yield: 86.7%). $^1$H-NMR (CDCl$_3$, 400 MHz) δ 7.61~7.94 (m, 3H), 7.36~7.47 (m, 1H), 7.10~7.14 (m, 2H), 5.88~6.13 (m, 1H), 4.28~4.35 (m, 1H), 3.91~4.01 (m, 2H), 3.66~3.72 (m, 4H), 3.37~3.50 (m, 1H), 3.19~3.32 (m, 2H), 2.94~2.98 (m, 6H), 2.57~2.78 (m, 1H), 1.88~2.14 (m, 1H), 1.39 (s, 9H). MS (M+H)$^+$: 604.

Step 6—Synthesis of (2S)-methyl 4-(2-(4-fluorophenyl)-3-(methylcarbamoyl)-6-(N-methylmethylsulfonamido)benzofuran-5-yl)pyrrolidine-2-carboxylate

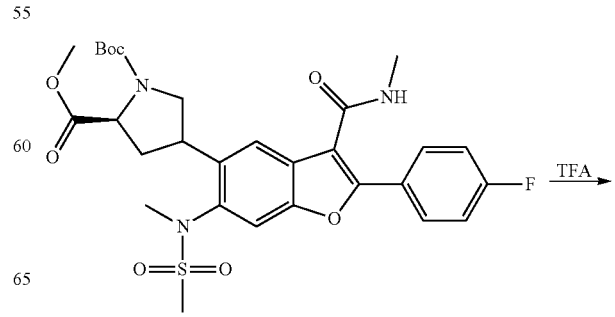

-continued

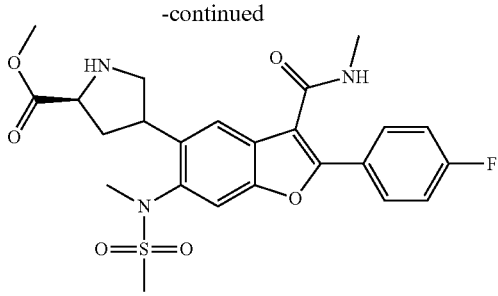

TFA (0.5 mL) was added into a solution of (2S)-1-tert-butyl 2-methyl 4-(2-(4-fluorophenyl)-3-(methylcarbamoyl)-6-(N-methylmethylsulfonamido)benzofuran-5-yl)pyrrolidine-1,2-dicarboxylate (200 mg, 0.33 mmol) in DCM (5 mL) under $N_2$ dropwise at 0° C. and stirred for 6 hours. After being diluted with $NaHCO_3$ (a.q.) and extracted with EtOAc (50 mL*3), the combined organic phase was washed with brine, dried over $Na_2SO_4$ and concentrated to give the desired product of (2S)-methyl 4-(2-(4-fluorophenyl)-3-(methylcarbamoyl)-6-(N-methylmethylsulfonamido)benzofuran-5-yl)pyrrolidine-2-carboxylate (150 mg, yield: 89.8%). MS (M+H)+: 504.

Step 7—Synthesis of (2S)-methyl 4-(2-(4-fluorophenyl)-3-(methylcarbamoyl)-6-(N-methylmethylsulfonamido)benzofuran-5-yl)-1-methylpyrrolidine-2-carboxylate

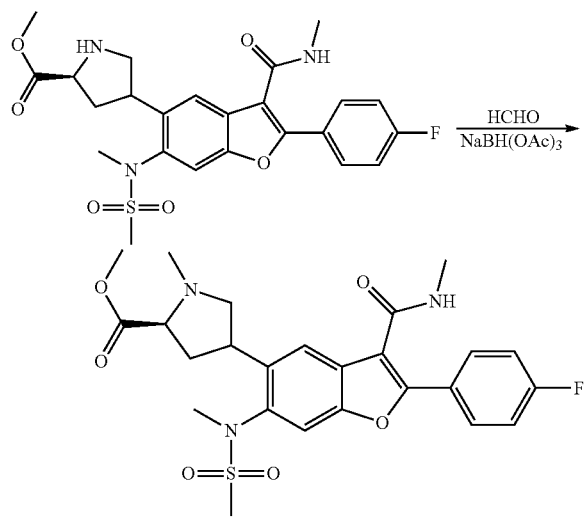

A solution of (2S)-methyl 4-(2-(4-fluorophenyl)-3-(methylcarbamoyl)-6-(N-methylmethylsulfonamido)benzofuran-5-yl)pyrrolidine-2-carboxylate (50 mg, 0.09 mmol), $CH_3CO_2Na$ (8 mg, 0.09 mmol) and HCHO (8 mg, 0.09 mmol) in MeOH (5 mL) was stirred at RT for 1 h under $N_2$. Then TEA (3 drops) and $NaBH(OAc)_3$ (105 mg, 0.5 mmol) were added to the mixture. After being stirred for 12 h, the mixture was diluted with water and extracted with DCM. The combined organic phases were washed with brine, dried over $Na_2SO_4$, filtered and evaporated to give (2S)-methyl 4-(2-(4-fluorophenyl)-3-(methylcarbamoyl)-6-(N-methylmethylsulfonamido)benzofuran-5-yl)-1-methylpyrrolidine-2-carboxylate (40 mg, yield: 78.4%). MS (M+H)+: 518.

Step 8—Synthesis of (2S)-4-(2-(4-fluorophenyl)-3-(methylcarbamoyl)-6-(N-methylmethyl sulfonamido)benzofuran-5-yl)-1-methylpyrrolidine-2-carboxylic acid

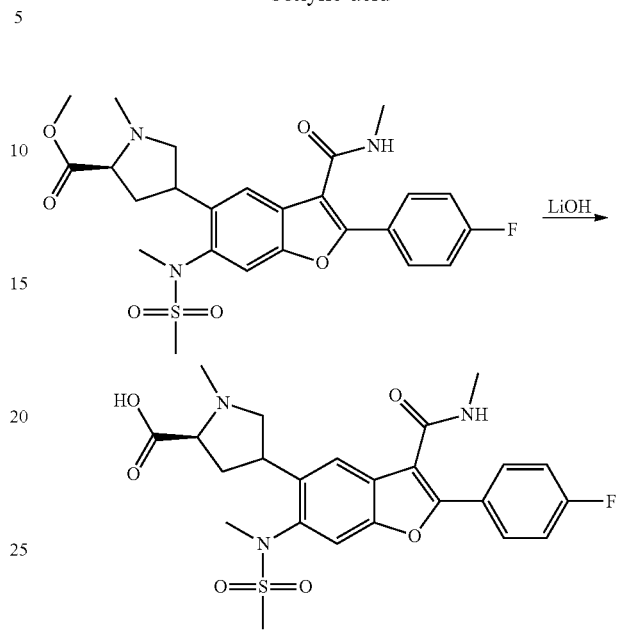

To a solution of (2S)-methyl 4-(2-(4-fluorophenyl)-3-(methylcarbamoyl)-6-(N-methylmethylsulfonamido)benzofuran-5-yl)-1-methylpyrrolidine-2-carboxylate (100 mg, 0.19 mmol) in dioxane (5 mL) and water (3 mL), LiOH $H_2O$ (82 mg, 1.93 mmol) was added, and the mixture was stirred overnight at 20° C. After being concentrated, $H_2O$ was added, the mixture was extracted with ether, and the aqueous phase was acidified by 1 N HCl. Then the mixture was extracted by EtOAc (50 mL*3), and the combined organic phase was washed with brine, dried over $Na_2SO_4$ and concentrated. The residue was dried to give the desired product of (2S)-4-(2-(4-fluorophenyl)-3-(methylcarbamoyl)-6-(N-methylmethylsulfonamido)benzofuran-5-yl)-1-methylpyrrolidine-2-carboxylic acid (90 mg, yield: 91.8%). $^1$H-NMR (CDCl$_3$, 400 MHz) δ 7.9~17.95 (m, 2H), 7.83~7.86 (m, 2H), 7.22~7.26 (m, 2H), 4.45~4.52 (m, 1H), 4.00~4.12 (m, 1H), 3.65~3.73 (m, 2H), 3.46~3.57 (m, 1H), 3.28~3.34 (m, 3H), 3.07 (d, J=8.0 Hz, 3H), 2.9~63.01 (m, 6H), 2.18~2.30 (m, 1H). MS (M+H)+: 504.

Step 9—Synthesis of (2S)—N-(2-fluoro-6-hydroxyphenyl)-4-(2-(4-fluorophenyl)-3-(methylcarbamoyl)-6-(N-methylmethylsulfonamido)benzofuran-5-yl)-1-methylpyrrolidine-2-carboxamide

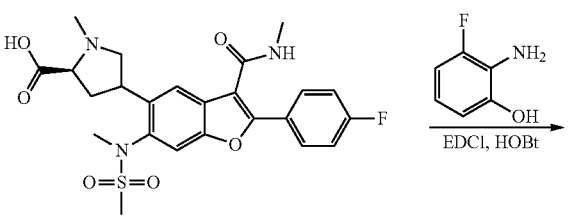

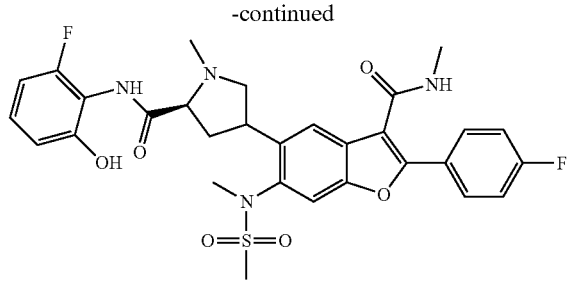

(2S)-4-(2-(4-fluorophenyl)-3-(methylcarbamoyl)-6-(N-methylmethylsulfonamido)benzofuran-5-yl)-1-methylpyrrolidine-2-carboxylic acid (57 mg, 0.11 mmol), HOBT (17 mg, 0.12 mmol), EDCI (33 mg, 0.16 mmol) and TEA (35 mg, 0.33 mmol) were dissolved in dry DMF (3 mL). The resulting solution was stirred for 30 minutes. Then 2-amino-3-fluorophenol (22 mg, 0.16 mmol) was added to the mixture. The mixture was stirred at 20° C. overnight. Then H$_2$O was added, and the reaction mixture filtered to give the crude solid. The crude product was purified by prep-TLC (DCM:MeOH=20:1) to give (2S)—N-(2-fluoro-6-hydroxyphenyl)-4-(2-(4-fluorophenyl)-3-(methylcarbamoyl)-6-(N-methylmethylsulfonamido)benzofuran-5-yl)-1-methylpyrrolidine-2-carboxamide (30 mg, yield: 43.4%), which was used for the next step without further purification. MS (M+H)$^+$: 613.

Step 10—Synthesis of 5-((5S)-5-(4-fluorobenzo[d]oxazol-2-yl)-1-methylpyrrolidin-3-yl)-2-(4-fluorophenyl)-N-methyl-6-(N-methylmethylsulfonamido)benzofuran-3-carboxamide (Example 12)

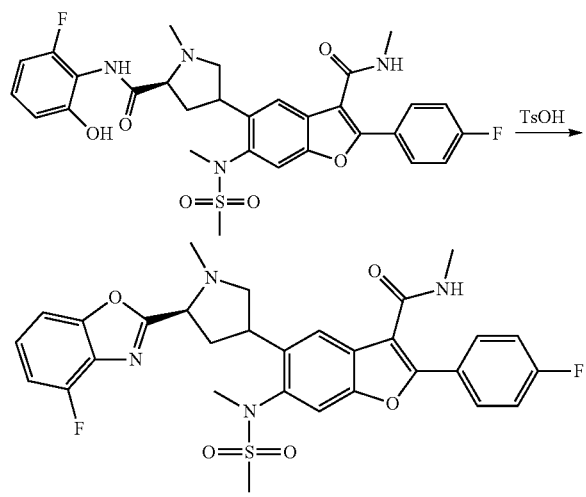

4-methylbenzene sulfonic acid (10 mg, 0.05 mmol) was added to a solution of (2S)—N-(2-fluoro-6-hydroxyphenyl)-4-(2-(4-fluorophenyl)-3-(methylcarbamoyl)-6-(N-methylmethylsulfonamido)benzofuran-5-yl)-1-methylpyrrolidine-2-carboxamide (30 mg, 0.05 mmol) in toluene (1 mL) under N$_2$. The mixture was stirred at reflux overnight. After being concentrated in vacuo, the residue was purified by prep-HPLC to give the product of 5-((5S)-5-(4-fluorobenzo[d]oxazol-2-yl)-1-methylpyrrolidin-3-yl)-2-(4-fluorophenyl)-N-methyl-6-(N-methylmethylsulfonamido)benzofuran-3-carboxamide (20 mg, yield: 68.9%). $^1$H-NMR (MeOD, 400 MHz) δ 7.87~7.99 (m, 4H), 7.49~7.58 (m, 2H), 7.22~7.29 (m, 3H), 5.25~5.41 (m, 1H), 4.54~4.72 (m, 1H), 3.95~4.22 (m, 1H), 3.61~3.92 (m, 1H), 3.21~3.38 (m, 6H), 3.10~3.17 (m, 4H), 3.08~2.87 (m, 3H), 2.70~2.80 (m, 1H). MS (M+H)$^+$: 595.

Example 13

5-(6-(4-fluoro-1H-indol-2-yl)piperazin-2-yl)-2-(4-fluorophenyl)-N-methyl-6-(N-methylmethylsulfonamido)benzofuran-3-carboxamide

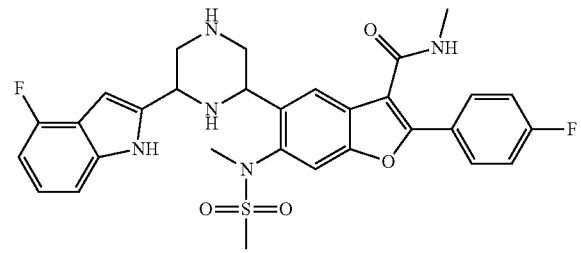 [SMILES: CNC(=O)c1c(-c2ccc(F)cc2)oc2cc(N(C)S(C)(=O)=O)c(C3CNCC(c4cc5c(F)cccc5[nH]4)N3)cc12]

Step 1—Synthesis of tert-butyl 4-fluoro-1H-indole-1-carboxylate

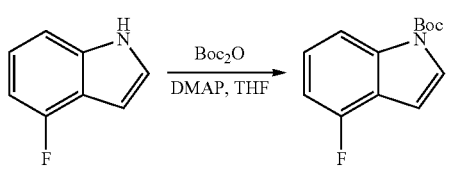 [SMILES: "Boc2O" ; Fc1cccc2[nH]ccc12 ; CC(C)(C)OC(=O)n1ccc2c(F)cccc21]

To a solution of 4-fluoro-1H-indole (150 g, 1.11 mol) and DMAP (4.5 g, 3% wt) in THF (2.5 L) was added (Boc)$_2$O (255 g, 1.16 mol) dropwise. The mixture was stirred at room temperature overnight. The organic solvent was removed in vacuum, and the residue was purified by column chromatography (PE) to give tert-butyl 4-fluoro-1H-indole-1-carboxylate (250 g, yield: 96%). $^1$H-NMR (CDCl$_3$, 400 MHz) δ 7.92 (d, J=8.4 Hz, 1H), 7.55 (d, J=3.6 Hz, 1H), 7.23 (m, 1H), 6.90 (m, 1H), 6.66 (d, J=3.6 Hz, 1H), 1.67 (s, 9H). MS (M+H)$^+$: 236.

Step 2—Synthesis of (1-(tert-butoxycarbonyl)-4-fluoro-1H-indol-2-yl)boronic acid

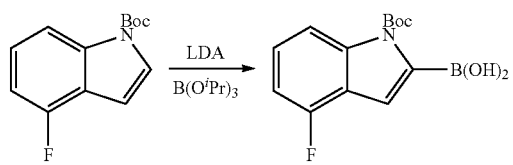

To a solution of diisopropylamine (175 mL, 1.25 mol) in THF (800 mL) at 0° C. was added n-BuLi (500 mL, 1.25 mol) dropwise. The mixture was stirred at 0° C. for 40 minutes. Then the mixture was cooled to –78° C. Tert-butyl 4-fluoro-1H-indole-1-carboxylate (118 g, 0.50 mol) in THF (300 mL) was added dropwise, followed by triisopropyl borate (231 mL, 1.00 mol). The mixture was stirred at –78°

C. for another 40 min. The reaction was monitored by HPLC. When the reaction was completed, the reaction was quenched with NH₄Cl (sat. 500 mL). Then the mixture was adjusted to pH=6 with 1 N HCl, extracted with EtOAc (2000 mL) and the combined organic layers were washed with brine (500 mL), dried over Na₂SO₄, filtered and concentrated. The obtained solid was recrystallized with EtOAc and PE to give (1-(tert-butoxycarbonyl)-4-fluoro-1H-indol-2-yl)boronic acid (93 g, yield: 64%). ¹H-NMR (CDCl₃, 400 MHz) δ 7.77 (d, J=8.4 Hz, 1H), 7.57 (s, 1H), 7.44 (s, 2H), 7.24 (m, 1H), 6.90 (m, 1H), 1.66 (s, 9H). MS (M+H)⁺: 280.

Step 3—Synthesis of tert-butyl 2-(6-chloropyrazin-2-yl)-4-fluoro-1H-indole-1-carboxylate

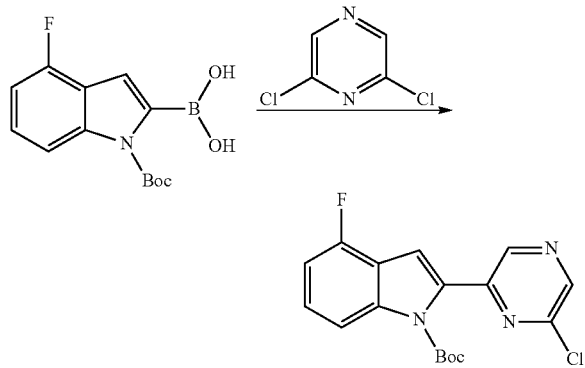

Pd(dppf)Cl₂ (53 mg, 0.072 mmol) was added to a mixture of 1-(tert-butoxycarbonyl)-4-fluoro-1H-indol-2-ylboronic acid (200 mg, 0.717 mmol), 2,6-dichloropyrazine (106 mg, 0.717 mmol) and K₃PO₄ (572 mg, 2.151 mmol) in DMF (2 mL) under N₂. The mixture was stirred at 80° C. overnight under N₂. The mixture was then diluted with water (40 mL) and extracted with EA (25 mL*3). The organic layer was washed with brine (30 mL*3), dried over Na₂SO₄ and concentrated. The residue was purified by prep-TLC (PE: EA=8:1) to afford the desired product of tert-butyl 2-(6-chloropyrazin-2-yl)-4-fluoro-1H-indole-1-carboxylate (150 mg, yield: 60.2%). ¹H-NMR (CDCl₃, 400 MHz) δ 8.65 (s, 1H), 8.50 (s, 1H), 7.91 (d, J=8.4 Hz, 1H), 7.24~7.30 (m, 1H), 6.88~6.94 (m, 2H), 1.35 (s, 9H). MS (M+H)⁺: 348/350.

Step 4—Synthesis of 2-(6-chloropyrazin-2-yl)-4-fluoro-1H-indole

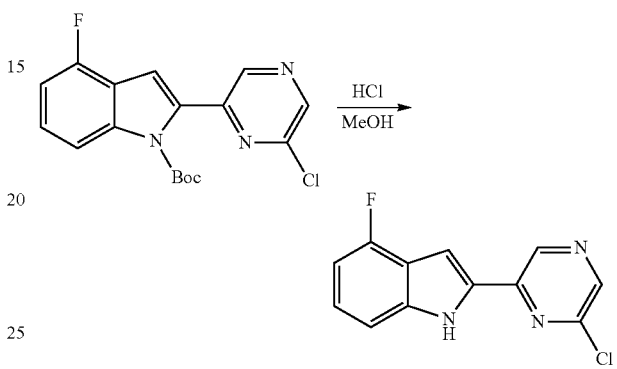

A mixture of tert-butyl 2-(6-chloropyrazin-2-yl)-4-fluoro-1H-indole-1-carboxylate (150 mg, 0.432 mmol) in HCl/CH₃OH (10 mL) was stirred at RT for 2 hours. The mixture was then concentrated to afford the product of 2-(6-chloropyrazin-2-yl)-4-fluoro-1H-indole (100 mg, yield: 93.4%). ¹H-NMR (CDCl₃, 400 MHz) δ 9.33 (s, 1H), 8.92 (s, 1H), 8.37 (s, 1H), 7.13~7.17 (m, 3H), 6.73~6.78 (m, 1H). MS (M+H)⁺: 248/250.

Step 5—Synthesis of 5-(6-(4-fluoro-1H-indol-2-yl)pyrazin-2-yl)-2-(4-fluorophenyl)-N-methyl-6-(N-methylmethylsulfonamido)benzofuran-3-carboxamide

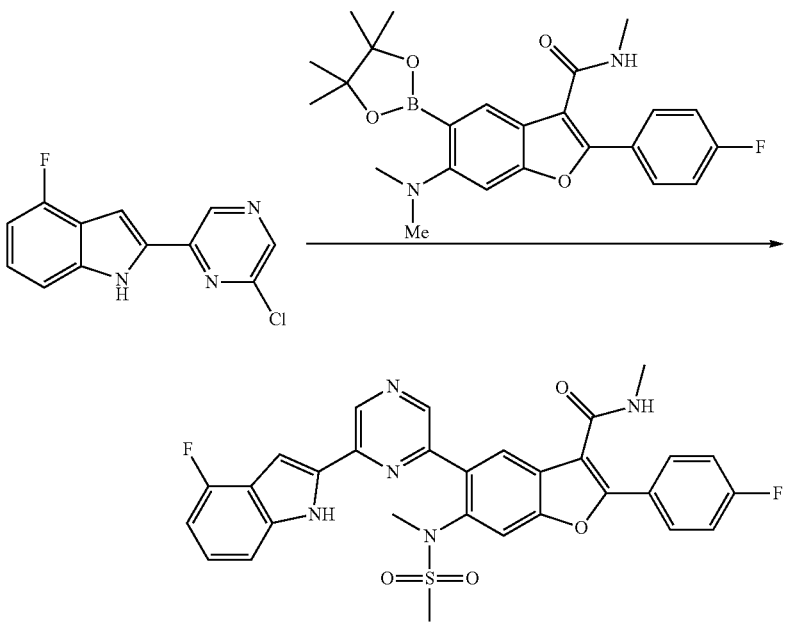

Pd$_2$(dba)$_3$ (10 mg, 0.011 mmol) and X-Phos (10 mg, 0.022 mmol) were added to a mixture of 2-(6-chloropyrazin-2-yl)-4-fluoro-1H-indole (58 mg, 0.241 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (121 mg, 0.241 mmol) and K$_3$PO$_4$ (175 mg, 0.657 mmol) in dioxane/H$_2$O (1.6 mL/0.4 mL) under N$_2$. The mixture was stirred at 110° C. overnight. The mixture was then diluted with water (3 mL) and extracted with EtOAc (20 mL*3). The organic layer was washed with brine (30 mL*3), dried over Na$_2$SO$_4$ and concentrated. The residue was purified by prep-TLC (PE:EA=1:1.5) to afford the desired product of 5-(6-(4-fluoro-1H-indol-2-yl)pyrazin-2-yl)-2-(4-fluorophenyl)-N-methyl-6-(N-methylmethylsulfonamido)benzofuran-3-carboxamide (80 mg, yield: 56.7%). $^1$H-NMR (DMSO-d$_6$, 400 MHz) δ 12.03 (s, 1H), 9.29 (s, 1H), 8.72 (s, 1H), 8.52 (d, J=4.4 Hz, 1H), 8.16 (s, 1H), 7.98~8.03 (m, 3H), 7.38~7.46 (m, 3H), 7.32 (d, J=8.4 Hz, 1H), 7.09~7.14 (m, 1H), 6.78~6.82 (m, 1H), 3.33 (s, 3H), 2.97 (s, 3H), 2.80 (d, J=5.2 Hz, 3H). MS (M+H)$^+$: 588.

Step 6—Synthesis of 5-(6-(4-fluoro-1H-indol-2-yl)piperazin-2-yl)-2-(4-fluorophenyl)-N-methyl-6-(N-methylmethylsulfonamido)benzofuran-3-carboxamide

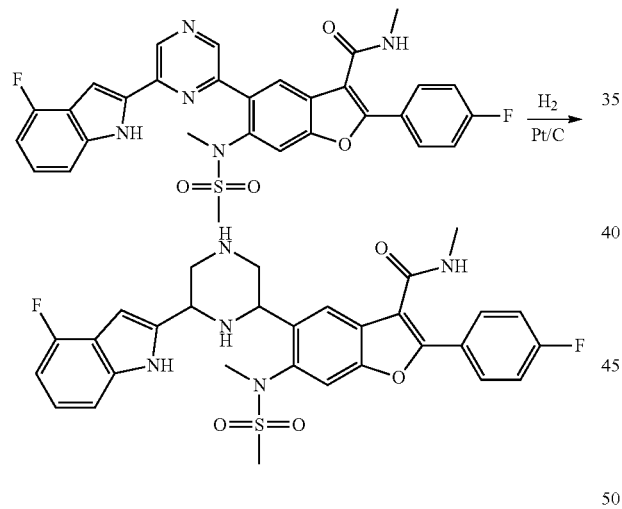

A mixture of 5-(6-(4-fluoro-1H-indol-2-yl)pyrazin-2-yl)-2-(4-fluorophenyl)-N-methyl-6-(N-methylmethylsulfonamido)benzofuran-3-carboxamide (30 mg, 0.051 mmol) and HCl/CH$_3$OH (20 mL) was concentrated in vacuum. The residue was then dissolved in CH$_3$OH (10 mL) and Pt/C (20 mg) was added to the solution. The mixture was stirred at 30° C. under H$_2$ (35 Psi) for 24 hours. The mixture was then filtered through Celite. The filtrate was concentrated and purified by prep-HPLC to afford 5-(6-(4-fluoro-1H-indol-2-yl)piperazin-2-yl)-2-(4-fluorophenyl)-N-methyl-6-(N-methylmethylsulfonamido)benzofuran-3-carboxamide (15 mg, yield: 50.0%). $^1$H-NMR (Methanol-d4, 400 MHz) δ 8.35 (d, J=11.2 Hz, 1H), 7.94~7.98 (m, 3H), 7.28~7.32 (m, 2H), 7.21~7.24 (m, 1H), 7.07~7.13 (m, 1H), 6.66~6.75 (m, 2H), 5.07~5.16 (m, 1H), 4.67~4.81 (m, 1H), 3.70~3.89 (m, 2H), 3.52~3.60 (m, 2H), 3.57 (s, 3H), 3.14 (d, J=18.0 Hz, 3H), 3.00 (s, 3H). MS (M+H)$^+$: 594.

Examples 14 and 15

5-(1-(4-fluoro-1-methyl-1H-indole-2-carbonyl)pyrrolidin-3-yl)-2-(4-fluorophenyl)-N-methyl-6-(N-methylmethylsulfonamido)benzofuran-3-carboxamide (enantiomers 1 and 2)

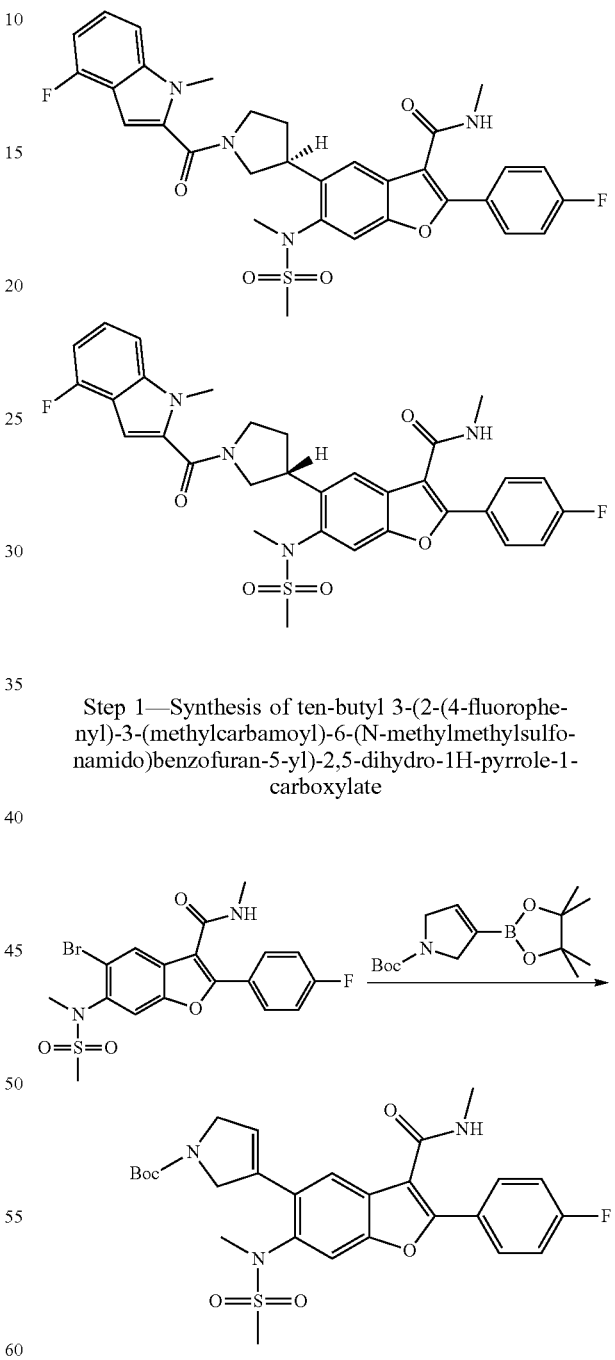

Step 1—Synthesis of ten-butyl 3-(2-(4-fluorophenyl)-3-(methylcarbamoyl)-6-(N-methylmethylsulfonamido)benzofuran-5-yl)-2,5-dihydro-1H-pyrrole-1-carboxylate To a solution of 5-bromo-2-(4-fluorophenyl)-N-methyl-6-(N-methylmethyl sulfonamido)benzofuran-3-carboxamide (100 mg, 0.22 mmol), tert-butyl 3-(4,4,5,5-tetramethyl-1,3,2-dioxaborolan-2-yl)-2,5-dihydro-1H-pyrrole-1-carboxylae (65 mg, 0.22 mmol) and K$_2$CO$_3$ (61 mg, 0.44 mmol) in 1,4-dioxane (5 mL) and H$_2$O (0.2 mL) was added Pd(dppf)Cl$_2$ (15 mg) under nitrogen. The reaction mixture was heated at 100° C. for 2 h. The mixture was diluted with water and extracted with EtOAc. The combined organic phase was washed with brine, dried over Na$_2$SO$_4$ and concentrated. The residue was purified by prep-HPLC to afford the product of tert-butyl 3-(2-(4-fluorophenyl)-3-(methylcarbamoyl)-6-(N-methylmethylsulfonamido)benzofuran-5-yl)-2,5-dihydro-1H-pyrrole-1-carboxylate (80 mg, yield: 67%). $^1$H-NMR (CDCl$_3$, 400 MHz) δ 7.85~7.92 (m, 2H), 7.75~7.79 (m, 1H), 7.52 (s, 1H), 7.15~7.19 (m, 2H), 6.05~6.18 (m, 1H), 5.75~5.80 (m, 1H), 4.50~4.54 (m, 2H), 4.29~4.33 (m, 2H), 3.25 (s, 3H), 3.00 (d, J=4.0 Hz, 6H), 1.48 (s, 9H). MS (M+H)$^+$: 544.

Step 2—Synthesis of 5-(2,5-dihydro-1H-pyrrol-3-yl)-2-(4-fluorophenyl)-N-methyl-6-(N-methylmethylsulfonamido)benzofuran-3-carboxamide

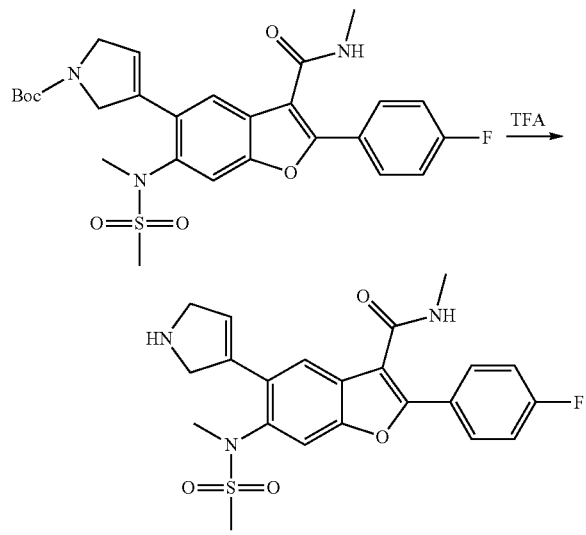

To a solution of tert-butyl 3-(2-(4-fluorophenyl)-3-(methylcarbamoyl)-6-(N-methylmethylsulfonamido)benzofuran-5-yl)-2,5-dihydro-1H-pyrrole-1-carboxylate (100 mg, 0.18 mmol) in DCM (5 mL) was added TFA (1 mL) under N$_2$ protection at 0° C. The mixture was stirred at room temperature for 2 h. After being concentrated, the residue was purified by prep-HPLC to give the product of 5-(2,5-dihydro-1H-pyrrol-3-yl)-2-(4-fluorophenyl)-N-methyl-6-(N-methylmethylsulfonamido)benzofuran-3-carboxamide (50 mg, yield: 62%). $^1$H-NMR (CDCl$_3$, 400 MHz) δ 7.87~7.92 (m, 2H), 7.76 (s, 1H), 7.51 (s, 1H), 7.18 (t, J=8.4 Hz, 2H), 6.72 (s, 1H), 5.82 (brs, 1H), 4.17 (s, 2H), 3.96 (s, 2H), 3.25 (s, 3H), 2.98~3.00 (m, 6H). MS (M+H)$^+$: 444.

Step 3—Synthesis of 5-(1-(4-fluoro-1-methyl-1H-indole-2-carbonyl)-2,5-dihydro-1H-pyrrol-3-yl)-2-(4-fluorophenyl)-N-methyl-6-(N-methylmethylsulfonamido)benzofuran-3-carboxamide

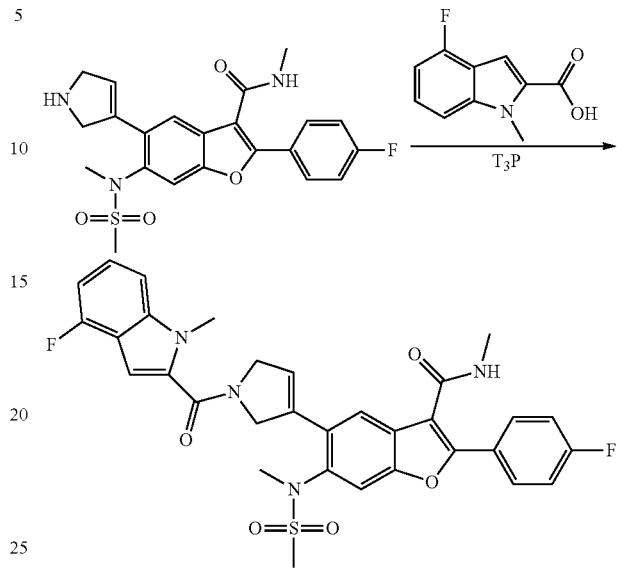

To a solution of 5-(2,5-dihydro-1H-pyrrol-3-yl)-2-(4-fluorophenyl)-N-methyl-6-(N-methylmethylsulfonamido)benzofuran-3-carboxamide (70 mg, 0.16 mmol), 4-fluoro-1-methyl-1H-indole-2-carboxylic acid (30.5 mg, 0.16 mmol) in THF (5 mL) was added Et$_3$N (48 mg, 0.47 mmol) and T$_3$P (152 mg, 0.24 mmol) at 0° C. under nitrogen. After being stirred at 0° C. for 30 minutes and RT overnight, the reaction mixture was quenched with H$_2$O, extracted with EA, dried over Na$_2$SO$_4$ and concentrated in vacuo. The crude product was purified by prep-HPLC to give 5-(1-(4-fluoro-1-methyl-1H-indole-2-carbonyl)-2,5-dihydro-1H-pyrrol-3-yl)-2-(4-fluorophenyl)-N-methyl-6-(N-methylmethylsulfonamido)benzofuran-3-carboxamide (34 mg, yield: 35%). $^1$H-NMR (CDCl$_3$, 400 MHz) δ 7.7~57.84 (m, 3H), 7.43~7.48 (m, 1H), 7.08~7.19 (m, 4H), 6.87~6.92 (m, 1H), 6.70~6.76 (m, 1H), 6.22~6.24 (m, 1H), 5.72~5.78 (m, 1H), 4.89 (brs, 2H), 4.63~4.68 (m, 2H), 3.93 (s, 3H), 3.22~3.27 (m, 3H), 2.90~2.97 (m, 6H). MS (M+H)$^+$: 619.

Step 4—Synthesis of (R) 5-(1-(4-fluoro-1-methyl-1H-indole-2-carbonyl)pyrrolidin-3-yl)-2-(4-fluorophenyl)-N-methyl-6-(N-methylmethylsulfonamido)benzofuran-3-carboxamide and (S) 5-(1-(4-fluoro-1-methyl-1H-indole-2-carbonyl)pyrrolidin-3-yl)-2-(4-fluorophenyl)-N-methyl-6-(N-methylmethylsulfonamido)benzofuran-3-carboxamide

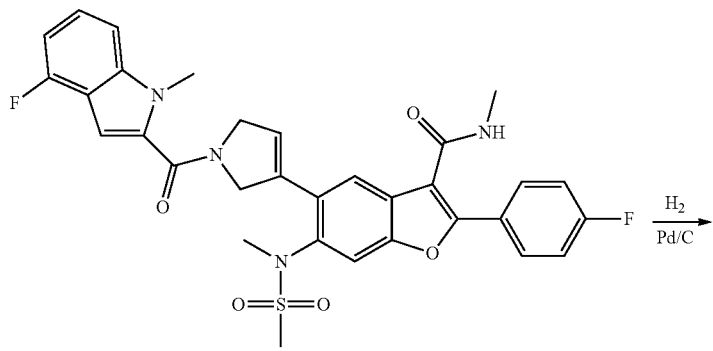

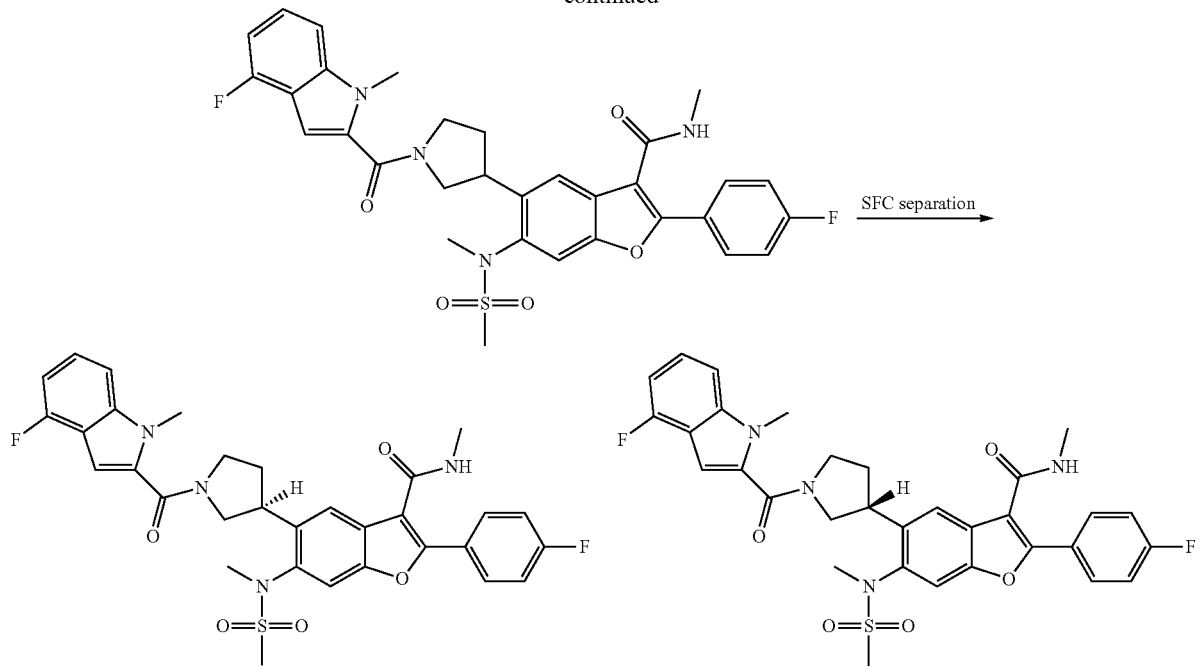

To a degassed solution of 5-(1-(4-fluoro-1-methyl-1H-indole-2-carbonyl)-2,5-dihydro-1H-pyrrol-3-yl)-2-(4-fluorophenyl)-N-methyl-6-(N-methylmethylsulfonamido)benzofuran-3-carboxamide (150 mg, 0.24 mmol) in EtOH (20 mL) was added Pd/C (30 mg) under $N_2$, then the mixture was stirred at RT under $H_2$ balloon for 10 hours. The reaction mixture was filtrated and the filtrate was concentrated. The residue was purified by SFC to give two single enantiomers.

Example 14 (enantiomer 1, peak 1 on SFC, OD-H_3 UM_3_5_40_4 ML_3 MIN, HPLC_RT=1.879 min) (50 mg, yield: 34%). $^1$H-NMR (CDCl$_3$, 400 MHz) δ 7.98 (s, 1H), 7.82~7.88 (m, 2H), 7.42~7.46 (m, 1H), 7.15~7.23 (m, 4H), 6.75~6.89 (m, 2H), 5.80~5.82 (m, 1H), 3.81~4.15 (m, 9H), 3.33~3.37 (m, 2H), 2.96~3.05 (m, 6H), 2.46~2.71 (m, 2H). MS (M+H)$^+$: 621.

Example 15 (enantiomer 2, peak 2 on SFC, OD-H_3 UM_3_5_40_4 ML_3 MIN, HPLC_RT=2.164 min) (50 mg, yield: 34%). $^1$H-NMR (CDCl$_3$, 400 MHz) δ 7.98 (s, 1H), 7.82~7.88 (m, 2H), 7.42~7.46 (m, 1H), 7.15~7.23 (m, 4H), 6.75~6.89 (m, 2H), 5.80~5.82 (m, 1H), 3.81~4.15 (m, 9H), 3.33~3.37 (m, 2H), 2.96~3.05 (m, 6H), 2.46~2.71 (m, 2H). MS (M+H)$^+$: 621.

Example 16

5-(2-(4-fluoro-1H-indol-2-yl)-1-methylpiperidin-4-yl)-2-(4-fluorophenyl)-N-methyl-6-(N-methylmethylsulfonamido)benzofuran-3-carboxamide

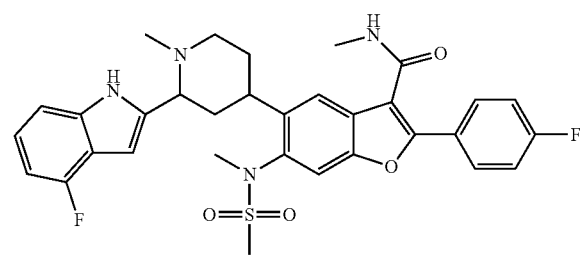 [SMILES: CNC(=O)c1c(-c2ccc(F)cc2)oc2cc(N(C)S(C)(=O)=O)c(C3CCN(C)C(c4cc5c(F)cccc5[nH]4)C3)cc12]

Step 1—Synthesis of 2-(4-fluoro-1H-indol-2-yl)-4-(2-(4-fluorophenyl)-3-(methylcarbamoyl)-6-(N-methylmethylsulfonamido)benzofuran-5-yl)-1-methylpyridinium iodide

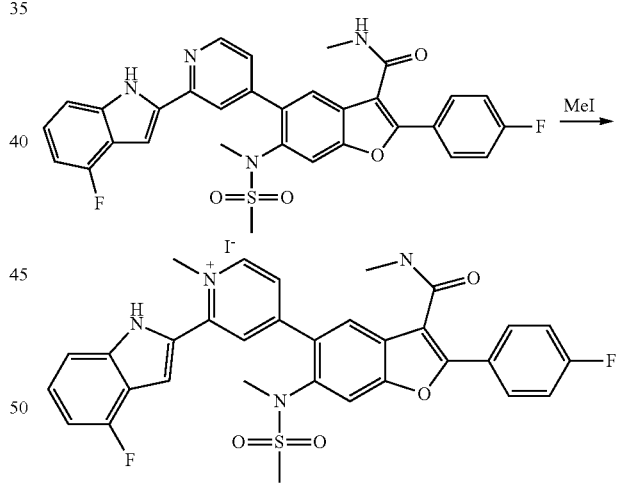

A mixture of 5-(2-(4-fluoro-1H-indol-2-yl)pyridin-4-yl)-2-(4-fluorophenyl)-N-methyl-6-(N-methylmethylsulfonamido)benzofuran-3-carboxamide (100 mg, 0.17 mmol, prepared from 2-(4-fluorophenyl)-N-methyl-6-(N-methylmethylsulfonamido)-5-(4,4,5,5-tetramethyl-1,3,2-dioxaborolan-2-yl)benzofuran-3-carboxamide according to previous patent) and CH$_3$I (50 mg, 0.35 mmol) in DMF (2 mL) was stirred at 80° C. overnight. The mixture was concentrated to afford a crude product of 2-(4-fluoro-1H-indol-2-yl)-4-(2-(4-fluorophenyl)-3-(methylcarbamoyl)-6-(N-methylmethylsulfonamido)benzofuran-5-yl)-1-methylpyridinium iodide (110 mg, yield: 89%), which was used in the next step without further purification. $^1$H-NMR (DMSO-d$_6$, 400 MHz) δ 12.47 (br s, 1H), 9.14 (d, J=6.4 Hz, 1H), 8.55 (d, J=4.0 Hz, 1H), 8.38 (s, 1H), 8.28 (s, 1H), 8.15 (d, J=6.0 Hz, 1H), 7.91~7.98 (m, 3H), 7.39~7.48 (m, 4H), 7.26~7.35 (m, 1H), 6.95 (t, J=9.2 Hz, 1H), 4.51 (s, 3H), 3.08 (br s, 3H), 2.87 (s, 3H), 2.82 (d, J=4.0 Hz, 3H). MS (M+H)$^+$: 601.

Step 2—Synthesis of 5-(2-(4-fluoro-1H-indol-2-yl)-1-methylpiperidin-4-yl)-2-(4-fluorophenyl)-N-methyl-6-(N-methylmethylsulfonamido)benzofuran-3-carboxamide

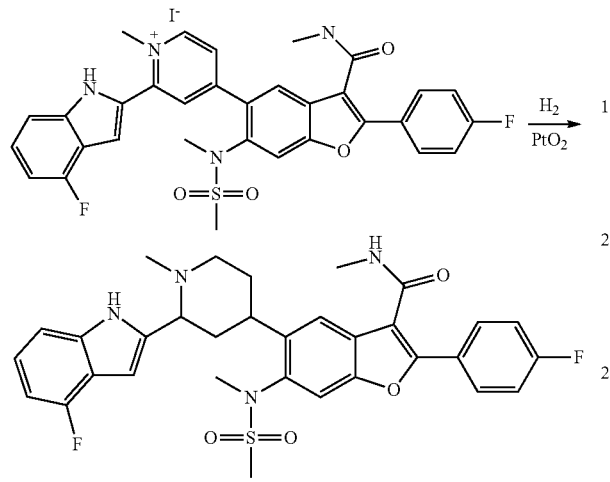

A mixture of 2-(4-fluoro-1H-indol-2-yl)-4-(2-(4-fluorophenyl)-3-(methylcarbamoyl)-6-(N-methylmethylsulfonamido)benzofuran-5-yl)-1-methylpyridinium iodide (50 mg, 0.07 mmol) and PtO$_2$ (30 mg) in CH$_3$OH (10 mL) was stirred at 50° C. for 2 days under H$_2$ (50 Psi). The mixture was filtered through Celite and concentrated, and the residue was purified by prep-TLC (DCM:MeOH=10:1) to give 5-(2-(4-fluoro-1H-indol-2-yl)-1-methylpiperidin-4-yl)-2-(4-fluorophenyl)-N-methyl-6-(N-methylmethylsulfonamido)benzofuran-3-carboxamide (20 mg, yield: 48%). $^1$H-NMR (MeOD, 400 MHz) δ 7.93 (dd, J=7.6, 5.5 Hz, 2H), 7.77~7.86 (m, 2H), 7.22~7.32 (m, 3H), 7.10~7.18 (m, 1H), 6.84 (s, 1H), 6.70~6.79 (m, 1H), 4.50~4.68 (m, 1H), 3.76~3.93 (m, 2H), 3.41~3.56 (m, 1H), 3.35 (d, J=17.6 Hz, 3H), 3.11 (d, J=10.8 Hz, 3H), 3.00 (s, 3H), 2.74 (s, 3H), 2.12~2.70 (m, 4H). MS (M+H)$^+$: 607.

Examples 17 and 18

2-(4-fluorophenyl)-5-(1-(2-(4-fluorophenyl)acetyl)piperidin-3-yl)-N-methyl-6-(N-methylmethylsulfonamido)benzofuran-3-carboxamide (enantiomers 1 and 2)

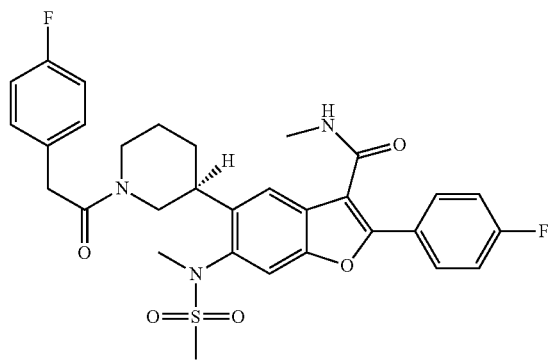

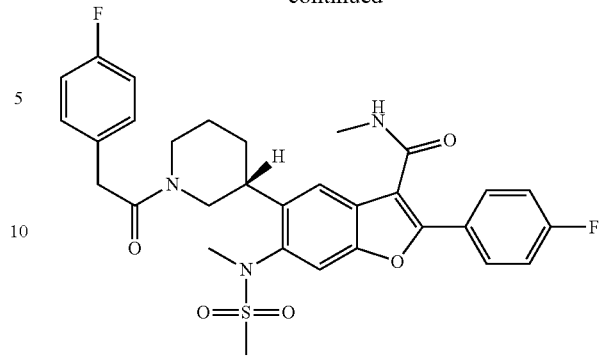

Synthesis of 2-(4-fluorophenyl)-5-(1-(2-(4-fluorophenyl)acetyl)piperidin-3-yl)-N-methyl-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (100 mg, 0.202 mmol), 4-fluorophenylacetic acid (62.2 mg, 0.403 mmol), DMAP (1.232 mg, 10.08 μmol), N,N-diisopropylethylamine (130 mg, 1.008 mmol) and 1-(3-dimethylaminopropyl)-3-ethylcarbodiimide (62.6 mg, 0.403 mmol) in DCM (5 mL) was stirred at RT overnight under N$_2$ protection. The reaction mixture was concentrated and separated by SFC on a AD-H, 2×25 cm, 35% MeOH/CO$_2$ to afford Example 17 (Enantiomer 1, peak 1 on SFC, HPLC_RT=3.43 min) as white solid 30 mg (50%) (LC-MS (ES, m/z) C$_{31}$H$_{31}$F$_2$N$_3$O$_5$S: 595; Found: 596 [M+H]$^+$) and Example 18 (Enantiomer 2, peak 2 on SFC, HPLC_RT=5.05 min) as white solid 33 mg (55%) (LC-MS (ES, m/z) C$_{31}$H$_{31}$F$_2$N$_3$O$_5$S: 595; Found: 596 [M+H]$^+$).

Examples 19 and 20

5-(1-(4-fluorobenzoyl)piperidin-3-yl)-2-(4-fluorophenyl)-N-methyl-6-(N-methylmethylsulfonamido)benzofuran-3-carboxamide (enantiomers 1 and 2)

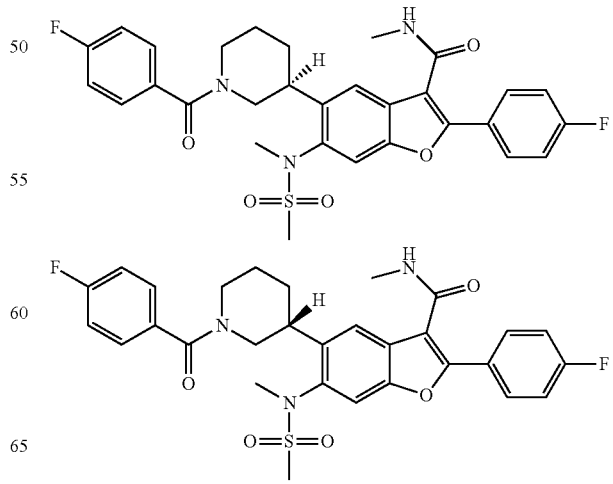

Synthesis of 5-(1-(4-fluorobenzoyl)piperidin-3-yl)-2-(4-fluorophenyl)-N-methyl-6-(N-methylmethylsulfonamido)benzofuran-3-carboxamide (Enantiomer 1) and (S)—S-(1-(4-fluorobenzoyl)piperidin-3-yl)-2-(4-fluorophenyl)-N-methyl-6-(N-methylmethylsulfonamido)benzofuran-3-carboxamide (Enantiomer 2)

A mixture of 2-(4-fluorophenyl)-N-methyl-6-(N-methylmethylsulfonamido)-5-(piperidin-3-yl)benzofuran-3-carboxamide (100 mg, 0.202 mmol), 4-fluorobenzoic acid (56.5 mg, 0.403 mmol), DMAP (1.232 mg, 10.08 μmol), N,N-diisopropylethylamine (130 mg, 1.008 mmol) and 1-(3-dimethylaminopropyl)-3-ethylcarbodiimide (62.6 mg, 0.403 mmol) in DCM (5 mL) was stirred at RT overnight under $N_2$ protection. The reaction mixture was concentrated and separated by SFC on a ChiralPak AS-H, 3×25 cm, 40% EtOH (0.1% $NH_3.H_2O$)/$CO_2$ to afford Example 19 (Enantiomer 1, peak 1 on SFC, HPLC_RT=2.26 min) as white solid 36 mg (59%) (LC-MS (ES, m/z) $C_{30}H_{29}F_2N_3O_5S$: 581; Found: 582 [M+H]$^+$) and Example 20 (Enantiomer 2, peak 2 on SFC, HPLC_RT=2.73 min) as white solid 38 mg (62.2%) (LC-MS (ES, m/z) $C_{30}H_{29}F_2N_3O_5S$: 581; Found: 582 [M+H]$^+$)

Example 21 and 22

5-(1-(1H-indole-2-carbonyl)piperidin-3-yl)-2-(4-fluorophenyl)-N-methyl-6-(N-methylmethylsulfonamido)benzofuran-3-carboxamide (enantiomers 1 and 2)

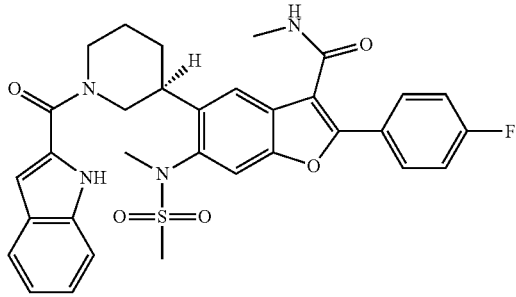

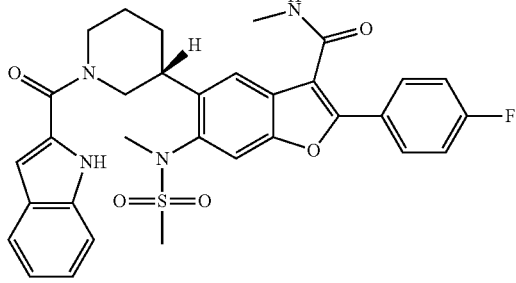

Synthesis of 5-(1-(1H-indole-2-carbonyl)piperidin-3-yl)-2-(4-fluorophenyl)-N-methyl-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (100 mg, 0.202 mmol), 1H-indole-2-carboxylic acid (65 mg, 0.403 mmol), DMAP (1.232 mg, 10.08 μmol), N,N-diisopropylethylamine (130 mg, 1.008 mmol) and 1-(3-dimethylaminopropyl)-3-ethylcarbodiimide (62.6 mg, 0.403 mmol) in DCM (5 mL) was stirred at RT overnight under $N_2$ protection. The reaction mixture was concentrated and separated by SFC on a ChiralPak AS-H, 3×25 cm, 40% MeOH (0.1% $NH_3.H_2O$)/$CO_2$ to afford Example 21 (Enantiomer 1, peak 1 on SFC, HPLC_RT=4.15 min) as white solid 41 mg (67.3%) (LC-MS (ES, m/z) $C_{32}H_{31}FN_4O_5S$: 602; Found: 603 [M+H]$^+$) and Example 22 (Enantiomer 2, peak 2 on SFC, HPLC_RT=5.49 min) as white solid 38 mg (62.4%) (LC-MS (ES, m/z) $C_{32}H_{31}FN_4O_5S$: 602; Found: 603 [M+H]$^+$).

Examples 23 and 24

2-(4-fluorophenyl)-N-methyl-5-(1-(1-methyl-1H-benzo[d]imidazole-2-carbonyl)piperidin-3-yl)-6-(N-methylmethylsulfonamido)benzofuran-3-carboxamide (enantiomers 1 and 2)

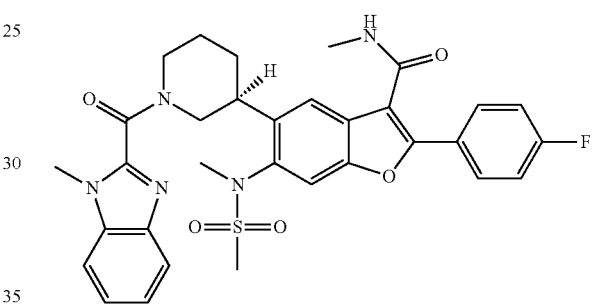

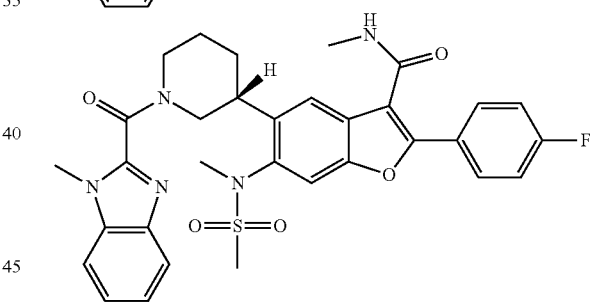

Synthesis of 2-(4-fluorophenyl)-N-methyl-5-(1-(1-methyl-1H-benzo[d]imidazole-2-carbonyl)piperidin-3-yl)-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (80 mg, 0.161 mmol), 1-methyl-1H-benzo[d]imidazole-2-carboxylic acid (56.8 mg, 0.323 mmol), DMAP (0.985 mg, 8.06 μmol), N,N-diisopropylethylamine (104 mg, 0.806 mmol) and 1-(3-dimethylaminopropyl)-3-ethylcarbodiimide (50.1 mg, 0.323 mmol) in DCM (5 mL) was stirred at RT overnight under $N_2$ protection. The reaction mixture was concentrated and separated by SFC on a ChiralPak AS-H, 4.6×25 cm, 5-40% MeOH(0.05% DEA)/$CO_2$ to afford Example 23 (Enantiomer 1, peak 1 on SFC, HPLC_RT=8.39 min) as white solid 65 mg (96%) (LC-MS (ES, m/z) $C_{33}H_{32}F_2N_4O_5S$: 634; Found: 635 [M+H]$^+$) and Example 24 (Enantiomer 2, peak 2 on SFC, HPLC_RT=9.32 min) as white solid 60 mg (93.8%) (LC-MS (ES, m/z) $C_{33}H_{32}F_2N_4O_5S$: 634; Found: 635 [M+H]$^+$).

Examples 25 and 26

5-(1-(4-fluoro-1-methyl-1H-indole-2-carbonyl)piperidin-3-yl)-2-(4-fluorophenyl)-N-methyl-6-(N-methylmethylsulfonamido)benzofuran-3-carboxamide (enantiomers 1 and 2)

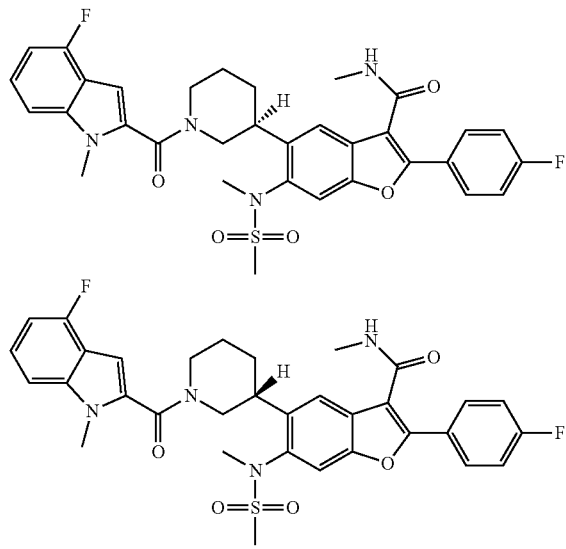

Synthesis of 5-(1-(4-fluoro-1-methyl-1H-indole-2-carbonyl)piperidin-3-yl)-2-(4-fluorophenyl)-N-methyl-6-(N-methylmethylsulfonamido)benzofuran-3-carboxamide (enantiomer 1) and 5-(1-(4-fluoro-1-methyl-1H-indole-2-carbonyl)piperidin-3-yl)-2-(4-fluorophenyl)-N-methyl-6-(N-methylmethylsulfonamido)benzofuran-3-carboxamide (enantiomer 2)

A mixture of 2-(4-fluorophenyl)-N-methyl-6-(N-methylmethylsulfonamido)-5-(piperidin-3-yl)benzofuran-3-carboxamide (100 mg, 0.202 mmol), 4-fluoro-1-methyl-1H-indole-2-carboxylic acid (67.8 mg, 0.403 mmol), DMAP (1.232 mg, 10.08 μmol), N,N-diisopropylethylamine (130 mg, 1.008 mmol) and 1-(3-dimethylaminopropyl)-3-ethylcarbodiimide (62.6 mg, 0.403 mmol) in DCM (5 mL) was stirred at RT overnight under $N_2$ protection. The reaction mixture was concentrated and separated by SFC on a ChiralPak AS-H, 3×25 cm, 40% MeOH(0.1% $NH_3.H_2O$)/$CO_2$ to afford Example 25 (Enantiomer 1, peak 1 on SFC, HPLC_RT=4.15 min) as white solid 41 mg (67.3%) (LC-MS (ES, m/z) $C_{32}H_{31}FN_4O_5S$: 602; Found: 603 [M+H]$^+$) and Example 26 (Enantiomer 2, peak 2 on SFC, HPLC_RT=5.49 min) as white solid 38 mg (62.4%) (LC-MS (ES, m/z) $C_{32}H_{31}FN_4O_5S$: 602; Found: 603 [M+H]$^+$).

Examples 27 and 28 tert-butyl ((1R)-1-(2-fluorophenyl)-2-(3-(2-(4-fluorophenyl)-3-(methylcarbamoyl)-6-(N-methylmethylsulfonamido)benzofuran-5-yl)piperidin-1-yl)-2-oxoethyl)carbamate (diastereomers 1 and 2)

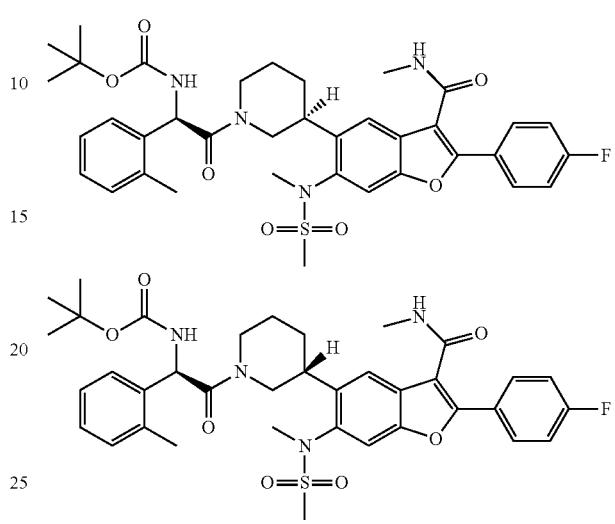

Synthesis of tert-butyl ((1R)-1-(2-fluorophenyl)-2-(3-(2-(4-fluorophenyl)-3-(methylcarbamoyl)-6-(N-methylmethylsulfonamido)benzofuran-5-yl)piperidin-1-yl)-2-oxoethyl)carbamate (diastereomers 1 and 2)

A mixture of 2-(4-fluorophenyl)-N-methyl-6-(N-methylmethylsulfonamido)-5-(piperidin-3-yl)benzofuran-3-carboxamide (110 mg, 0.222 mmol), (R)-2-((tert-butoxycarbonyl)amino)-2-(2-fluorophenyl)acetic acid (119 mg, 0.444 mmol), DMAP (1.355 mg, 0.011 mmol), N,N-diisopropylethylamine (143 mg, 1.109 mmol) and 1-(3-dimethylaminopropyl)-3-ethylcarbodiimide (68.9 mg, 0.444 mmol) in DCM (5 mL) was stirred at RT overnight under $N_2$ protection. The reaction mixture was concentrated and separated by SFC on a ChiralPak AS-H, 3×25 cm, 25% EtOH(0.1% $NH_3.H_2O$)/$CO_2$ to afford Example 27 (Diasteromer 1, peak 1 on SFC, HPLC_RT=7.16 min) as white solid 31.5 mg (40%) (LC-MS (ES, m/z) $C_{36}H_{40}F_2N_4O_7S$: 710; Found: 711 [M+H]$^+$) and Example 28 (Diasteromer 2, peak 2 on SFC, HPLC_RT=7.84 min) as white solid 47.2 mg (60%) (LC-MS (ES, m/z) $C_{36}H_{40}F_2N_4O_7S$: 710; Found: 711 [M+H]$^+$)

Examples 29 and 30

5-(1-((R)-2-amino-2-(2-fluorophenyl)acetyl)piperidin-3-yl)-2-(4-fluorophenyl)-N-methyl-6-(N-methylmethylsulfonamido)benzofuran-3-carboxamide (diastereomers 1 and 2)

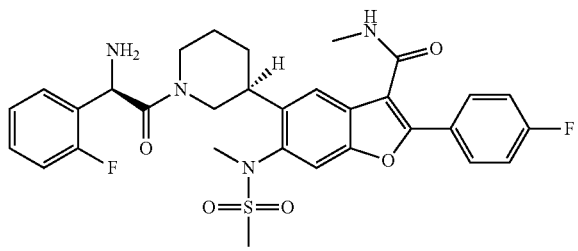

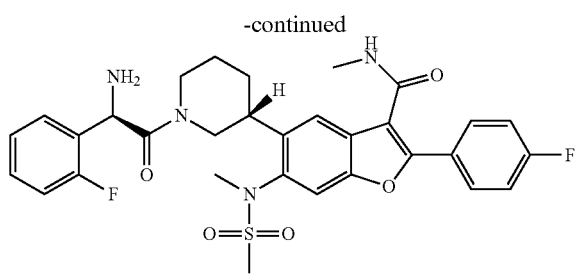

Synthesis of 5-(1-((R)-2-amino-2-(2-fluorophenyl)
acetyl)piperidin-3-yl)-2-(4-fluorophenyl)-N-methyl-
6-(N-methylmethylsulfonamido)benzofuran-3-car-
boxamide (diastereomers 1 and 2)

A mixture of tert-butyl ((1R)-1-(2-fluorophenyl)-2-(3-(2-(4-fluorophenyl)-3-(methylcarbamoyl)-6-(N-methylmethylsulfonamido)benzofuran-5-yl)piperidin-1-yl)-2-oxoethyl)carbamate (130 mg, 0.183 mmol), and hydrochloric acid (0.457 ml, 1.829 mmol) in 1,4-Dioxane (0.5 ml) was stirred at RT overnight under $N_2$ protection. The reaction mixture was concentrated and separated by SFC on a ChiralPak OD, 4.6×25 cm, 30% (3:1 MeOH/MeCN+0.2% DEA)/$CO_2$ to afford Example 29 (Diasteromer 1, peak 1 on SFC, HPLC_RT=3.99 min) as white solid 28 mg (56%) (LC-MS (ES, m/z) $C_{31}H_{32}F_2N_4O_5S$: 610; Found: 611 [M+H]$^+$) and Example 30 (Diasteromer 2, peak 2 on SFC, HPLC_RT=4.64 min) as white solid 28 mg (56%) (LC-MS (ES, m/z) $C_{31}H_{32}F_2N_4O_5S$: 610; Found: 611 [M+H]$^+$)

Example 31

(R)-5-(1-(7-fluoro-1H-indole-2-carbonyl)piperidin-
3-yl)-2-(4-fluorophenyl)-N-methyl-6-(N-methylm-
ethylsulfonamido)benzofuran-3-carboxamide

31

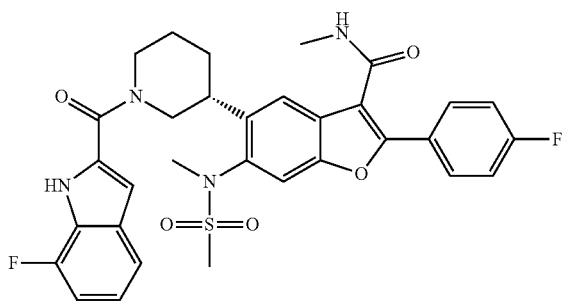

Synthesis of (R)-5-(1-(7-fluoro-1H-indole-2-carbo-
nyl)piperidin-3-yl)-2-(4-fluorophenyl)-N-methyl-6-
(N-methylmethylsulfonamido)benzofuran-3-carbox-
amide To a solution of 7-fluoro-1H-indole-2-carboxylic acid (78 mg, 0.435 mmol), (R)-2-(4-fluorophenyl)-N-methyl-6-(N-methylmethylsulfonamido)-5-(piperidin-3-yl)benzofuran-3-carboxamide (100 mg, 0.218 mmol) in DCM (1 ml) was added N,N-diisopropylethylamine (169 mg, 1.306 mmol), and the reaction mixture stirred for 5 min at RT. Then 2,4,6-tripropyl-1,3,5,2,4,6-trioxatriphosphinane 2,4,6-trioxide (415 mg, 0.653 mmol) was added to the reaction mixture and stirred at RT overnight under $N_2$ protection. The reaction mixture was concentrated under vacuum, then applied onto a silica gel column and eluted with 0-30% MeOH/EtOAc. This resulted in 68 mg (50.3%) of (R)-5-(1-(7-fluoro-1H-indole-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{32}H_{30}F_2N_4O_5S$: 620; Found: 621 [M+H]$^+$.

Example 32

(S)-5-(1-(7-fluoro-1H-indole-2-carbonyl)piperidin-3-
yl)-2-(4-fluorophenyl)-N-methyl-6-(N-methylmeth-
ylsulfonamido)benzofuran-3-carboxamide

32

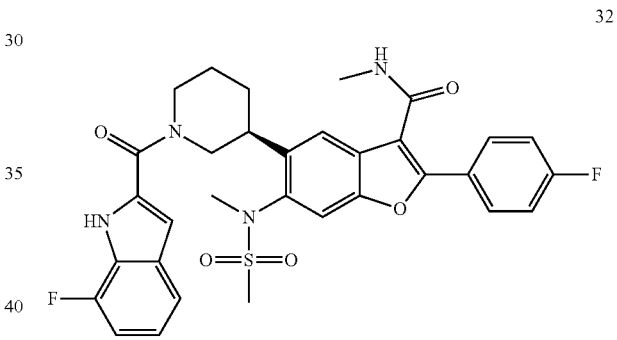

Synthesis of (S)-5-(1-(7-fluoro-1H-indole-2-carbo-
nyl)piperidin-3-yl)-2-(4-fluorophenyl)-N-methyl-6-
(N-methylmethylsulfonamido)benzofuran-3-carbox-
amide To a solution of 7-fluoro-1H-indole-2-carboxylic acid (78 mg, 0.435 mmol), (S)-2-(4-fluorophenyl)-N-methyl-6-(N-methylmethylsulfonamido)-5-(piperidin-3-yl)benzofuran-3-carboxamide (100 mg, 0.218 mmol) in DCM (1 ml) was added N,N-diisopropylethylamine (169 mg, 1.306 mmol), and the reaction mixture stirred for 5 min at RT. Then 2,4,6-tripropyl-1,3,5,2,4,6-trioxatriphosphinane 2,4,6-trioxide (415 mg, 0.653 mmol) was added to the reaction mixture and stirred at RT overnight under $N_2$ protection. The reaction mixture was concentrated under vacuum, then applied onto a silica gel column and eluted with 0-30% MeOH/EtOAc. This resulted in 78 mg (58%) of (S)-5-(1-(7-fluoro-1H-indole-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{32}H_{30}F_2N_4O_5S$: 620; Found: 621 [M+H]$^+$.

Example 33

(S)-5-(1-(1-ethyl-4-fluoro-1H-indole-2-carbonyl) piperidin-3-yl)-2-(4-fluorophenyl)-N-methyl-6-(N-methylmethylsulfonamido)benzofuran-3-carboxamide

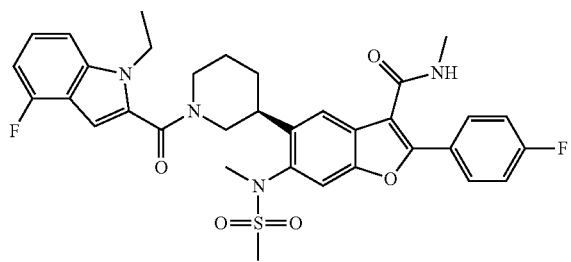

Synthesis of (S)-5-(1-(1-ethyl-4-fluoro-1H-indole-2-carbonyl)piperidin-3-yl)-2-(4-fluorophenyl)-N-methyl-6-(N-methylmethylsulfonamido)benzofuran-3-carboxamide A mixture of (S)-2-(4-fluorophenyl)-N-methyl-6-(N-methylmethylsulfonamido)-5-(piperidin-3 yl)benzofuran-3-carboxamide (60 mg, 0.131 mmol), 1-ethyl-4-fluoro-1H-indole-2-carboxylic acid (54.1 mg, 0.261 mmol), DMAP (0.798 mg, 6.53 μmol), N,N-diisopropylethylamine (84 mg, 0.653 mmol) and 1-(3-dimethylaminopropyl)-3-ethylcarbodiimide (40.5 mg, 0.261 mmol) in DCM (2 mL) was stirred at RT overnight under $N_2$ protection. The reaction mixture was concentrated under vacuum, then applied onto a silica gel column and eluted with 0-10% MeOH/EtOAc. This resulted in 46 mg (54.3%) of (S)-5-(1-(1-ethyl-4-fluoro-1H-indole-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{34}H_{34}F_2N_4O_5S$: 648; Found: 649 $[M+H]^+$.

Example 34

(R)-5-(1-(1-ethyl-4-fluoro-1H-indole-2-carbonyl) piperidin-3-yl)-2-(4-fluorophenyl)-N-methyl-6-(N-methylmethylsulfonamido)benzofuran-3-carboxamide

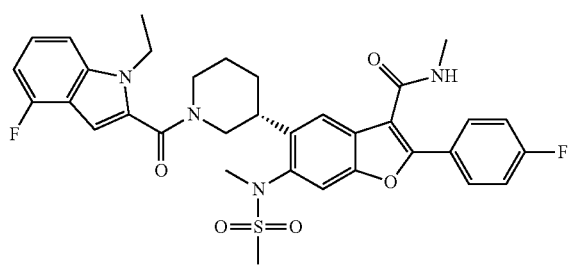

Synthesis of (R)-5-(1-(1-ethyl-4-fluoro-1H-indole-2-carbonyl)piperidin-3-yl)-2-(4-fluorophenyl)-N-methyl-6-(N-methylmethylsulfonamido)benzofuran-3-carboxamide A mixture of (R)-2-(4-fluorophenyl)-N-methyl-6-(N-methylmethylsulfonamido)-5-(piperidin-3 yl)benzofuran-3-carboxamide (60 mg, 0.131 mmol), 1-ethyl-4-fluoro-1H-indole-2-carboxylic acid (54.1 mg, 0.261 mmol), DMAP (0.798 mg, 6.53 μmol), N,N-diisopropylethylamine (84 mg, 0.653 mmol) and 1-(3-dimethylaminopropyl)-3-ethylcarbodiimide (40.5 mg, 0.261 mmol) in DCM (2 mL) was stirred at RT overnight under $N_2$ protection. The reaction mixture was concentrated under vacuum, then applied onto a silica gel column and eluted with 0-10% MeOH/EtOAc. This resulted in 38 mg (44.9%) of (R)-5-(1-(1-ethyl-4-fluoro-1H-indole-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{34}H_{34}F_2N_4O_5S$: 648; Found: 649 $[M+H]^+$.

Example 35

(S)-5-(1-(1H-imidazo[4,5-b]pyridine-2-carbonyl) piperidin-3-yl)-2-(4-fluorophenyl)-N-methyl-6-(N-methylmethylsulfonamido)benzofuran-3-carboxamide

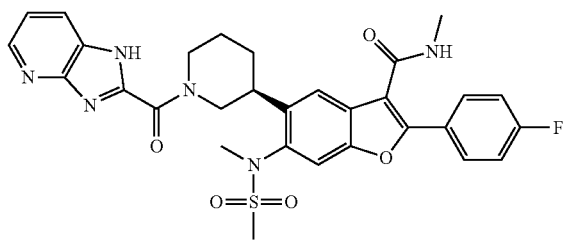

Synthesis of (S)-5-(1-(1H-imidazo[4,5-b]pyridine-2-carbonyl)piperidin-3-yl)-2-(4-fluorophenyl)-N-methyl-6-(N-methylmethylsulfonamido)benzofuran-3-carboxamide A mixture of (S)-2-(4-fluorophenyl)-N-methyl-6-(N-methylmethylsulfonamido)-5-(piperidin-3 yl)benzofuran-3-carboxamide (70 mg, 0.152 mmol), 1H-imidazo[4,5-b]pyridine-2-carboxylic acid (49.7 mg, 0.305 mmol), DMAP (0.93 mg, 7.62 μmol), N,N-diisopropylethylamine (98 mg, 0.762 mmol) and 1-(3-dimethylaminopropyl)-3-ethylcarbodiimide (47.3 mg, 0.305 mmol) in DCM (2 mL) was stirred at RT overnight under $N_2$ protection. The reaction mixture was concentrated under vacuum, then applied onto a silica gel column and eluted with 0-10% MeOH/EtOAc. This resulted in 45 mg (48.9%) of (S)-5-(1-(1H-imidazo[4,5-b]pyridine-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{30}H_{29}FN_6O_5S$: 604; Found: 605 $[M+H]^+$.

Example 36

(R)-5-(1-(1H-imidazo[4,5-b]pyridine-2-carbonyl)piperidin-3-yl)-2-(4-fluorophenyl)-N-methyl-6-(N-methylmethylsulfonamido)benzofuran-3-carboxamide

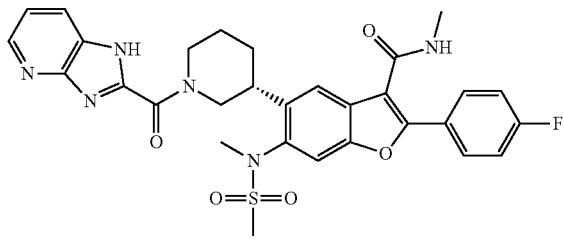

36

Synthesis of (R)-5-(1-(1H-imidazo[4,5-b]pyridine-2-carbonyl)piperidin-3-yl)-2-(4-fluorophenyl)-N-methyl-6-(N-methylmethylsulfonamido)benzofuran-3-carboxamide A mixture of (R)-2-(4-fluorophenyl)-N-methyl-6-(N-methylmethylsulfonamido)-5-(piperidin-3 yl)benzofuran-3-carboxamide (70 mg, 0.152 mmol), 1H-imidazo[4,5-b]pyridine-2-carboxylic acid (49.7 mg, 0.305 mmol), DMAP (0.93 mg, 7.62 μmol), N,N-diisopropylethylamine (98 mg, 0.762 mmol) and 1-(3-dimethylaminopropyl)-3-ethylcarbodiimide (47.3 mg, 0.305 mmol) in DCM (2 mL) was stirred at RT overnight under $N_2$ protection. The reaction mixture was concentrated under vacuum, then applied onto a silica gel column and eluted with 0-10% MeOH/EtOAc. This resulted in 58 mg (63%) of (R)-5-(1-(1H-imidazo[4,5-b]pyridine-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{30}H_{29}FN_6O_5S$: 604; Found: 605 [M+H]$^+$.

Example 37

Synthesis of (S)-5-(1-(7-fluoro-3-methyl-1H-indole-2-carbonyl)piperidin-3-yl)-2-(4-fluorophenyl)-N-methyl-6-(N-methylmethylsulfonamido)benzofuran-3-carboxamide

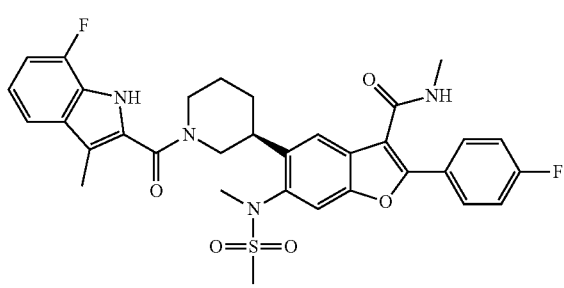

37

Synthesis of (S)-5-(1-(7-fluoro-3-methyl-1H-indole-2-carbonyl)piperidin-3-yl)-2-(4-fluorophenyl)-N-methyl-6-(N-methylmethylsulfonamido)benzofuran-3-carboxamide A mixture of (S)-2-(4-fluorophenyl)-N-methyl-6-(N-methylmethylsulfonamido)-5-(piperidin-3 yl)benzofuran-3-carboxamide (75 mg, 0.163 mmol), 7-fluoro-3-methyl-1H-indole-2-carboxylic acid (63.1 mg, 0.326 mmol), DMAP (0.997 mg, 8.16 μmol), N,N-diisopropylethylamine (105 mg, 0.816 mmol) and 1-(3-dimethylaminopropyl)-3-ethylcarbodiimide (50.7 mg, 0.326 mmol) in DCM (2 mL) was stirred at RT overnight under $N_2$ protection. The reaction mixture was concentrated under vacuum, then applied onto a silica gel column and eluted with 0-12% MeOH/EtOAc. This resulted in 58 mg (56%) of (S)-5-(1-(7-fluoro-3-methyl-1H-indole-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{33}H_{32}F_2N_4O_5S$: 634; Found: 635 [M+H]$^+$.

Example 38

(R)-5-(1-(7-fluoro-3-methyl-1H-indole-2-carbonyl)piperidin-3-yl)-2-(4-fluorophenyl)-N-methyl-6-(N-methylmethylsulfonamido)benzofuran-3-carboxamide

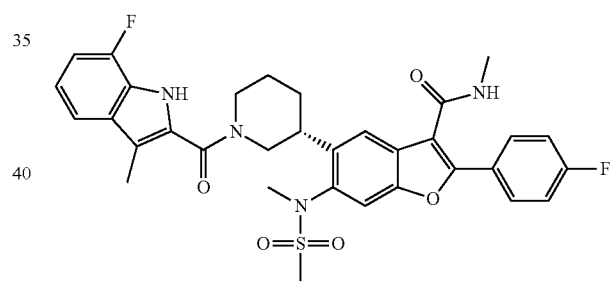

38

Synthesis of (R)-5-(1-(7-fluoro-3-methyl-1H-indole-2-carbonyl)piperidin-3-yl)-2-(4-fluorophenyl)-N-methyl-6-(N-methylmethylsulfonamido)benzofuran-3-carboxamide A mixture of (R)-2-(4-fluorophenyl)-N-methyl-6-(N-methylmethylsulfonamido)-5-(piperidin-3 yl)benzofuran-3-carboxamide (75 mg, 0.163 mmol), 7-fluoro-3-methyl-1H-indole-2-carboxylic acid (63.1 mg, 0.326 mmol), DMAP (0.997 mg, 8.16 μmol), N,N-diisopropylethylamine (105 mg, 0.816 mmol) and 1-(3-dimethylaminopropyl)-3-ethylcarbodiimide (50.7 mg, 0.326 mmol) in DCM (2 mL) was stirred at RT overnight under $N_2$ protection. The reaction mixture was concentrated under vacuum, then applied onto a silica gel column and eluted with 0-12% MeOH/EtOAc. This resulted in 58 mg (56%) of (R)-5-(1-(7-fluoro-3-methyl-1H-indole-2-carbonyl)piperidin-3-yl)-2-(4-fluorophenyl)-N-methyl-6-(N-methylmethylsulfonamido)benzofuran-3-carboxamide as white solid. LC-MS (ES, m/z) $C_{33}H_{32}F_2N_4O_5S$: 634; Found: 635 [M+H]$^+$.

Example 39

(S)-2-(4-fluorophenyl)-N-methyl-6-(N-methylmethylsulfonamido)-5-(1-(7-(trifluoromethyl)-1H-indole-2-carbonyl)piperidin-3-yl)benzofuran-3-carboxamide

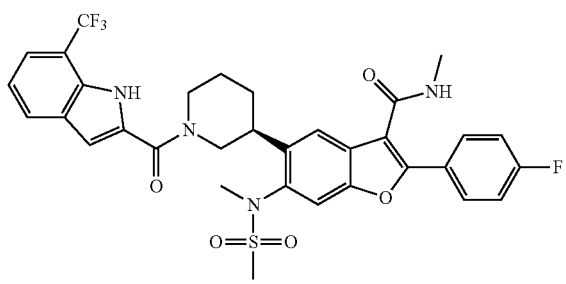

Synthesis of (S)-2-(4-fluorophenyl)-N-methyl-6-(N-methylmethylsulfonamido)-5-(1-(7-(trifluoromethyl)-1H-indole-2-carbonyl)piperidin-3-yl)benzofuran-3-carboxamide A mixture of (S)-2-(4-fluorophenyl)-N-methyl-6-(N-methylmethylsulfonamido)-5-(piperidin-3 yl)benzofuran-3-carboxamide (75 mg, 0.163 mmol), 7-(trifluoromethyl)-1H-indole-2-carboxylic acid (74.8 mg, 0.326 mmol), DMAP (0.997 mg, 8.16 µmol), N,N-diisopropylethylamine (105 mg, 0.816 mmol) and 1-(3-dimethylaminopropyl)-3-ethylcarbodiimide (50.7 mg, 0.326 mmol) in DCM (2 mL) was stirred at RT overnight under $N_2$ protection. The reaction mixture was concentrated under vacuum, then applied onto a silica gel column and eluted with 0-100% EtOAc/Hexane. This resulted in 78 mg (71.3%) of (S)-2-(4-fluorophenyl)-N-methyl-6-(N-methylmethylsulfonamido)-5-(1-(7-(trifluoromethyl)-1H-indole-2-carbonyl)piperidin-3-yl)benzofuran-3-carboxamide as white solid. LC-MS (ES, m/z) $C_{33}H_{30}F_4N_4O_5S$: 670; Found: 671[M+H]$^+$.

Example 40

(R)-2-(4-fluorophenyl)-N-methyl-6-(N-methylmethylsulfonamido)-5-(1-(7-(trifluoromethyl)-1H-indole-2-carbonyl)piperidin-3-yl)benzofuran-3-carboxamide

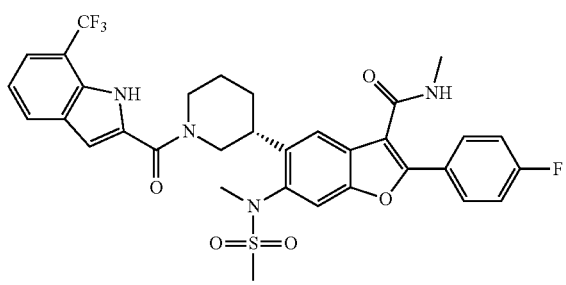

Synthesis of (R)-2-(4-fluorophenyl)-N-methyl-6-(N-methylmethylsulfonamido)-5-(1-(7-(trifluoromethyl)-1H-indole-2-carbonyl)piperidin-3-yl)benzofuran-3-carboxamide A mixture of (R)-2-(4-fluorophenyl)-N-methyl-6-(N-methylmethylsulfonamido)-5-(piperidin-3 yl)benzofuran-3-carboxamide (75 mg, 0.163 mmol), 7-(trifluoromethyl)-1H-indole-2-carboxylic acid (74.8 mg, 0.326 mmol), DMAP (0.997 mg, 8.16 µmol), N,N-diisopropylethylamine (105 mg, 0.816 mmol) and 1-(3-dimethylaminopropyl)-3-ethylcarbodiimide (50.7 mg, 0.326 mmol) in DCM (2 mL) was stirred at RT overnight under $N_2$ protection. The reaction mixture was concentrated under vacuum, then applied onto a silica gel column and eluted with 0-100% EtOAc/Hexane. This resulted in 88 mg (80%) of (R)-2-(4-fluorophenyl)-N-methyl-6-(N-methylmethylsulfonamido)-5-(1-(7-(trifluoromethyl)-1H-indole-2-carbonyl)piperidin-3-yl)benzofuran-3-carboxamide as white solid. LC-MS (ES, m/z) $C_{33}H_{30}F_4N_4O_5S$: 670; Found: 671[M+H]$^+$.

Examples 41 and 42

2-(4-fluorophenyl)-5-(1-(7-methoxy-1H-indole-2-carbonyl)piperidin-3-yl)-N-methyl-6-(N-methylmethylsulfonamido)benzofuran-3-carboxamide (enantiomers 1 and 2)

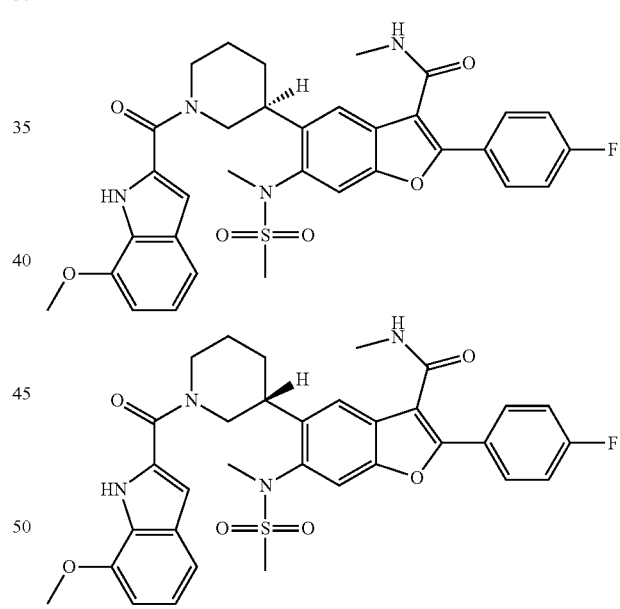

Synthesis of (R)-2-(4-fluorophenyl)-5-(1-(7-methoxy-1H-indole-2-carbonyl)piperidin-3-yl)-N-methyl-6-(N-methylmethylsulfonamido)benzofuran-3-carboxamide and (S)-2-(4-fluorophenyl)-5-(1-(7-methoxy-1H-indole-2-carbonyl)piperidin-3-yl)-N-methyl-6-(N-methylmethylsulfonamido)benzofuran-3-carboxamide A mixture of 2-(4-fluorophenyl)-N-methyl-6-(N-methylmethylsulfonamido)-5-(piperidin-3-yl)benzofuran-3-carboxamide (100 mg, 0.218 mmol), 7-methoxy-1H-indole-2-carboxylic acid (83 mg, 0.435 mmol), DMAP (1.329 mg, 10.88 μmol), N,N-diisopropylethylamine (141 mg, 1.088 mmol) and 1-(3-dimethylaminopropyl)-3-ethylcarbodiimide (67.6 mg, 0.435 mmol) in DCM (5 mL) was stirred at RT overnight under $N_2$ protection. The reaction mixture was concentrated and separated by SFC on a ChiralPak AS-H, 3×25 cm, 40% MeOH (0.1% $NH_3.H_2O$)/$CO_2$ to afford Example 41 (Enantiomer 1, peak 1 on SFC, HPLC_RT=3.52 min) as white solid 24 mg (35%) (LC-MS (ES, m/z) $C_{33}H_{33}FN_4O_6S$: 632; Found: 633 [M+H]$^+$) and Example 42 (Enantiomer 2, peak 2 on SFC, HPLC_RT=6.21 min) as white solid 26 mg (37%) (LC-MS (ES, m/z) $C_{33}H_{33}FN_4O_6S$: 632; Found: 633 [M+H]$^+$).

Examples 43 and 44

2-(4-fluorophenyl)-N-methyl-5-(1-(1-methyl-1H-benzo[d]imidazol-2-yl)piperidin-3-yl)-6-(N-methylmethylsulfonamido)benzofuran-3-carboxamide

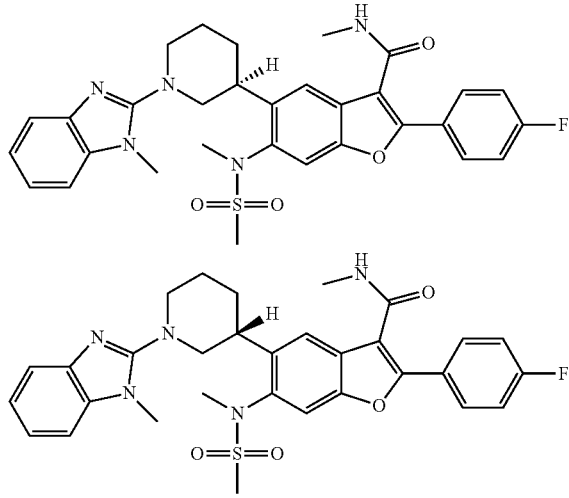

Synthesis of 2-(4-fluorophenyl)-N-methyl-5-(1-(1-methyl-1H-benzo[d]imidazol-2-yl)piperidin-3-yl)-6-(N-methylmethylsulfonamido)benzofuran-3-carboxamide A mixture of 2-(4-fluorophenyl)-N-methyl-6-(N-methylmethylsulfonamido)-5-(piperidin-3-yl)benzofuran-3-carboxamide (80 mg, 0.174 mmol), 2-chloro-1-methyl-1H-benzo[d]imidazole (58 mg, 0.348 mmol) and triethylamine (106 mg, 1.045 mmol) in DMF (1 ml) was heated to 170° C. for 10 min. The reaction mixture was cooled to RT and partitioned between EtOAc and water, the organic layer dried in $Na_2SO_4$ and concentrated under vacuum. Then the reaction mixture separated by SFC on a ChiralCel OJ-H, 4.6×25 cm, 5-40% EtOH(0.05% DEA)/$CO_2$ to afford Example 43 (Enantiomer 1, peak 1 on SFC, HPLC_RT=8.28 min) as white solid 12.3 mg (24%) (LC-MS (ES, m/z) $C_{31}H_{32}FN_5O_4S$: 589; Found: 590 [M+H]$^+$) and Example 44 (Enantiomer 2, peak 2 on SFC, HPLC_RT=9.13 min) as white solid 14.3 mg (27%) (LC-MS (ES, m/z) $C_{31}H_{32}FN_5O_4S$: 589; Found: 590 [M+H]$^+$).

Examples 45 and 46

5-(1-(1H-benzo[d]imidazol-2-yl)piperidin-3-yl)-2-(4-fluorophenyl)-N-methyl-6-(N-methylmethylsulfonamido)benzofuran-3-carboxamide (enantiomers 1 and 2)

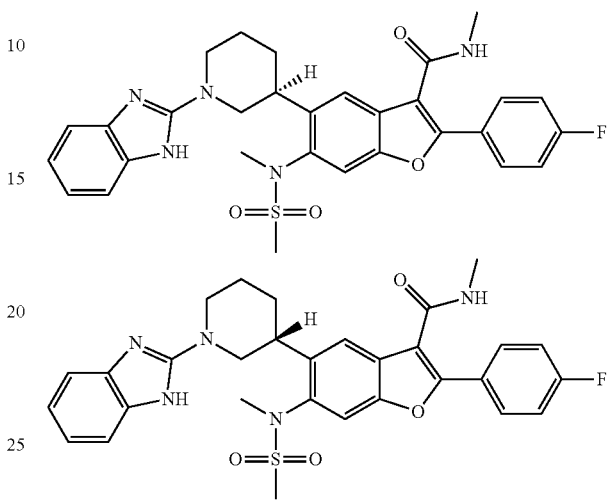

Synthesis of 5-(1-(1H-benzo[d]imidazol-2-yl)piperidin-3-yl)-2-(4-fluorophenyl)-N-methyl-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (80 mg, 0.174 mmol), 2-chloro-1H-benzo[d]imidazole (34.5 mg, 0.226 mmol) and triethylamine (90 mg, 0.696 mmol) in DMF (1 ml) was heated to 170° C. for 40 min. The reaction mixture was cooled to RT and partitioned between EtOAc and water, the organic layer dried in $Na_2SO_4$ and concentrated under vacuum. Then the reaction mixture separated by SFC on a ChiralCel OJ-3, 4.6×15 cm, 40% EtOH(0.05% DEA)/$CO_2$ to afford Example 45 (Enantiomer 1, peak 1 on SFC, HPLC_RT=1.89 min) as white solid 30 mg (60%) (LC-MS (ES, m/z) $C_{30}H_{30}FN_5O_4S$: 575; Found: 576 [M+H]$^+$) and Example 46 (Enantiomer 2, peak 2 on SFC, HPLC_RT=2.68 min) as white solid 31 mg (62%) (LC-MS (ES, m/z) $C_{30}H_{30}FN_5O_4S$: 575; Found: 576 [M+H]$^+$).

Examples 47 and 48

5-(1-(benzo[d]oxazol-2-yl)piperidin-3-yl)-2-(4-fluorophenyl)-N-methyl-6-(N-methylmethylsulfonamido)benzofuran-3-carboxamide (enantiomers 1 and 2)

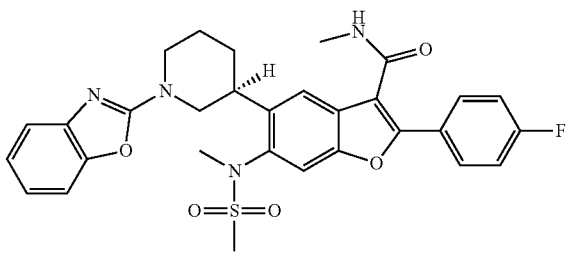

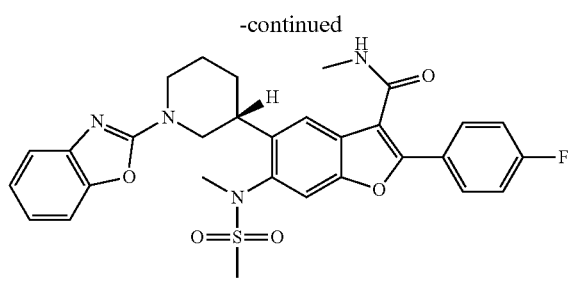

Synthesis of 5-(1-(benzo[d]oxazol-2-yl)piperidin-3-yl)-2-(4-fluorophenyl)-N-methyl-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (80 mg, 0.174 mmol), 2-chlorobenzo[d]oxazole (34.8 mg, 0.226 mmol) and potassium carbonate (72.2 mg, 0.522 mmol) in DMF (1 ml) was heated to 60° C. overnight under $N_2$ protection. The reaction mixture was cooled to RT and partitioned between EtOAc and water, the organic layer dried in $Na_2SO_4$ and concentrated under vacuum. Then the reaction mixture separated by SFC on a ChiralCel OJ-H, 4.6×25 cm, 5-40% EtOH (0.05% DEA)/$CO_2$ to afford Example 47 (Enantiomer 1, peak 1 on SFC, HPLC_RT=8.68 min) as white solid 38 mg (76%) (LC-MS (ES, m/z) $C_{30}H_{29}FN_4O_5S$: 576; Found: 577 [M+H]$^+$) and Example 48 (Enantiomer 2, peak 2 on SFC, HPLC_RT=11.12 min) as white solid 30 mg (60%) (LC-MS (ES, m/z) $C_{30}H_{29}FN_4O_5S$: 576; Found: 577 [M+H]$^+$).

Examples 49 and 50

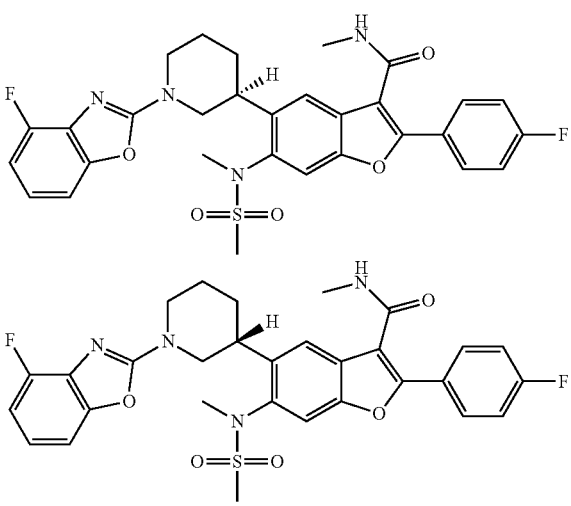

Synthesis of 5-(1-(4-fluorobenzo[d]oxazol-2-yl)piperidin-3-yl)-2-(4-fluorophenyl)-N-methyl-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (80 mg, 0.174 mmol), 2-chloro-4-fluorobenzo[d]oxazole (38.8 mg, 0.226 mmol) and potassium carbonate (72.2 mg, 0.522 mmol) in DMF (1 ml) was heated to 60° C. overnight under $N_2$ protection. The reaction mixture was cooled to RT and partitioned between EtOAc and water, the organic layer dried in $Na_2SO_4$ and concentrated under vacuum. Then the reaction mixture separated by SFC on a ChiralCel OJ-H, 4.6×25 cm, 35% EtOH (0.1% $NH_3.H_2O$)/$CO_2$ to afford Example 49 (Enantiomer 1, peak 1 on SFC, HPLC_RT=2.68 min) as white solid 42 mg (81%) (LC-MS (ES, m/z) $C_{30}H_{28}F_2N_4O_5S$: 594; Found: 595 [M+H]$^+$) and Example 50 (Enantiomer 2, peak 2 on SFC, HPLC_RT=3.37 min) as white solid 38 mg (73%) (LC-MS (ES, m/z) $C_{30}H_{28}F_2N_4O_5S$: 594; Found: 595 [M+H]$^+$).

Examples 51 and 52

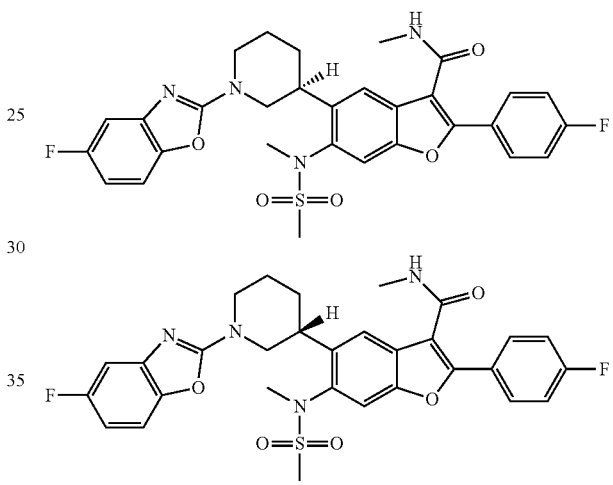

Synthesis of 5-(1-(5-fluorobenzo[d]oxazol-2-yl)piperidin-3-yl-2-(4-fluorophenyl)-N-methyl-6-(N-methylmethylsulfonamido)benzofuran-3-carboxamide (enantiomer 1) and (S)-5-(1-(5-fluorobenzo[d]oxazol-2-yl)piperidin-3-yl)-2-(4-fluorophenyl)-N-methyl-6-(N-methylmethylsulfonamido)benzofuran-3-carboxamide (enantiomer 2)

A mixture of 2-(4-fluorophenyl)-N-methyl-6-(N-methylmethylsulfonamido)-5-(piperidin-3-yl)benzofuran-3-carboxamide (120 mg, 0.261 mmol), 2-chloro-5-fluorobenzo[d]oxazole (58.2 mg, 0.339 mmol) and potassium carbonate (108 mg, 0.783 mmol) in DMF (1 ml) was heated to 60° C. overnight under $N_2$ protection. The reaction mixture was cooled to RT and partitioned between EtOAc and water, the organic layer dried in $Na_2SO_4$ and concentrated under vacuum. Then the reaction mixture separated by SFC on a ChiralCel OJ-H, 3×25 cm, 45% EtOH(0.1% $NH_3.H_2O$)/$CO_2$ to afford Example 51 (Enantiomer 1, peak 1 on SFC, HPLC_RT=2.54 min) as white solid 23 mg (29.6%) (LC-MS (ES, m/z) $C_{30}H_{28}F_2N_4O_5S$: 594; Found: 595 [M+H]$^+$) and Example 52 (Enantiomer 2, peak 2 on SFC, HPLC_RT=3.93 min) as white solid 31 mg (40%) (LC-MS (ES, m/z) $C_{30}H_{28}F_2N_4O_5S$: 594; Found: 595 [M+H]$^+$).

Examples 53 and 54

2-(4-fluorophenyl)-N-methyl-6-(N-methylmethylsulfonamido)-5-(1-(oxazolo[4,5-b]pyridin-2-yl)piperidin-3-yl)benzofuran-3-carboxamide (enantiomers 1 and 2)

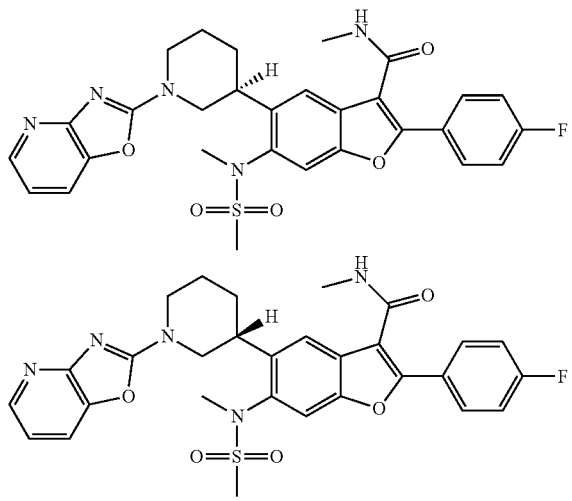

Synthesis of 2-(4-fluorophenyl)-N-methyl-6-(N-methylmethylsulfonamido)-5-(1-(oxazolo[4,5-b]pyridin-2-yl)piperidin-3-yl)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (120 mg, 0.261 mmol), 2-chlorooxazolo[4,5-b]pyridine (60.5 mg, 0.392 mmol) and potassium carbonate (108 mg, 0.783 mmol) in DMF (1 ml) was heated to 60° C. overnight under $N_2$ protection. The reaction mixture was cooled to RT and partitioned between EtOAc and water, the organic layer dried in $Na_2SO_4$ and concentrated under vacuum. Then the reaction mixture separated by SFC on a ChiralCel OJ-H, 3×25 cm, 40% Isopropanol (0.1% $NH_3.H_2O)/CO_2$ to afford Example 53 (Enantiomer 1, peak 1 on SFC, HPLC_RT=3.37 min) as white solid 22 mg (29.3%) (LC-MS (ES, m/z) $C_{29}H_{28}FN_5O_5S$: 577; Found: 578 [M$^+$H]$^+$) and Example 54 (Enantiomer 2, peak 2 on SFC, HPLC_RT=4.19 min) as white solid 20 mg (26.7%) (LC-MS (ES, m/z) $C_{29}H_{28}FN_5O_5S$: 577; Found: 578 [M+H]$^+$).

Examples 55 and 56

5-(1-(4-fluoro-1H-benzo[d]imidazol-2-yl)piperidin-3-yl)-2-(4-fluorophenyl)-N-methyl-6-(N-methylmethylsulfonamido)benzofuran-3-carboxamide (enantiomers 1 and 2)

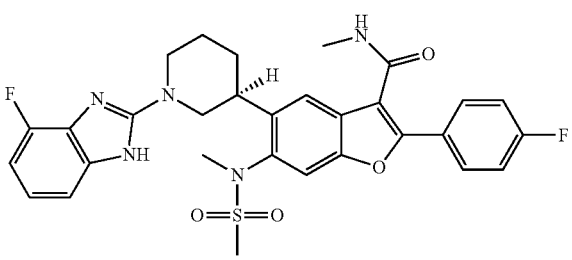

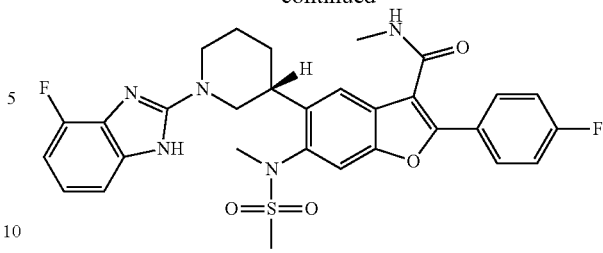

Synthesis of 5-(1-(4-fluoro-1H-benzo[d]imidazol-2-yl)piperidin-3-yl)-2-(4-fluorophenyl)-N-methyl-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (80 mg, 0.174 mmol), 2-chloro-4-fluoro-1H-benzo[d]imidazole (47.5 mg, 0.279 mmol) and triethylamine (90 mg, 0.696 mmol) in DMF (1 ml) was heated to 170° C. for 40 min. The reaction mixture was cooled to RT and partitioned between EtOAc and water. The organic layer was dried in $Na_2SO_4$ and concentrated under vacuum. Then the reaction mixture separated by SFC on a ChiralPark AD, 3×25 cm, 40% MeOH(0.1% $NH_3.H_2O)/CO_2$ to afford Example 55 (Enantiomer 1, peak 1 on SFC, HPLC_RT=3.91 min) as white solid 5 mg (10%) (LC-MS (ES, m/z) $C_{30}H_{29}F_2N_5O_4S$: 593; Found: 594 [M+H]$^+$) and Example 56 (Enantiomer 2, peak 2 on SFC, HPLC_RT=6.34 min) as white solid 5 mg (10%) (LC-MS (ES, m/z) $C_{30}H_{29}F_2N_5O_4S$: 593; Found: 594 [M+H]$^+$).

Examples 57 and 58

2-(4-fluorophenyl)-5-(1-(5-(4-fluorophenyl)oxazol-2-yl)piperidin-3-yl)-N-methyl-6-(N-methylmethylsulfonamido)benzofuran-3-carboxamide (enantiomers 1 and 2)

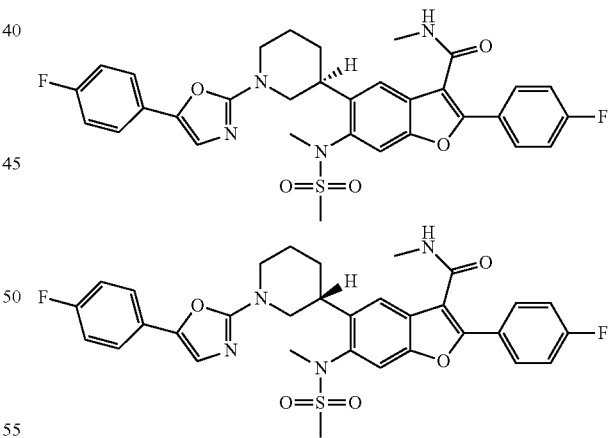

Synthesis of 2-(4-fluorophenyl)-5-(1-(5-(4-fluorophenyl)oxazol-2-yl)piperidin-3-yl)-N-methyl-6-(N-methylmethylsulfonamido)benzofuran-3-carboxamide (enantiomers 1 and 2)

A mixture of 2-(4-fluorophenyl)-N-methyl-6-(N-methylmethylsulfonamido)-5-(piperidin-3-yl)benzofuran-3-carboxamide (120 mg, 0.261 mmol), 2-chloro-5-(4-fluorophenyl)oxazole (61.9 mg, 0.313 mmol) and DIEA (67.5 mg, 0.522 mmol) in DMF (1 ml) was heated to 160° C. for 30 min. The reaction mixture was cooled to RT and partitioned between EtOAc and water The organic layer was dried in Na₂SO₄ and concentrated under vacuum. Then the reaction mixture separated by SFC on a WHELK-O1(S,S), 3×25 cm, 50% MeOH (0.1% NH₃H₂O)/CO₂ to afford Example 57 (Enantiomer 1, peak 1 on SFC, HPLC_RT=9.19 min) as white solid 33 mg (40.7%) (LC-MS (ES, m/z) C₃₂H₃₀F₂N₄O₅S: 620; Found: 621 [M+H]⁺) and Example 58 (Enantiomer 2, peak 2 on SFC, HPLC_RT=13.04 min) as white solid 30 mg (37%) (LC-MS (ES, m/z) C₃₂H₃₀F₂N₄O₅S: 620; Found: 621 [M+H]⁺).

Examples 59-78

These examples were synthesized using library format. To individual acid (0.078 mmol) in DMF (1 ml) was added DIEA (0.027 ml) then 0.266 ml T3P solution (50% in EtOAc). The solution was then treated with a 0.025 ml solution of amine (24 mg, from a solution of 576 mg amine 4 in 0.6 ml DMF). The solution was stirred at room temp for 16 h.

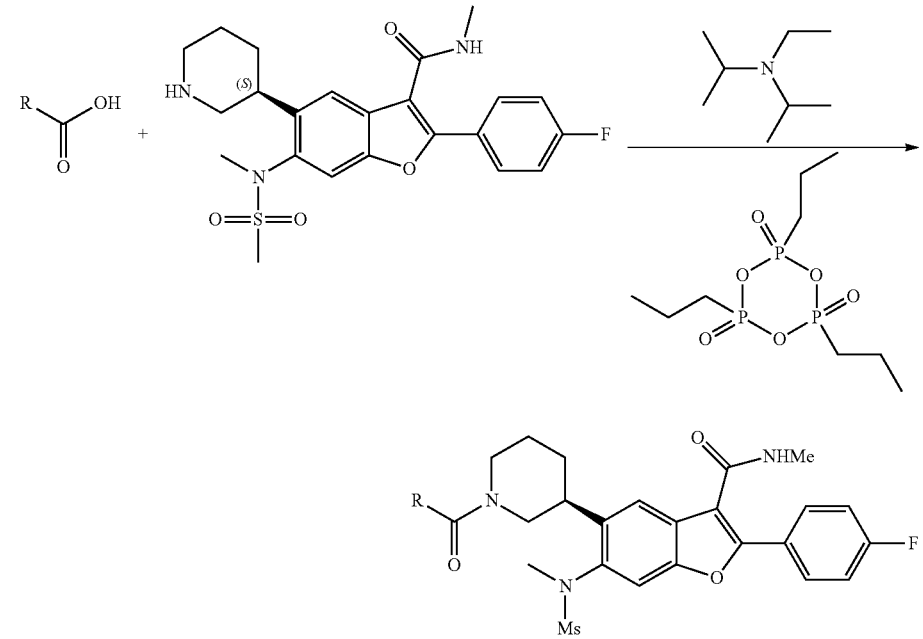

The reaction was filtered into a 96 well plate and submitted to high throughput purification.

Purification Method for Amides:
Column: Waters Sunfire C18, 5u, 19×100 mm
50 ml/min
8 minute run time
Mobile phase A=Water+0.1% Formic Acid
Mobile phase B=MeCN+0.1% Formic Acid
Gradient from 10 to 75% MeCN.
This work resulted in Examples 59 to 78.

| Ex. | Product Structure | IUPAC Name | Exact Mass [M + H]+ |
|---|---|---|---|
| 59 | | 2-(4-fluorophenyl)-N-methyl-6-[methyl(methylsulfonyl)amino]-5-[1-(3-oxabicyclo[3.1.0]hex-6-ylcarbonyl)piperidin-3-yl]-1-benzofuran-3-carboxamide | 570 |

| Ex. | Product Structure | IUPAC Name | Exact Mass [M + H]+ |
|---|---|---|---|
| 60 | 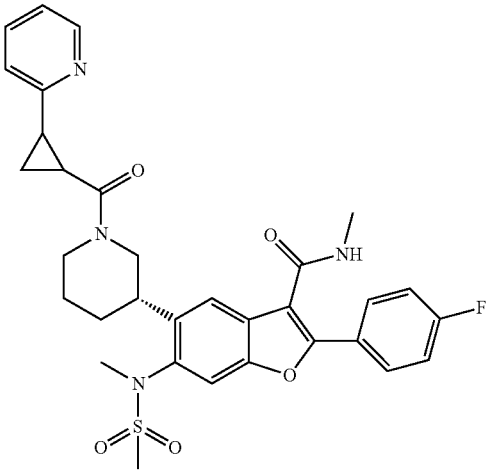 [SMILES: CNC(=O)c1c(-c2ccc(F)cc2)oc2cc(N(C)S(C)(=O)=O)c([C@@H]3CCCN(C(=O)C4CC4c4ccccn4)C3)cc12] | 2-(4-fluorophenyl)-N-methyl-6-[methyl(methylsulfonyl)amino]-5-{1-[(2-pyridin-2-ylcyclopropyl)carbonyl]piperidin-3-yl}-1-benzofuran-3-carboxamide | 605 |
| 61 | 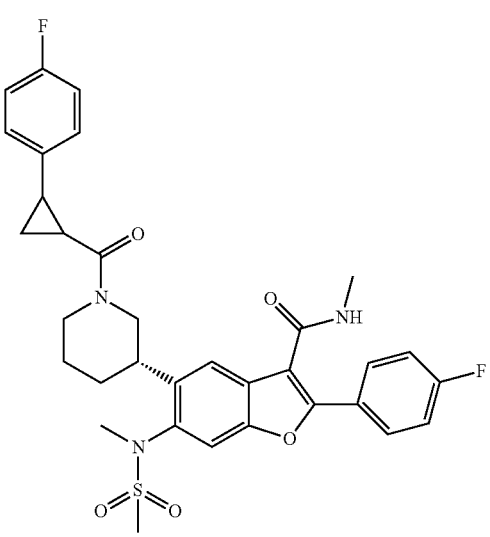 [SMILES: CNC(=O)c1c(-c2ccc(F)cc2)oc2cc(N(C)S(C)(=O)=O)c([C@@H]3CCCN(C(=O)C4CC4c4ccc(F)cc4)C3)cc12] | 2-(4-fluorophenyl)-5-(1-{[2-(4-fluorophenyl)cyclopropyl]carbonyl}piperidin-3-yl)-N-methyl-6-[methyl(methylsulfonyl)amino]-1-benzofuran-3-carboxamide | 622 |
| 62 | 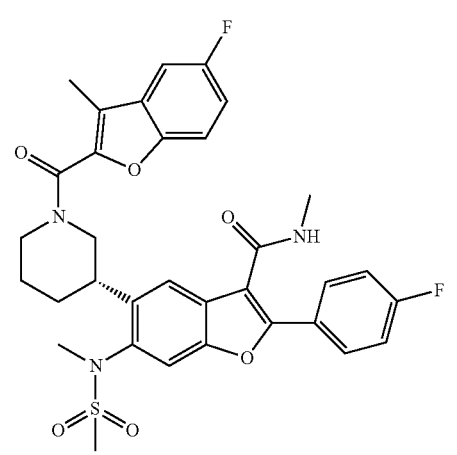 [SMILES: CNC(=O)c1c(-c2ccc(F)cc2)oc2cc(N(C)S(C)(=O)=O)c([C@@H]3CCCN(C(=O)c4oc5ccc(F)cc5c4C)C3)cc12] | 5-{1-[(5-fluoro-3-methyl-1-benzofuran-2-yl)carbonyl]piperidin-3-yl}-2-(4-fluorophenyl)-N-methyl-6-[methyl(methylsulfonyl)amino]-1-benzofuran-3-carboxamide | 636 |

-continued

| Ex. | Product Structure | IUPAC Name | Exact Mass [M + H]+ |
|---|---|---|---|
| 63 | | 2-(4-fluorophenyl)-N-methyl-5-[1-(3-methylbut-2-enoyl)piperidin-3-yl]-6-[methyl(methylsulfonyl)amino]-1-benzofuran-3-carboxamide | 542 |
| 64 | | 2-(4-fluorophenyl)-5-{1-[(4-methoxy-1H-indol-2-yl)carbonyl]piperidin-3-yl}-N-methyl-6-[methyl(methylsulfonyl)amino]-1-benzofuran-3-carboxamide | 633 |
| 65 | | 2-(4-fluorophenyl)-N-methyl-6-[methyl(methylsulfonyl)amino]-5-[1-(1H-pyrrolo[3,2-b]pyridin-2-ylcarbonyl)piperidin-3-yl]-1-benzofuran-3-carboxamide | 604 |

-continued

| Ex. | Product Structure | IUPAC Name | Exact Mass [M + H]+ |
|---|---|---|---|
| 66 | | 2-(4-fluorophenyl)-N-methyl-6-[methyl(methylsulfonyl)amino]-5-[1-(1H-pyrrolo[2,3-b]pyridin-2-ylcarbonyl)piperidin-3-yl]-1-benzofuran-3-carboxamide | 604 |
| 67 | | 2-(4-fluorophenyl)-N-methyl-5-{1-[(1-methyl-1H-indol-2-yl)carbonyl]piperidin-3-yl}-6-[methyl(methylsulfonyl)amino]-1-benzofuran-3-carboxamide | 617 |
| 68 | | 5-[1-(cyclohexylacetyl)piperidin-3-yl]-2-(4-fluorophenyl)-N-methyl-6-[methyl(methylsulfonyl)amino]-1-benzofuran-3-carboxamide | 584 |

| Ex. | Product Structure | IUPAC Name | Exact Mass [M + H]+ |
| --- | --- | --- | --- |
| 69 | | 5-[1-(1,3-benzothiazol-2-ylcarbonyl)piperidin-3-yl]-2-(4-fluorophenyl)-N-methyl-6-[methyl(methylsulfonyl)amino]-1-benzofuran-3-carboxamide | 621 |
| 70 | | 2-(4-fluorophenyl)-5-{1-[(5-fluoropyridin-2-yl)acetyl]piperidin-3-yl}-N-methyl-6-[methyl(methylsulfonyl)amino]-1-benzofuran-3-carboxamide | 597 |
| 71 | | 2-(4-fluorophenyl)-5-(1-{[4-(4-fluorophenyl)-1H-pyrrol-3-yl]carbonyl}piperidin-3-yl)-N-methyl-6-[methyl(methylsulfonyl)amino]-1-benzofuran-3-carboxamide | 647 |

| Ex. | Product Structure | IUPAC Name | Exact Mass [M + H]+ |
|---|---|---|---|
| 72 | | 2-(4-fluorophenyl)-5-(1-{[2-(4-fluorophenyl)-1,3-oxazol-4-yl]carbonyl}piperidin-3-yl)-N-methyl-6-[methyl(methylsulfonyl)amino]-1-benzofuran-3-carboxamide | 649 |
| 73 | | 2-(4-fluorophenyl)-5-(1-{[3-(4-fluorophenyl)-1H-pyrazol-5-yl]carbonyl}piperidin-3-yl)-N-methyl-6-[methyl(methylsulfonyl)amino]-1-benzofuran-3-carboxamide | 648 |
| 74 | | 2-(4-fluorophenyl)-N-methyl-6-[methyl(methylsulfonyl)amino]-5-{1-[(4-methyl-4H-thieno[3,2-b]pyrrol-5-yl)carbonyl]piperidin-3-yl}-1-benzofuran-3-carboxamide | 623 |

-continued

| Ex. | Product Structure | IUPAC Name | Exact Mass [M + H]+ |
|---|---|---|---|
| 75 | | 5-{1-[(6-fluoro-1,3-benzothiazol-2-yl)carbonyl]piperidin-3-yl}-2-(4-fluorophenyl)-N-methyl-6-[methyl(methylsulfonyl)amino]-1-benzofuran-3-carboxamide | 639 |
| 76 | | 5-{1-[(6-fluoro-1H-benzimidazol-2-yl)carbonyl]piperidin-3-yl}-2-(4-fluorophenyl)-N-methyl-6-[methyl(methylsulfonyl)amino]-1-benzofuran-3-carboxamide | 622 |
| 77 | | 5-[1-(1,3-benzoxazol-2-ylcarbonyl)piperidin-3-yl]-2-(4-fluorophenyl)-N-methyl-6-[methyl(methylsulfonyl)amino]-1-benzofuran-3-carboxamide | 605 |

| Ex. | Product Structure | IUPAC Name | Exact Mass [M + H]+ |
|---|---|---|---|
| 78 | | 2-(4-fluorophenyl)-N-methyl-6-[methyl(methylsulfonyl)amino]-5-{1-[(2-pyridin-2-ylcyclopropyl)carbonyl]piperidin-3-yl}-1-benzofuran-3-carboxamide | 605 |

Examples 79-84

These examples were synthesized using library format. To individual sulfonyl chlorides (0.109 mmol each) was added 1 ml MeCN solution of amine (25 mg) followed by DIEA (0.047 ml). The reactions were shaken for 16 h. Then the reactions were filtered using a filter plate to a 96 well plate, which was sealed and submitted to High Throughput Purification.

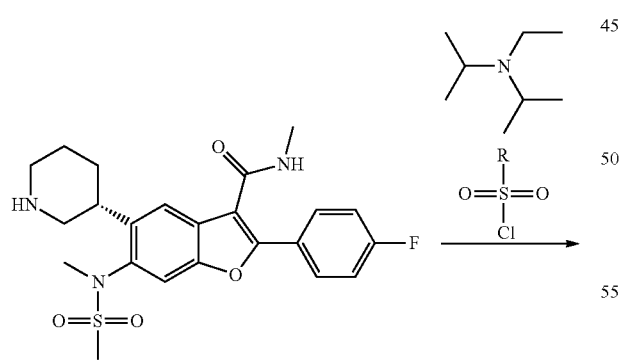

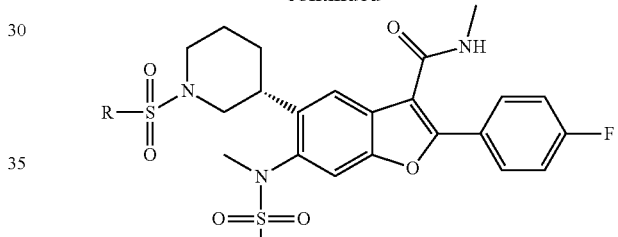

Purification Method:

Waters Sunfire C18, 5u, 19×100 mm 25 ml/min 10-12 minute run time

Mobile phase A=Water+0.1% Formic Acid

Mobile phase B=MeCN+0.1% Formic Acid

Gradient from 10 to 75% MeCN

This work resulted in Examples 79 to 84.

| Example | Product Structure | IUPAC Name | Mass [M + H]+ |
|---------|-------------------|------------|----------------|
| 79 | | 2-(4-fluorophenyl)-N-methyl-6-[methyl(methylsulfonyl)amino]-5-[(3R)-1-{[(E)-2-phenylethenyl]sulfonyl}piperidin-3-yl]-1-benzofuran-3-carboxamide | 626 |
| 80 | | 5-{(3R)-1-[(4-fluorobenzyl)sulfonyl]piperidin-3-yl}-2-(4-fluorophenyl)-N-methyl-6-[methyl(methylsulfonyl)amino]-1-benzofuran-3-carboxamide | 632 |
| 81 | | 5-{(3R)-1-[(2-fluorobenzyl)sulfonyl]piperidin-3-yl}-2-(4-fluorophenyl)-N-methyl-6-[methyl(methylsulfonyl)amino]-1-benzofuran-3-carboxamide | 632 |

| Example | Product Structure | IUPAC Name | Mass [M + H]+ |
|---|---|---|---|
| 82 | | 5-{(3R)-1-[(3-fluorobenzyl)sulfonyl]piperidin-3-yl}-2-(4-fluorophenyl)-N-methyl-6-[methyl(methylsulfonyl)amino]-1-benzofuran-3-carboxamide | 632 |
| 83 | | 5-[(3R)-1-(1-benzofuran-2-ylsulfonyl)piperidin-3-yl]-2-(4-fluorophenyl)-N-methyl-6-[methyl(methylsulfonyl)amino]-1-benzofuran-3-carboxamide | 640 |
| 84 | | 5-{(3R)-1-[(3,4-difluorobenzyl)sulfonyl]piperidin-3-yl}-2-(4-fluorophenyl)-N-methyl-6-[methyl(methylsulfonyl)amino]-1-benzofuran-3-carboxamide | 650 |

Examples 85-108

Examples 85 to 108 were prepared in library format. The procedure is exemplified by the synthesis of Example 85. To 5-fluoro-1-methyl-1H-indole-2-carboxylic acid (16 mg, was added a solution of (R)-2-(4-fluorophenyl)-N-methyl-6-(N-methylmethylsulfonamido)-5-(piperindin-3-yl)benzofuran-3-carboxamide (25 mg, 0.054 mmol), O-(benzotriazol-1yl)-N,N,N',N'-tetramethyluronium tetrafluoroborate (34.9 mg, 0.109 mmol) and Hunig's base (14.1 mg, 0.109 mmol) in 1 ml DMF. The mixture was stirred at room temperature for 18 h. The crude mixture was purified using mass directed reverse phase HPLC, Waters XBridge C18, 5u, 30×100 mm, 50 ml/min, 8 min run time, mobile phase A=water and ammonium, mobile phase B=acetonitrile and ammonium, gradient from 35% to 75% acetonitrile to give 5-{(3R)-1-

[(5-fluoro-1-methyl-1H-indol-2-yl)carbonyl]piperidin-3-yl}-2-(4-fluorophenyl)-N-methyl-6-[methyl(methylsulfonyl)amino]-1-benzofuran-3-carboxamide (25 mg, 71% yield). MS (M+H)⁺: 635.

| Example | Structure | IUPAC Name | Mass [M + H]+ |
|---|---|---|---|
| 85 | 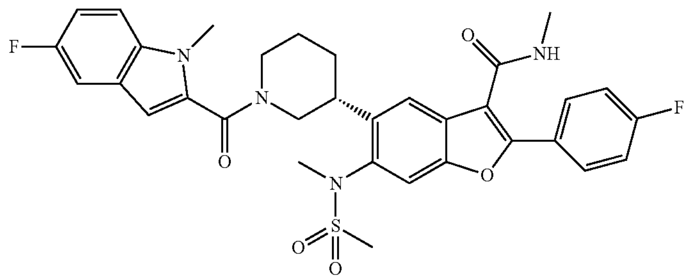 [SMILES: CNC(=O)c1c(-c2ccc(F)cc2)oc2cc(N(C)S(C)(=O)=O)c([C@H]3CCCN(C(=O)c4cc5cc(F)ccc5n4C)C3)cc12] | 5-{(3R)-1-[(5-fluoro-1-methyl-1H-indol-2-yl)carbonyl]piperidin-3-yl}-2-(4-fluorophenyl)-N-methyl-6-[methyl(methylsulfonyl)amino]-1-benzofuran-3-carboxamide | 635 |
| 86 | 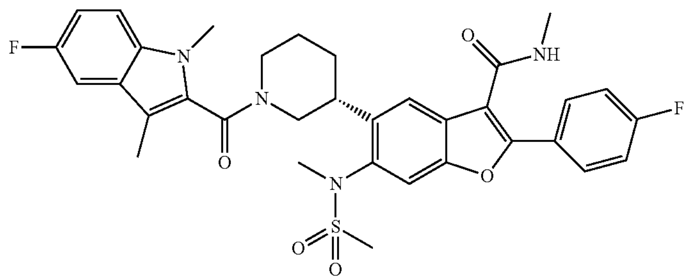 [SMILES: CNC(=O)c1c(-c2ccc(F)cc2)oc2cc(N(C)S(C)(=O)=O)c([C@H]3CCCN(C(=O)c4c(C)c5cc(F)ccc5n4C)C3)cc12] | 5-{(3R)-1-[(5-fluoro-1,3-dimethyl-1H-indol-2-yl)carbonyl]piperidin-3-yl}-2-(4-fluorophenyl)-N-methyl-6-[methyl(methylsulfonyl)amino]-1-benzofuran-3-carboxamide | 649 |
| 87 | 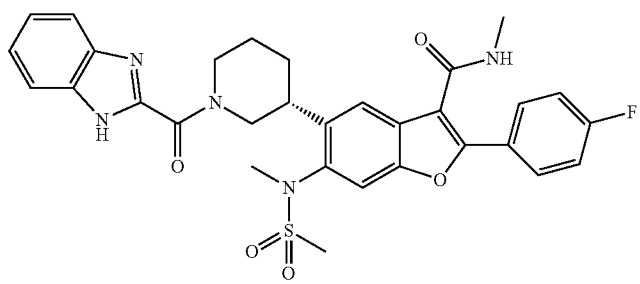 [SMILES: CNC(=O)c1c(-c2ccc(F)cc2)oc2cc(N(C)S(C)(=O)=O)c([C@H]3CCCN(C(=O)c4nc5ccccc5[nH]4)C3)cc12] | 5-[(3R)-1-(1H-benzimidazol-2-ylcarbonyl)piperidin-3-yl]-2-(4-fluorophenyl)-N-methyl-6-[methyl(methylsulfonyl)amino]-1-benzofuran-3-carboxamide | 604 |
| 88 | 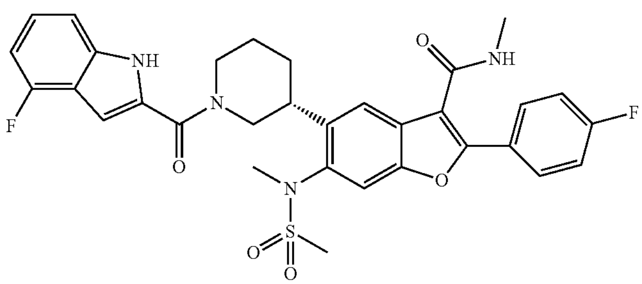 [SMILES: CNC(=O)c1c(-c2ccc(F)cc2)oc2cc(N(C)S(C)(=O)=O)c([C@H]3CCCN(C(=O)c4cc5c(F)cccc5[nH]4)C3)cc12] | 5-{(3R)-1-[(4-fluoro-1H-indol-2-yl)carbonyl]piperidin-3-yl}-2-(4-fluorophenyl)-N-methyl-6-[methyl(methylsulfonyl)amino]-1-benzofuran-3-carboxamide | 621 |
| 89 | 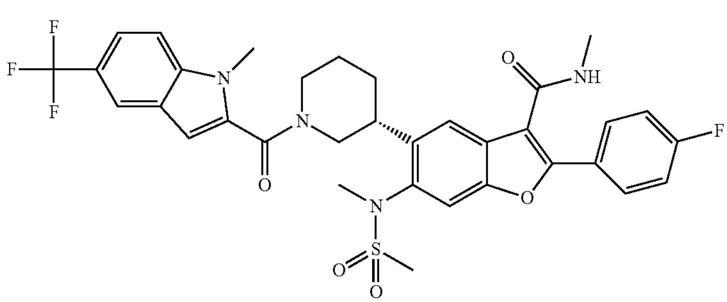 [SMILES: CNC(=O)c1c(-c2ccc(F)cc2)oc2cc(N(C)S(C)(=O)=O)c([C@H]3CCCN(C(=O)c4cc5cc(C(F)(F)F)ccc5n4C)C3)cc12] | 2-(4-fluorophenyl)-N-methyl-6-[methyl(methylsulfonyl)amino]-5-[(3R)-1-{[1-methyl-5-(trifluoromethyl)-1H-indol-2-yl]carbonyl}piperidin-3-yl]-1-benzofuran-3-carboxamide | 685 |

-continued

| Example | Structure | IUPAC Name | Mass [M + H]+ |
|---|---|---|---|
| 90 | 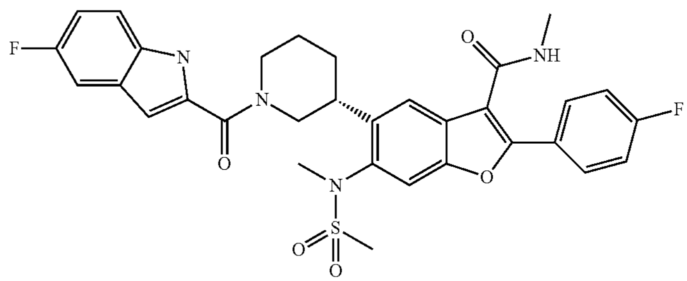 [SMILES: CNC(=O)c1c(-c2ccc(F)cc2)oc2cc(N(C)S(C)(=O)=O)c([C@H]3CCCN(C(=O)c4cc5cc(F)ccc5[nH]4)C3)cc12] | (R)-5-(1-(5-fluoro-1H-indole-2-carbonyl)piperidin-3-yl)-2-(4-fluorophenyl)-N-methyl-6-(N-methylmethylsulfonamido)benzofuran-3-carboxamide | 621 |
| 91 | 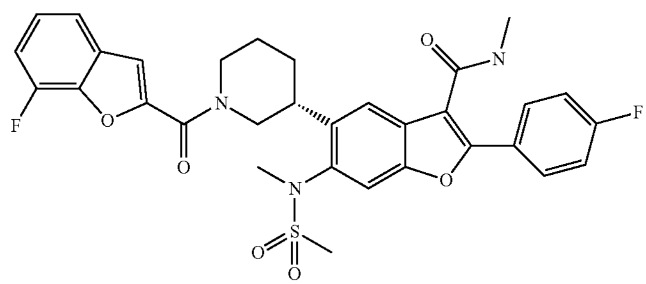 [SMILES: CNC(=O)c1c(-c2ccc(F)cc2)oc2cc(N(C)S(C)(=O)=O)c([C@H]3CCCN(C(=O)c4cc5cccc(F)c5o4)C3)cc12] | (R)-5-(1-(7-fluorobenzofuran-2-carbonyl)piperidin-3-yl)-2-(4-fluorophenyl)-N-methyl-6-(N-methylmethylsulfonamido)benzofuran-3-carboxamide | 622 |
| 92 | 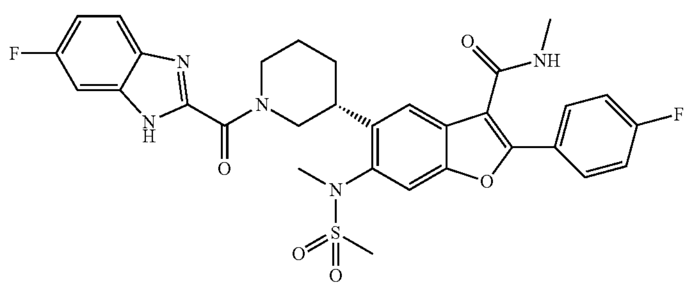 [SMILES: CNC(=O)c1c(-c2ccc(F)cc2)oc2cc(N(C)S(C)(=O)=O)c([C@H]3CCCN(C(=O)c4nc5ccc(F)cc5[nH]4)C3)cc12] | 5-{(3R)-1-[(6-fluoro-1H-benzimidazol-2-yl)carbonyl]piperidin-3-yl}-2-(4-fluorophenyl)-N-methyl-6-[methyl(methylsulfonyl)amino]-1-benzofuran-3-carboxamide | 622 |
| 93 | 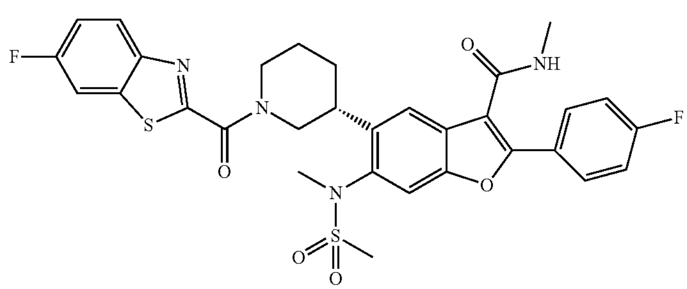 [SMILES: CNC(=O)c1c(-c2ccc(F)cc2)oc2cc(N(C)S(C)(=O)=O)c([C@H]3CCCN(C(=O)c4nc5ccc(F)cc5s4)C3)cc12] | 5-{(3R)-1-[(6-fluoro-1,3-benzothiazol-2-yl)carbonyl]piperidin-3-yl}-2-(4-fluorophenyl)-N-methyl-6-[methyl(methylsulfonyl)amino]-1-benzofuran-3-carboxamide | 639 |
| 94 | 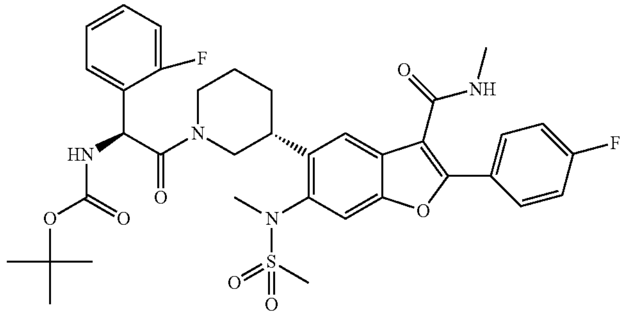 [SMILES: CNC(=O)c1c(-c2ccc(F)cc2)oc2cc(N(C)S(C)(=O)=O)c([C@H]3CCCN(C(=O)[C@@H](NC(=O)OC(C)(C)C)c4ccccc4F)C3)cc12] | tert-butyl {(1S)-1-(2-fluorophenyl)-2-[(3R)-3-{2-(4-fluorophenyl)-3-(methylcarbamoyl)-6-[methyl(methylsulfonyl)amino]-1-benzofuran-5-yl}piperidin-1-yl]-2-oxoethyl}carbamate | 711 |

| Example | Structure | IUPAC Name | Mass [M + H]+ |
|---|---|---|---|
| 95 | 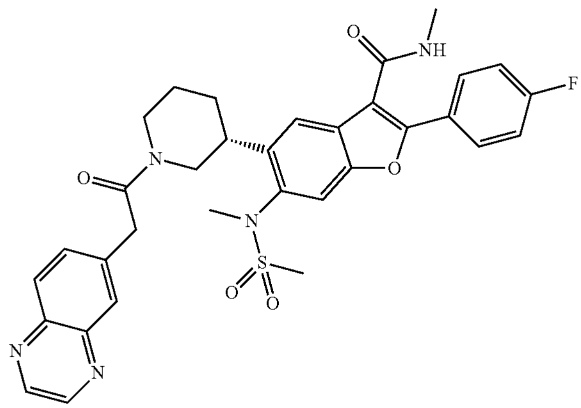 [SMILES: CNC(=O)c1c(-c2ccc(F)cc2)oc2cc(N(C)S(C)(=O)=O)c([C@H]3CCCN(C(=O)Cc4ccc5nccnc5c4)C3)cc12] | 2-(4-fluorophenyl)-N-methyl-6-[methyl(methylsulfonyl)amino]-5-[(3R)-1-(quinoxalin-6-ylacetyl)piperidin-3-yl]-1-benzofuran-3-carboxamide | 630 |
| 96 | 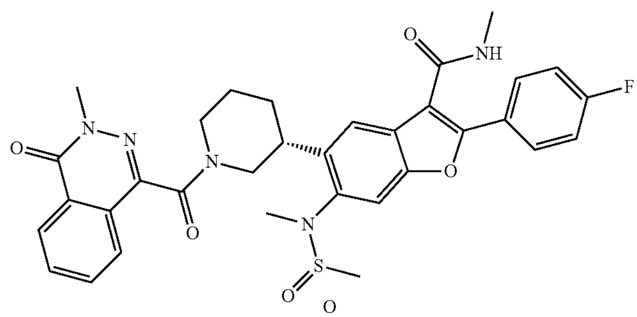 | 2-(4-fluorophenyl)-N-methyl-6-[methyl(methylsulfonyl)amino]-5-{(3R)-1-[(3-methyl-4-oxo-3,4-dihydrophthalazin-1-yl)carbonyl]piperidin-3-yl}-1-benzofuran-3-carboxamide | 646 |
| 97 | 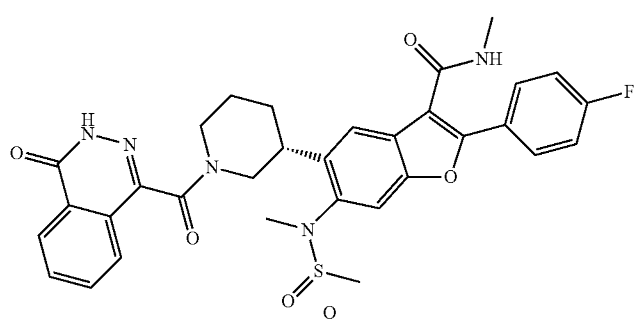 | 2-(4-fluorophenyl)-N-methyl-6-[methyl(methylsulfonyl)amino]-5-{(3R)-1-[(4-oxo-3,4-dihydrophthalazin-1-yl)carbonyl]piperidin-3-yl}-1-benzofuran-3-carboxamide | 632 |
| 98 | 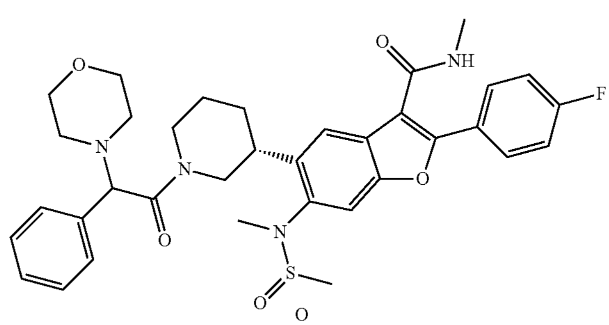 | 2-(4-fluorophenyl)-N-methyl-6-[methyl(methylsulfonyl)amino]-5-{(3R)-1-[morpholin-4-yl(phenyl)acetyl]piperidin-3-yl}-1-benzofuran-3-carboxamide | 663 |

| Example | Structure | IUPAC Name | Mass [M + H]+ |
|---|---|---|---|
| 99 | 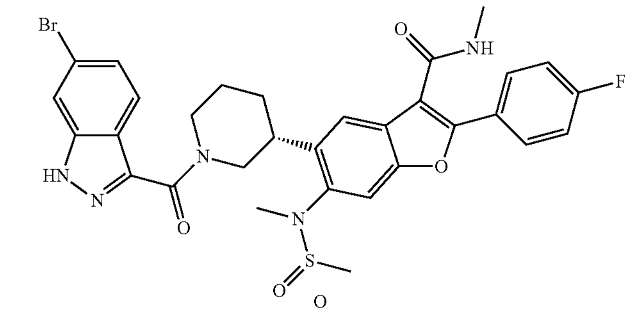 | 5-{(3R)-1-[(6-bromo-1H-indazol-3-yl)carbonyl]piperidin-3-yl}-2-(4-fluorophenyl)-N-methyl-6-[methyl(methylsulfonyl)amino]-1-benzofuran-3-carboxamide | 682 |
| 100 | 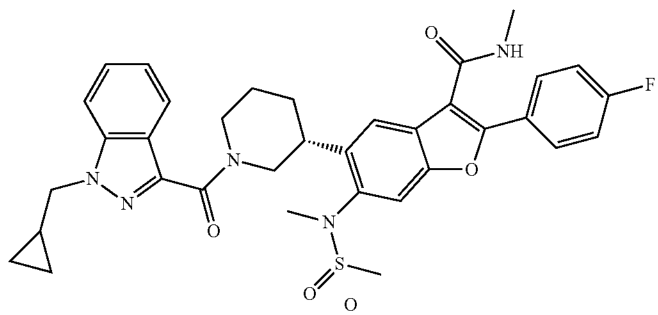 | 5-[(3R)-1-{[1-(cyclopropylmethyl)-1H-indazol-3-yl]carbonyl}piperidin-3-yl]-2-(4-fluorophenyl)-N-methyl-6-[methyl(methylsulfonyl)amino]-1-benzofuran-3-carboxamide | 658 |
| 101 | 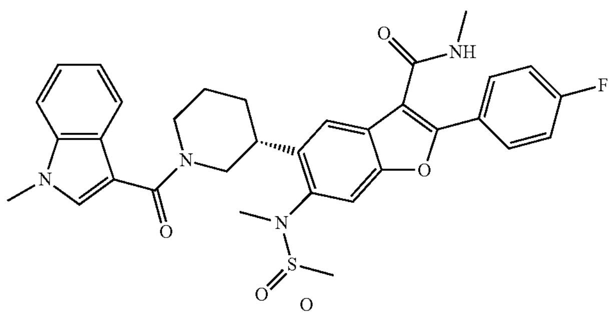 | 2-(4-fluorophenyl)-N-methyl-5-{(3R)-1-[(1-methyl-1H-indol-3-yl)carbonyl]piperidin-3-yl}-6-[methyl(methylsulfonyl)amino]-1-benzofuran-3-carboxamide | 617 |
| 102 | 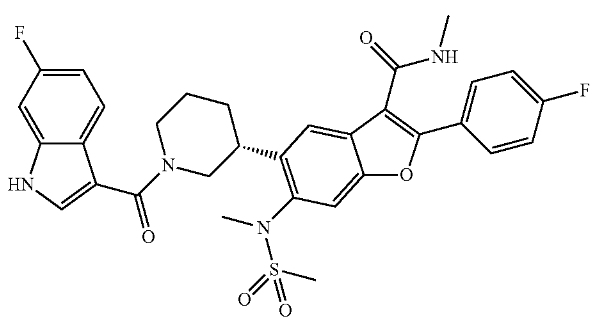 [SMILES: CNC(=O)c1c(-c2ccc(F)cc2)oc2cc(N(C)S(C)(=O)=O)c([C@H]3CCCN(C(=O)c4c[nH]c5cc(F)ccc45)C3)cc12] | 5-{(3R)-1-[(6-fluoro-1H-indol-3-yl)carbonyl]piperidin-3-yl}-2-(4-fluorophenyl)-N-methyl-6-[methyl(methylsulfonyl)amino]-1-benzofuran-3-carboxamide | 621 |
| 103 | 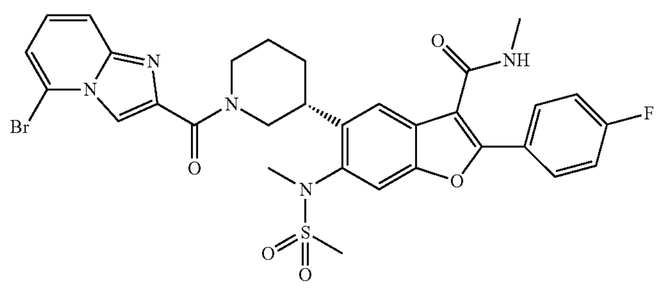 | 5-{(3R)-1-[(5-bromoimidazo[1,2-a]pyridin-2-yl)carbonyl]piperidin-3-yl}-2-(4-fluorophenyl)-N-methyl-6-[methyl(methylsulfonyl)amino]-1-benzofuran-3-carboxamide | 682 |

-continued

| Example | Structure | IUPAC Name | Mass [M + H]+ |
|---|---|---|---|
| 104 | 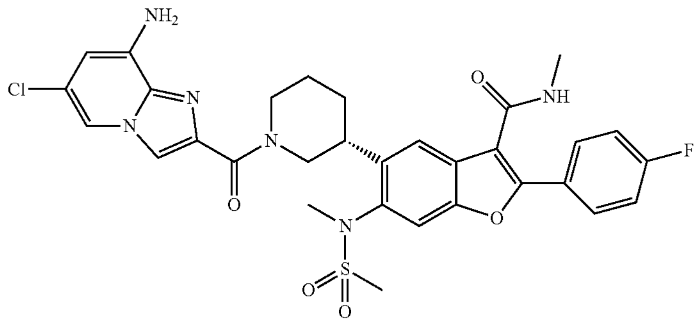 [SMILES: CNC(=O)c1c(-c2ccc(F)cc2)oc2cc(N(C)S(C)(=O)=O)c([C@H]3CCCN(C(=O)c4cn5cc(Cl)cc(N)c5n4)C3)cc12] | 5-{(3R)-1-[(8-amino-6-chloroimidazo[1,2-a]pyridin-2-yl)carbonyl]piperidin-3-yl}-2-(4-fluorophenyl)-N-methyl-6-[methyl(methylsulfonyl)amino]-1-benzofuran-3-carboxamide | 653 |
| 105 | 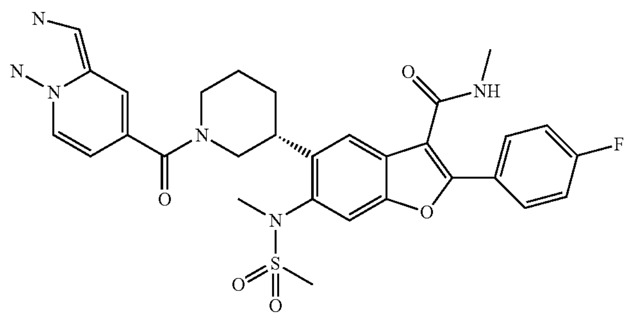 [SMILES: CNC(=O)c1c(-c2ccc(F)cc2)oc2cc(N(C)S(C)(=O)=O)c([C@H]3CCCN(C(=O)C4=C/C(=C/N)N(N)C=C4)C3)cc12] | 2-(4-fluorophenyl)-N-methyl-6-[methyl(methylsulfonyl)amino]-5-[(3R)-1-([1,2,3]triazolo[1,5-a]pyridin-5-ylcarbonyl)piperidin-3-yl]-1-benzofuran-3-carboxamide | 605 |
| 106 | 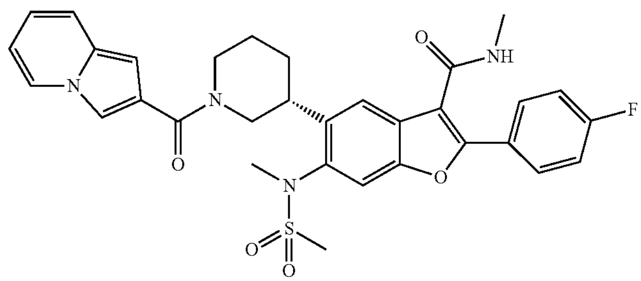 [SMILES: CNC(=O)c1c(-c2ccc(F)cc2)oc2cc(N(C)S(C)(=O)=O)c([C@H]3CCCN(C(=O)c4cc5ccccn5c4)C3)cc12] | 2-(4-fluorophenyl)-5-[(3R)-1-(indolizin-2-ylcarbonyl)piperidin-3-yl]-N-methyl-6-[methyl(methylsulfonyl)amino]-1-benzofuran-3-carboxamide | 603 |
| 107 | 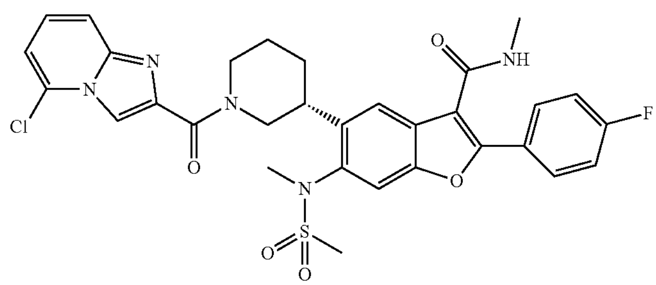 [SMILES: CNC(=O)c1c(-c2ccc(F)cc2)oc2cc(N(C)S(C)(=O)=O)c([C@H]3CCCN(C(=O)c4cn5c(Cl)cccc5n4)C3)cc12] | 5-{(3R)-1-[(5-chloroimidazo[1,2-a]pyridin-2-yl)carbonyl]piperidin-3-yl}-2-(4-fluorophenyl)-N-methyl-6-[methyl(methylsulfonyl)amino]-1-benzofuran-3-carboxamide | 638 |
| 108 | 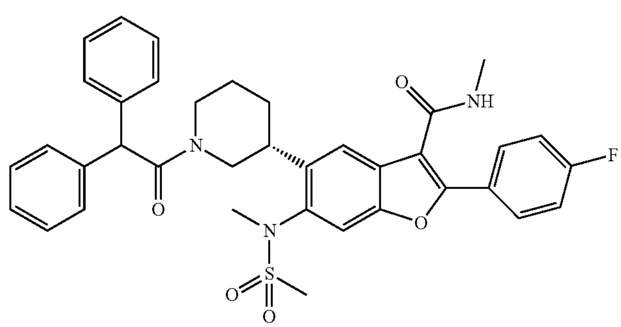 [SMILES: CNC(=O)c1c(-c2ccc(F)cc2)oc2cc(N(C)S(C)(=O)=O)c([C@H]3CCCN(C(=O)C(c4ccccc4)c4ccccc4)C3)cc12] | 5-[(3R)-1-(diphenylacetyl)piperidin-3-yl]-2-(4-fluorophenyl)-N-methyl-6-[methyl(methylsulfonyl)amino]-1-benzofuran-3-carboxamide | 654 |

Examples 109 to 144

Examples 109 to 144 were prepared in library format. The procedure is exemplified by the synthesis of Example 111. To a solution of (S)-2-(4-fluorophenyl)-N-methyl-6-(N-methylmethylsulfonamido)-5-(piperidin-3-yl)benzofuran-3-carboxamide (20 mg, 0.044 mmol) and Hunig's base (11.3 mg, 0.087 mmol) in DCM was added 2-methylbenzene-1-sufonyl chloride (17 mg, 0.089 mmol). The mixture was stirred uncapped for 18 hours. The crude mixture was purified using mass directed reverse phase HPLC, Waters Sunfire C18, 5u, 19×100 mm, 25 ml/min, 8 min run time, mobile phase A=water and 0.1% formic acid, mobile phase B=acetonitrile and 0.1% formic acid, gradient from 35% to 70% acetonitrile (14 mg, 51% yield) to afford 2-(4-fluorophenyl)-N-methyl-6-[methyl(methylsulfonyl)amino]-5-{(3S)-1-[(2-methylphenyl)sulfonyl]piperidin-3-yl}-1-benzofuran-3-carboxamide. MS (M+H)$^+$: 614.

| Example | Structure | IUPAC Name | Mass [M + H]+ |
|---|---|---|---|
| 109 | 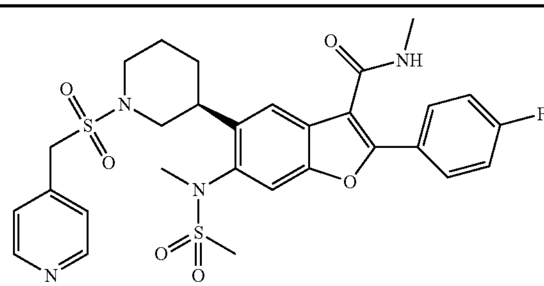 | 2-(4-fluorophenyl)-N-methyl-6-[methyl(methylsulfonyl)amino]-5-{(3S)-1-[(pyridin-4-ylmethyl)sulfonyl]piperidin-3-yl}-1-benzofuran-3-carboxamide | 615 |
| 110 | 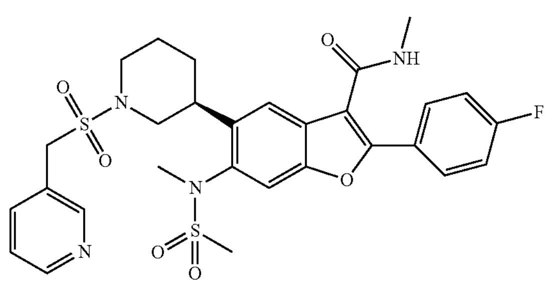 [SMILES: CNC(=O)c1c(-c2ccc(F)cc2)oc2cc(N(C)S(C)(=O)=O)c([C@@H]3CCCN(S(=O)(=O)Cc4cccnc4)C3)cc12] | 2-(4-fluorophenyl)-N-methyl-6-[methyl(methylsulfonyl)amino]-5-{(3S)-1-[(pyridin-3-ylmethyl)sulfonyl]piperidin-3-yl}-1-benzofuran-3-carboxamide | 615 |
| 111 | 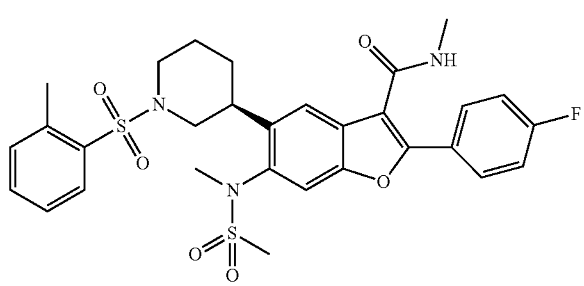 [SMILES: CNC(=O)c1c(-c2ccc(F)cc2)oc2cc(N(C)S(C)(=O)=O)c([C@@H]3CCCN(S(=O)(=O)c4ccccc4C)C3)cc12] | 2-(4-fluorophenyl)-N-methyl-6-[methyl(methylsulfonyl)amino]-5-{(3S)-1-[(2-methylphenyl)sulfonyl]piperidin-3-yl}-1-benzofuran-3-carboxamide | 614 |
| 112 | 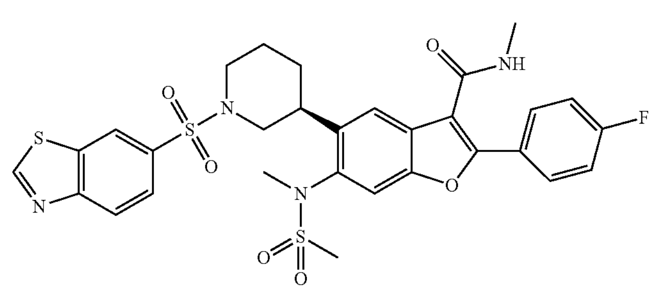 [SMILES: CNC(=O)c1c(-c2ccc(F)cc2)oc2cc(N(C)S(C)(=O)=O)c([C@@H]3CCCN(S(=O)(=O)c4ccc5ncsc5c4)C3)cc12] | 5-[(3S)-1-(1,3-benzothiazol-6-ylsulfonyl)piperidin-3-yl]-2-(4-fluorophenyl)-N-methyl-6-[methyl(methylsulfonyl)amino]-1-benzofuran-3-carboxamide | 657 |

| Example | Structure | IUPAC Name | Mass [M + H]+ |
|---|---|---|---|
| 113 | 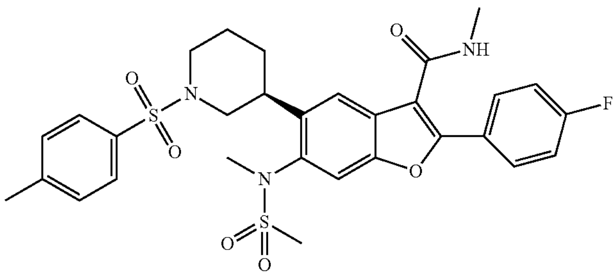 [SMILES: CNC(=O)c1c(-c2ccc(F)cc2)oc2cc(N(C)S(C)(=O)=O)c([C@@H]3CCCN(S(=O)(=O)c4ccc(C)cc4)C3)cc12] | 2-(4-fluorophenyl)-N-methyl-6-[methyl(methylsulfonyl)amino]-5-{(3S)-1-[(4-methylphenyl)sulfonyl]piperidin-3-yl}-1-benzofuran-3-carboxamide | 614 |
| 114 | 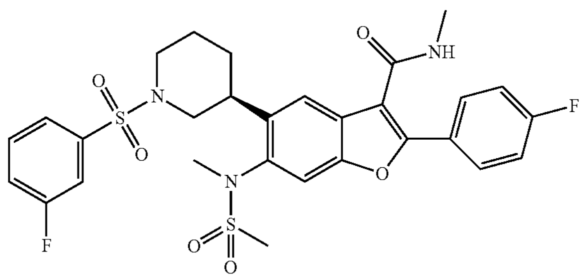 | 2-(4-fluorophenyl)-5-{(3S)-1-[(3-fluorophenyl)sulfonyl]piperidin-3-yl}-N-methyl-6-[methyl(methylsulfonyl)amino]-1-benzofuran-3-carboxamide | 618 |
| 115 | 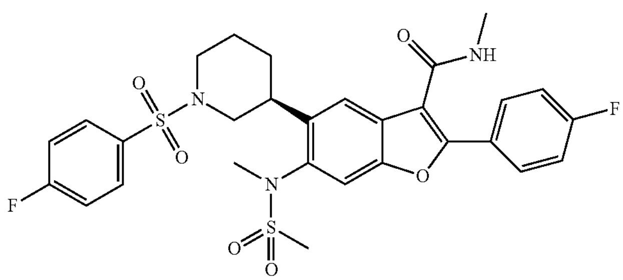 [SMILES: CNC(=O)c1c(-c2ccc(F)cc2)oc2cc(N(C)S(C)(=O)=O)c([C@@H]3CCCN(S(=O)(=O)c4ccc(F)cc4)C3)cc12] | 2-(4-fluorophenyl-5-{(3S)-1-[(4-fluorophenyl)sulfonyl]piperidin-3-yl}-N-methyl-6-[methyl(methylsulfonyl)amino]-1-benzofuran-3-carboxamide | 618 |
| 116 | 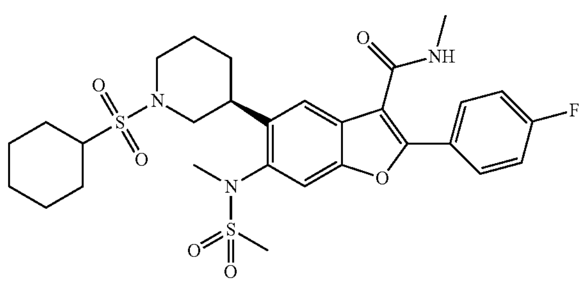 [SMILES: CNC(=O)c1c(-c2ccc(F)cc2)oc2cc(N(C)S(C)(=O)=O)c([C@@H]3CCCN(S(=O)(=O)C4CCCCC4)C3)cc12] | 5-[(3S)-1-(cyclohexylsulfonyl)piperidin-3-yl]-2-(4-fluorophenyl)-N-methyl-6-[methyl(methylsulfonyl)amino]-1-benzofuran-3-carboxamide | 606 |
| 117 | 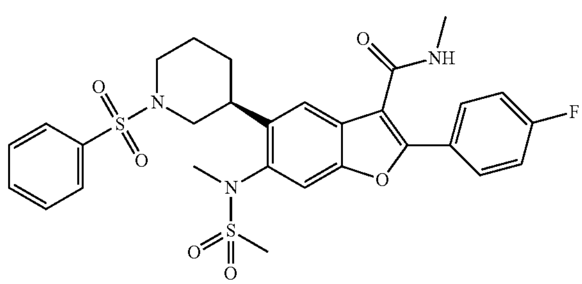 [SMILES: CNC(=O)c1c(-c2ccc(F)cc2)oc2cc(N(C)S(C)(=O)=O)c([C@@H]3CCCN(S(=O)(=O)c4ccccc4)C3)cc12] | 2-(4-fluorophenyl)-N-methyl-6-[methyl(methylsulfonyl)amino]-5-[(3S)-1-(phenylsulfonyl)piperidin-3-yl]-1-benzofuran-3-carboxamide | 600 |

| Example | Structure | IUPAC Name | Mass [M + H]+ |
|---|---|---|---|
| 118 | 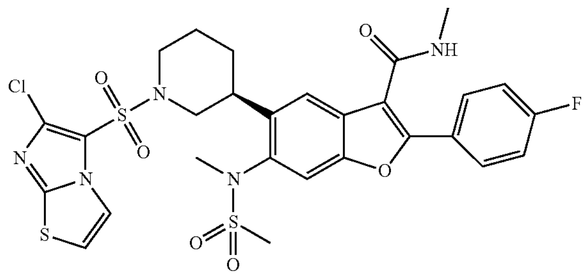 [SMILES: CNC(=O)c1c(-c2ccc(F)cc2)oc2cc(N(C)S(C)(=O)=O)c([C@@H]3CCCN(S(=O)(=O)c4c(Cl)nc5sccn45)C3)cc12] | 5-{(3S)-1-[(6-chloroimidazo[2,1-b][1,3]thiazol-5-yl)sulfonyl]piperidin-3-yl}-2-(4-fluorophenyl)-N-methyl-6-[methyl(methylsulfonyl)amino]-1-benzofuran-3-carboxamide | 680 |
| 119 | 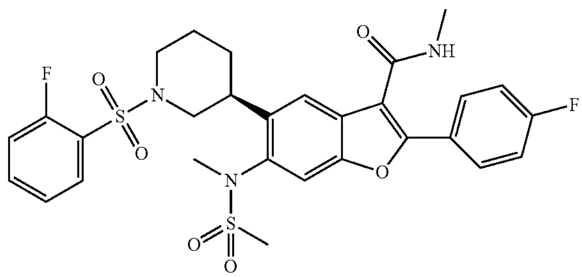 [SMILES: CNC(=O)c1c(-c2ccc(F)cc2)oc2cc(N(C)S(C)(=O)=O)c([C@@H]3CCCN(S(=O)(=O)c4ccccc4F)C3)cc12] | 2-(4-fluorophenyl)-5-{(3S)-1-[(2-fluorophenyl)sulfonyl]piperidin-3-yl}-N-methyl-6-[methyl(methylsulfonyl)amino]-1-benzofuran-3-carboxamide | 618 |
| 120 | 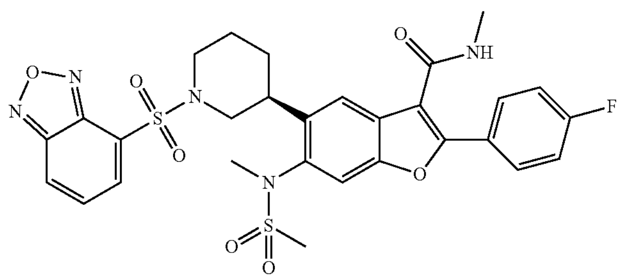 [SMILES: CNC(=O)c1c(-c2ccc(F)cc2)oc2cc(N(C)S(C)(=O)=O)c([C@@H]3CCCN(S(=O)(=O)c4cccc5nonc45)C3)cc12] | 5-[(3S)-1-(2,1,3-benzoxadiazol-4-ylsulfonyl)piperidin-3-yl]-2-(4-fluorophenyl)-N-methyl-6-[methyl(methylsulfonyl)amino]-1-benzofuran-3-carboxamide | 642 |
| 121 | 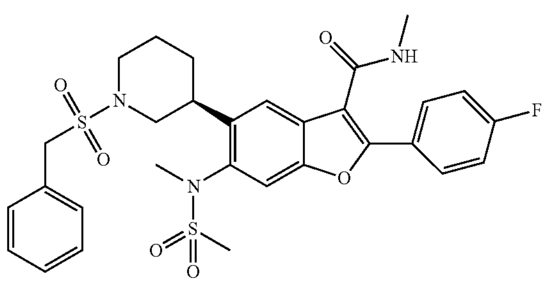 [SMILES: CNC(=O)c1c(-c2ccc(F)cc2)oc2cc(N(C)S(C)(=O)=O)c([C@@H]3CCCN(S(=O)(=O)Cc4ccccc4)C3)cc12] | 5-[(3S)-1-(benzylsulfonyl)piperidin-3-yl]-2-(4-fluorophenyl)-N-methyl-6-[methyl(methylsulfonyl)amino]-1-benzofuran-3-carboxamide | 614 |
| 122 | 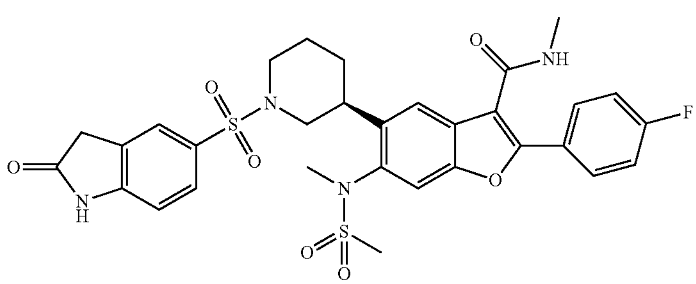 [SMILES: CNC(=O)c1c(-c2ccc(F)cc2)oc2cc(N(C)S(C)(=O)=O)c([C@@H]3CCCN(S(=O)(=O)c4ccc5c(c4)CC(=O)N5)C3)cc12] | 2-(4-fluorophenyl)-N-methyl-6-[methyl(methylsulfonyl)amino]-5-{(3S)-1-[(2-oxo-2,3-dihydro-1H-indol-5-yl)sulfonyl]piperidin-3-yl}-1-benzofuran-3-carboxamide | 655 |

| Example | Structure | IUPAC Name | Mass [M + H]+ |
|---|---|---|---|
| 123 | 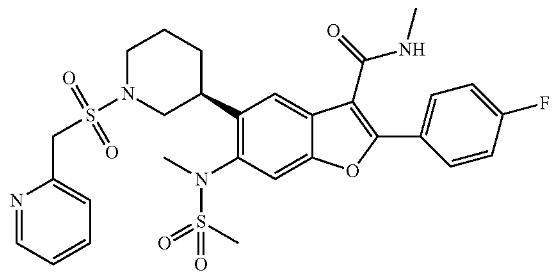 [SMILES: CNC(=O)c1c(-c2ccc(F)cc2)oc2cc(N(C)S(C)(=O)=O)c([C@@H]3CCCN(S(=O)(=O)Cc4ccccn4)C3)cc12] | 2-(4-fluorophenyl)-N-methyl-6-[methyl(methylsulfonyl)amino]-5-{(3S)-1-[(pyridin-2-ylmethyl)sulfonyl]piperidin-3-yl}-1-benzofuran-3-carboxamide | 615 |
| 124 | 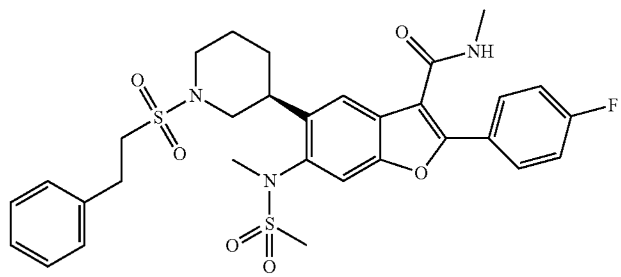 [SMILES: CNC(=O)c1c(-c2ccc(F)cc2)oc2cc(N(C)S(C)(=O)=O)c([C@@H]3CCCN(S(=O)(=O)CCc4ccccc4)C3)cc12] | 2-(4-fluorophenyl)-N-methyl-6-[methyl(methylsulfonyl)amino]-5-{(3S)-1-[(2-phenylethyl)sulfonyl]piperidin-3-yl}-1-benzofuran-3-carboxamide | 628 |
| 125 | 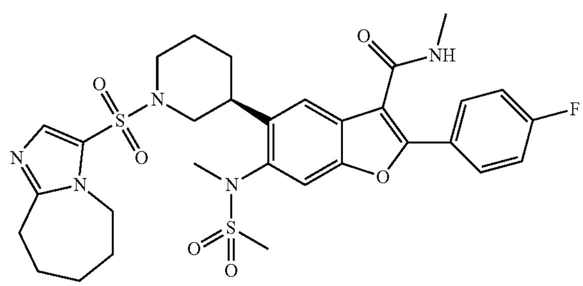 [SMILES: CNC(=O)c1c(-c2ccc(F)cc2)oc2cc(N(C)S(C)(=O)=O)c([C@@H]3CCCN(S(=O)(=O)c4cnc5n4CCCCC5)C3)cc12] | 2-(4-fluorophenyl)-N-methyl-6-[methyl(methylsulfonyl)amino]-5-[(3S)-1-(6,7,8,9-tetrahydro-5H-imidazo[1,2-a]azepin-3-ylsulfonyl)piperidin-3-yl]-1-benzofuran-3-carboxamide | 658 |
| 126 | 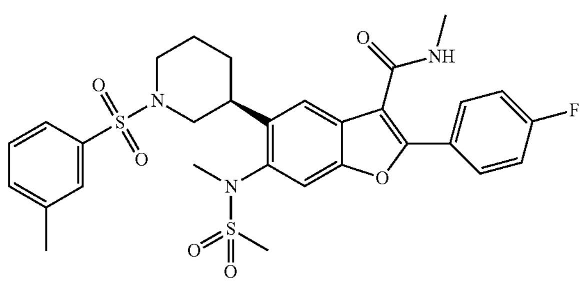 [SMILES: CNC(=O)c1c(-c2ccc(F)cc2)oc2cc(N(C)S(C)(=O)=O)c([C@@H]3CCCN(S(=O)(=O)c4cccc(C)c4)C3)cc12] | 2-(4-fluorophenyl)-N-methyl-6-[methyl(methylsulfonyl)amino]-5-{(3S)-1-[(3-methylphenyl)sulfonyl]piperidin-3-yl}-1-benzofuran-3-carboxamide | 614 |
| 127 | 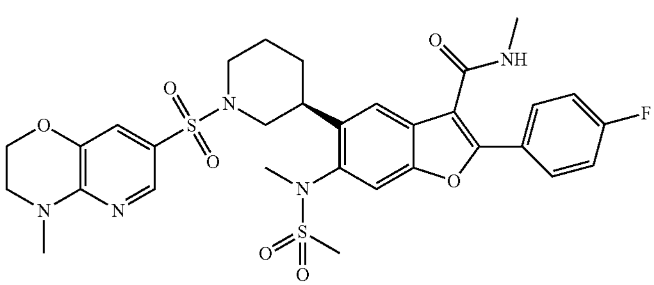 [SMILES: CNC(=O)c1c(-c2ccc(F)cc2)oc2cc(N(C)S(C)(=O)=O)c([C@@H]3CCCN(S(=O)(=O)c4cnc5c(c4)OCCN5C)C3)cc12] | 2-(4-fluorophenyl)-N-methyl-5-{(3S)-1-[(4-methyl-3,4-dihydro-2H-pyrido[3,2-b][1,4]oxazin-7-yl)sulfonyl]piperidin-3-yl}-6-[methyl(methylsulfonyl)amino]-1-benzofuran-3-carboxamide | 672 |

-continued

| Example | Structure | IUPAC Name | Mass [M + H]+ |
|---|---|---|---|
| 128 | 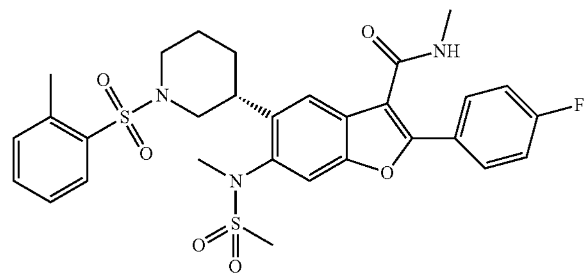 [SMILES: CNC(=O)c1c(-c2ccc(F)cc2)oc2cc(N(C)S(C)(=O)=O)c([C@H]3CCCN(S(=O)(=O)c4ccccc4C)C3)cc12] | 2-(4-fluorophenyl)-N-methyl-6-[methyl(methylsulfonyl)amino]-5-{(3R)-1-[(2-methylphenyl)sulfonyl]piperidin-3-yl}-1-benzofuran-3-carboxamide | 614 |
| 129 | 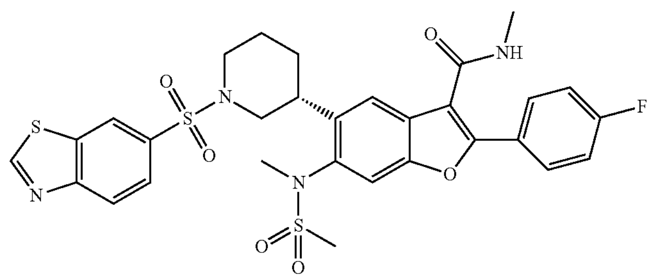 [SMILES: CNC(=O)c1c(-c2ccc(F)cc2)oc2cc(N(C)S(C)(=O)=O)c([C@H]3CCCN(S(=O)(=O)c4ccc5ncsc5c4)C3)cc12] | 5-[(3R)-1-(1,3-benzothiazol-6-ylsulfonyl)piperidin-3-yl]-2-(4-fluorophenyl)-N-methyl-6-[methyl(methylsulfonyl)amino]-1-benzofuran-3-carboxamide | 657 |
| 130 | 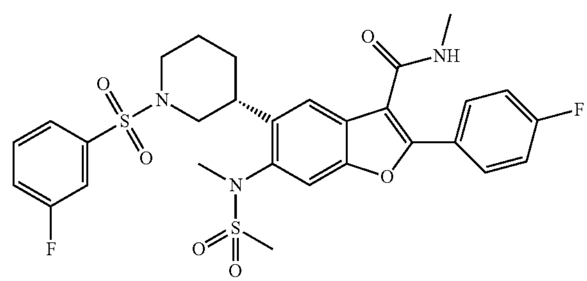 | 2-(4-fluorophenyl)-5-{(3R)-1-[(3-fluorophenyl)sulfonyl]piperidin-3-yl}-N-methyl-6-[methyl(methylsulfonyl)amino]-1-benzofuran-3-carboxamide | 618 |
| 131 | 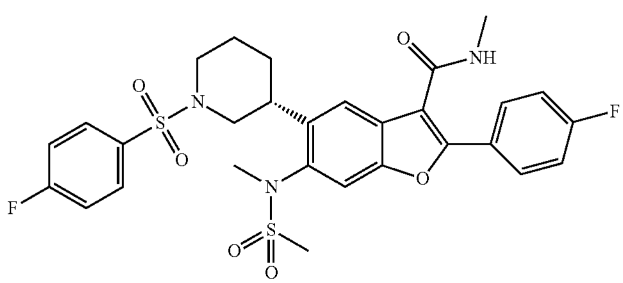 [SMILES: CNC(=O)c1c(-c2ccc(F)cc2)oc2cc(N(C)S(C)(=O)=O)c([C@H]3CCCN(S(=O)(=O)c4ccc(F)cc4)C3)cc12] | 2-(4-fluorophenyl)-5-{(3R)-1-[(4-fluorophenyl)sulfonyl]piperidin-3-yl}-N-methyl-6-[methyl(methylsulfonyl)amino]-1-benzofuran-3-carboxamide | 618 |
| 132 | 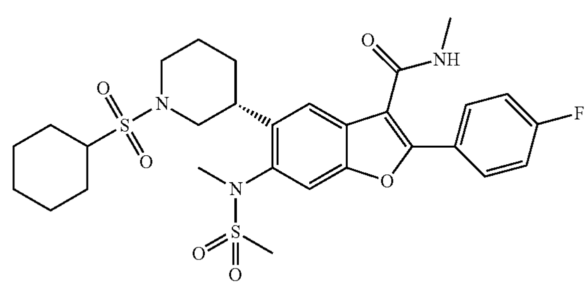 [SMILES: CNC(=O)c1c(-c2ccc(F)cc2)oc2cc(N(C)S(C)(=O)=O)c([C@H]3CCCN(S(=O)(=O)C4CCCCC4)C3)cc12] | 5-[(3R)-1-(cyclohexylsulfonyl)piperidin-3-yl]-2-(4-fluorophenyl)-N-methyl-6-[methyl(methylsulfonyl)amino]-1-benzofuran-3-carboxamide | 606 |

| Example | Structure | IUPAC Name | Mass [M + H]+ |
|---|---|---|---|
| 133 | 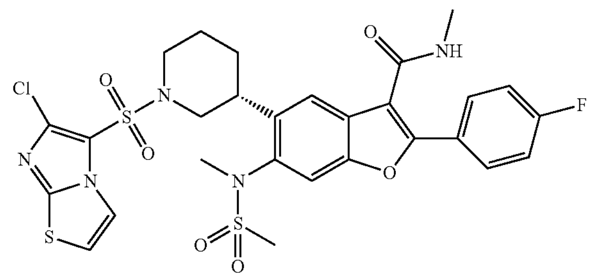 [SMILES: CNC(=O)c1c(-c2ccc(F)cc2)oc2cc(N(C)S(C)(=O)=O)c([C@H]3CCCN(S(=O)(=O)c4c(Cl)nc5sccn45)C3)cc12] | 5-{(3R)-1-[(6-chloroimidazo[2,1-b][1,3]thiazol-5-yl)sulfonyl]piperidin-3-yl}-2-(4-fluorophenyl)-N-methyl-6-[methyl(methylsulfonyl)amino]-1-benzofuran-3-carboxamide | 680 |
| 134 | 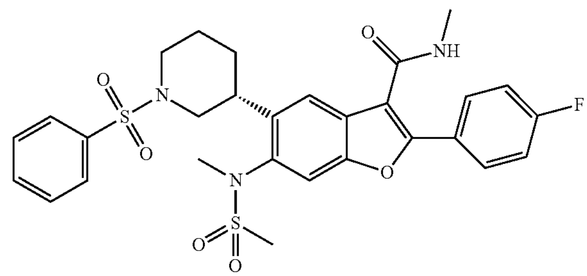 [SMILES: CNC(=O)c1c(-c2ccc(F)cc2)oc2cc(N(C)S(C)(=O)=O)c([C@H]3CCCN(S(=O)(=O)c4ccccc4)C3)cc12] | 2-(4-fluorophenyl)-N-methyl-6-[methyl(methylsulfonyl)amino]-5-[(3R)-1-(phenylsulfonyl)piperidin-3-yl]-1-benzofuran-3-carboxamide | 600 |
| 135 | 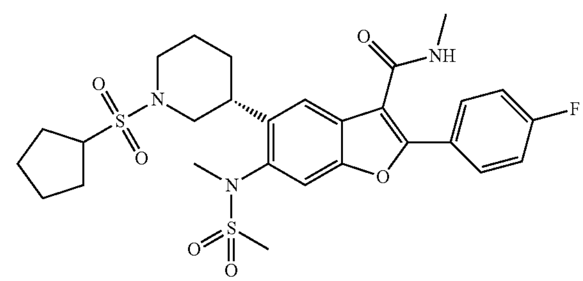 [SMILES: CNC(=O)c1c(-c2ccc(F)cc2)oc2cc(N(C)S(C)(=O)=O)c([C@H]3CCCN(S(=O)(=O)C4CCCC4)C3)cc12] | 5-[(3R)-1-(cyclopentylsulfonyl)piperidin-3-yl]-2-(4-fluorophenyl)-N-methyl-6-[methyl(methylsulfonyl)amino]-1-benzofuran-3-carboxamide | 592 |
| 136 | 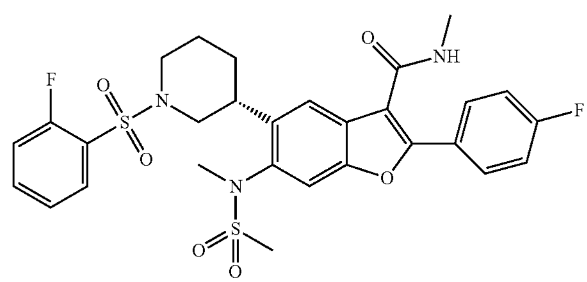 [SMILES: CNC(=O)c1c(-c2ccc(F)cc2)oc2cc(N(C)S(C)(=O)=O)c([C@H]3CCCN(S(=O)(=O)c4ccccc4F)C3)cc12] | 2-(4-fluorophenyl)-5-{(3R)-1-[(2-fluorophenyl)sulfonyl]piperidin-3-yl}-N-methyl-6-[methyl(methylsulfonyl)amino]-1-benzofuran-3-carboxamide | 618 |
| 137 | 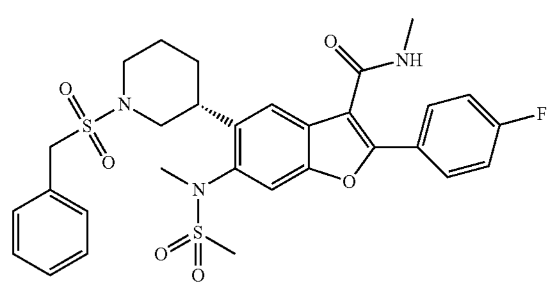 | 5-[(3R)-1-(benzylsulfonyl)piperidin-3-yl]-2-(4-fluorophenyl)-N-methyl-6-[methyl(methylsulfonyl)amino]-1-benzofuran-3-carboxamide | 614 |

| Example | Structure | IUPAC Name | Mass [M + H]+ |
|---|---|---|---|
| 138 | 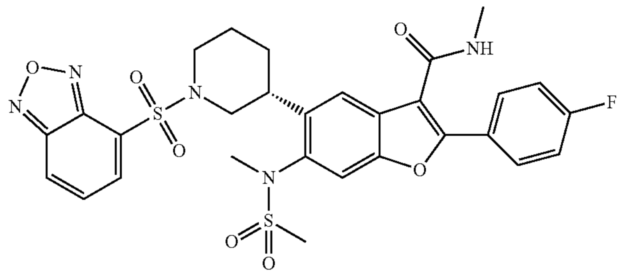 [SMILES: CNC(=O)c1c(-c2ccc(F)cc2)oc2cc(N(C)S(C)(=O)=O)c([C@H]3CCCN(S(=O)(=O)c4cccc5nonc45)C3)cc12] | 5-[(3R)-1-(2,1,3-benzoxadiazol-4-ylsulfonyl)piperidin-3-yl]-2-(4-fluorophenyl)-N-methyl-6-[methyl(methylsulfonyl)amino]-1-benzofuran-3-carboxamide | 642 |
| 139 | 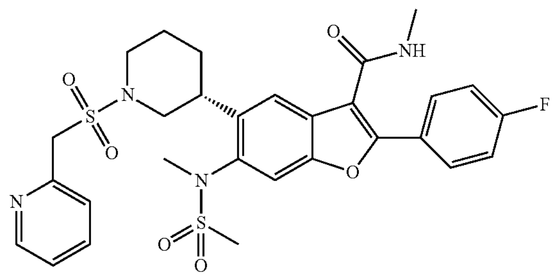 [SMILES: CNC(=O)c1c(-c2ccc(F)cc2)oc2cc(N(C)S(C)(=O)=O)c([C@H]3CCCN(S(=O)(=O)Cc4ccccn4)C3)cc12] | 2-(4-fluorophenyl)-N-methyl-6-[methyl(methylsulfonyl)amino]-5-{(3R)-1-[(pyridin-2-ylmethyl)sulfonyl]piperidin-3-yl}-1-benzofuran-3-carboxamide | 615 |
| 140 | 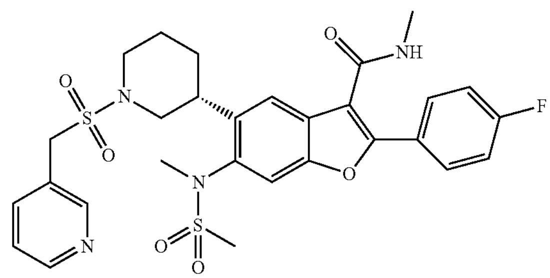 | 2-(4-fluorophenyl)-N-methyl-6-[methyl(methylsulfonyl)amino]-5-{(3R)-1-[(pyridin-3-ylmethyl)sulfonyl]piperidin-3-yl}-1-benzofuran-3-carboxamide | 615 |
| 141 | 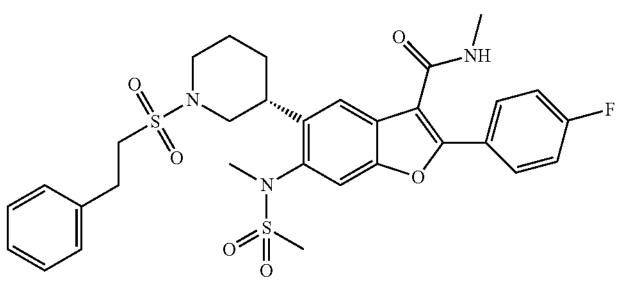 [SMILES: CNC(=O)c1c(-c2ccc(F)cc2)oc2cc(N(C)S(C)(=O)=O)c([C@H]3CCCN(S(=O)(=O)CCc4ccccc4)C3)cc12] | 2-(4-fluorophenyl)-N-methyl-6-[methyl(methylsulfonyl)amino]-5-{(3R)-1-[(2-phenylethyl)sulfonyl]piperidin-3-yl}-1-benzofuran-3-carboxamide | 628 |
| 142 | 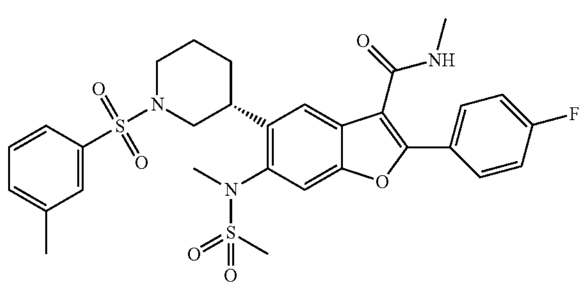 [SMILES: CNC(=O)c1c(-c2ccc(F)cc2)oc2cc(N(C)S(C)(=O)=O)c([C@H]3CCCN(S(=O)(=O)c4cccc(C)c4)C3)cc12] | 2-(4-fluorophenyl)-N-methyl-6-[methyl(methylsulfonyl)amino]-5-{(3R)-1-[(3-methylphenyl)sulfonyl]piperidin-3-yl}-1-benzofuran-3-carboxamide | 614 |

| Example | Structure | IUPAC Name | Mass [M + H]+ |
|---|---|---|---|
| 143 | 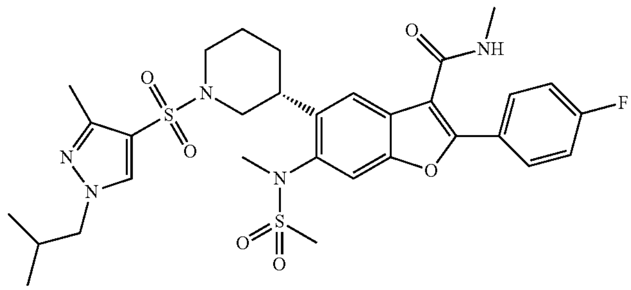 [SMILES: CNC(=O)c1c(-c2ccc(F)cc2)oc2cc(N(C)S(C)(=O)=O)c([C@H]3CCCN(S(=O)(=O)c4cn(CC(C)C)nc4C)C3)cc12] | 2-(4-fluorophenyl)-N-methyl-5-[(3R)-1-{[3-methyl-1-(2-methylpropyl)-1H-pyrazol-4-yl]sulfonyl}piperidin-3-yl]-6-[methyl(methylsulfonyl)amino]-1-benzofuran-3-carboxamide | 660 |
| 144 | 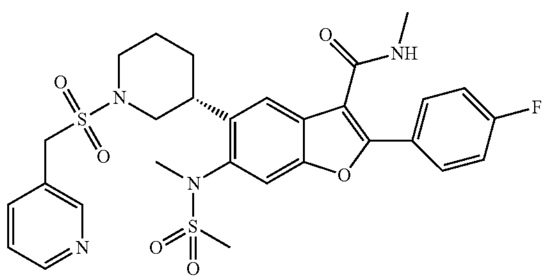 [SMILES: CNC(=O)c1c(-c2ccc(F)cc2)oc2cc(N(C)S(C)(=O)=O)c([C@H]3CCCN(S(=O)(=O)Cc4cccnc4)C3)cc12] | 2-(4-fluorophenyl)-N-methyl-6-[methyl(methylsulfonyl)amino]-5-{(3R)-1-[(pyridin-4-ylmethyl)sulfonyl]piperidin-3-yl}-1-benzofuran-3-carboxamide | 615 |

Example 145

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278(14) J. BIOLOGICAL CHEMISTRY 11979 (2003). However, the underlying principles are common to all of these determinations, and are outlined below.

Stable neomycin phosphotransferase encoding replicons-harboring cell lines were used, so all cell lines were maintained under G418 selection prior to the assay. Potency was deteremined using a cell ELISA assay with an antibody to the replicons encoded NS3/4a protease. See Caterina Trozzi et al., *In Vitro Selection and Characterization of Hepatitis C Virus Serine Protease Variants Resistant to an Active-Site Peptide Inhibitor*, 77(6) J. Virol. 3669 (2003). To initiate an assay, replicon cells were plated in the presence of a dilution series of test compound in the absence of G418. Typically, the assays were performed in a 96-well plate formate for manual operation, or a 384-well plate format for automated assay. Replicon cells and compound were incubated for 96 hours. At the end of the assay, cells were washed free of media and compound, and the cells were then lysed. RNA was quantified indirectly through detection of replicon-encoded NS3/4A protein levels, through an ELISA-based assay with an antibody specific for NS3/4A. $IC_{50}$ determinations were calculated as a percentage of a DMSO control by fitting the data to a four-parameter fit function and the data obtained is provided in the table below.

Data for selected compounds of the present invention was obtained for genotypes 1a and 1b using this method and is provided in the table below:

| Example# | 1a $IC_{50}$ (nM) | 1b $IC_{50}$ (nM) |
|---|---|---|
| 1 | 56.91 | 34.3 |
| 2 | 84.07 | 41.04 |
| 3 | 148.2 | 109.4 |
| 4 | 7.026 | 6.525 |
| 5 | 53.68 | 19.34 |
| 6 | 11.12 | 17.37 |
| 7 | 5.79 | 11.59 |
| 8 | 28.22 | 36.89 |
| 9 | 53.98 | 67.85 |
| 10 | 16 | 26.58 |
| 11 | 21.36 | 17.23 |
| 12 | 92.81 | 37.76 |
| 13 | 140.5 | 165.2 |
| 14 | 25.87 | 2.768 |
| 15 | 125.4 | 11.25 |
| 16 | 332.6 | 106.4 |
| 17 | 137.7 | 58.2 |
| 18 | 187.8 | 72.25 |
| 19 | 43.76 | 50.83 |
| 20 | 48.04 | 46.9 |
| 21 | 16.22 | 9.96 |
| 22 | 40.84 | 18.77 |
| 23 | 45.47 | 57.71 |
| 24 | 32.68 | 40.46 |
| 25 | 16.43 | 5.259 |
| 26 | 15.79 | 12.59 |
| 27 | 44.41 | 35.21 |
| 28 | 23.86 | 21.39 |
| 29 | 83.13 | 147.8 |
| 30 | 122.3 | 215.1 |
| 31 | 17.08 | 9.38 |
| 32 | 53.12 | 19.18 |
| 33 | 129.8 | 196.5 |
| 34 | 84.09 | 65.3 |
| 35 | 71.59 | 48.93 |
| 36 | 269.4 | 285.6 |
| 37 | 162.4 | 92.77 |

-continued

| Example# | 1a IC$_{50}$ (nM) | 1b IC$_{50}$ (nM) |
|---|---|---|
| 38 | 277.4 | 115.5 |
| 39 | 268.3 | 36.44 |
| 40 | 141.8 | 27.63 |
| 41 | 30.67 | 13.47 |
| 42 | 105.6 | 23.94 |
| 43 | 41.23 | 92.96 |
| 44 | 70.97 | 82.36 |
| 45 | 224.6 | 70.9 |
| 46 | 11.94 | 9.474 |
| 47 | 8.368 | 5.372 |
| 48 | 40.19 | 24.75 |
| 49 | 5.764 | 7.439 |
| 50 | 81.65 | 20.06 |
| 51 | 4.99 | 7.118 |
| 52 | 32.64 | 42.64 |
| 53 | 14.57 | 15.7 |
| 54 | 7.383 | 13.87 |
| 55 | 5.652 | 3.626 |
| 56 | 53.66 | 23.85 |
| 57 | 19.88 | 22.2 |
| 58 | 132.5 | 36.15 |
| 59 | 307.6 | 119.7 |
| 60 | 115.9 | 40.31 |
| 61 | 251.4 | 99.55 |
| 62 | 192.1 | 41.18 |
| 63 | 156 | 68.11 |
| 64 | 135.2 | 40.72 |
| 65 | 140.1 | 46.26 |
| 66 | 92.59 | 21.21 |
| 67 | 156.2 | 87.42 |
| 68 | 97.95 | 88.95 |
| 69 | 74.44 | 22.76 |
| 70 | 206.8 | 67.94 |
| 71 | 168.3 | 95.43 |
| 72 | 124.9 | 23.62 |
| 73 | 50.5 | 23.36 |
| 74 | 54.75 | 43.37 |
| 75 | 72.29 | 12.02 |
| 76 | 49.36 | 9.961 |
| 77 | 64.3 | 19.24 |
| 78 | 248.2 | 81.15 |
| 79 | 64.78 | 33.12 |
| 80 | 3.165 | 4.5 |
| 81 | 14.13 | 11.63 |
| 82 | 2.203 | 3.262 |
| 83 | 38.22 | 22.45 |
| 84 | 2.774 | 3.035 |
| 85 | 25.99 | 12.49 |
| 86 | 233.7 | 115.2 |
| 87 | 267.1 | 111.6 |
| 88 | 70.72 | 38.69 |
| 89 | 84.36 | 45.18 |
| 90 | 41.59 | 20.72 |
| 91 | 180.1 | 62.56 |
| 92 | 274.2 | 96.96 |
| 93 | 180.7 | 102 |
| 94 | 299.9 | 167.6 |
| 95 | 175.8 | 105.9 |
| 96 | 423.3 | 218.6 |
| 97 | 335.6 | 470.3 |
| 98 | 240.6 | 111.8 |
| 99 | 136.8 | 66.74 |
| 100 | 65.04 | 20.39 |
| 101 | 103.2 | 55.87 |
| 102 | 345.3 | 295.2 |
| 103 | 212.5 | 109.9 |
| 104 | 283.8 | 136.4 |
| 105 | 347 | 219.4 |
| 106 | 122.9 | 51.5 |
| 107 | 388.8 | 116.5 |
| 108 | 265.7 | 52.97 |
| 109 | 103.6 | 26.16 |
| 110 | 163.7 | 38.38 |
| 111 | 68.1 | 17.23 |
| 112 | 24.98 | 6.785 |
| 113 | 64.62 | 21.92 |

-continued

| Example# | 1a IC$_{50}$ (nM) | 1b IC$_{50}$ (nM) |
|---|---|---|
| 114 | 34.19 | 8.202 |
| 115 | 36.61 | 7.995 |
| 116 | 194.5 | 31.67 |
| 117 | 32.34 | 9.373 |
| 118 | 41.04 | 8.357 |
| 119 | 24.53 | 10.92 |
| 120 | 22.44 | 8.37 |
| 121 | 47.54 | 23.82 |
| 122 | 78.77 | 22.15 |
| 123 | 105.5 | 29.77 |
| 124 | 182 | 72.92 |
| 125 | 172.5 | 67.61 |
| 126 | 46.86 | 13.17 |
| 127 | 90.19 | 32.35 |
| 128 | 34.24 | 24.2 |
| 129 | 193.7 | 109.6 |
| 130 | 174.1 | 95.47 |
| 131 | 175.6 | 88.94 |
| 132 | 93.34 | 56.11 |
| 133 | 105.8 | 74.65 |
| 134 | 85.9 | 58.31 |
| 135 | 80.38 | 45.63 |
| 136 | 58.48 | 40.45 |
| 137 | 2.15 | 3.04 |
| 138 | 139.2 | 55.67 |
| 139 | 35.04 | 21.07 |
| 140 | 20.46 | 16.51 |
| 141 | 10.61 | 14.23 |
| 142 | 198.2 | 91.72 |
| 143 | 314.7 | 213.6 |
| 144 | 36.17 | 28.56 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:
1. A compound having the formula:

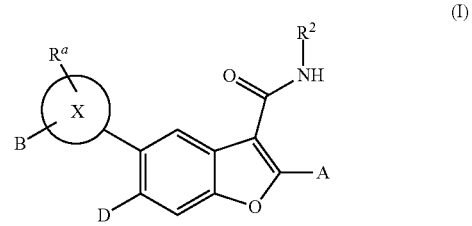

or a pharmaceutically acceptable salt thereof,
wherein:
X is a 5 or 6-membered saturated monocyclic ring with 1 or 2 heteroatom ring atoms independently selected from N and O;
A is fluorophenyl;
B is a) hydrogen;
  b) —C(O)CH=C(CH$_3$)$_2$;
  c) Ar;
  d) —C(O)—Ar;
  e) —C(O)CHR$^y$—Ar;
  f) —C(O)CH(NHR$^x$)—Ar;
  g) —SO$_2$(CH$_2$)$_{0-2}$—Ar;
  h) —SO$_2$—CH=CH—Ar;

i) —CO-Cyc;

j) —COCH$_2$-Cyc;

k) —SO$_2$-Cyc;

Ar is an aromatic ring system selected from:
(i) 5-6 membered monocyclic ring with 0, 1, or 2 heteroatom ring atoms independently selected from N or O, optionally substituted with 1 or 2 substituents independently selected from fluorophenyl, C$_1$-C$_6$ alkyl, and halo; and
(ii) 8-10 membered bicyclic rings with 1, 2 or 3 heteroatom ring atoms selected from N, O and S, optionally substituted with 1, 2 or 3 substituents independently selected from C$_1$-C$_6$ alkyl, C$_1$-C$_6$ alkoxy, halo, CF$_3$, cyano, oxo, —NH$_2$, and cyclopropylmethyl;

Cyc is C$_3$-C$_6$ cycloalkyl optionally substituted with fluorophenyl or pyridine; or 3-oxabicyclo[3.1.0]hexane;

D is H or NR$^3$SO$_2$R$^4$;

R$^2$, R$^3$, and R$^4$ are independently C$_1$-C$_6$ alkyl;

R$^a$ is hydrogen or C$_1$-C$_6$ alkyl;

R$^x$ is hydrogen or C(O)OC(CH$_3$)$_3$; and

R$^y$ is hydrogen, morpholinyl or Ar.

2. The compound of claim 1, or a pharmaceutically acceptable salt thereof, wherein X is

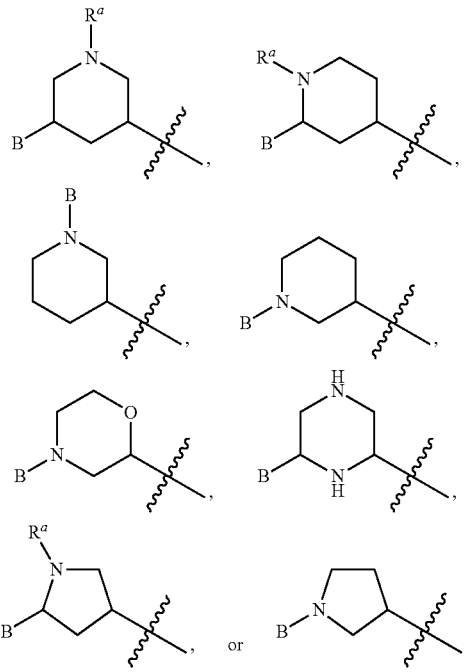

3. The compound of claim 2, or a pharmaceutically acceptable salt thereof, wherein R$^2$, R$^3$ and R$^4$ are methyl.

4. The compound of claim 3, or a pharmaceutically acceptable salt thereof, wherein D is N(CH$_3$)SO$_2$CH$_3$.

5. The compound of claim 4, or a pharmaceutically acceptable salt thereof, wherein each halo is F.

6. The compound of claim 1, or a pharmaceutically acceptable salt thereof, having the formula:

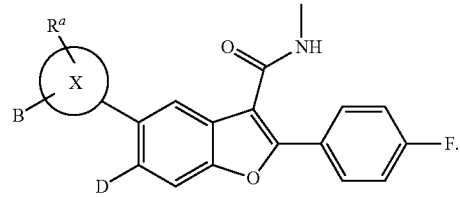

7. The compound of claim 6, or a pharmaceutically acceptable salt thereof, wherein X is

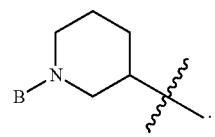

8. The compound of claim 7, or a pharmaceutically acceptable salt thereof, wherein B is Ar, —C(O)—Ar, or —SO$_2$—Ar; wherein Ar is a 9-membered bicyclic ring with 1, 2, or 3 heteroatom ring atoms selected from N, O and S, optionally substituted with 1, 2 or 3 substituents independently selected from C$_1$-C$_6$ alkyl, C$_1$-C$_6$ alkoxy, F, CF$_3$, and cyano.

9. The compound of claim 8, or a pharmaceutically acceptable salt thereof, wherein Ar is

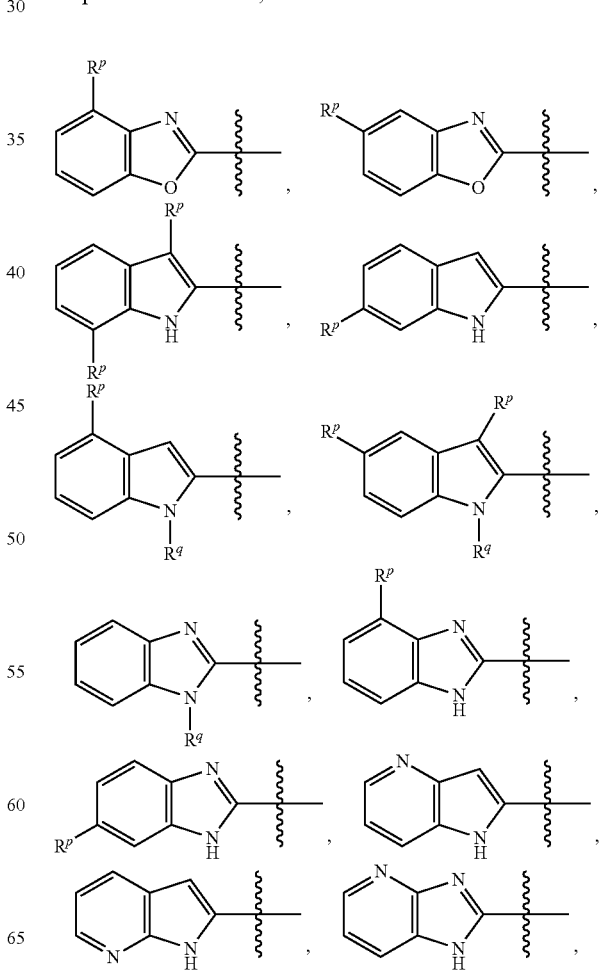

-continued

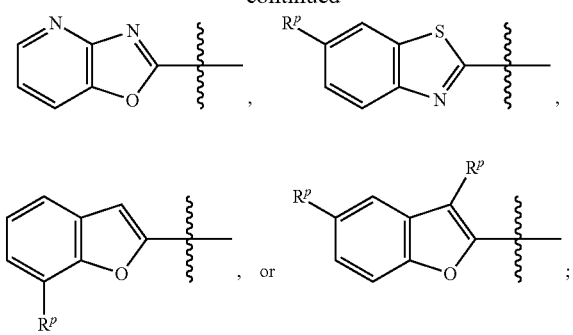

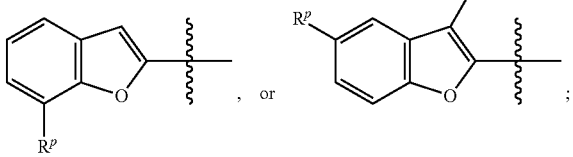

wherein each $R^p$ is independently selected from hydrogen, methyl, methoxy, F, $CF_3$, or cyano, and $R^q$ is hydrogen, methyl or ethyl.

10. The compound of claim 7, or a pharmaceutically acceptable salt thereof, wherein B is —$SO_2$—Ar, —$SO_2CH_2$—Ar, —$SO_2CH_2CH_2$—Ar, —C(O)—Ar; or —C(O)$CH_2$—Ar; wherein Ar is phenyl, methylphenyl, fluorophenyl, difluorophenyl, pyridine, or fluoropyridine.

11. The compound of claim 1 which is any one of:

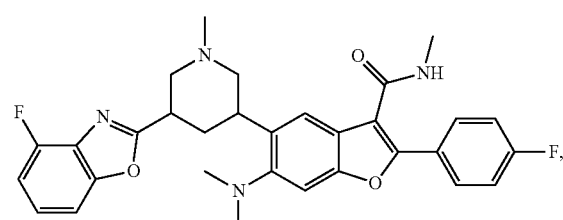

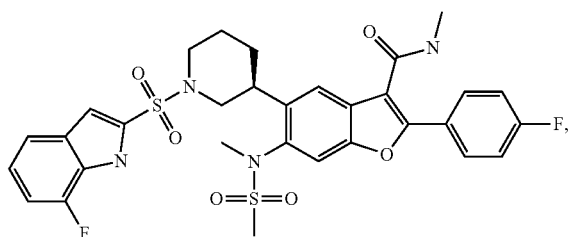

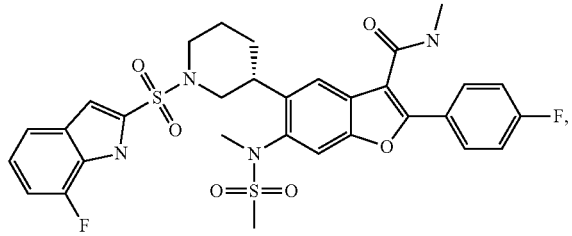

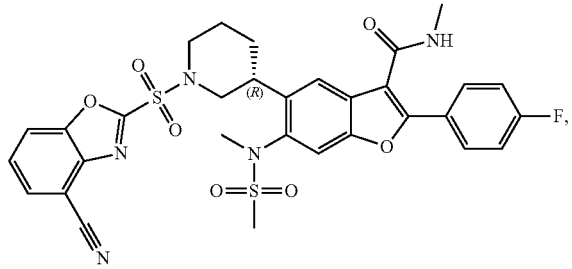

-continued

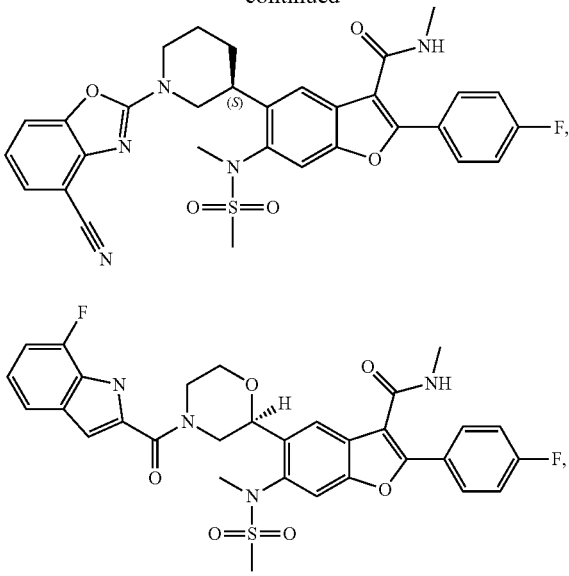

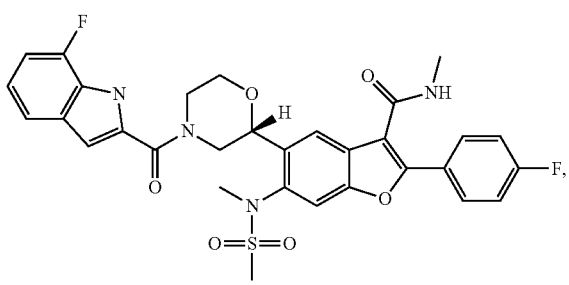

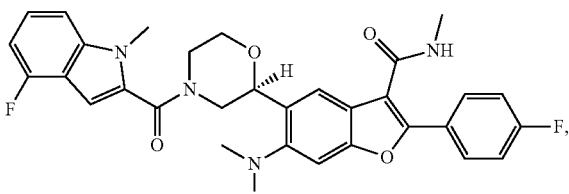

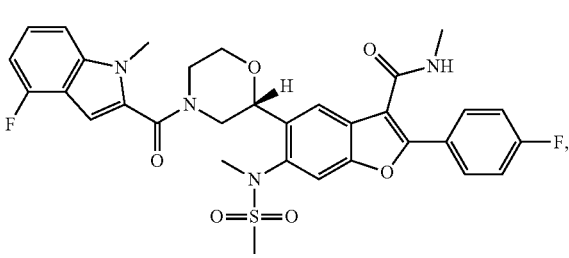

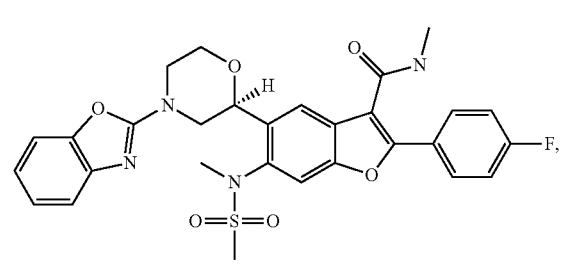

149
-continued
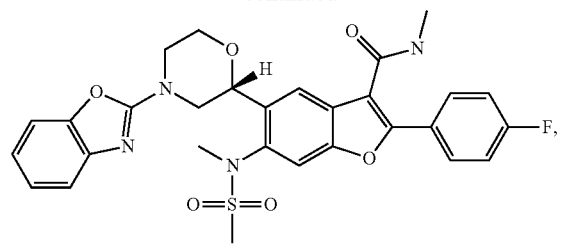
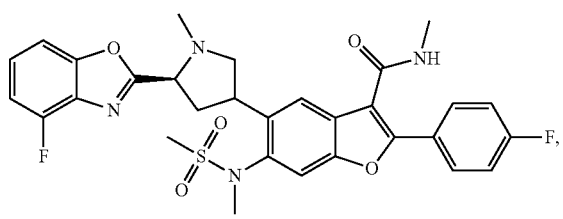
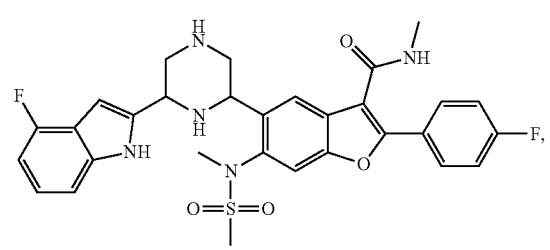
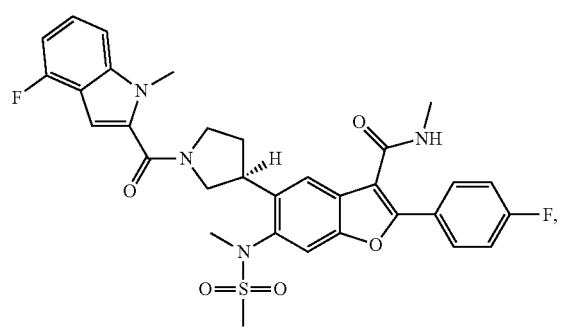
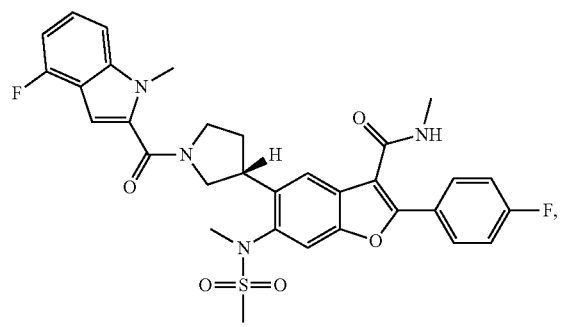
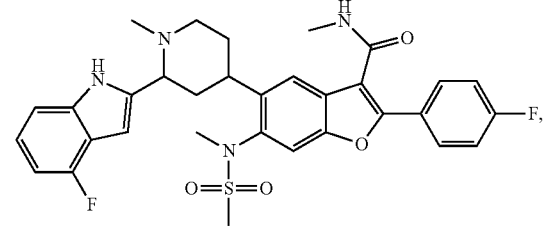
150
-continued
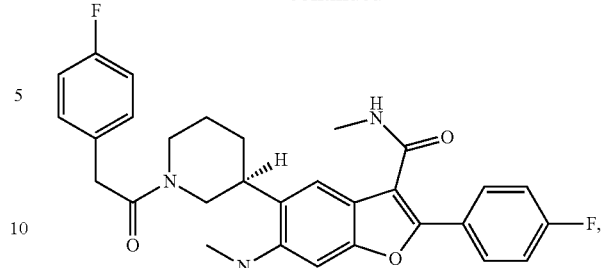
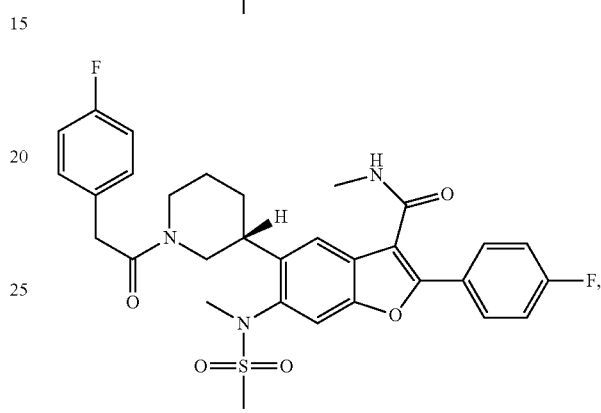
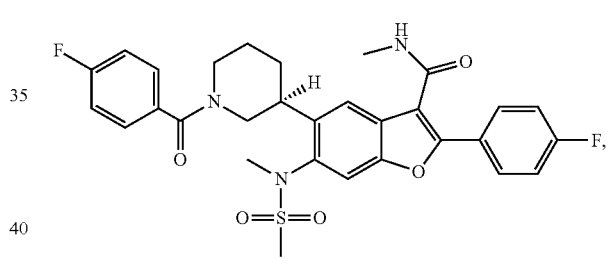
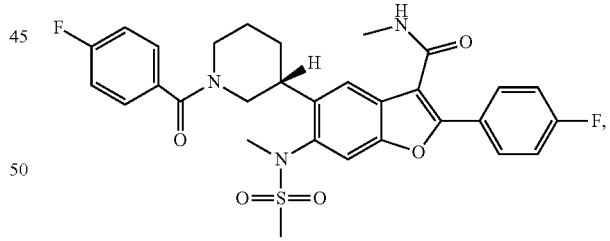
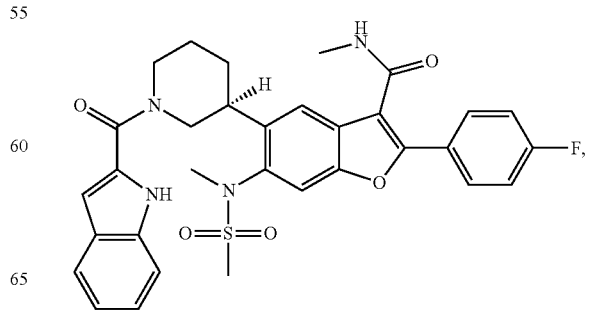

151
-continued
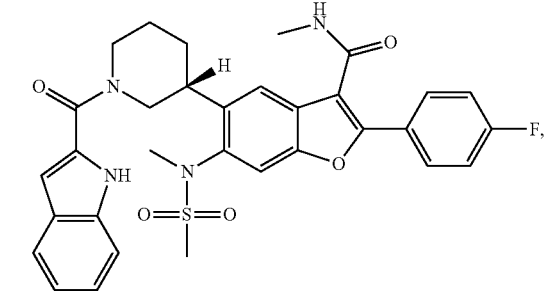
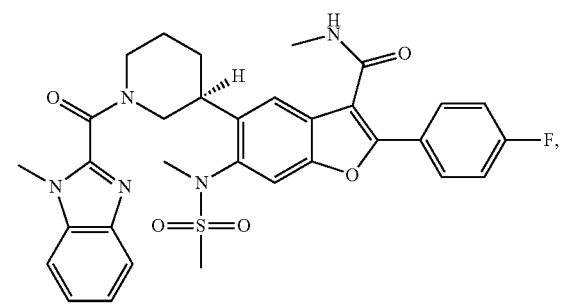
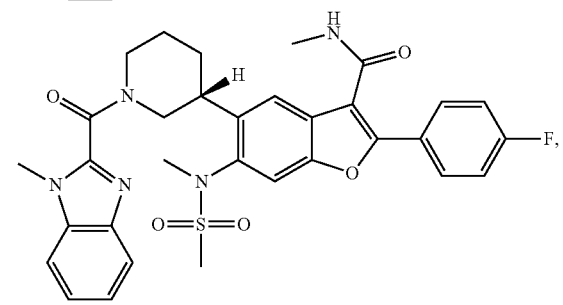
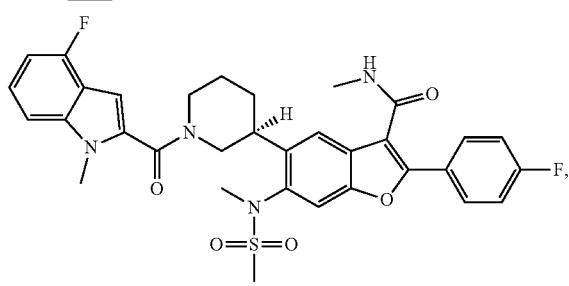
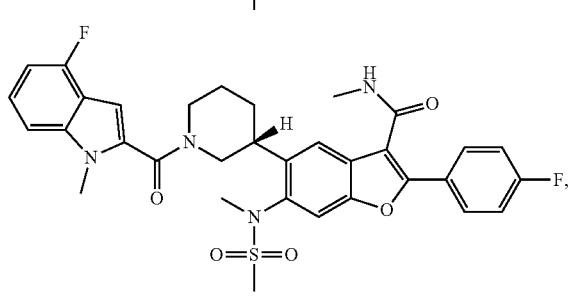
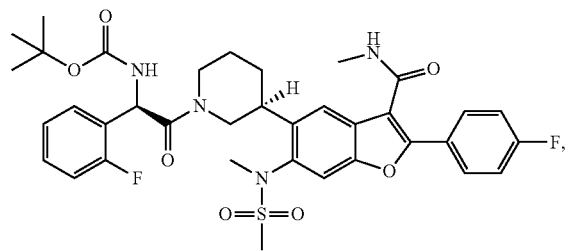
152
-continued
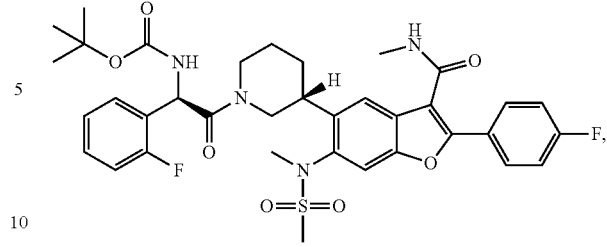
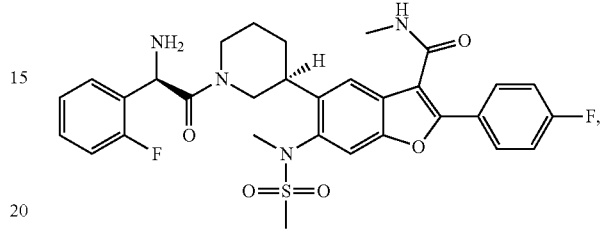
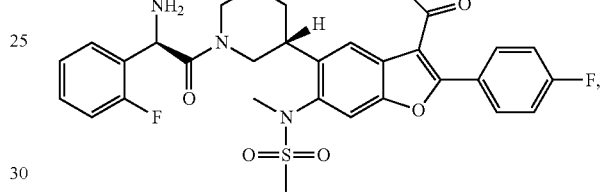
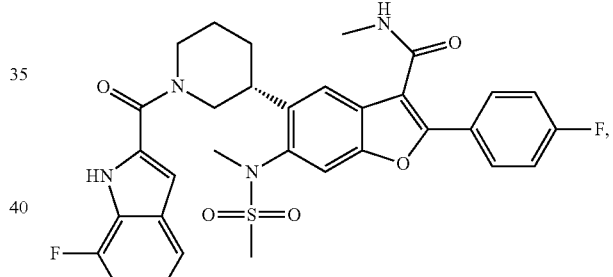
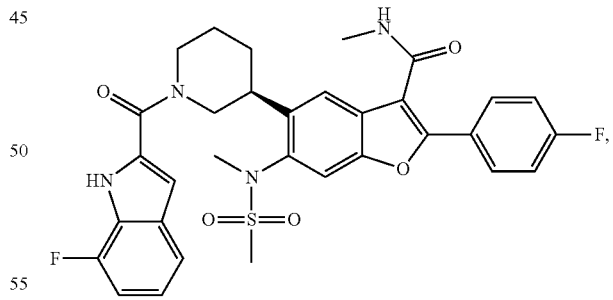
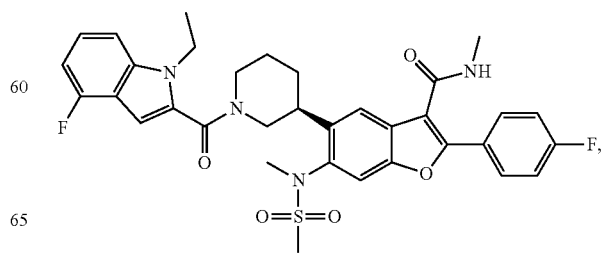

153
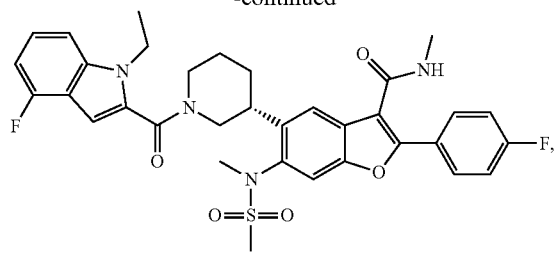
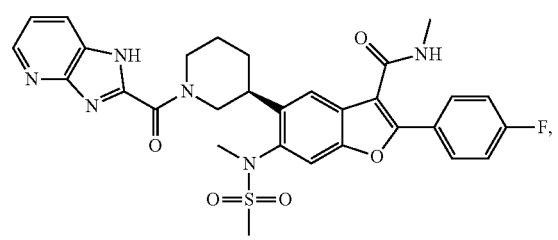
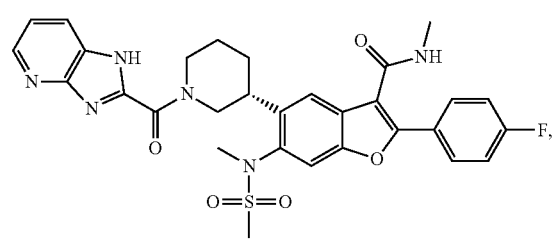
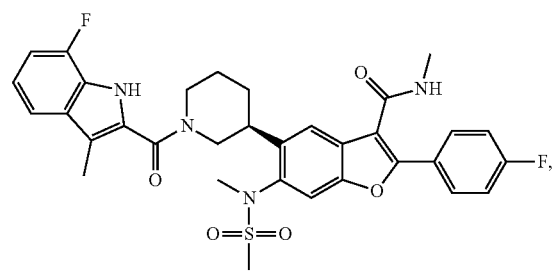
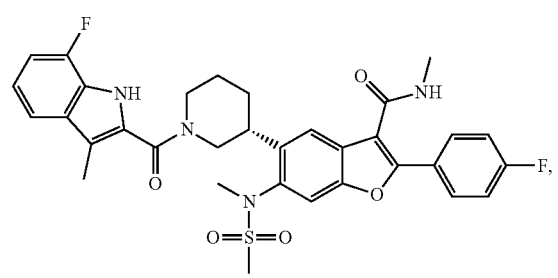
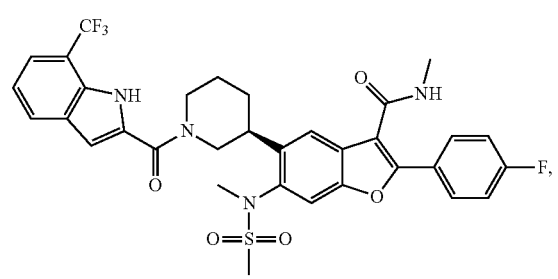
154
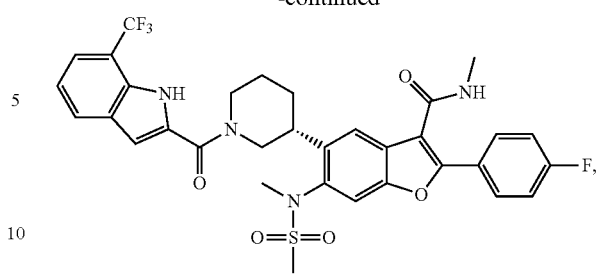
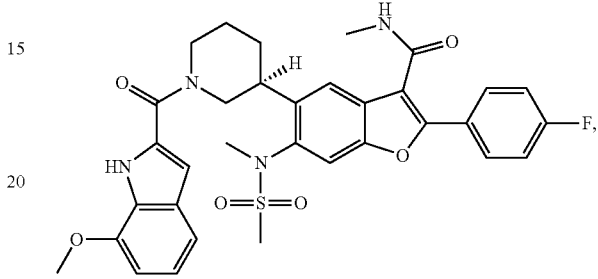
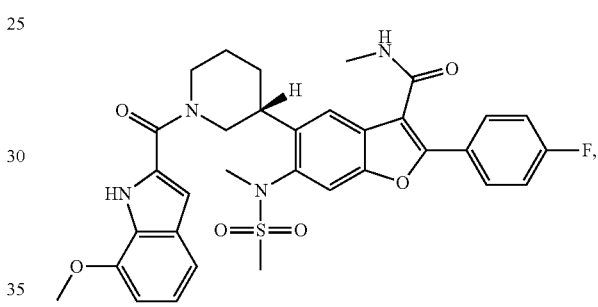
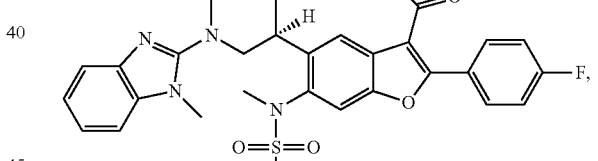
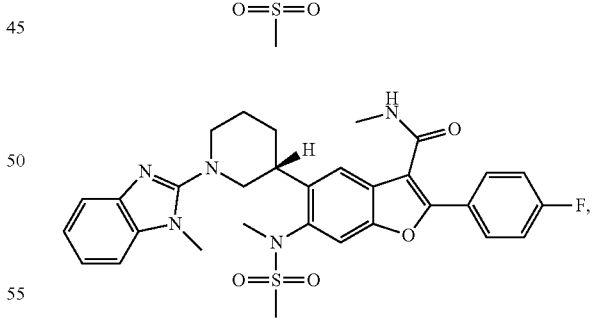
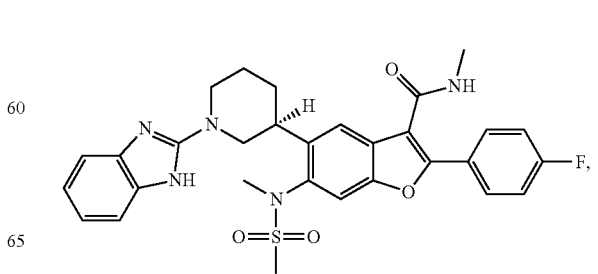

155
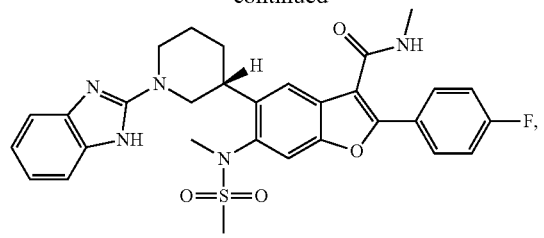
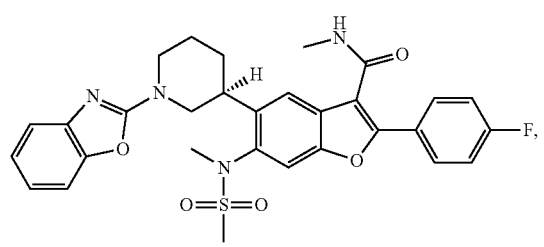
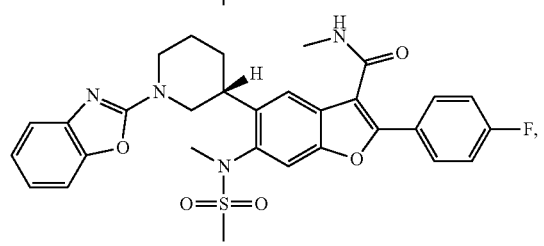
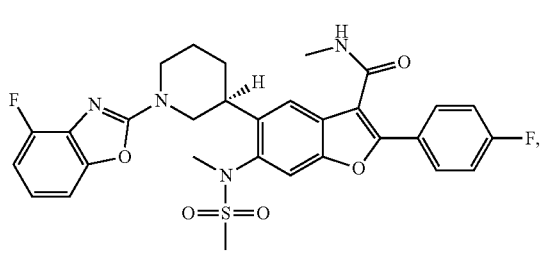
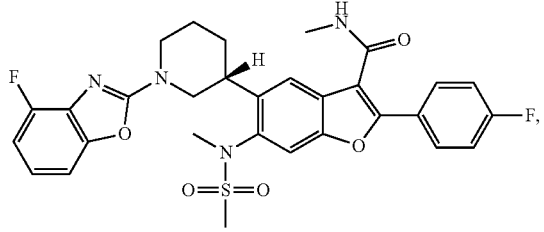
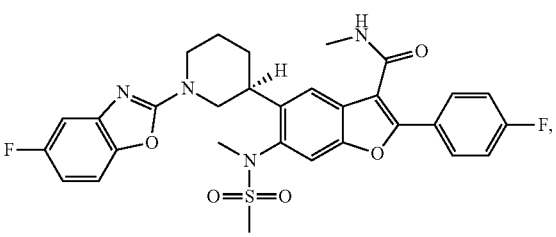
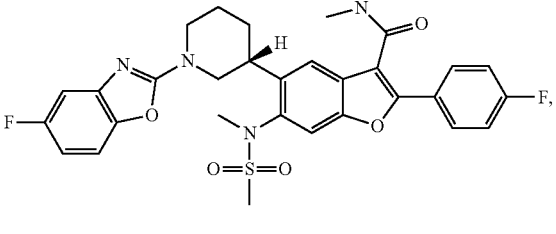
156
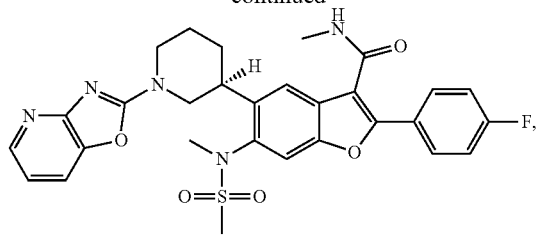
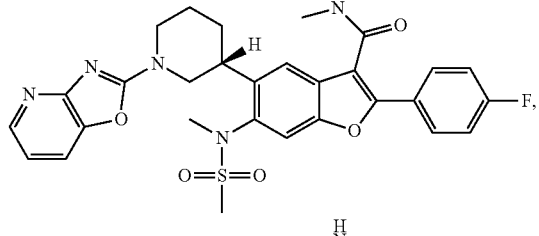
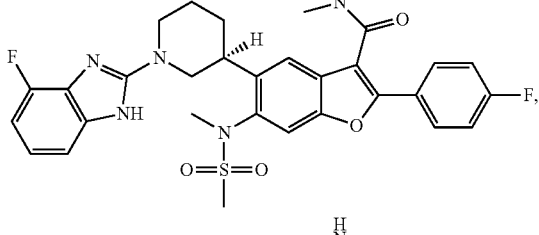
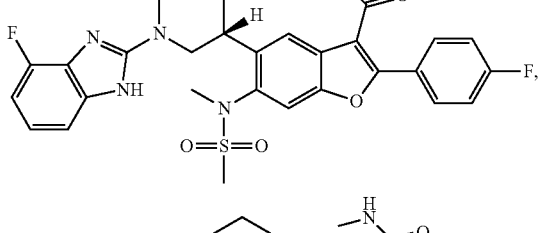
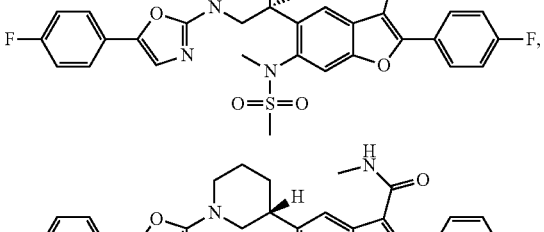
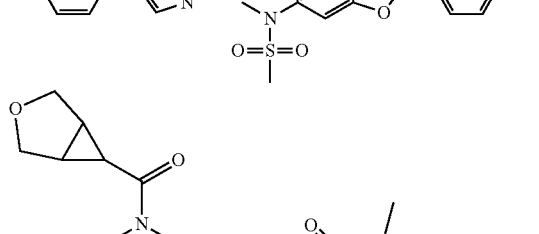
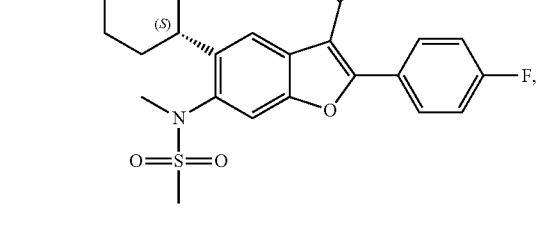

157
-continued
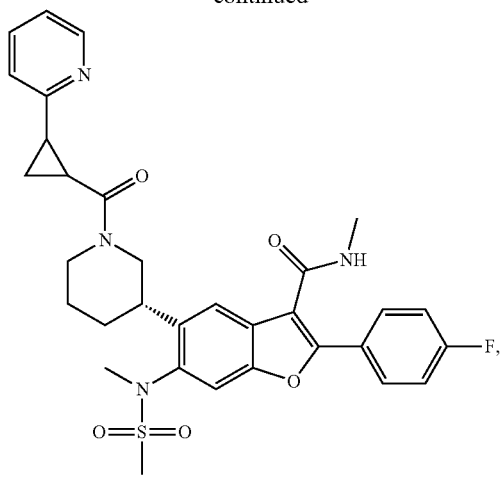
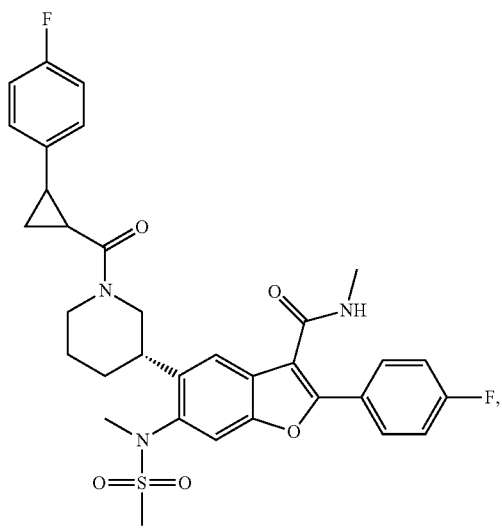
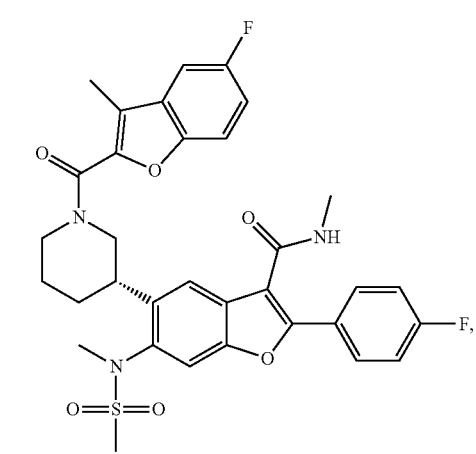
158
-continued
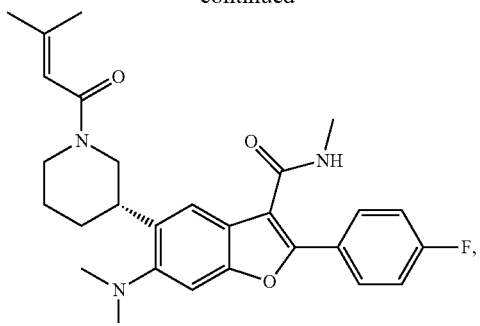
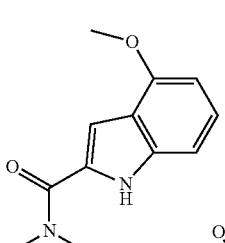
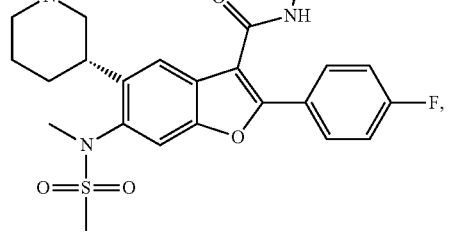
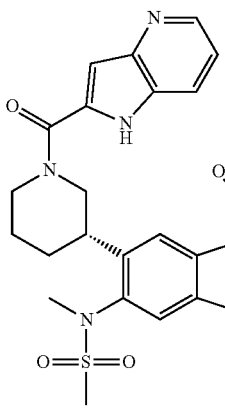
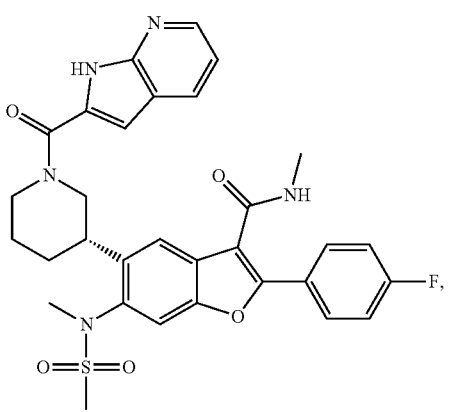

159
-continued
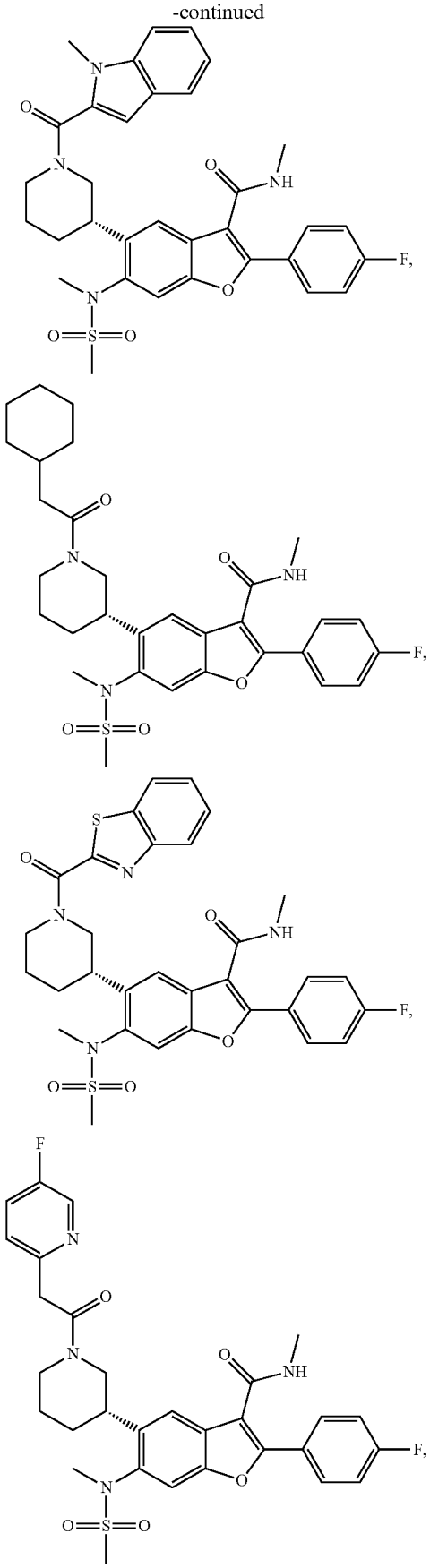
160
-continued
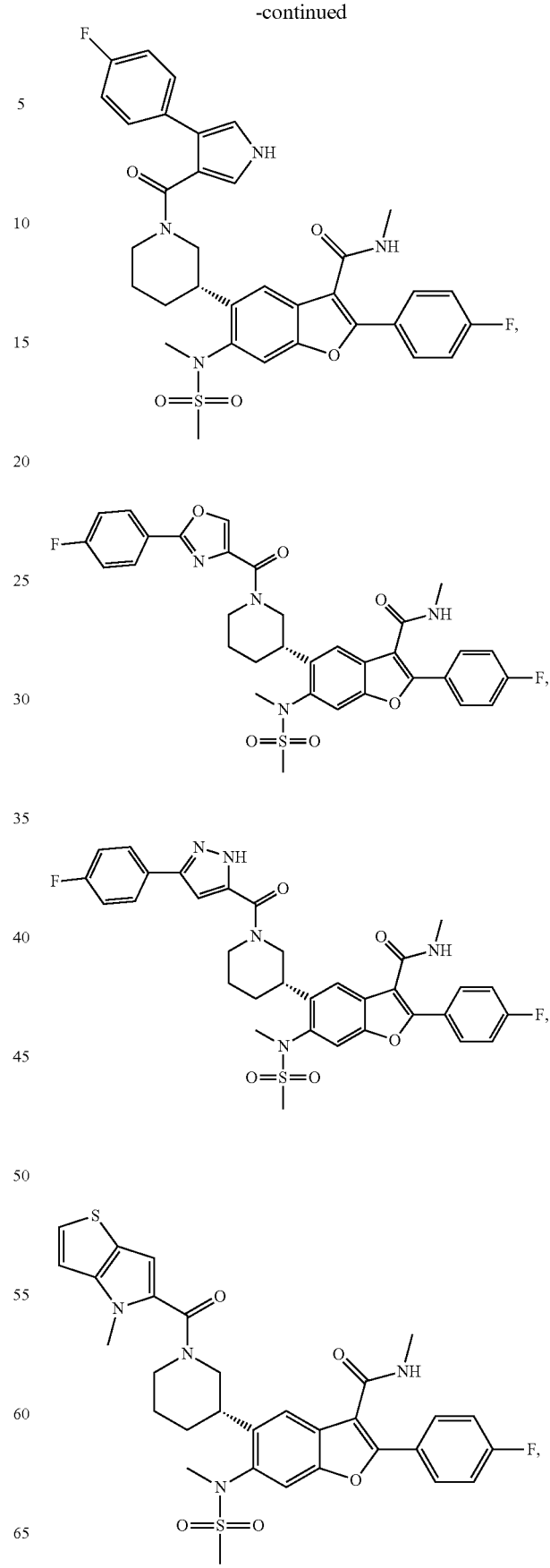

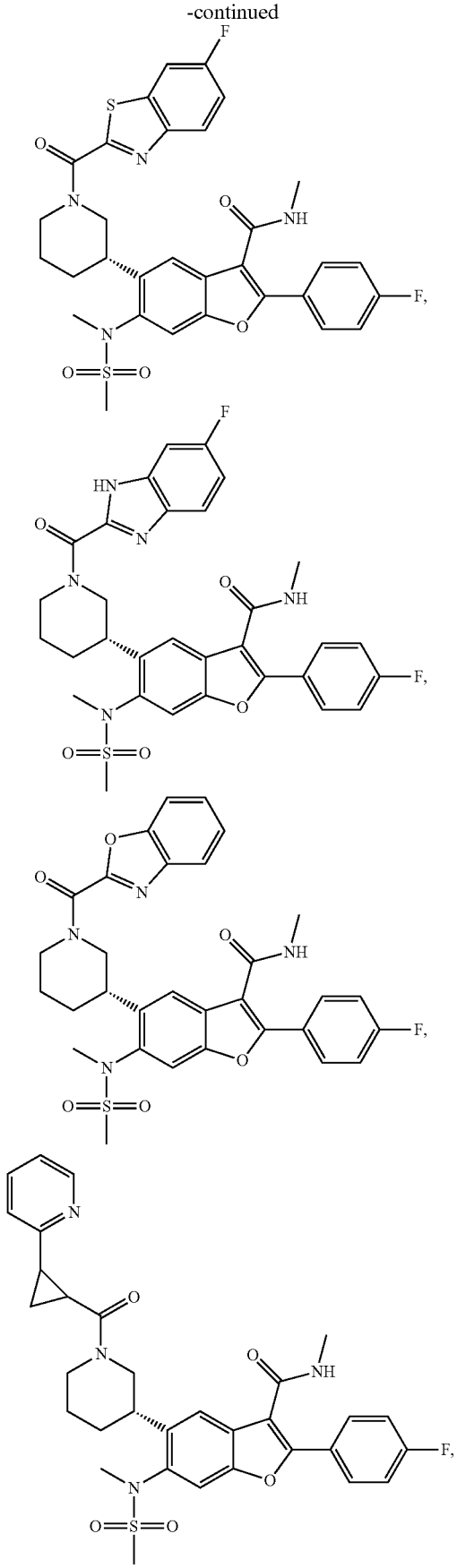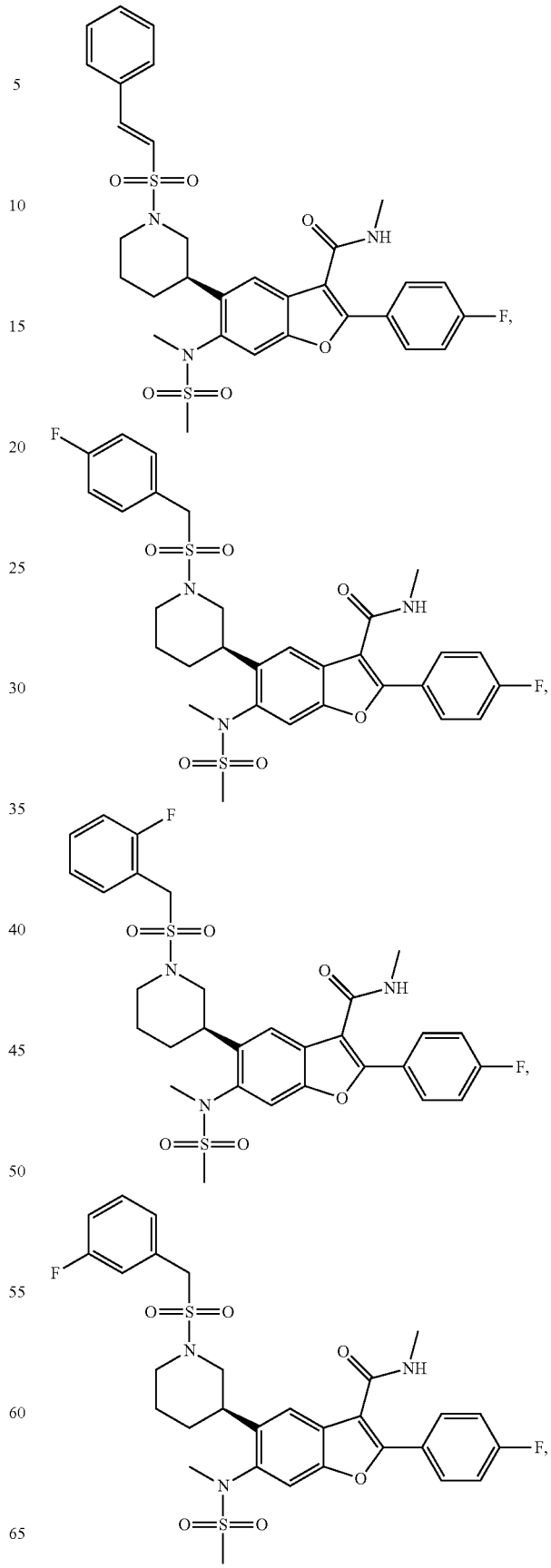

163
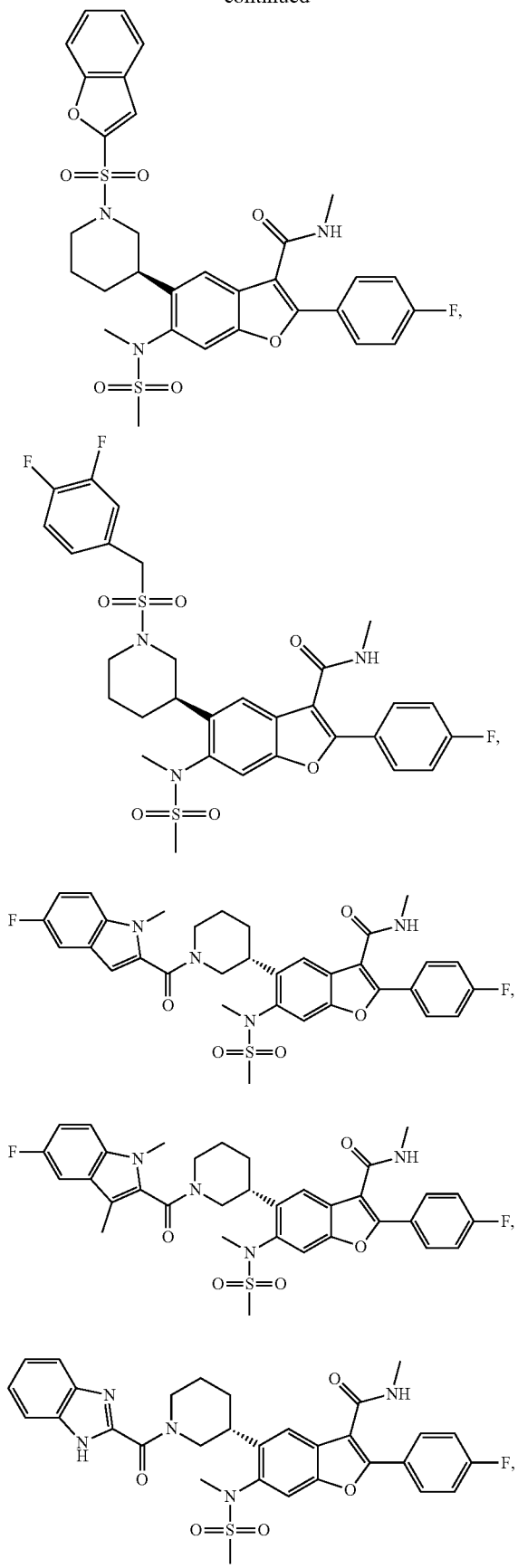
164
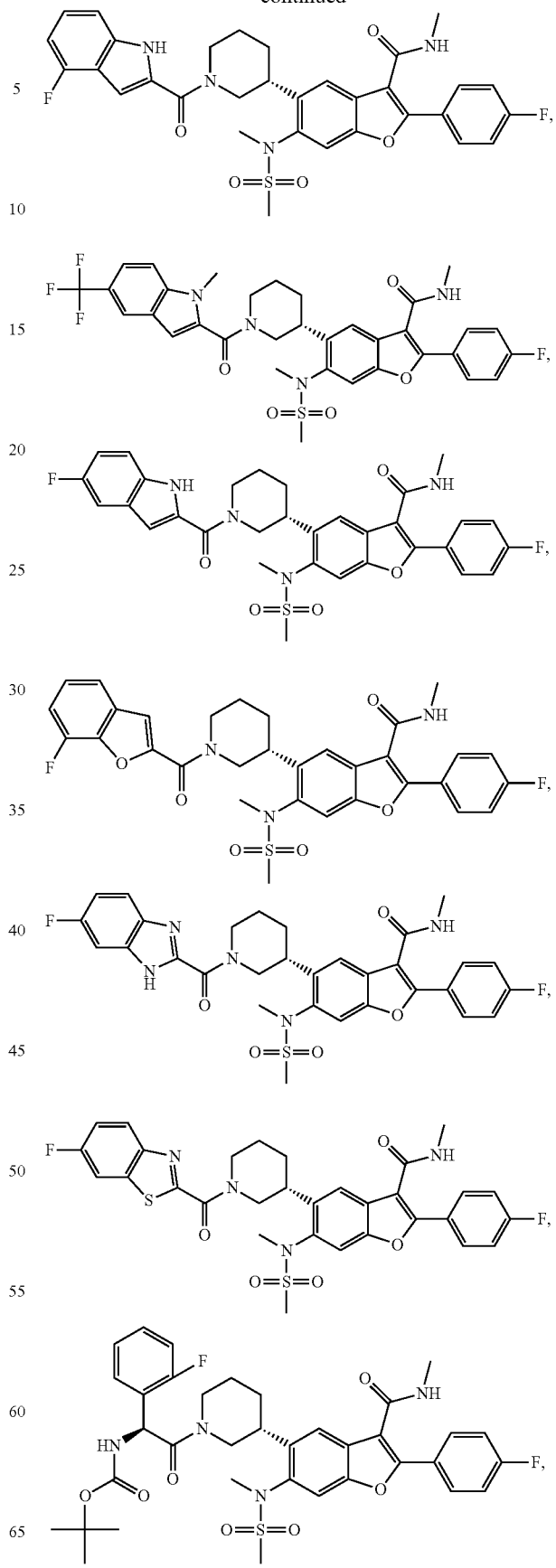

165
-continued
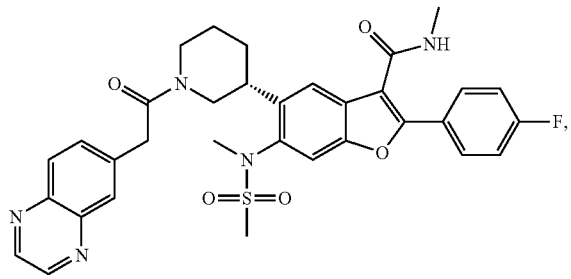
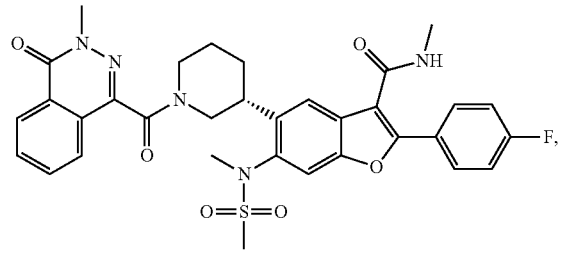
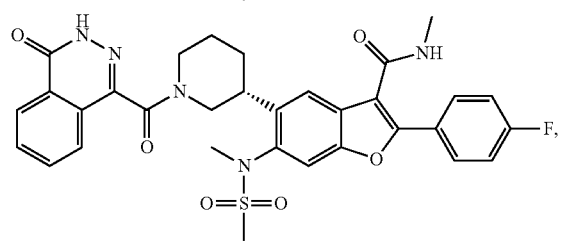
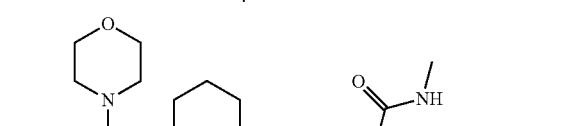
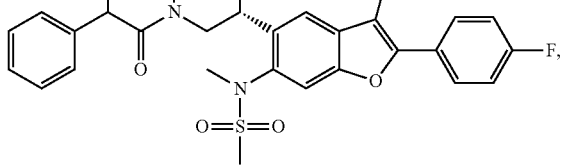
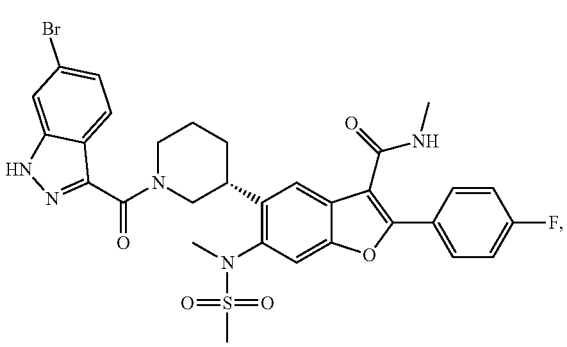
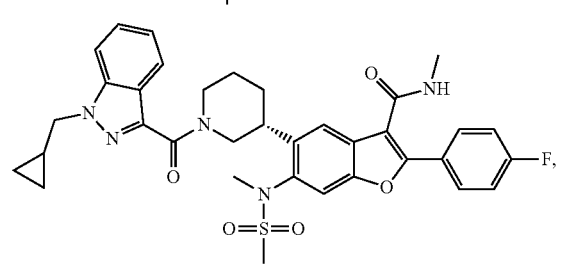
166
-continued
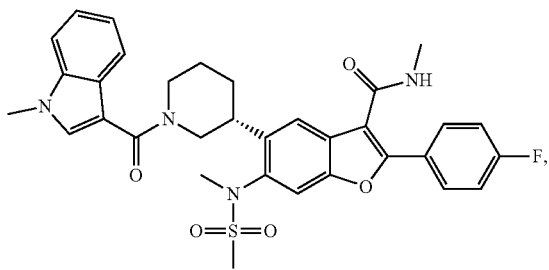
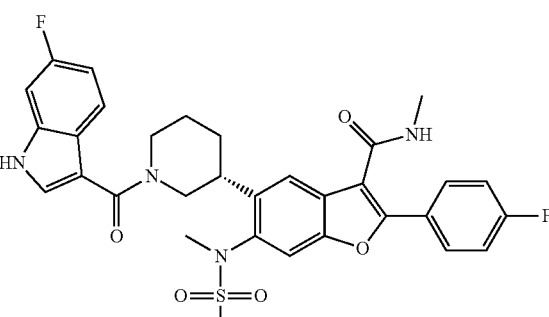
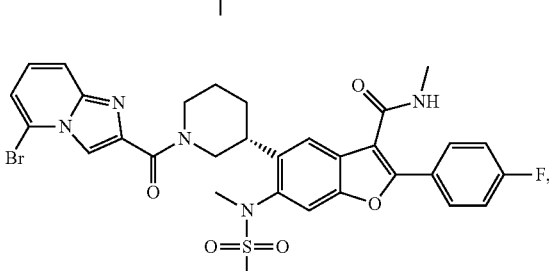
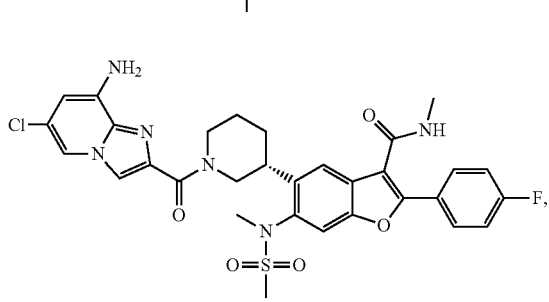
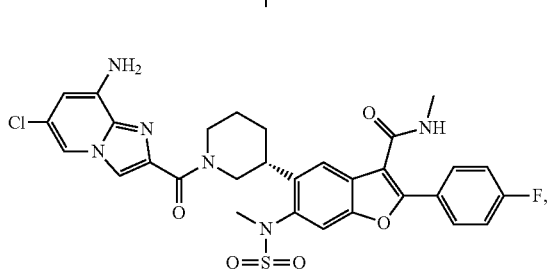
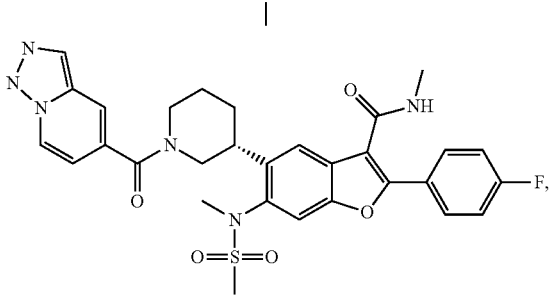

167
-continued
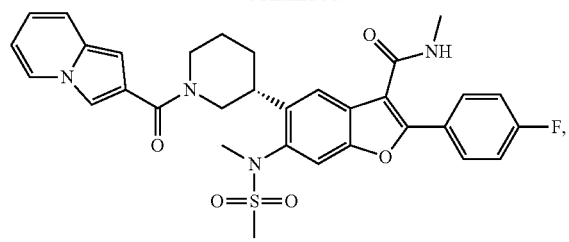
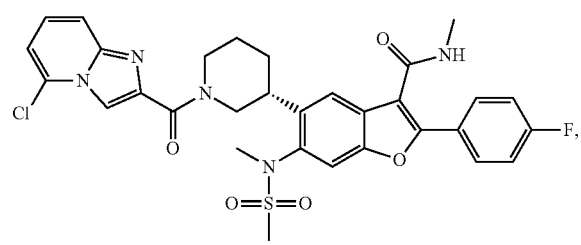
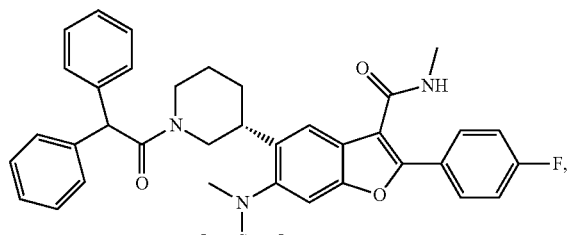
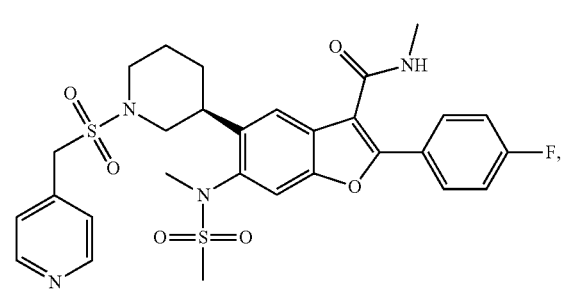
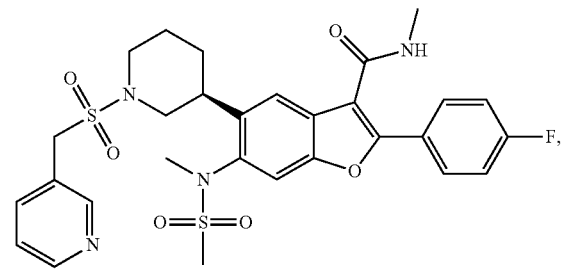
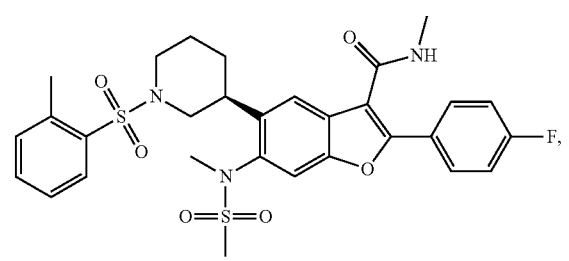
168
-continued
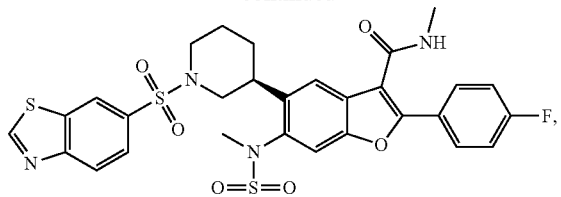
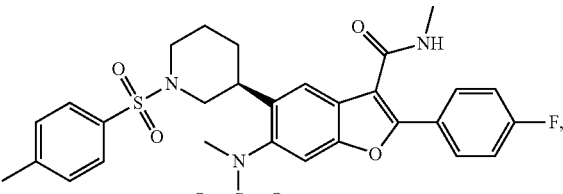
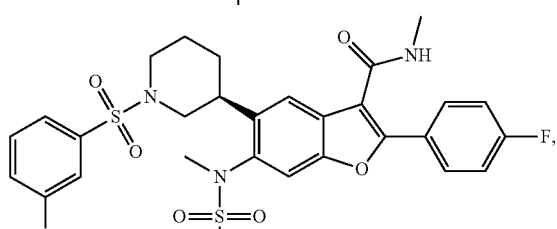
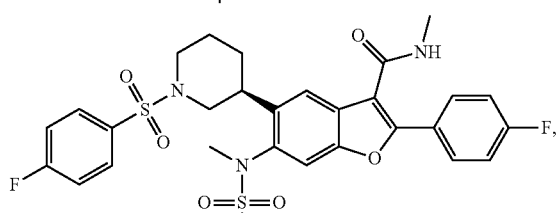
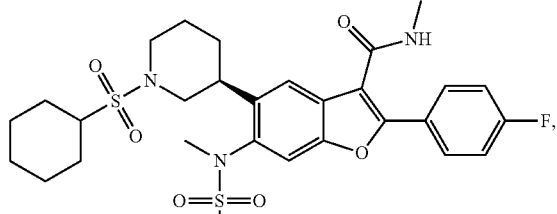
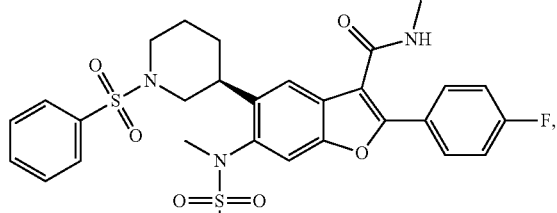
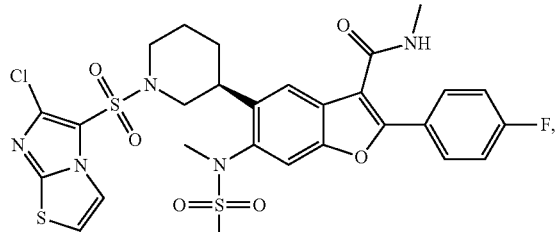

169
-continued
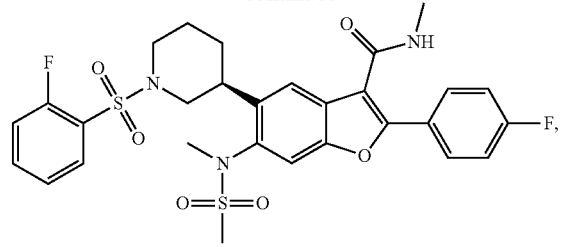
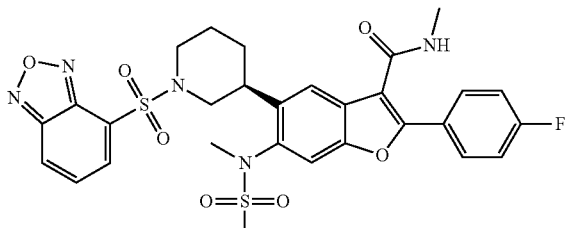
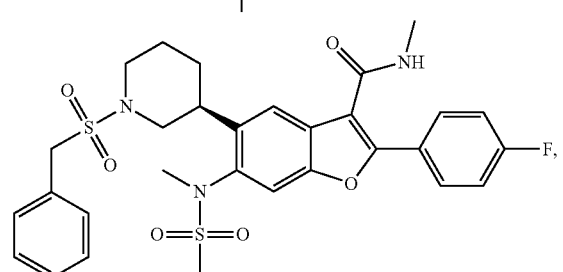
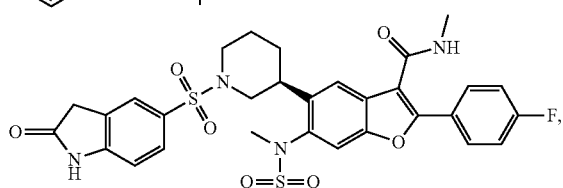
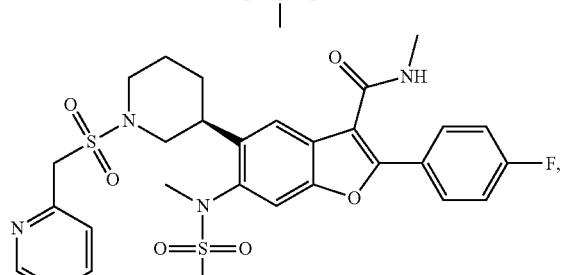
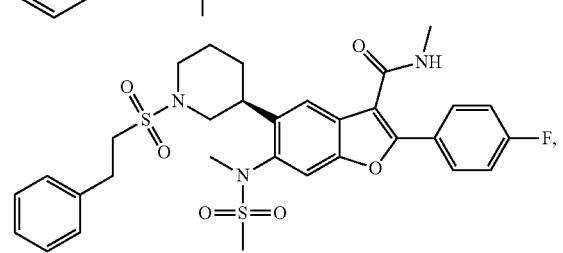
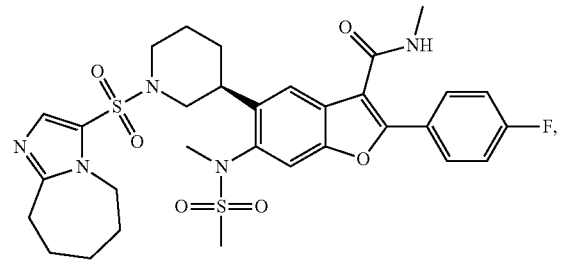
170
-continued
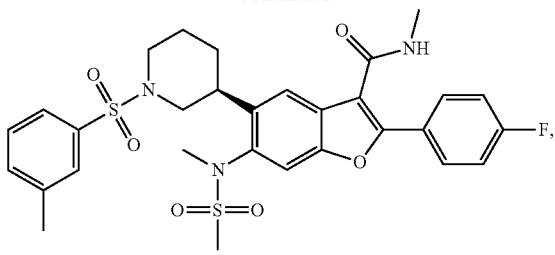
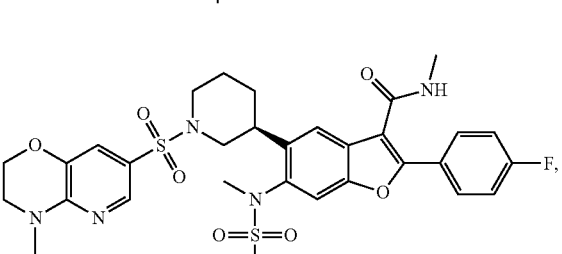
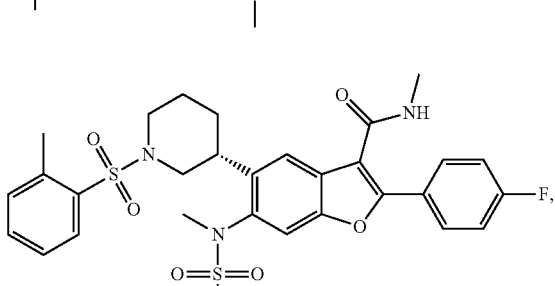
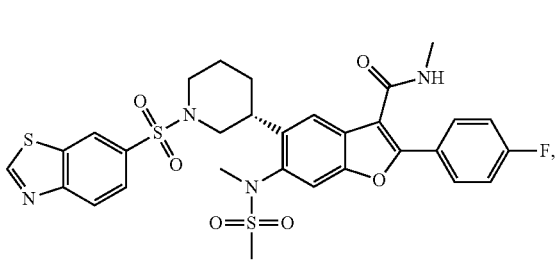
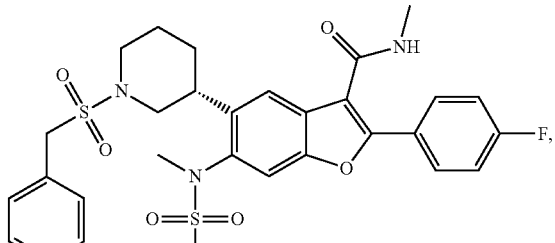
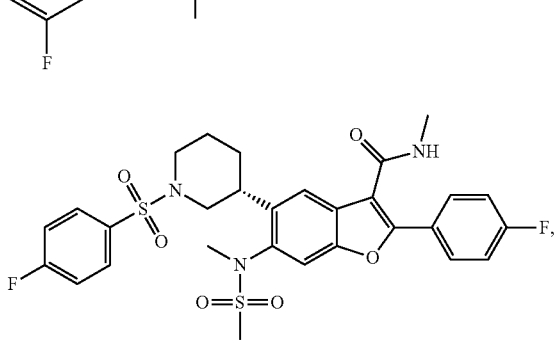

171
-continued
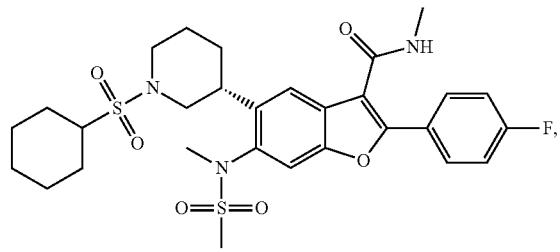
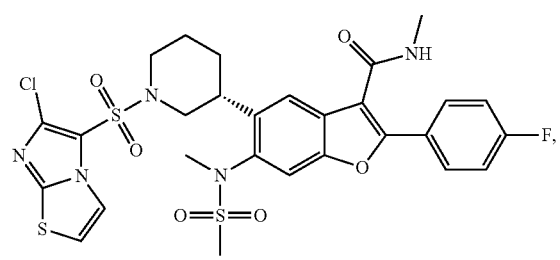
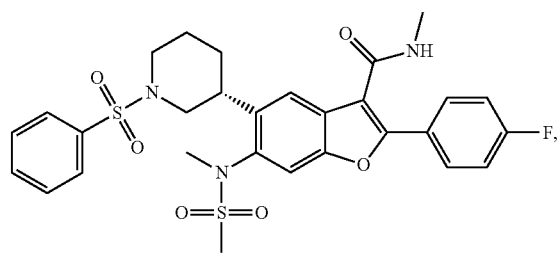
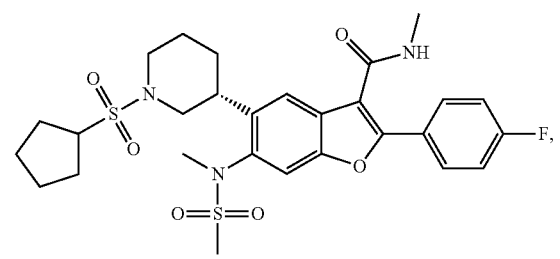
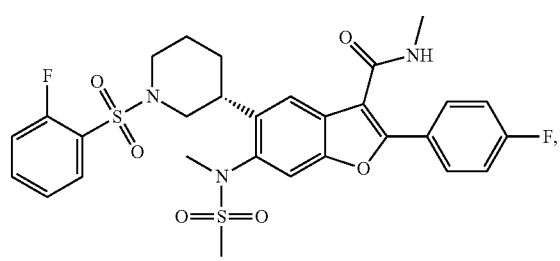
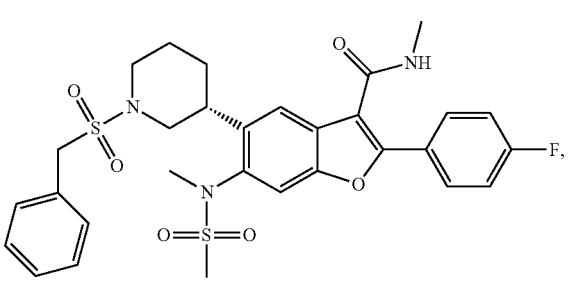
172
-continued
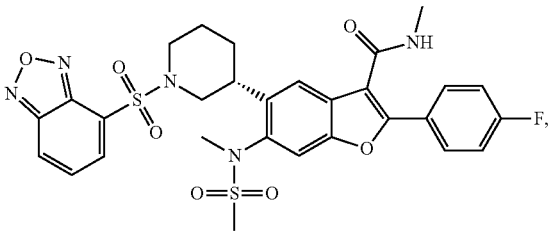
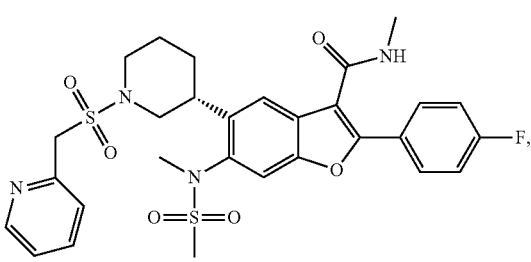
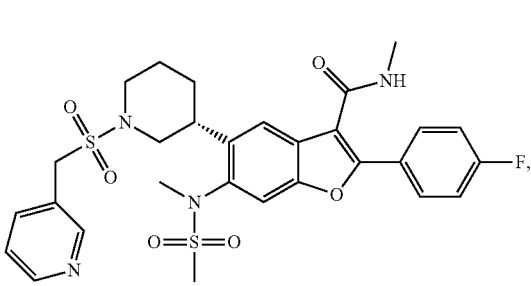
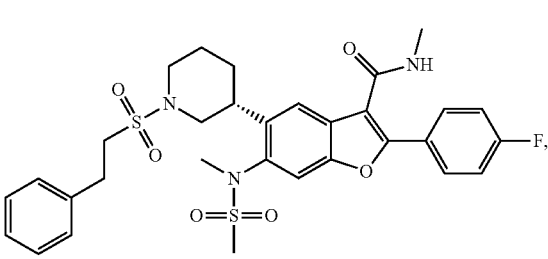
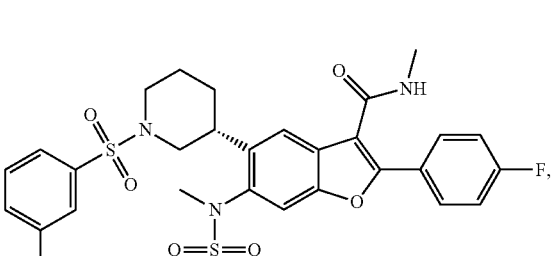
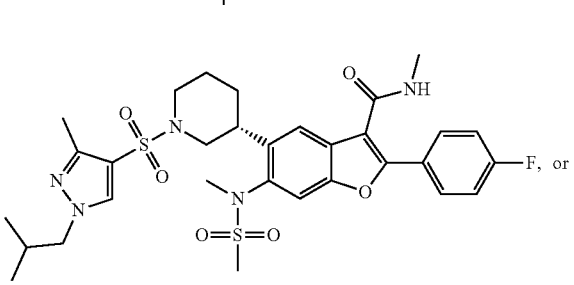

173
-continued
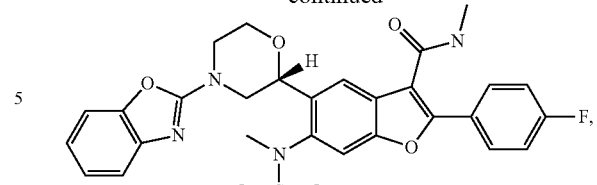
or a pharmaceutically acceptable salt thereof.
12. The compound of claim 1 which is any one of
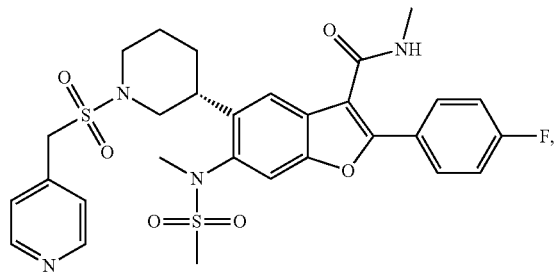
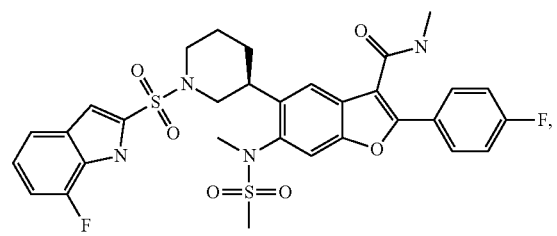
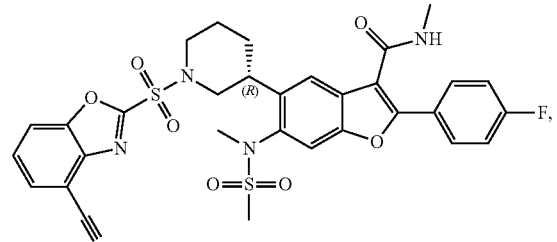
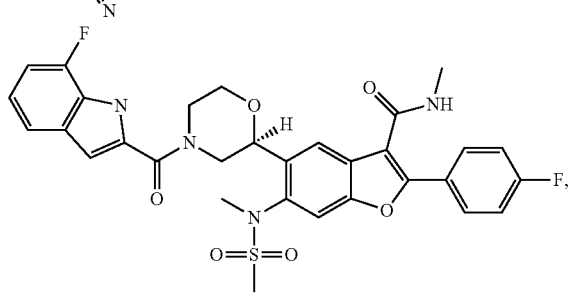
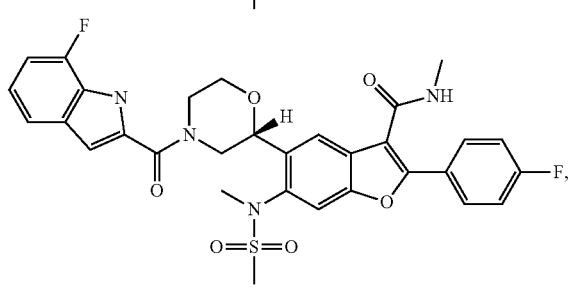
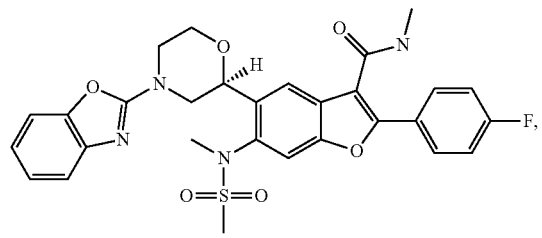
174
-continued
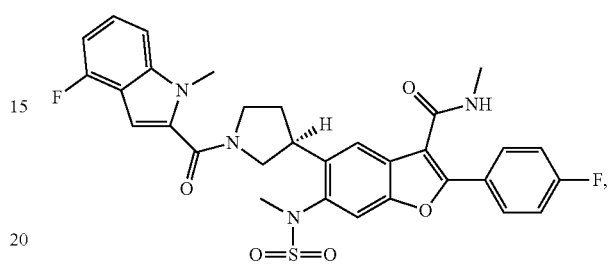
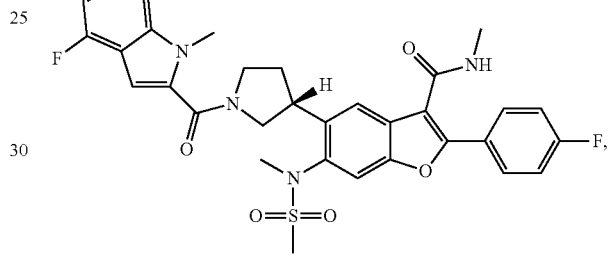
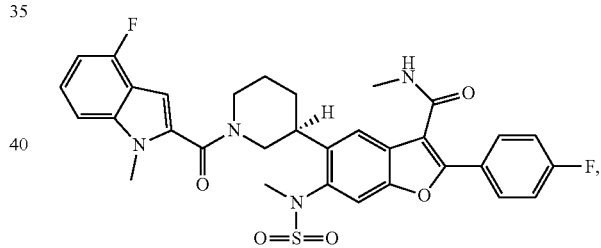
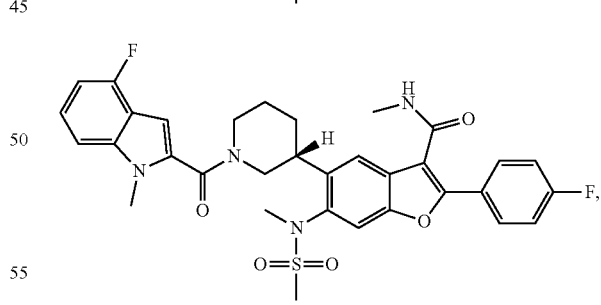
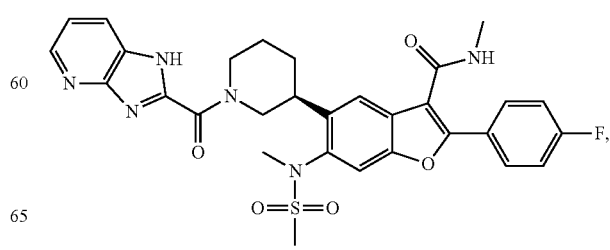

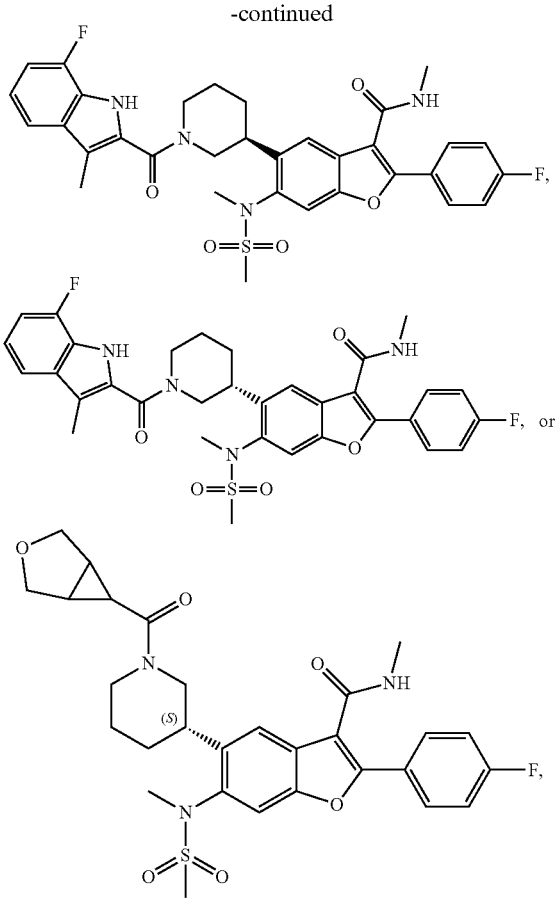

or a pharmaceutically acceptable salt thereof.

13. A pharmaceutical composition comprising (i) a pharmaceutically acceptable carrier and (ii) an amount of the compound of claim 1 or a pharmaceutically acceptable salt thereof effective to treat hepatitis C virus (HCV) infection.

14. The pharmaceutical composition of claim 13, further comprising a second therapeutic agent selected from the group consisting of HCV antiviral agents, immunomodulators, and anti-infective agents.

15. The pharmaceutical composition of claim 14, wherein the second therapeutic agent is selected from the group consisting of HCV NS3 and NS3/4A protease inhibitors, HCV NS5A inhibitors and HCV NS5B polymerase inhibitors.

16. A method of treating a patient infected with hepatitis C (HCV), the method comprising administering to the patient the compound of claim 1, or a pharmaceutically acceptable salt thereof, in an amount effective to treat infection by HCV in the patient.

17. The method of claim 16, further comprising administering to said patient an effective amount of at least one second therapeutic agent selected from the group consisting of HCV NS3 and NS3/4A protease inhibitors, HCV NS5A inhibitors and HCV NS5B polymerase inhibitors.

* * * * *

UNITED STATES PATENT AND TRADEMARK OFFICE
CERTIFICATE OF CORRECTION

PATENT NO. : 9,549,921 B2  
APPLICATION NO. : 14/897966  
DATED : January 24, 2017  
INVENTOR(S) : He et al.

Page 1 of 1

It is certified that error appears in the above-identified patent and that said Letters Patent is hereby corrected as shown below:

On the Title Page

In item (71) Applicant, replace:
"Shuwen He, Fanwood, NJ (US); Zhong Lai, East Brunswick, NJ (US); Xing Dai, Cranford, NJ (US); Dong Xiao, Warren, NJ (US); Clare London, Chatham, NJ (US); Nicolas Zorn, Durmenach (FR); Ravi Nargund, East Brunswick, NJ (US); Anandan Palani, Bridgewater, NJ (US); Casey C. McComas, Phoenixville, PA (US); Peng Li, Shanghai (CN); Xuanjia Peng, Shanghai (CN); Richard Soll, Middleton, MA (US)"

With:
--Merck Sharp & Dohme Corp., Rahway, NJ (US)--

Signed and Sealed this  
Twenty-fourth Day of July, 2018

Andrei Iancu  
*Director of the United States Patent and Trademark Office*